US009815849B2

(12) United States Patent
Bradner et al.

(10) Patent No.: US 9,815,849 B2
(45) Date of Patent: *Nov. 14, 2017

(54) COMPOSITIONS AND METHODS FOR TREATING LEUKEMIA

(71) Applicants: Dana-Farber Cancer Institute, Inc., Boston, MA (US); Cold Spring Harbor Laboratory, Cold Spring Harbor, NY (US)

(72) Inventors: James Elliott Bradner, Weston, MA (US); Johannes Zuber, Cold Spring Harbor, NY (US); Junwei Shi, Cold Spring Harbor, NY (US); Christopher R. Vakoc, Cold Spring Harbor, NY (US); Scott W. Lowe, New York, NY (US); Constantine S. Mitsiades, Boston, MA (US)

(73) Assignees: Dana-Farber Cancer Institute, Inc., Boston, MA (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,843

(22) Filed: Jul. 3, 2013

(65) Prior Publication Data
US 2014/0011862 A1    Jan. 9, 2014

Related U.S. Application Data

(63) Continuation of application No. 13/697,968, filed as application No. PCT/US2011/036672 on May 16, 2011, now abandoned.
(Continued)

(51) Int. Cl.
A61K 31/55     (2006.01)
C07D 495/14    (2006.01)
(Continued)

(52) U.S. Cl.
CPC ........ *C07D 495/14* (2013.01); *A61K 31/5517* (2013.01); *C12N 15/111* (2013.01);
(Continued)

(58) Field of Classification Search
CPC ........................... A61K 31/551; C07D 495/14
(Continued)

(56) References Cited

U.S. PATENT DOCUMENTS 3,681,343 A    8/1972    Hester, Jr.
3,709,898 A    1/1973    Hester, Jr.
(Continued)

FOREIGN PATENT DOCUMENTS

CA    2020806 A1    1/1991
CA    2710740 A1    7/2009
(Continued)

OTHER PUBLICATIONS

Abbate, E. A., et al., "Structure of the papillomavirus DNA-tethering complex E2:Brd4 and a peptide that ablates HPV chromosomal association," *Mol Cell* 24, 877-889, (2006).
(Continued)

*Primary Examiner* — Shengjun Wang
(74) *Attorney, Agent, or Firm* — Foley Hoag LLP

(57) ABSTRACT

The invention provides compositions, methods, and kits for the treatment of acute myeloid leukemia in a subject.

13 Claims, 55 Drawing Sheets

Related U.S. Application Data

(60) Provisional application No. 61/334,991, filed on May 14, 2010, provisional application No. 61/370,745, filed on Aug. 4, 2010, provisional application No. 61/375,863, filed on Aug. 22, 2010, provisional application No. 61/467,376, filed on Mar. 24, 2011, provisional application No. 61/467,342, filed on Mar. 24, 2011.

(51) Int. Cl.
    *C12N 15/11* (2006.01)
    *C12N 15/113* (2010.01)
    *A61K 31/5517* (2006.01)
    *C12Q 1/68* (2006.01)

(52) U.S. Cl.
    CPC ........ *C12N 15/113* (2013.01); *C12N 15/1137* (2013.01); *C12Q 1/6886* (2013.01); *C12N 2310/11* (2013.01); *C12N 2310/14* (2013.01); *C12N 2310/141* (2013.01); *C12N 2310/531* (2013.01); *C12N 2330/51* (2013.01)

(58) Field of Classification Search
    USPC ...................................................... 514/220
    See application file for complete search history.

(56) References Cited

U.S. PATENT DOCUMENTS

| | | |
|---|---|---|
| 3,812,259 A | 5/1974 | Collins |
| 4,621,083 A | 11/1986 | Casals-Stenzel et al. |
| 5,104,543 A | 4/1992 | Brandt et al. |
| 5,593,988 A | 1/1997 | Tahara et al. |
| 5,712,274 A | 1/1998 | Sueoka et al. |
| 5,753,649 A | 5/1998 | Tahara et al. |
| 5,854,238 A | 12/1998 | Kempen |
| 6,444,664 B1 | 9/2002 | Princen et al. |
| 7,015,213 B1 | 3/2006 | Bigg et al. |
| 7,589,167 B2 | 9/2009 | Zhou et al. |
| 8,044,042 B2 | 10/2011 | Adachi et al. |
| 8,476,260 B2 | 7/2013 | Miyoshi et al. |
| 8,981,083 B2 | 3/2015 | Bradner et al. |
| 9,320,711 B2 | 4/2016 | Natoli et al. |
| 9,320,741 B2 | 4/2016 | Bradner et al. |
| 2002/0169158 A1 | 11/2002 | Hunt, III et al. |
| 2003/0130268 A1 | 7/2003 | Sagara et al. |
| 2004/0043378 A1 | 3/2004 | Zhou et al. |
| 2006/0142257 A1 | 6/2006 | Nieschlag et al. |
| 2006/0223055 A1 | 10/2006 | Howley et al. |
| 2007/0218135 A1 | 9/2007 | Mukharya et al. |
| 2008/0004308 A1* | 1/2008 | Dhanak et al. ............... 514/300 |
| 2008/0081781 A1 | 4/2008 | Lippa et al. |
| 2009/0012064 A1 | 1/2009 | Sagara et al. |
| 2010/0286127 A1 | 11/2010 | Miyoshi et al. |
| 2012/0202798 A1 | 8/2012 | Sagara |
| 2013/0184264 A1 | 7/2013 | Bradner et al. |
| 2013/0210813 A1 | 8/2013 | Bradner et al. |
| 2013/0252331 A1 | 9/2013 | Bradner et al. |
| 2014/0011862 A1 | 1/2014 | Bradner et al. |

FOREIGN PATENT DOCUMENTS

| | | |
|---|---|---|
| CH | 622019 A5 | 3/1981 |
| CN | 1227555 A | 9/1999 |
| DE | 3724164 A1 | 2/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 2 239 264 A1 | 10/2010 |
| FR | 7532815 A1 | 5/1977 |
| JP | 61-87684 | 5/1986 |
| JP | 1-299231 | 12/1989 |
| JP | 6-157316 | 6/1994 |
| JP | 11-228576 | 8/1999 |
| JP | 11-512107 | 10/1999 |
| JP | 3001979 | 11/1999 |
| JP | 3096299 | 8/2000 |
| WO | WO 97/47622 A1 | 12/1997 |
| WO | WO 98/11111 A1 | 3/1998 |
| WO | WO 01/95912 A1 | 12/2001 |
| WO | WO 2008/083056 A2 | 7/2008 |
| WO | WO 2008/137081 A1 | 11/2008 |
| WO | WO 2009/084693 A1 | 7/2009 |
| WO | WO 2010/015387 A1 | 2/2010 |
| WO | WO 2010/049466 A1 | 5/2010 |
| WO | WO 2011/143651 A1 | 11/2011 |
| WO | WO 2011/143657 A1 | 11/2011 |
| WO | WO 2011/143660 A2 | 11/2011 |
| WO | WO 2011/143669 A2 | 11/2011 |
| WO | WO 2012/075456 A1 | 6/2012 |
| WO | WO 2013/033268 A2 | 3/2013 |
| WO | WO 2013/033269 A1 | 3/2013 |
| WO | WO 2013/033270 A2 | 3/2013 |
| WO | WO 2013/148197 A1 | 10/2013 |

OTHER PUBLICATIONS

Arango, O., et al., "Reversible Azoospermia in a Patient Treated with Triazolam," *Eur J Contracept Reprod Health Care*, 1(3):293-294 (1996).

Berkovits, B.D. and Wolgemuth, D.J., "The First Bromodomain of the Testis-Specific Double Bromodomain Protein Brdt is Required for Chromocenter Organization That is Modulated by Genetic Background," *Dev Biol.*, 360(2):358-368 (2011).

Berkovits, B.D. and Wolgemuth, D.J., "The Role of the Double Bromodomain-Containing BET Genes During Mammalian Spermatogenesis," *Current Topics in Developmental Biology*, 102: 293-326 (2013).

Buchdunger, E. et al., "Inhibition of the Abl Protein-Tyrosine Kinase in Vitro and in Vivo by a 2-Phenylaminopyrimidine Derivative," *Cancer Res*, 56:100-104 (1996).

Buchdunger, E. et al., "Selective inhibition of the platelet-derived growth factor signal transduction pathway by a protein-tyrosine kinase inhibitor of the 2-phenylaminopyrimidine class," *Proc Natl Acad Sci*, 92:2558-2562 (1995).

Bullock, A. N. et al., "Structural basis of Inhibitor Specificity of the Human Protooncogene Proviral Insertion site in Moloney Murine 1Leukemia virus (PIM-1) kinase," *J Med Chem*, 48:7604-7614 (2005).

Cellai, C., et al., "Mechanistic Insight Into WEB-2170-induced Apoptosis in Human Acute Myelogenous Leukemia Cells: the Crucial Role of PTEN," *Exp Hematol*, 37(10):1176-1185 (2009).

Cole, P. A., "Chemical probes for histone-modifying enzymes," *Nat Chem Biol* 4, 590-597, (2008).

Crawford, N. P. et al., "Bromodomain 4 activation predicts breast cancer survival," *Proc Natl Acad Sci*, 105, 6380-6385, (2008).

Denis, G.V., et al., "An Emerging Role for Bromodomain-Containing Proteins in Chromatin Regulation and Transcriptional Control of Adipogenesis," *FEBS Lett.*, 584(15): 3260-3268 (2010).

Dey, A., et al., "Brd4 Marks Select Genes of Mitotic Chromatin and Directs Postmitotic Transcription," *Molecular Biology of the Cell*, 20:4899-4909 (2009).

Druker, B. J. et al., "Effects of a selective inhibitor of the Abl Tyrosine kinase on the Growth of Bcr-Abl positive cells," *Nat Med*, 2:561-566 (1996).

Druker, B. J. et al., "Efficacy and safety of a specific inhibitor of the BCR-ABL tyrosine kinase in chronic myeloid leukemia," *N Engl J Med* 344, 1031-1037 (2001).

Fedorov, O. et al., "A Systematic Interaction Map of Validated Kinase Inhibitors with Ser/Thr kinases," *Proc Natl Acad Sci.*, 104(51):20523-20528 (2007).

Filippakopoulos, P., et al., "Selective Inhibition of BET Bromodomains," *Nature*, 468(7327): 1067-1073 (2010).

(56) References Cited

OTHER PUBLICATIONS

French, C. A. et al. "BRD4-NUT Fusion Oncogene: a Novel Mechanism in Aggressive Carcinoma," Cancer Res, 63:304-307 (2003).
French, C. A., "Demystified Molecular pathology of NUT Midline Carcinomas," J Clin Pathol, 63:492-496 (2010).
French, C. A., et al., "BRD4 Bromodomain Gene Rearrangement in Aggressive Carcinoma with Translocation t(15;19)," Am J Pathol, 159(6):1987-1992 (2001).
French, C. A., et al., "BRD-NUT Oncoproteins: a Family of Closely Related Nuclear Proteins that Block Epithelial Differentiation and Maintain the Growth of Carcinoma Cells," Oncogene, 27:2237-2242 (2008).
Greenwald, R.J., et al., "Eµ-BRD2 Transgenic Mice Develop B-Cell Lymphoma and Leukemia," Blood, 103(4):1475-1484 (2004).
Haack, H. et al., "Diagnosis of NUT Midline Carcinoma Using a NUT-specific Monoclonal Antibody," Am J Surg Pathol, 33:984-991 (2009).
Huang, B., et al., "Brd4 Coactivates Transcriptional Activation of NF-κB via Specific Binding to Acetylated RelA," Mol Cell Biol, 29(5):1375-1387 (2009).
Kadota, M. et al. "Identification of Novel Gene Amplifications in Breast Cancer and Coexistence of Gene Amplification with an Activating Mutation of PIK3CA," Cancer Res, 69: 7357-7365 (2009).
Kim, W.S., et al., "Berberine Improves Lipid Dysregulation in Obesity by Controlling Central and Peripheral AMPK Activity," Am. J. Physiol. Endocrinol. Metab., 296: E812-E819 (2009).
Le Coutre, P. et al. In vivo eradication of human BCR/ABL-positive leukemia cells with an ABL kinase inhibitor. J Natl Cancer Inst, 91:163-168 (1999).
Lee, Y.S., et al., "Berberine, a Natural Plant Product, Activates AMP-Activated Protein Kinase with Beneficial Metabolic Effects in Diabetic and Insulin-Resistant States," Diabetes, 55: 2256-2264 (2006).
Marushige, K., "Activation of Chromatin by Acetylation of Histone Side Chains," Proc. Nat'l. Acad. Sci., 73(11): 3937-3941 (1976).
Matzuk, M., "Small-Molecule Inhibition of BRDT for Male Contraception," Cell: 150: 673-684 (2012).
Meguro, K., et al., "Heterocycles. VI.[1]) Synthesis of 4H-s-Triazolo[4,3-a][1,4]benzodiazepines, Novel Tricyclic Psychosedatives," Chem. Pharm. Bull., 21(11):2382-2390 (1973).
Meng-er, H., et al., "Use of All-Trans Retinoic Acid in the Treatment of Acute Promyelocytic Leukemia," BLOOD, 72(2): 567-572 (1988).
Mochizuki, K. et al., "The Bromodomain Protein Brd4 Stimulates $G_1$ Gene Transcription and Promotes Progression to S Phase," J Biol Chem, 283(14):9040-9048 (2008).
Niesen, F. H., et al., "The use of Differential Scanning Fluorimetry to Detect Ligand Interactions that Promote Protein Stability," Nat Protoc, 2(9):2212-2221 (2007).
Owen, D.J., et al., "The Structural Basis for the Recognition of Acetylated Histone R4 by the Bromodomain of Histone Acetyltransferase Gcn5p," The EMBO Journal, 19(22): 6141-6149 (2000).
Patani, G.A. and LaVoie, E.L., "Bioisosterism: A Rational Approach in Drug Design," Chem. Rev. 96:3147-3176 (1996).
Phelps, M., et al., "Clinical Response and Pharmacokinetics from a Phase 1 Study of an Active Dosing Schedule of Flavopiridol in Relapsed Chronic Lymphocytic Leukemia," BLOOD, 113(12):2637-2645 (2009).
Preisler, H.D., et al., "Assessment of c-myc Expression in Individual Leukemic Cells," Leuk Res, 12(6): 507-516 (1988).
Ptashne, M., "Binding Reactions: Epigenetic Switches, Signal Transduction and Cancer," Current Biology, 19(6):R234-R241 (2009).
Quinn, A. M. et al. "A homogeneous method for investigation of methylation-dependent protein-protein interactions in epigenetics," Nucleic Acids Res, 38(2):e11(1-10) (2010).
Rahl, P., et al., "c-Myc Regulates Transcriptional Pause Release," Cell, 141:432-445 (2010).
Schindler, T. et al. "Structural mechanism for STI-571 Inhibition of Abelson Tyrosine kinase. Science," 289:1938-1942 (2000).
Schreiber, S.L., et al., "Signaling Network Model of Chromatin," Cell, 111:771-778 (2002).
Shang, et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).
Taskinen, M., et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).
Vollmuth, F., et al., "Structures of the dual bromodomains of the P-TEFb-activating protein Brd4 at atomic resolution," J Biol Chem, 284:36547-36556 (2009).
VonVoigtlander, P.F. and Straw, R.N., "Alprazolam: Review of Pharmacological, Pharmacokinetic and Clinical Data," Drug Development Research, 6:1-12 (1985).
Yang, et al., "Multisite Protein Modification and Intramolecular Signaling," Oncogene, 24:1653-1662 (2005).
Yang, Z., et al., "Brd4 recruits P-TEFb to chromosomes at late mitosis to promote $G_1$ gene expression and cell cycle progression," Mol Cell Biol, 28(3):967-976 (2008).
Yang, Z., et al., "Recruitment of P-TEFb for Stimulation of Transcriptional Elongation by the Bromodomain Protein Brd4," Molecular Cell, 16:535-545 (2005).
You, J. et al. "Regulation of Aurora B Expression by the Bromodomain Protein Brd4," Mol Cell Biol, 29:5094-5103 (2009).
You, J. et al., "Kaposi's sarcoma-associated herpesvirus latency-associated nuclear antigen interacts with bromodomain protein Brd4 on host mitotic chromosomes," J Virol 80, 8909-8919, (2006).
Zeng, L. et al., "Bromodomain: an Acetyl-lysine Binding Domain," FEBS Letters, 513:124-128 (2002).
Zhang, G., et al., "Down-Regulation of NF-κB Transcriptional Activity in HIV-Associated Kidney Disease by BRD4 Inhibition," J. Biol Chem, 287(34):28840-28851 (2012).
Zhang, G., et al., "Down-Regulation of NF-κB Transcriptional Activity in HIV-Associated Kidney Disease by BRD4 Inhibition," J. Biol Chem, 287(46):38956 (2012).
Zuber, J., et al., "RNAi Screen Identifies Brd4 as a Therapeutic Target in Acute Myeloid Leukaemia," Nature: 478: 524-528 (2011), with "Supplementary Information" from www.nature.com/nature, pp. 1-33.
Notification of Transmittal of the International Search Report and the Written Opinion of the International Searching Authority, International Application No. PCT/US11/36667, Titled: "Male Contraceptive Compositions and Methods of Use", dated Aug. 15, 2011.
Notification of Transmittal of the International Search Report and the Written Opinion of the International Searching Authority, International Application No. PCT/US11/36647, Titled: "Compositions and Methods of Modulating Metabolism", dated Aug. 17, 2011.
Notification of Transmittal of the International Search Report and the Written Opinion of the International Searching Authority, International Application No. PCT/US11/36672, Titled: "Compositions and Methods for Treating Leukemia", dated Jan. 27, 2012.
Notification of Transmittal of the International Search Report and the Written Opinion of the International Searching Authority, International Application No. PCT/US11/36701, Titled: "Compositions and Methods for Treating Neoplasia, Inflammatory Disease and Other Disorders", dated Feb. 1, 2012.
Notification Concerning Transmittal of International Preliminary Report on Patentability, International Application No. PCT/US2011/036647, Titled: "Compositions and Methods of Modulating Metabolism", dated Nov. 29, 2012.
Notification Concerning Transmittal of International Preliminary Report on Patentability, International Application No. PCT/US2011/036701, Titled: "Compositions and Methods for Treating Neoplasia, Inflammatory Disease and Other Disorders", dated Nov. 29, 2012.

(56) References Cited

OTHER PUBLICATIONS

Notification Concerning Transmittal of International Preliminary Report on Patentability, International Application No. PCT/US2011/036672, Titled: "Compositions and Methods for Treating Leukemia", dated Nov. 29, 2012.
Notification Concerning Transmittal of International Preliminary Report on Patentability, International Application No. PCT/US2011/036667, Titled: "Male Contraceptive Compositions and Methods of Use", dated Nov. 29, 2012.
Office Action, U.S. Appl. No. 13/698,006, dated Sep. 26, 2013.
Examination Report, AU Application No. 2011252808, dated Aug. 5, 2013.
Cellai, C., et al., "Specific PAF Antagonist WEB-2086 Induces Terminal Differentiation of Murine and Human Leukemia Cells," *FASEB*, 16:733-735 (2002).
Hu, G-X, et al., "Adjudin Targeting Rabbit Germ Cell Adhesion as a Male Contraceptive: A Pharmacokinetics Study," *J Androl*, 30(1):87-3 (2009).
Lawless, M.W., et al., "Histone Deacetylase Inhibitors Target Diabetes Via Chromatin Remodeling or as Chemical Chaperones?," *Curr Diabetes Rev*, 5(3):201-209 (2009).
Santillan, D.A., et al., "Bromodomain and Histone Acetyltransferase Domain Specificities Control Mixed Lineage Leukemia Phenotype," *Cancer Res*, 66(20):10032-10039 (2006).
Seyrig, J.A., et al., "Effects of a Chronic Administration of Two Benzodiazepines on Food Intake in Rats Given a Highly Palatable Diet," *Pharmacology Biochemistry & Behavior*, 25:913-918 (1986).
Wang, C.Q.F. and Cheng C.Y., "A Seamless Trespass: Germ Cell Migration Across the Seminiferous Epithelium During Spermatogenesis," JCB, 178(4):549-556 (2007).
Wang, F., et al., "Brd2 Disruption in Mice Causes Severe Obesity Without Type 2 Diabetes," *Biochem. J.*, 425:71-83 (2010).
Zhao, W., et al., "Research Development on Fusion Protein Transcription Factor siRNA Specifically Targeting Leukemia," *Sciencepaper Online*:1-6 and *J. Med Res.*, 39(2):6-9 (Feb. 2010) (English-language translation entitled "Progress of Research on siRNA that Targets Leukemia Specific Transcription Regulation Factor Fusion Proteins," pp. 1-10).
Office Action, U.S. Appl. No. 13/698,006, dated Apr. 10, 2014.
Notice of Allowance, U.S. Appl. No. 13/698,010, dated Aug. 21, 2014.
Office Action, U.S. Appl. No. 13/698,006, dated Oct. 23, 2014.
Office Action, U.S. Appl. No. 13/697,963, dated Nov. 21, 2014.
Office Action, U.S. Appl. No. 13/934,843, dated Mar. 23, 2015.
U.S. Appl. No. 15/061,576, filed Mar. 4, 2016, "Compositions and Methods for Treating Neoplasia, Inflammatory Disease and Other Disorders".
Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo," Blood, 110(6): 2034-2040 (2007).
Notice of Allowance, U.S. Appl. No. 14/502,840, dated Dec. 4, 2015.

\* cited by examiner

Figure 2A
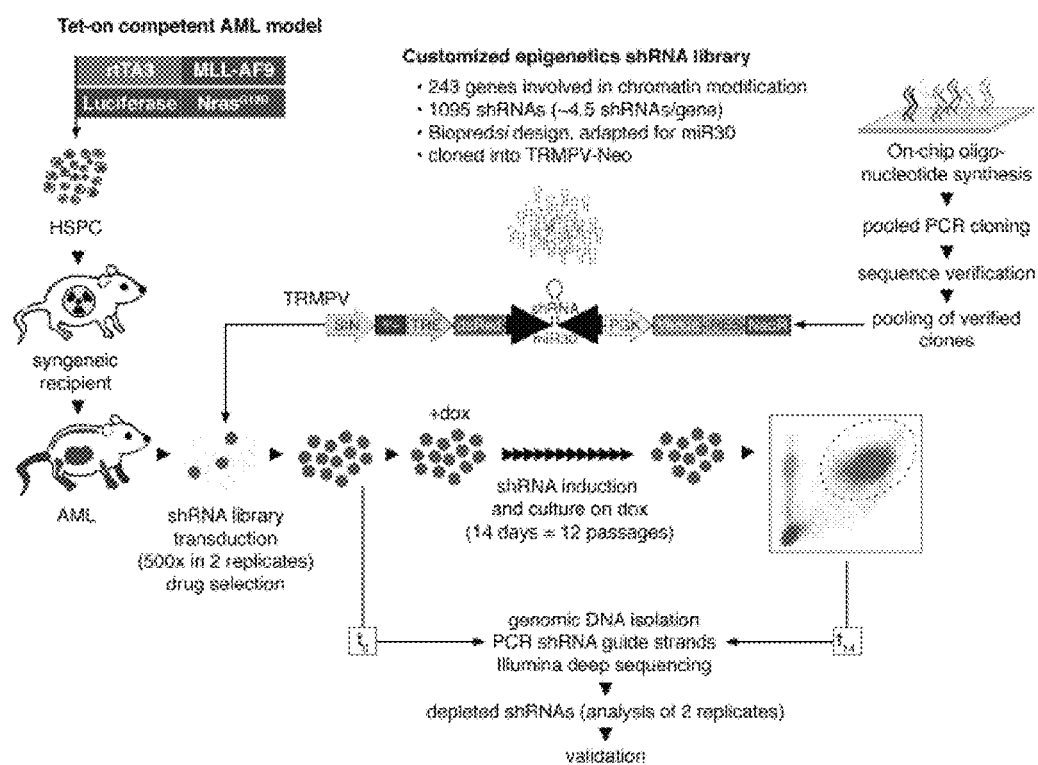
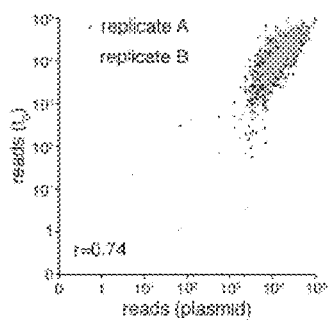
Figure 2B
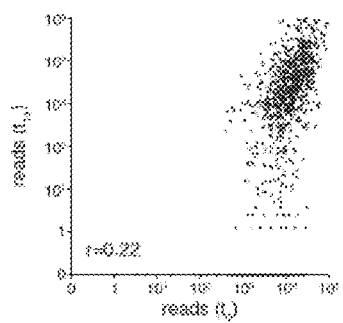
Figure 2C
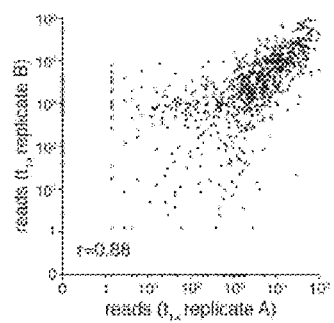
Figure 2D

Figure 8A

| AML: | F/M | Age | FAB | WHO | WBC 10^9/L | % Blast cells PB | BM | Karyotype | Mutations |
|---|---|---|---|---|---|---|---|---|---|
| 1* | F | 32 | M1 | AML with t(9;11) | 0.4* | 80% | 73% | 46,XX, t(9;11) | MLL1-AF9 |
| 2 | M | 61 | M5 | AML monoblastic | 35.1 | 33% | 72% | 46,XY, t(11;17) | MLL1-MSF |
| 3 | M | 65 | M5 | AML with t(9;11)/NPM1m | 94.8 | 6% | 90% | 47,XY, t(9;11),+8 | MLL1-AF9, FLT3-D835, NPM1m |
| 4 | M | 80 | M4 | AML with NPM1m | 198.5 | 25% | 52% | 46,XY | FLT3 ITD, KIT D816V, NPM1m |
| 5 | M | 54 | M1 | AML with NPM1m | 361.5 | 95% | 92% | 46,XY | FLT3 ITD, NPM1m |
| 6 | F | 49 | M4 | AML myelomonocytic | 15.4 | 16% | 63% | 46,XX | FLT3 ITD |
| 7 | M | 67 | M1 | AML with myelodysplasia | 74.6 | 95% | 84% | complex | - |
| 8* | F | 81 | M5 | AML with myelodysplasia | 82.1* | 77% | 74% | 46,XX,del12p,del20q | - |
| 9 | F | 39 | M5 | AML monoblastic | 37.7 | 65% | 84% | 47,XX,t(3;11),+8 | -- |
| 10 | F | 49 | M4 | AML with inv16 | 94.2 | 47% | 87% | 46,XX,inv16 | FLT3 ITD |
| 11 | M | 58 | M2 | AML with t(8;21) | 100 | 60% | 58% | 46,XY,t(8;21) | -- |
| 12 | M | 23 | M2 | AML with t(8;21) | 13.7 | 52% | 59% | 45,X,-Y, t(8;21) | - |

*These patients were analyzed at relapse. Abbreviations: WBC, white blood count; F, female, M, male, FAB, French-American-British cooperative study group; WHO, World Health Organization; PB, peripheral blood; BM, bone marrow; NPM1m, mutated NPM1;

Figure 8B

| AML: | source | 3H-thymidine-uptake +cytokines* IC50 (nM) | -cytokines IC50 (nM) | Induction of Apoptosis** % Apoptotic Cells (Giemsa) 500 nM JQ1 | 1,000 nM JQ1 | Maturation |
|---|---|---|---|---|---|---|
| 1 | PB | 280 | n.t. | n.t. | n.t. | n.t. |
| 2 | BM | 90 | 70 | 14 | 22 | + (macrophage) |
| 3 | BM | 160 | 240 | n.t. | n.t. | n.t. |
| 4 | PB | 1030 | 420 | 14 | 18 | ++ (macrophage) |
| 5 | BM | 420 | n.t. | 30 | 50 | + (myeloid) |
| 6 | BM | 1420 | 140 | 14 | 37 | ++ (myeloid) |
| 7 | BM | 40 | n.t. | 23 | 28 | + (myeloid) |
| 8 | PB | 40 | 50 | 33 | 27 | - |
| 9 | BM | 50 | 50 | n.t. | n.t. | n.t. |
| 10 | BM | 150 | 60 | 36 | 55 | ++ (macrophage) |
| 11 | BM | 40 | n.t. | n.t. | n.t. | n.t. |
| 12 | BM | 60 | n.t. | n.t. | n.t. | n.t. |
| HL60 | + ctl | | 200 | | | |
| MOLM13 | + ctl | | 135 | | | |

*Cells were incubated with JQ1 in the presence of G-CSF (100 ng/ml), SCF (100 ng/ml), and IL-3 (100 ng/ml).
**The percentage of apoptotic cells was determined on cytospin slides by Wright-Giemsa staining; percentages of apoptotic cells measured in control medium (usually <10% of cells) was subtracted in each case.

Figure 9A

| Sample ID | Age Group | Phenotype | Molecular/Cytogenetic | WST1 IC50 (nM) | Induction of Apoptosis* % Apoptotic Cells (AVB) 500 nM JQ1 | 1,000 nM JQ1 | Maturation |
|---|---|---|---|---|---|---|---|
| PED025 | Infant | MPAL (B/myeloid) | MLL-ENL | 163 | 32 | 33 | ++ (Lymphoid) |
| PED095 | Infant | MPAL (B/myeloid) | MLL-AF4 | 174 | 32 | 18 | ++ (Myeloid) |
| PED051 | Child | AML | FLT3/ITD | 596 | 21 | 24 | - |
| PED004 | Child | AML | monosomy 7, BCR-ABL | 451 | 19 | 34 | + (Myeloid) |
| 801343 | Infant | pre-B ALL | MLL-ENL | 345 | 13 | 20 | ++ (Lymphoid) |
| PED063 | Child | AML | CBFB-MYH11 | 136 | 21 | 24 | - |
| MV4-11 | cell | AML | MLL-AF4, FLT3/ITD | 165 | 80 | 86 | n.t. |

Abbreviations: MPAL: Mixed Phenotype Acute Leukemia, n.t: not tested
*The percentage of apoptotic cells was determined Annexin V binding flow cytometry (AVB); percentages of apoptotic cells measured in control medium was subtracted in each case.

Figure 9B

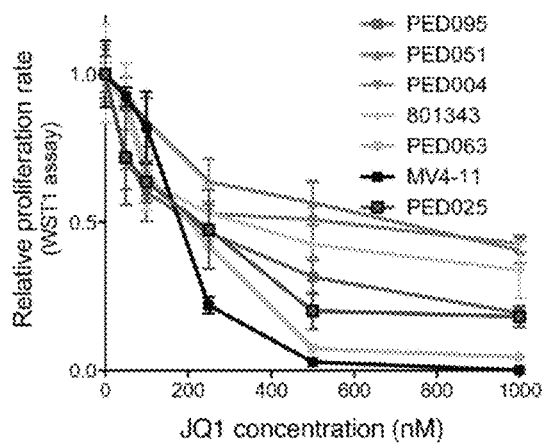

| Individual and mean plasma concentration-time data of (S)-JQ1 after an IP dose of 50 mg/kg in male CD1 mice ||||||||
| Dose (mg/kg) | Dose route | Sampling time (hr) | Concentration (ng/mL) Individual ||| Mean (ng/mL) | SD | CV(%) |
| --- | --- | --- | --- | --- | --- | --- | --- | --- |
| 50 | IP | 0 | BQL | BQL | BQL | BQL | NA | NA |
| | | 0.033 | 7270 | 9480 | 5470 | 7407 | 2008 | 27.1 |
| | | 0.083 | 11000 | 12600 | 9510 | 11037 | 1548 | 14.0 |
| | | 0.25 | 8660 | 8930 | 11400 | 9663 | 1510 | 15.6 |
| | | 0.5 | 8540 | 6950 | 9920 | 8470 | 1486 | 17.5 |
| | | 1 | 5690 | 4270 | 4680 | 4880 | 731 | 15.0 |
| | | 2 | 3590 | 4370 | 4450 | 4137 | 475 | 11.5 |
| | | 4 | 2620 | 1280 | 2060 | 1987 | 673 | 33.9 |
| | | 6 | 65.7 | 523 | 801 | 463 | 371 | 80.1 |
| | | 8 | 151 | 595 | 446 | 397 | 226 | 56.9 |
| | | 12 | 4.54 | 5.02 | 10.9 | 6.82 | 3.54 | 51.9 |
| | | 24 | BQL | BQL | BQL | BQL | NA | NA |
| PK parameters | Unit | Estimate ||||||| 
| $T_{max}$ | hr | 0.0830 |||||||
| $C_{max}$ | ng/mL | 11000 |||||||
| Terminal $t_{1/2}$ | hr | 1.24 |||||||
| $AUC_{last}$ | hr*ng/mL | 22700 |||||||
| $AUC_{inf}$ | hr*ng/mL | 22700 |||||||

# COMPOSITIONS AND METHODS FOR TREATING LEUKEMIA

CROSS-REFERENCE TO RELATED APPLICATIONS

This application is a continuation application of U.S. application Ser. No. 13/697,968, which is the U.S. National Stage of International Application No. PCT/US2011/036672, filed May 16, 2011, which designates the U.S., published in English, and claims the benefit of U.S. Provisional Application No. 61/334,991, filed May 14, 2010; U.S. Provisional Application No. 61/370,745, filed Aug. 4, 2010, U.S. Provisional Application No. 61/375,863, filed Aug. 22, 2010, U.S. Provisional Application No. 61/467,376, filed Mar. 24, 2011 and U.S. Provisional Application No. 61/467,342, filed Mar. 24, 2011. The entire teachings of the above applications are incorporated herein by reference.

STATEMENT OF RIGHTS TO INVENTIONS MADE UNDER FEDERALLY SPONSORED RESEARCH

This invention was made with government support under grant numbers K08CA128972, CA174793 and CA045508 awarded by The National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

File name. 48051002010SeqList.txt; created Jul. 2, 2013, 35 KB in size.

Parties to Joint Research Agreement: Cold Spring Harbor Laboratory and Dana-Farber Cancer Institute, Inc.

BACKGROUND OF THE INVENTION

Acute Myeloid Leukemia (AML) represents a paradigm for understanding how complex patterns of cooperating genetic and epigenetic alterations lead to tumorigenesis. While this complexity poses a challenge for the development of targeted therapy, diverse AML gene mutations generally converge functionally in deregulating similar core cellular processes. One key event in AML initiation is the corruption of cell-fate programs to generate Leukemic Stem Cells (LSCs) that aberrantly self-renew and thereby maintain and propagate the disease. While incompletely understood, this process has been linked to changes in regulatory chromatin modifications whose impact on gene expression is well characterized. Hence, common oncogenes in AML, such as AML1-ETO and MLL fusion proteins induce self-renewal programs, at least in part, through reprogramming of epigenetic pathways. Several epigenetic regulators are targets of somatic mutation. Since epigenetic alterations induced by oncogenic stimuli are potentially reversible, chromatin regulators are being explored as candidate drug targets.

SUMMARY OF THE INVENTION

The invention provides compositions, methods, and kits for the detection and treatment of leukemia and related disorders (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes).

In one aspect, the invention generally provides a method for treating a leukemia or related disorder (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes) in a subject, the method involving administering to the subject an effective amount of an agent that inhibits Brd4 (e.g., an inhibitory nucleic acid that target Brd4, JQ1) or a derivative thereof.

In another aspect, the invention provides a method for reducing the growth, proliferation or survival of a leukemic cell, the method involving contacting the cell with an effective amount of an agent that inhibits Brd4 or a derivative thereof, thereby reducing the growth, proliferation or survival of a leukemic cell.

In yet another aspect, the invention provides a method of inducing cell death or terminal differentiation in a leukemic cell, the method comprising contacting the cell with an effective amount of an agent that inhibits Brd4 or a derivative thereof, thereby inducing cell death or terminal differentiation in the leukemic cell.

In yet another aspect, the invention provides a method of treating acute myeloid leukemia in a subject, the method involving administering to a subject in need thereof an effective amount of an agent that inhibits Brd4, thereby treating acute myeloid leukemia in a subject.

In yet another aspect, the invention provides a pharmaceutical composition containing a therapeutically effective amount of an agent that inhibits Brd4 or a derivative thereof in a pharmaceutically effective excipient.

In yet another aspect, the invention provides a kit for the treatment of leukemia, the kit containing a therapeutically effective amount of an agent that inhibits Brd4, and written instructions for administration of the compound for use in the method of claim 8.

In yet another aspect, the invention provides a method for detecting the clinical responsiveness of a leukemic cell, the method involving contacting a leukemic cell with a Brd4 inhibitory agent or derivative thereof and detecting expression of a macrophage specific differentiation marker in the cell, wherein an increase in the expression of the macrophage specific differentiation marker indicates that the cell is responsive to the agent.

In yet another aspect, the invention provides a method for selecting a treatment regimen for a subject identified as having leukemia, the method involving contacting a leukemic cell of the subject with a Brd4 inhibitory agent or derivative thereof and detecting expression of a macrophage specific differentiation marker in the cell, wherein an increase in the expression of the macrophage specific differentiation marker is indicative that a treatment regimen including that agent should be selected for the subject.

In yet another aspect, the invention provides a method for detecting the clinical responsiveness of a leukemic cell, the method comprising contacting a leukemic cell with a Brd4 inhibitory agent or derivative thereof and detecting expression of myc in the cell, wherein a decrease in myc expression indicates that the cell is responsive to the agent.

In yet another aspect, the invention provides a method for selecting a treatment regimen for a subject, the method comprising contacting a leukemic cell with a Brd4 inhibitory agent or derivative thereof and detecting expression of myc, wherein a decrease in myc expression is indicative that a treatment regimen including that agent should be selected for the subject.

In various embodiments of any of the above aspects or any other aspect of the invention delineated herein, the agent is a small compound (e.g., JQ1 or a derivative thereof) or inhibitory nucleic acid molecule (e.g., siRNA, shRNA or antisense nucleic acid molecule). In other embodiments of the above aspects, the subject is a mammal (e.g., a human patient). In other embodiments, the subject is an adult mammal (e.g., adult human patient). In other embodiments, the subject is a child mammal (e.g., child human patient). In other embodiments of the above aspects, the method reduces the growth, proliferation or survival of a leukemic cell in a subject. In various embodiments of any of the above aspects, the agent is a compound of any of Formulas I-XXII or any other formula described herein. In particular embodiments of the above aspects, the cell is in a subject. In other embodiments of the above aspects, the leukemia is acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia or Myeloproliferative Disorders. In other embodiments of the above aspects, the leukemic cell is derived from an acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia or Myeloproliferative Disorders. In another aspect, the invention generally provides a method for treating a leukemia or related disorder (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes) in a subject, the method comprising administering to the subject an effective amount of an agent that inhibits Brd4 (e.g., an inhibitory nucleic acid that target Brd4, JQ1) or a derivative thereof.

In another aspect, the invention provides a method for reducing the growth, proliferation or survival of a leukemic cell, the method comprising contacting the cell with an effective amount of an agent that inhibits Brd4 or a derivative thereof, thereby reducing the growth, proliferation or survival of a leukemic cell.

In yet another aspect, the invention provides a method of inducing cell death or terminal differentiation in a leukemic cell, the method comprising contacting the cell with an effective amount of an agent that inhibits Brd4 or a derivative thereof, thereby inducing cell death or terminal differentiation in the leukemic cell.

In yet another aspect, the invention provides a method of treating acute myeloid leukemia in a subject, the method comprising administering to a subject in need thereof an effective amount of an agent that inhibits Brd4, thereby treating acute myeloid leukemia in a subject.

In yet another aspect, the invention provides a pharmaceutical composition comprising a therapeutically effective amount of an agent that inhibits Brd4 or a derivative thereof in a pharmaceutically effective excipient.

In yet another aspect, the invention provides a kit for the treatment of leukemia, the kit comprising a therapeutically effective amount of an agent that inhibits Brd4, and written instructions for administration of the compound for use in the method of claim 8.

In yet another aspect, the invention provides a method for detecting the clinical responsiveness of a leukemic cell, the method comprising contacting a leukemic cell with a Brd4 inhibitory agent or derivative thereof and detecting expression of a macrophage specific differentiation marker in the cell, wherein an increase in the expression of the macrophage specific differentiation marker indicates that the cell is responsive to the agent.

In yet another aspect, the invention provides a method for selecting a treatment regimen for a subject identified as having leukemia, the method comprising contacting a leukemic cell of the subject with a Brd4 inhibitory agent or derivative thereof and detecting expression of a macrophage specific differentiation marker in the cell, wherein an increase in the expression of the macrophage specific differentiation marker is indicative that a treatment regimen including that agent should be selected for the subject.

In yet another aspect, the invention provides a method for detecting the clinical responsiveness of a leukemic cell, the method comprising contacting a leukemic cell with a Brd4 inhibitory agent or derivative thereof and detecting expression of myc in the cell, wherein a decrease in myc expression indicates that the cell is responsive to the agent.

In yet another aspect, the invention provides a method for selecting a treatment regimen for a subject, the method comprising contacting a leukemic cell with a Brd4 inhibitory agent or derivative thereof and detecting expression of myc, wherein a decrease in myc expression is indicative that a treatment regimen including that agent should be selected for the subject.

In various embodiments of any of the above aspects or any other aspect of the invention delineated herein, the agent is a small compound (e.g., JQ1 or a derivative thereof) or inhibitory nucleic acid molecule (e.g., siRNA, shRNA or antisense nucleic acid molecule). In other embodiments of the above aspects, the subject is a mammal (e.g., a human patient). In other embodiments of the above aspects, the method reduces the growth, proliferation or survival of a leukemic cell in a subject. In various embodiments of any of the above aspects, the agent is a compound of any of Formulas I-XXII or any other formula described herein. In particular embodiments of the above aspects, the cell is in a subject. In other embodiments of the above aspects, the leukemia is acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia or Myeloproliferative Disorders. In other embodiments of the above aspects, the leukemic cell is derived from an acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia or Myeloproliferative Disorders.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

FIG. 1A includes a pie chart showing the distribution of genes involved in chromatin modification and a graph showing pooled negative selection screening in MLL-AF9/Nras$^{G12D}$ leukemia depicting changes in representation of 1072 informative shRNAs during fourteen days in culture (FIG. 1B). Numbers indicate the number of genes in each category. For each gene, six shRNAs were designed using the BIOPREDsi algorithm (Huesken et al., Nat Biotech 2005; 23:995-1001) and adapted for the miR30-context. The library was constructed using large-scale on-chip oligonucleotide synthesis, followed by pooled PCR cloning and sequence verification of individual clones, which yielded a total of 1095 shRNAs (three to six per gene). FIG. 1B includes a plot showing changes in representation of the 1072 informative shRNAs during 14 days of culture. Pooled negative selection screening was performed on MLL-AF9/Nras$^{G12D}$ leukemic cells, and shRNA abundance ratios were calculated as the number of reads after fourteen days of doxycycline administration ($T_{14}$) divided by reads prior to doxycycline administration ($T_0$). The results were and plotted as a mean of two replicates in ascending order. Completely depleted shRNAs (zero reads at $T_{14}$, n=71) were plotted as a ratio of $10^{-5}$; highlighted shRNAs in this group are shown with even spacing in alphabetical order. Positive scoring shRNAs (having greater than twenty fold depletion in both replicates, n=177) are marked in dark grey. Positive controls include shRNAs targeting Rpa1, Rpa3, Pcna, or Polr2b. Negative control shRNAs target *Renilla* luciferase (Ren) or Braf.

FIGS. 2A-2D show RNAi screening in a Tet-On competent AML model. FIG. 2A is a schematic diagram describing the RNAi screening strategy. The screen was performed in a Tet-On competent Acute Myeloid Leukemia (AML) model generated by retroviral co-transduction of vectors encoding rtTA3-IRES-MLL-AF9 and Luciferase-IRES-Nras$^{G12D}$ into hematopoietic stem and progenitor cells (HSPC). Leukemic cells retrieved from terminally ill mice were placed in culture and utilized for the screen. A customized shRNA library targeting chromatin-regulating genes was synthesized using On-chip oligonucleotide synthesis, and cloned in a pooled format. A library pool of 1095 sequence verified shRNAs was subcloned into TRMPV-Neo (Zuber et al., Nat Biotechnol 2011; 29:79-83) and transduced into leukemia cells, followed by G418 selection. Cells were then treated with doxycycline for fourteen days (equivalent to twelve cell passages), followed by fluorescence-activated cell sorting (FACS) to isolate the dsRed-positive/shRNA-expressing cells. Genomic DNA was prepared from sorted ($T_{14}$), as well as pre-treated ($T_0$) leukemia cells and used as a template for PCR amplification of shRNA guide strands, which was subjected to deep-sequencing to quantify the relative abundance of each shRNA in the library. Top hits were defined in the screen as genes for which at least two shRNA showed greater than twenty-fold depletion. Thirty-eight genes satisfied these criteria and were subjected to one-by-one validation using a different MLL-AF9/Nras$^{G12D}$ induced AML cell line and a constitutive shRNA expression vector (LMN). FIG. 2B is a scatter plot illustrating the correlation of normalized reads per shRNA between the plasmid pool and two replicates of library transduced leukemia cells following drug selection ($T_0$). The correlation verifies that the library representation is largely unaffected by retroviral transduction and drug selection. FIG. 2C is a scatter plot of normalized reads per shRNA in $T_0$ compared to $T_{14}$ in one trial. The low correlation suggests substantial changes in shRNA representation. FIG. 2D is a scatter plot illustrating the correlation of normalized reads per shRNA at $T_{14}$ in two independent replicates. The high correlation indicates that changes in shRNA abundance are due to specific effects. r, Pearson correlation coefficient.

FIG. 3A is a schematic diagram describing an RNAi screen validation strategy. Each gene positively scoring in the primary pooled screen (criteria: at least two shRNAs depleted greater than twenty fold in two independent replicates) was subject to one-by-one validation. The shRNAs designed to target that gene were subcloned into the LMN vector, which expresses miR30-shRNAs under control of the constitutive LTR promoter and features GFP and NeoR reporters. LMN-shRNAs were transduced into an independently derived MLL-AF9/Nras$^{G12D}$ leukemia cell line with an average infection efficiency of 20%. The relative change in GFP % was monitored over ten days by flow cytometry and used as a readout of cell growth inhibition, plotted as fold depletion [GFP % (d2) divided by GFP % (d12)]. FIG. 3B is a bar chart showing the fold depletion of all LMN-shRNAs targeting the thirty-eight identified hits in the primary screen. The fold depletion of all LMN-shRNAs targeting the thirty-eight identified hits in the primary screen. Several genes failed to validate, which might be due to (i) true false-positives in the primary screen, (ii) variable effects in the independent leukemia line, or (iii) differences between the shRNA expression systems. Based on the total number of identified shRNAs displaying maximum depletion (twenty-five-fold), Brd4 was identified as the top hit in the screen.

FIG. 4A includes charts showing the results of RT-qPCR of Brd4 mRNA levels following 48 hours of dox treatment. (n=4). FIG. 4B includes charts showing the results from competitive proliferation assays. Selected cells were mixed with untransduced cells at an 8:1 ratio, and subsequently cultured with doxycycline. The relative percentage of Venus-positive/TurboRFP-positive (i.e., shRNA expressing) cells was determined at indicated time points and changes used to readout growth inhibitory effects (n=3). Error bars represent s.e.m. FIG. 4C includes flow cytometry plots from cell cycle analyses (BrdU/7-AAD double staining) of cells assayed in FIG. 4B, following five days of doxycycline administration. FIG. 4D includes plots showing apoptosis measurements using Annexin V/DAPI double staining of cells assayed in FIG. 4A, following five days of doxycycline administration. Gating was first applied to live cells (FSC/SSC), followed by gating RFP+/shRNA+ cells. This accounts for the lack of accumulated dead (Annexing V+/DAPI+) cells. FIG. 4E includes charts showing the degree of GFP depletion of LMN-shRNAs performed in G1E as depicted in FIG. 3A. (n=3). Error bars represent s.e.m.

FIG. 5A includes a graph showing the knockdown efficiency of BRD4 upon conditional RNAi suppressigion. RT-qPCR was performed on TRMPV-MOLM-13 lines following 48 hours of dox treatment (n=3). Error bars represent s.e.m. FIGS. 5B and 5C include graphs showing the results from competitive proliferation assays of MOLM-13 and THP-1. Selected cells were mixed with untranduced cells and subsequently cultured on dox. The relative percentage of dsRed+/shRNA+ cells was determined at indicated time points and changes were used to measure growth inhibitory effects. Results are the average of two independent experiments. All results were normalized to a control shRNA (shRen.713). Error bars represent s.e.m. FIG. 5D include flow cytometry from cell cycle analysis (BrdU/DAPI double staining) of cells from FIGS. 5B and 5C after 5 days of dox treatment. Events were gated on dsRed+/shRNA+ cells.

FIG. 6A (top panel) includes a representative Western blot of whole-cell lysates prepared from murine embryonic fibroblast (MEF) cultures transduced with the indicated TtTMPV-shRNAs and induced with doxycycline for five days. FIG. 6A (bottom panel) displays the relative change in GFP % following transduction of MLL-AF9/Nras$^{G12D}$ leukemia cultures with LMN-shRNAs. FIGS. 6B-6E show inhibition of cell proliferation in murine (FIGS. 6B and 6D) and human (FIGS. 6C and 6E) cells upon treatment with JQ1. FIGS. 6B and 6C include graphs showing the proliferation rates of JQ1-treated cells. Curves were generated by measuring the increase in viable cell number after three days in culture and fitting data to an exponential growth curve. Results were plotted relative to the proliferation rate of control cells, set to 1 (n=3). Results were normalized to the proliferation rate of vehicle/DMSO-treated cells, set to 1. (n=3). The term CML-BC denotes chronic myeloid leukemia blast crisis. The term T-ALL denotes T-cell acute lymphoblastic leukemia. FIGS. 6D and 6E include charts showing quantified S-phase (BrdU-positive) percentages after JQ1 treatment for forty-eight hours at the indicated concentrations (n=3). BrdU was pulsed for thirty minutes in all experiments shown. All error bars represent s.e.m.

FIGS. 7A and 7B include graphs showing the proliferation rates of JQ1 treated cell lines. Curves were generated by measuring the increase in viable cell number after 3 days in culture and fitting data to an exponential growth curve. Results are plotted relative to the proliferation rate of control (DMSO treated) cells, set to 1. (n=3). Error bars represent s.e.m. A majority of human myeloid leukemia cell lines display an IC50<500 nM.

FIGS. 8A-8D show JQ1 sensitivity of patient-derived adult AML samples. FIG. 8A includes a table of clinical and pathological information about the AML specimens analyzed. FIG. 8B includes a table summarizing the impact of JQ1 on proliferation (3H-thymidine-uptake), apoptosis (Giemsa stain), and cell maturation (Wright-Giemsa staining). Since the proliferation assay is different from those utilized in FIG. 7, HL-60 and MOLM-13 lines were included to ensure that IC50 measurements were consistent with the other findings. FIG. 8C includes graphs showing the proliferation curves of JQ1-treated AML specimens, in the presence of cytokines. (n=3). Error bars represent s.e.m. FIG. 8D includes an image of a Wright-Giemsa cytospin of AML sample #4, demonstrating morphologic features of macrophage differentiation.

FIGS. 9A-9C show JQ1 sensitivity of patient-derived pediatric leukemia samples. FIG. 9A includes a table summarizing patient leukemia sample information and sensitivity data from the JQ1 experiments. The MV4-11 cell line was included as a control to ensure that proliferation measurements with WST1 assay were comparable to results shown in FIG. 7. Samples were treated with JQ1 for 72 hours, followed by analysis with WST-1 reagent or analysis with Annexin V staining. Wright-Giemsa staining of cytospins was performed on specimens treated with 250 nM JQ1 for 48 hours. FIG. 9B includes a graph showing the proliferation curves. Results were normalized to control cells treated with DMSO. (n=3). Error bars represent s.e.m. FIG. 9C includes an image of a Wright-Giemsa cytospin of sample PED025, demonstrating features of lymphoid differentiation.

FIGS. 10A and 10B include graphs showing cell death quantification for murine cells (FIG. 10A) and human cells (FIG. 10B). Cells were treated with 250 nM JQ1 for forty-eight hours, followed by staining with propidium iodide (PI). Cells positive for PI staining were quantified by FACS; n=3. All error bars represent s.e.m. FIG. 10C includes plots that show the apoptosis measurements for MLL-AF9/Nras$^{G12D}$ leukemia cells treated with JQ1 for forty-eight hours. (n=3). Results from representative experiments are shown.

FIG. 11A includes a schematic describing the in vivo RNAi and JQ1 experiments. Tet-On competent leukemia cells were transduced with TRMPV-Neo-shRNAs, followed by G418 selection, and subsequently transplanted into sublethally irradiated recipient mice. Upon disease onset (determined using bioluminescent imaging, typically after five or six days), shRNA expression was induced by doxycycline supplementation in drinking water and food. An animal's disease burden was then evaluated using bioluminescent imaging, overall survival, and quantification of dsRed-positive cells. FIG. 11B includes FACS plots of doxycycline-treated leukemia clones. The results verify the high percentage of Venus+/dsRed+ cells in these cellular populations. Identified clones are >99.9% positive, although TRMPV-Neo pools are typically ~85% Venus+/dsRed+ (see FIG. 12). FIG. 11C includes bioluminescent images of leukemia burden. Doxycycline was administered following disease onset (day 5-6 post transplant). FIG. 11D includes a graph showing quantitation of bioluminescent imaging responses following dox treatment. Number of mice in each treatment arm is indicated and error bars represent s.e.m. FIG. 11E includes a graph showing Kaplan-Meier survival curves of recipient mice transplanted with the indicated TRMPV-shRNA leukemia clones. Interval of dox treatment is indicated by arrow. Overall survival benefit of clonal shBrd4 disease is 9-10 days, whereas with non-clonal pools median survival is 4 days. FIG. 11F includes flow cytometry plots of donor-derived (CD45.2+) bone marrow cells in terminally diseased dox-treated mice. Gate shown includes dsRed+/shRNA+ cells.

FIG. 12A includes bioluminescent images of mice administered doxycycline upon disease onset, i.e., six days post-transplant. Day zero is the first day of doxycycline administration. FIG. 12B includes a graph showing the quantification of bioluminescent imaging responses following doxycycline administration. Shown are mean values of four replicate mice. FIG. 12C includes a graph showing Kaplan-Meier survival curves of recipient mice transplanted with the indicated TRMPV-shRNA leukemia cell line. The period of doxycycline administration is indicated by an arrow. Statistical significance relative to shRNAs that target Renilla luciferase (shRen) was calculated using a Log-rank test; *p=0.0001, **p<0.0001. FIG. 12D includes flow cytometry of donor-derived (CD45.2-positive) bone marrow cells in terminally diseased doxycycline-administered mice. Gate shown includes dsRed-positive/shRNA-positive cells. FIG. 12E includes a graph showing the quantification of dsRed-positive/shRNA-positive percentage in CD45.2-positive terminal leukemia burden. FIG. 12F includes bioluminescent images of MLL-AF9/Nras$^{G12D}$ leukemia recipient mice treated with JQ1 (50 mg/kg/d) or DMSO carrier. FIG. 12G includes a graph showing quantitation of bioluminescent imaging responses to JQ1 treatment. Shown are mean values of 6 DMSO- and 7 JQ1-treated mice. p-values were calculated using a two-tailed Student's paired t-test. FIG. 12H includes a graph showing Kaplan-Meier survival curves of control and JQ1-treated mice. Statistical significance was calculated using a Log-rank test. In 12F, 12G, and 12H, JQ1 treatment was initiated on day 1 following transplant of 50,000 leukemia cells. FIG. 12I includes a graph showing quantitation of bioluminescent imaging responses to JQ1 treatment in established disease. Mice were transplanted with 500,000 leukemia cells, followed by initiation of treatment 6 days post-transplant, when disease could first be imaged. Shown are mean values of 6 DMSO- and 7 JQ1-treated mice. p-values were calculated using a two-tailed Student's paired t-test. All error bars shown represent s.e.m.

FIG. 13A includes bioluminescent images of leukemic mice treat with 100 mg/kg/d JQ1. Mice were transplanted with 1 million leukemia cells, followed by treatment initiation on day 4 (when disease becomes visible by imaging). FIG. 13B includes a graph showing quantitation of the bioluminescent images. (n=8 in each group). Error bars represent s.e.m. FIG. 13C includes a graph showing Kaplan-Meier survival curves of control and JQ1-treated mice. Treatment was initiated on day 4 post transplant (indicated by horizontal line). Statistical significance was calculated using a Log-rank test. FIG. 13D includes bioluminescent images of leukemic mice treat with 50 mg/kg/d JQ1. Mice were transplanted with 500,000 leukemia cells, followed by treatment initiation on day 6 (when disease became visible by imaging). Quantitation is shown in FIG. 12I. FIG. 13E includes a graph showing Kaplan-Meier survival curves of control and JQ1-treated mice shown in FIG. 13D. Treatment was initiated on day 6 post transplant (indicated by horizontal line). Statistical significance was calculated using a Log-rank test.

FIG. 14A is a schematic showing the experimental strategy. p53$^{-/-}$ HSPCs were cotransduced with AML1-ETO9a and Luciferase-IRES-NrasG12D constructs, followed by transplantation of cells into a sublethally irradiated recipient mouse. With high-penetrance, mice succumb to AML as has been described previously (Dick, J. E., Blood 2008; 112:4793-807). Splenic leukemia material derived from moribund mice was transplanted into secondary recipient animals. 50 mg/kg/d JQ1 treatment was initiated following 5 days of disease onset, confirmed by bioluminescent imaging. FIG. 14B includes bioluminescent images of leukemic mice at indicated timepoints. FIG. 14C includes a graph showing quantitation of bioluminescent imaging responses to JQ1 treatment. Shown are mean values of 8 mice in each treatment group, error bars represent s.e.m, p-values were calculated using a two-tailed Student's paired t-test.

FIG. 17A includes representative FACS plots of bone marrow cells demonstrating gating used to discriminate and quantify percentages Lin–, ckit+ cells (LK progenitors) and Lin-Sca1+ckit+ (LSK stem cells). FIG. 17B includes graphs showing the percentage of total bone marrow cells staining for the indicated antibodies. (n=3). Error bars indicate s.e.m.

FIGS. 18A and 18B include light microscopy images of May-Grunwald/Giemsa-stained MLL-AF9/NrasG12D leukemia cells following 2 days of dox-induced shRNA expression or 2 days of 100 nM JQ1 treatment. shRNA expression was induced in TRMPV-transduced leukemia cells. Imaging was performed with a 40× objective. FIGS. 18C and 18D include FACS plots of Mac-1 and c-kit surface expression after 4 days of shRNA expression or following 2 days of 100 nM JQ1 treatment. FIGS. 18E-18H include Gene Set Enrichment Analysis (GSEA) plots evaluating changes in macrophage and LSC gene signatures upon Brd4 inhibition. In FIGS. 18E and 18G, RNA for expression arrays was obtained from sorted dsRed+/shRNA+ cells (Ren vs three different Brd4 shRNAs) after 2 days of dox induction. In FIGS. 18F and 18H, microarray data was obtained from leukemia cells treated for 2 days with DMSO or 100 nM JQ1. NES=normalized enrichment score. FDR q-val=False Discovery Rate q-value, which is the probability that a gene set with a given NES represents a false-positive finding. FIG. 18I includes graphs showing RT-qPCR results. RTqPCR was performed to analyze the genes involved in macrophage functions following 2 days of dox-induced shRNA expression or 2 days of 100 nM JQ1 treatment. shRNA expression was induced using the TRMPV vector. For shRNA experiments, dsRed+/shRNA+ cells were FACS-sorted to prepare RNA. Brd4 shRNA data shown are an average of Brd4.552, 1448, and 2097 shRNA samples. Signals were normalized to GAPDH, with control samples set to 1. (n=3). Error bars indicate s.e.m.

FIGS. 20A and 20B include graphs showing RT-qPCR results of relative Myc RNA levels in mouse (FIG. 20A) or human (FIG. 20B) cells after 48 hour treatment with JQ1. Results were normalized to GAPDH, with RNA levels in untreated cells set to 1 (n=3). FIG. 20C includes a Western blot of whole cell lystates prepared from MLL-AF9/Nras$^{G12D}$ leukemia cells treated for 48 hours with DMSO or 250 nM JQ1. FIG. 20D includes a graph showing RT-qPCR results. RT-qPCR was performed at the indicated timepoints following treatment of MLL-AF9/Nras$^{G12D}$ leukemia cells with 250 nM JQ1. Results were normalized to GAPDH, with mRNA levels in untreated cells set at 1 (n=3). FIG. 20E includes a graph showing ChIP-qPCR results. ChIP-qPCR was performed in MLL-AF9/Nras$^{G12D}$ leukemia cells with indicated antibodies and primer locations (n=6 for DMSO; n=4 for JQ1 treated). TSS=transcription start site. FIG. 20F includes a Western blot of whole cell lystates prepared from MLL-AF9/Nras$^{G12D}$ leukemia cells transduced with empty vector or Myc cDNA containing MSCV retrovirus. Cells were treated for 48 hours with DMSO or 250 nM JQ1. FIG. 20G includes a graph showing quantitation of BrdU incorporation after a 30 minute pulse in MLL-AF9/Nras$^{G12D}$ leukemia cells transduced with empty control vector or the Myc-cDNA. Cells were treated with JQ1 for 5 days at the indicated concentrations. (n=3). FIG. 20H includes light microscopy images of May-Grunwald/Giemsa-stained MLL-AF9/Nras$^{G12D}$ leukemia cells transduced with an empty vector or containing the Myc cDNA. Cells were treated for 5 days with 50 nM JQ1. Representative images taken at 40× objective are shown. All error bars shown represent s.e.m.

FIGS. 21A and 21B include graphs showing the results of RT-qPCR analysis of Brd4 (FIG. 21A) and Myc (FIG. 21B) mRNA levels prepared from sorted TurboRFP+ (shRNA expressing) leukemia cells transduced with the indicated TtTMPV-shRNA constructs. Cells were treated with dox for 3 days. Results were normalized to GAPDH. FIG. 21C includes a Western blot of extracts prepared from Brd4-shRNA expressing cells. TRMPV-transduced MLL-AF9/Nras leukemia clones were used. Cells were treated with dox for 3 days. FIG. 21D includes GSEA plots evaluating changes in Myc downstream target gene expression. Microarray data was obtained from RNA samples described in FIG. 21A. Myc target gene sets have been described previously (Kim et al., *Cell* 2010; 143:313-24; and Schuhmacher et al., *Nucleic Acids Res* 2001; 29:397-406).

FIG. 22 includes GSEA plots evaluating JQ1-induced alteration in gene signatures downstream of Myc. Microarray data was obtained from MLL-AF9/Nras$^{G12D}$ leukemia cells treated for 48 hours with DMSO or 100 nM JQ1.

FIGS. 23A and 23B include graphs showing RT-qPCR results. RT-qPCR was performed to determine Myc RNA levels in mouse (FIG. 23A) or human (FIG. 23B) cell lines. Results were normalized to GAPDH, with RNA levels in untreated cells set at 1 (n=3). Error bars indicate s.e.m.

FIG. 24A includes a schematic of the retroviral vectors used for Myc overexpression. FIG. 24B includes a graph showing RT-qPCR results. RT-qPCR was performed to evaluate macrophage-related genes upon 5 day JQ1 treatment of leukemia cells overexpressing Myc or empty vector control. n=3. Error bars represent s.e.m. FIG. 24C includes a graph showing cumulative cell number in control and Myc-transduced MLL-AF9/Nras$^{G12D}$ leukemia cells in the presence of 50 nM JQ1 or DMSO carrier control. FIG. 24D includes a graph showing cell death quantitation of JQ1-treated cells on day 4. PI+ cells were quantified by FACS (n=3). Error bars represent s.e.m.

FIG. 25A includes representative flow cytometry plots showing cell cycle analysis (BrdU/DAPI double staining) of MLL-AF9/Nras$^{G12D}$ leukemia cultures cotransduced with MSCV-Myc or empty vector together with TtTMPV conditional shRNA vector, and subsequently selected with puromycin and G418. Cells were treated with dox for 3 days to induce shRNA expression. Events were gated on dsRed+/shRNA+ cells. FIG. 25B includes a graph showing quantitation of BrdU incorporation in shRNA+/dsRed+ population. n=3. Error bars represent s.e.m. FIG. 25C includes light microscopy images of May-Grunwald/Giemsa stained MLL-AF9/Nras$^{G12D}$ leukemia cells. Dox treatment was administered for 2 days. The images were taken with 40× objective. FIG. 24D includes a graph showing RT-qPCR results. RT-qPCR was performed to evaluate macrophage-related genes after 2.5 days of dox-induced Brd4-shRNA expression in Tet-On competent leukemia cells transduced with MSCV-Myc or empty MSCV vector. shRNAs were expressed using the TtTMPV vector. n=3. Error bars represent s.e.m.

FIG. 26A includes a row-normalized heat map representation of relative abundance of mRNAs encoding genes selected based on whether they upregulate (left) or downregulate (right) 2-fold in empty vector control leukemia cells following JQ1 treatment. The modest level of Myc overexpression utilized here influences gene expression prior to JQ1-treatment. FIG. 26B includes heat map representations demonstrating the influence of Myc overexpression on gene expression changes of indicated gene sets. Color scale in FIGS. 26A and 26B indicates row-normalized expression values. FIG. 26C includes charts showing the categorization of JQ1-induced gene expression changes based on the relationship to Myc expression. Genes that change 2-fold in expression following JQ1 treatment of control cells, were classified as Myc-independent if they are still able to change 2-fold in expression in leukemia cells transduced with MSCV-Myc. Genes were classified as Myc-dependent if they failed to change 2-fold in expression in JQ1-treated MSCV-Myc cells.

FIG. 27A includes a graph showing cell growth inhibition when LMN-shRNAs were transduced into an MLL-AF9/Nras$^{G12D}$ leukemia cell line. The relative change in GFP % was monitored over 6 days by flow cytometry and used as a measure of cell growth inhibition. FIG. 27B includes FACS plots showing c-kit and Mac-1 surface expression of LMN-transduced leukemia cells on day 4 post-infection. All events were gated on GFP+/shRNA+ cells. FIG. 27C includes light microscopy images of May-Grunwald/Giemsa-stained clonal MLL-AF9/Nras$^{G12D}$ leukemia cells following 2 days of doxycycline-induced TRMPV-shRNA expression. FIG. 28D includes a graph showing RT-qPCR results. RT-qPCR was performed to analyze the genes involved in macrophage functions following 2 days of dox-induced shRNA expression. shRNA expression was induced using the TRMPV vector. Signals were normalized to GAPDH, with control samples set to 1. (n=3). Error bars represent s.e.m.

FIGS. 28A and 28B include graphs showing RT-qPCR results. RT-qPCR was performed on the indicated mouse (FIG. 28A) or human (FIG. 28B) cell lines. Results were normalized to GAPDH. n=3. Error bars represent s.e.m.

FIG. 29A includes a table of pharmacokinetic data and measured parameters. Plasma drug concentrations were measured by triple quadrupole LCMS-MS (API-2000) following a single intraperitoneal injection of (+)-JQ1 (50 mg/kg) into adult C1 male mice, at prespecified time points, as presented. Administration of (+)-JQ1 at this dose yields an excellent peak plasma concentration (Cmax>20 uM) and total drug exposure (AUC>20,000 h*ng/mL). BQL indicates samples where (+)-JQ1 was beyond the quantifiable limit of the pharmacokinetic detection assay (1.00 ng/mL). FIG. 29B includes a graph showing plasma concentration-time profile for (+)-JQ1 using data listed in FIG. 29A. Data represent mean measurements and error bars indicate the standard deviation, both from triplicate independent measurements. Plasma concentrations of drug above the biologically active concentration observed in vitro (100 nM; horizontal red line) are observed for more than 10 hours by extrapolation.

FIG. 30A includes GSEA plots evaluating transcriptional signatures downstream of MLL-AF9 and Myb. MLL-AF9_500 and Myb_500 were defined using RMA as the top 500 downregulated genes based on fold-change upon either Tet-Off mediated MLL-AF9 downregulation or Myb shRNA knockdown, respectively. The 500 gene cutoff corresponds to a $Log_2$ fold-change of −1.17 for Myb and −1.77 for MLL-AF9. FIG. 30B includes a heat map representation of Myc expression in the indicated microarray replicates. $Log_2$ fold-change and adj.P.Val were calculated using Limma algorithm, implemented using Bioconductor. FIG. 30C includes a graph showing RT-qPCR results. RT-qPCR was performed to validate that JQ1 treatment does not influence expression of Hoxa7, Hoxa9, and Meis1 expression, which are well established direct targets of MLL-AF9. This indicates that Brd4 inhibition does not neutralize the global function of MLL-AF9, but instead suppresses a large subsets of other downstream targets, e.g., Myc. n=3. Error bars represent s.e.m.

Definitions

Figure 1A:
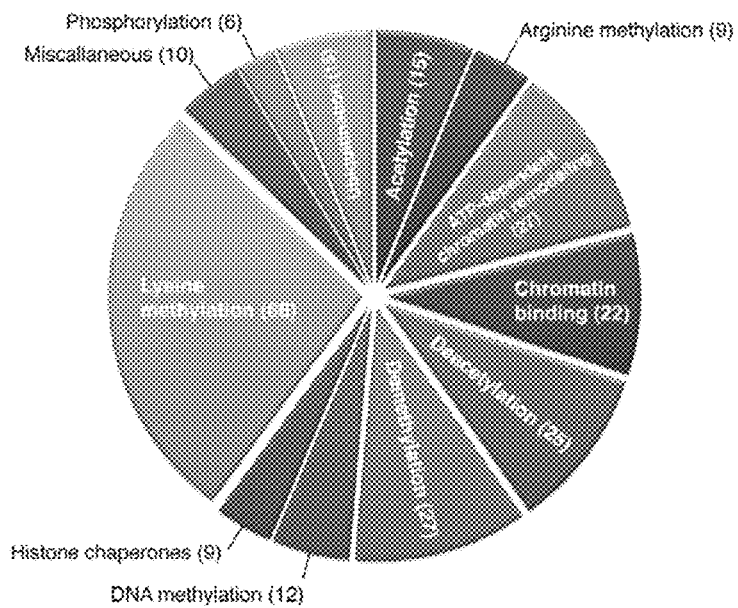
FIGS. 1A and 1B show chromatin regulators sensitive to Brd4-inhibition.

By "agent" is meant any small molecule chemical compound, antibody, nucleic acid molecule, or polypeptide, or fragments thereof.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, arylamino, heteroarylamino, alkoxy, alkylthio, oxo, halo, acyl, nitro, hydroxyl, cyano, aryl, heteroaryl, alkylaryl, alkylheteroaryl, aryloxy, heteroaryloxy, arylthio, heteroarylthio, arylamino, heteroarylamino, carbocyclyl, carbocyclyloxy, carbocyclylthio, carbocyclylamino, heterocyclyl, heterocyclyloxy, heterocyclylamino, heterocyclylthio, and the like. Lower alkyls are typically preferred for the compounds of this invention.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains at least some of the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7, 8-tetrahydronaphthyl. An aryl group can be unsubstituted or optionally is substituted with one or more substituents, e.g., substituents as described herein for alkyl groups (including without limitation alkyl (preferably, lower alkyl or alkyl substituted with one or more halo), hydroxy, alkoxy (preferably, lower alkoxy), alkylthio, cyano, halo, amino, boronic acid (—B(OH)$_2$, and nitro). In certain embodiments, the aryl group is a monocyclic ring, wherein the ring comprises 6 carbon atoms.

By "bromodomain" is meant a portion of a polypeptide that recognizes acetylated lysine residues. In one embodiment, a bromodomain of a BET family member polypeptide comprises approximately 110 amino acids and shares a conserved fold comprising a left-handed bundle of four alpha helices linked by diverse loop regions that interact with chromatin.

By "BET family polypeptide" is meant a polypeptide comprising two bromodomains and an extraterminal (ET) domain or a fragment thereof having transcriptional regulatory activity or acetylated lysine binding activity. Exemplary BET family members include BRD2, BRD3, BRD4 and BRDT.

By "BRD2 polypeptide" is meant a protein or fragment thereof having at least 85% identity to NP_005095 (SEQ ID NO: 1) that is capable of binding chromatin or regulating transcription.

The sequence of an exemplary BRD2 polypeptide follows:

MLQNVTPHNKLPGEGNAGLLGLGPEAAAPGKRIRKPSLLYEGFESPTMASVPALQLTPANPPPPEVSNPK

KPGRVTNQLQYLHKVVMKALWKHQFAWPFRQPVDAVKLGLPDYHKIIKQPMDMGTIKRRLENNYYWAASE

CMQDFNTMFTNCYIYNKPTDDIVLMAQTLEKIFLQKVASMPQEEQELVVTIPKNSHKKGAKLAALQGSVT

SAHQVPAVSSVSHTALYTPPPEIPTTVLNIPHPSVISSPLLKSLHSAGPPLLAVTAAPPAQPLAKKKGVK

RKADTTTPTPTAILAPGSPASPPGSLEPKAARLPPMRRESGRPIKPPRKDLPDSQQQHQSSKKGKLSEQL

KHCNGILKELLSKKHAAYAWPFYKPVDASALGLHDYHDIIKHPMDLSTVKRKMENRDYRDAQEFAADVRL

MFSNCYKYNPPDHDVVAMARKLQDVFEFRYAKMPDEPLEPGPLPVSTAMPPGLAKSSSESSSEESSSESS

SEEEEEEDEEDEEEEESESSDSEEERAHRLAELQEQLRAVHEQLAALSQGPISKPKRKREKKEKKKKRKA

EKHRGRAGADEDDKGPRAPRPPQPKKSKKASGSGGGSAALGPSGFGPSGGSGTKLPKKATKTAPPALPTG

YDSEEEEESRPMSYDEKRQLSLDINKLPGEKLGRVVHIIQAREPSLRDSNPEEIEIDFETLKPSTLRELE

RYVLSCLRKKPRKPYTIKKPVGKTKEELALEKKRELEKRLQDVSGQLNSTKKPPKKANEKTESSSAQQVA

VSRLSASSSSSDSSSSSSSSSSSDTSDSDSG

By "BRD2 nucleic acid molecule" is meant a polynucleotide encoding a BRD2 polypeptide or fragment thereof.

By "BRD3 polypeptide" is meant a protein or fragment thereof having at least 85% identity to NP_031397.1 that is capable of binding chromatin or regulating transcription.

The sequence (SEQ ID NO: 2) of an exemplary BRD3 polypeptide follows:

```
  1    mstattvapa gipatpgpvn ppppevsnps kpgrktnqlq
       ymqnvvvktl wkhqfawpfy
 61    qpvdaiklnl pdyhkiiknp mdmgtikkrl ennyywsase
       cmqdfntmft ncyiynkptd
121    divlmaqale kiflqkvaqm pqeevellpp apkgkgrkpa
       agaqsagtqq vaavssvspa
181    tpfqsvpptv sqtpviaatp vptitanvts vpvppaaapp
       ppatpivpvv pptppvvkkk
241    gvkrkadttt pttsaitasr sespppplsdp kqakvvarre
       sggrpikppk kdledgevpq
301    hagkkgklse hlrycdsilr emlskkhaay awpfykpvda
       ealelhdyhd iikhpmdlst
361    vkrkmdgrey pdaqgfaadv rlmfsncyky nppdhevvam
       arklqdvfem rfakmpdepv
421    eapalpapaa pmvskgaess rsseesssds gssdseeera
       trlaelqeql kavheqlaal
481    sqapvnkpkk kkekkekekk kkdkekekek hkvkaeeekk
       akvappakqa qqkkapakka
541    nstttagrql kkggkqasas ydseeeeegl pmsydekrql
       sldinrlpge klgrvvhiiq
601    srepslrdsn pdeieidfet lkpttlrele ryvksclqkk
       qrkpfsasgk kqaakskeel
661    aqekkkelek rlqdvsgqls sskkparkek pgsapsggps
       rlssssssses gssssgsss
721    dssdse
```

By "Brd3 nucleic acid molecule" is meant a polynucleotide encoding a BRD3 polypeptide.

By "BRD4 polypeptide" is meant a protein or fragment thereof having at least 85% identity to NP_055114 (SEQ ID NO: 3) that is capable of binding chromatin or regulating transcription.

```
  1    msaesgpgtr lrnlpvmgdg letsqmsttq aqaqpqpana
       astnppppet snpnkpkrqt
 61    nqlqyllrvv lktlwkhqfa wpfqqpvdav klnlpdyyki
       iktpmdmgti kkrlennyyw
121    naqeciqdfn tmftncyiyn kpgddivlma ealeklflqk
       inelpteete imivqakgrg
181    rgrketgtak pgvstvpntt gastppqtqt pqpnpppvqa
       tphpfpavtp dlivqtpvmt
```

-continued

```
241   vvppqpiqtp ppvppqpqpp papapqpvqs hppiiaatpq
      pvktkkgvkr kadttptti 301   dpiheppslp pepkttklgq rressrpvkp pkkdvpdsqq
      hpapeksskv seqlkccsgi 361   lkemfakkha ayawpfykpv dvealglhdy cdiikhpmdm
      stiksklear eyrdaqefga 421   dvrlmfsncy kynppdhevv amarklqdvf emrfakmpde
      peepvvavss pavppptkvv 481   appsssdsss dsssdsdsst ddseeeraqr laelqeqlka
      vheqlaalsq pqqnkpkkke 541   kdkkekkkek hkrkeeveen kkskakeppp kktkknnssn
      snvskkepap mkskppptye 601   seeedkckpm syeekrqlsl dinklpgekl grvvhiiqsr
      epslknsnpd eieidfetlk 661   pstlrelery vtsclrkkrk pqaekvdvia gsskmkgfss
      sesesssess ssdsedsetg 721   pa
```

By "Brd4 nucleic acid molecule" is meant a polynucleotide that encodes a BRD4 polypeptide.

By "BRDT polypeptide is meant a protein or fragment thereof having at least 85% identity to NP_001717 (SEQ ID NO: 4) that is capable of binding chromatin or regulating transcription.

```
1     mslpsrqtai ivnppppeyi ntkkngrltn qlgylqkvvl
      kdlwkhsfsw pfqrpvdavk 61    lqlpdyytii knpmdlntik krlenkyyak aseciedfnt
      mfsncylynk pgddivlmaq 121   aleklfmqkl sqmpqeeqvv gvkerikkgt qqniayssak
      eksspsatek vfkqqeipsv 181   fpktsispln vvqgasvnss sqtaaqvtkg vkrkadtttp
      atsavkasse fsptfteksv 241   alppikenmp knvlpdsqqq ynvvktvkvt eqlrhcseil
      kemlakkhfs yawpfynpvd 301   vnalglhnyy dvvknpmdlg tikekmdnqe ykdaykfaad
      vrlmfmncyk ynppdhevvt 361   marmlqdvfe thfskipiep vesmplcyik tditettgre
      ntneassegn ssddsederv 421   krlaklqeql kavhqqlqvl sqvpfrklnk kkekskkekk
      kekvnnsnen prkmceqmrl 481   kekskrnqpk krkqqfiglk sedednakpm nydekrqlsl
      ninklpgdkl grvvhiiqsr 541   epslsnsnpd eieidfetlk astlreleky vsaclrkrpl
      kppakkimms keelhsqkkq 601   elekrlldvn nqlnsrkrqt ksdktqpska venvsrlses
      sssssssses essssdlsss 661   dssdsesemf pkftevkpnd spskenvkkm knecilpegr
      tgvtqigycv qdttsanttl 721   vhqttpshvm ppnhhqlafn ygelehlqtv knisplqilp
      psgdseqlsn gitvmhpsgd 781   sdttmlesec qapvqkdiki knadswkslg kpvkpsgvmk
      ssdelfnqfr kaaiekevka
```

```
841   rtqelirkhl eqntkelkas qenqrdlgng ltvesfsnki
      qnkcsgeeqk ehqqsseaqd 901   ksklwllkdr dlarwkewer rrreamvgti dmtlqsdimt
      mfennfd
```

By "BRDT nucleic acid molecule" is meant a polynucleotide encoding a BRDT polypeptide.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

By "compound" is meant any small molecule chemical compound, antibody, nucleic acid molecule, or polypeptide, or fragments thereof.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By "computer readable media" is meant any media which can be read and accessed directly by a computer e.g. so that the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

By a "computer system" is meant the hardware means, software means and data storage means used to analyse atomic coordinate data. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

The term "diastereomers" refers to stereoisomers with two or more centers of dissymmetry and whose molecules are not mirror images of one another.

By "disease" is meant any condition or disorder that damages or interferes with the normal function of a cell, tissue, or organ. Examples of diseases susceptible to treatment with compounds delineated herein include leukemias and related disorders (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes).

By "effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "enantiomers" refers to two stereoisomers of a compound which are non-superimposable mirror images of one another. An equimolar mixture of two enantiomers is called a "racemic mixture" or a "racemate."

By "fitting" is meant determining by automatic, or semi-automatic means, interactions between one or more atoms of an agent molecule and one or more atoms or binding sites of a BET family member (e.g., a bromodomain of BRD2, BRD3, BRD4 and BRDT), and determining the extent to which such interactions are stable. Various computer-based methods for fitting are described further herein.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents, e.g., substituents as described herein for aryl groups. Examples of heteroaryl groups include, but are not limited to, pyridyl, furanyl, benzodioxolyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heteroatom" as used herein means an atom of any element other than carbon or hydrogen. Preferred heteroatoms are nitrogen, oxygen, sulfur and phosphorus. The term "isomers" or "stereoisomers" refers to compounds which have identical chemical constitution, but differ with regard to the arrangement of the atoms or groups in space.

The term "heterocyclic" as used herein, refers to organic compounds that contain at least at least one atom other than carbon (e.g., S, O, N) within a ring structure. The ring structure in these organic compounds can be either aromatic or, in certain embodiments, non-aromatic. Some examples of heterocyclic moeities include, are not limited to, pyridine, pyrimidine, pyrrolidine, furan, tetrahydrofuran, tetrahydrothiophene, and dioxane.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The term "hydroxyl" means —OH.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

By "leukemic cell" is meant a cell derived from a leukemia.

By "marker" is meant any protein or polynucleotide having an alteration in expression level or activity that is associated with a disease or disorder.

The language "inhibiting the growth" of a cancer cell includes the slowing, interrupting, arresting or stopping its growth and metastases and does not necessarily indicate a total elimination of the growth.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

The term "optical isomers" as used herein includes molecules, also known as chiral molecules, that are exact non-superimposable mirror images of one another.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "polymorph" as used herein, refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. Both configurations, cis/trans and/or Z/E are encompassed by the compounds of the present invention.

By "reduces" or "increases" is meant a negative or positive alteration, respectively, of at least about 10%, 25%, 50%, 75%, or 100% relative to a reference.

By "reducing cell survival" is meant to inhibit the viability of a cell or to induce cell death relative to a reference cell.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "root mean square deviation" is meant the square root of the arithmetic mean of the squares of the deviations from the mean.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

By "substantially identical" is meant a polypeptide or nucleic acid molecule exhibiting at least 85% identity to a reference amino acid sequence (for example, any one of the amino acid sequences described herein) or nucleic acid sequence (for example, any one of the nucleic acid sequences described herein). Preferably, such a sequence is at least 85%, 90%, 95%, 99% or even 100% identical at the amino acid level or nucleic acid to the sequence used for comparison The term "sulfhydryl" or "thiol" means —SH.

As used herein, the term "tautomers" refers to isomers of organic molecules that readily interconvert by tautomerization, in which a hydrogen atom or proton migrates in the reaction, accompanied in some occasions by a switch of a single bond and an adjacent double bond.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"An effective amount" refers to an amount of a compound, which confers a therapeutic effect on the treated subject. The therapeutic effect may be objective (i.e., measurable by some test or marker) or subjective (i.e., subject gives an indication of or feels an effect). An effective amount of a compound described herein may range from about 1 mg/Kg to about 5000 mg/Kg body weight. Effective doses will also vary depending on route of administration, as well as the possibility of co-usage with other agents.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. By "ameliorate" is meant decrease, suppress, attenuate, diminish, arrest, or stabilize the development or progression of a disease. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention features compositions and methods useful for treating leukemia and related disorders (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes).

The invention is based, at least in part, on the discovery that agents that inhibit Brd4 are useful for inhibiting the growth or progression of acute myeloid leukemia. This inhibition can involve suppressing Myc activity. These findings also highlight the utility of RNAi screening as a discovery platform for revealing epigenetic vulnerabilities for direct pharmacologic intervention in cancer.

As reported in detail below, the discovery that Brd4 inhibition is useful for the treatment of leukemia was made using a non-biased approach to probe epigenetic vulnerabilities in acute myeloid leukemia (AML)—an aggressive hematopoietic malignancy that is associated with aberrant chromatin. By screening a customized shRNA library targeting known chromatin regulators in genetically defined leukemias, the bromodomain-containing protein Brd4 was identified as a critical requirement for AML disease maintenance Suppression of Brd4 using shRNAs or the small-molecule inhibitor JQ1 led to robust anti-leukemic effects in vitro and in vivo, accompanied by terminal myeloid differentiation and elimination of leukemia stem cells (LSCs). These effects were due to the requirement of Brd4 in maintaining Myc expression and promoting aberrant self-renewal.

Bromodomain-Containing Proteins

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins each possessing one or more evolutionarily conserved effector modules, which recognize covalent modifications of histone proteins or DNA. The E-N-acetylation of lysine residues (Kac) on histone tails is associated with an open chromatin architecture and transcriptional activation (Marushige *Proc Natl Acad Sci USA* 73, 3937-3941, (1976)). Context-specific molecular recognition of acetyl-lysine is principally mediated by bromodomains.

Bromodomain-containing proteins are of substantial biological interest, as components of transcription factor complexes (TAF1, PCAF, Gcn5 and CBP) and determinants of epigenetic memory (Dey et al., *Mol Biol Cell* 20, 4899-4909, (2009)). There are 41 human proteins containing a total of 57 diverse bromodomains. Despite large sequence variations, all bromodomains share a conserved fold comprising a left-handed bundle of four alpha helices ($\alpha_Z$, $\alpha_A$, $\alpha_B$, $\alpha_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains (Owen, D. J. et al. The structural basis for the recognition of acetylated histone H4 by the bromodomain of histone acetyltransferase gcn5p. *Embo J* 19, 6141-6149, (2000)). The bromodomain and extra-terminal (BET)-family (BRD2, BRD3, BRD4 and BRDT) shares a common domain architecture comprising two N-terminal bromodomains that exhibit high level of sequence conservation, and a more divergent C-terminal recruitment domain (Zeng et al., *FEBS Lett* 513, 124-128, (2002).

The invention features compositions and methods that are useful for inhibiting human bromodomain proteins.

Compounds of the Invention

The invention provides compounds (e.g., JQ1 and compounds of formulas delineated herein) that bind in the binding pocket of the apo crystal structure of the first bromodomain of a BET family member (e.g., BRD2, BRD3, BRD4). Without wishing to be bound by theory, these compounds may be particularly effective in inhibiting leukemias, including but not limited to acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes. In one approach, compounds useful for the treatment of leukemias and related disorders are selected using a molecular docking program to identify compounds that are expected to bind to a bromodomain structural binding pocket. In certain embodiments, a compound of the invention can prevent, inhibit, or disrupt, or reduce by at least 10%, 25%, 50%, 75%, or 100% the biological activity of a BET family member (e.g., BRD2, BRD3, BRD4, BRDT) and/or disrupt the subcellular localization of such proteins, e.g., by binding to a binding site in a bromodomain apo binding pocket.

In certain embodiments, a compound of the invention is a small molecule having a molecular weight less than about 1000 daltons, less than 800, less than 600, less than 500, less than 400, or less than about 300 daltons. Examples of compounds of the invention include JQ1 and other compounds that bind the binding pocket of the apo crystal structure of the first bromodomain of a BET family member (e.g., BRD4 (hereafter referred to as BRD4(1); PDB ID 2OSS). JQ1 is a novel thieno-triazolo-1,4-diazepine. The invention further provides pharmaceutically acceptable salts of such compounds.

In certain embodiments, a compound of the invention is a small molecule having a molecular weight less than about 1000 daltons, less than 800, less than 600, less than 500, less than 400, or less than about 300 daltons. Examples of compounds of the invention include JQ1 and other compounds that bind the binding pocket of the apo crystal structure of the first bromodomain of a BET family member (e.g., BRD4 (hereafter referred to as BRD4(1); PDB ID 2OSS). JQ1 is a novel thieno-triazolo-1,4-diazepine. The invention further provides pharmaceutically acceptable salts of such compounds.

In one aspect, the compound is a compound of Formula I:

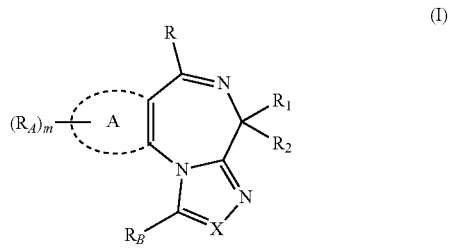

wherein
X is N or $CR_5$;
$R_5$ is H, alkyl, cycloalkyl, heterocycloalkyl, aryl, or heteroaryl, each of which is optionally substituted;
$R_B$ is H, alkyl, hydroxylalkyl, aminoalkyl, alkoxyalkyl, haloalkyl, hydroxy, alkoxy, or —COO—$R_3$, each of which is optionally substituted;
ring A is aryl or heteroaryl;
each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

R is alkyl, cycloalkyl, heterocycloalkyl, aryl, or heteroaryl; each of which is optionally substituted;

$R_1$ is —$(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;

$R_2$ is H, D (deuterium), halogen, or optionally substituted alkyl;

each $R_3$ is independently selected from the group consisting of:
  (i) H, aryl, substituted aryl, heteroaryl, or substituted heteroaryl;
  (ii) heterocycloalkyl or substituted heterocycloalkyl;
  (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
  (iv) $NH_2$, $N=CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that
  (a) if ring A is thienyl, X is N, R is phenyl or substituted phenyl, $R_2$ is H, $R_B$ is methyl, and $R_1$ is —$(CH_2)_n$-L, in which n is 1 and L is —CO—$N(R_3R_4)$, then $R_3$ and $R_4$ are not taken together with the nitrogen atom to which they are attached to form a morpholino ring;
  (b) if ring A is thienyl, X is N, R is substituted phenyl, $R_2$ is H, $R_B$ is methyl, and $R_1$ is —$(CH_2)_n$-L, in which n is 1 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and
  (c) if ring A is thienyl, X is N, R is substituted phenyl, $R_2$ is H, $R_B$ is methyl, and $R_1$ is —$(CH_2)_n$-L, in which n is 1 and L is —COO—$R_3$, then $R_3$ is not methyl or ethyl;

or a salt, solvate or hydrate thereof.

In certain embodiments, R is aryl or heteroaryl, each of which is optionally substituted.

In certain embodiments, L is H, —COO—$R_3$, —CO—N$(R_3R_4)$, —$S(O)_2$—$R_3$, —$S(O)_2$—$N(R_3R_4)$, $N(R_3R_4)$, $N(R_4)C(O)R_3$ or optionally substituted aryl. In certain embodiments, each $R_3$ is independently selected from the group consisting of: H, —$C_1$-$C_8$ alkyl, containing 0, 1, 2, or 3 heteroatoms selected from O, S, or N; or $NH_2$, $N=CR_4R_6$.

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxymethyl, methoxymethyl, trifluoromethyl, COOH, COOMe, COOEt, or $COOCH_2OC(O)CH_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In another aspect, the compound is a compound of Formula II:

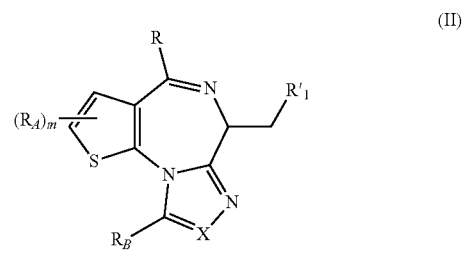

(II)

wherein
  X is N or $CR_5$;
  $R_5$ is H, alkyl, cycloalkyl, heterocycloalkyl, aryl, or heteroaryl, each of which is optionally substituted;
  $R_B$ is H, alkyl, hydroxylalkyl, aminoalkyl, alkoxyalkyl, haloalkyl, hydroxy, alkoxy, or —COO—$R_3$, each of which is optionally substituted;
  each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  R is alkyl, cycloalkyl, heterocycloalkyl, aryl, or heteroaryl, each of which is optionally substituted;
  $R'_1$ is H, —COO—$R_3$, —CO—$R_3$, optionally substituted aryl, or optionally substituted heteroaryl;
  each $R_3$ is independently selected from the group consisting of:
    (i) H, aryl, substituted aryl, heteroaryl, substituted heteroaryl;
    (ii) heterocycloalkyl or substituted heterocycloalkyl;
    (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;
  m is 0, 1, 2, or 3;
  provided that if $R'_1$ is —COO—$R_3$, X is N, R is substituted phenyl, and $R_B$ is methyl, then $R_3$ is not methyl or ethyl;
  or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, $R'_1$ is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, $R'_1$ is —COO—$R_3$, and $R_3$ is methyl, ethyl, propyl, i-propyl, butyl, sec-butyl, or t-butyl; or $R'_1$ is H or optionally substituted phenyl.

In certain embodiments, $R_B$ is methyl, ethyl, hydroxy methyl, methoxymethyl, trifluoromethyl, COOH, COOMe, COOEt, COOCH$_2$OC(O)CH$_3$.

In certain embodiments, $R_B$ is methyl, ethyl, hydroxy methyl, methoxymethyl, trifluoromethyl, COOH, COOMe, COOEt, or COOCH$_2$OC(O)CH$_3$.

In certain embodiments, each $R_A$ is independently an optionally substituted alkyl, or any two $R_A$ together with the atoms to which each is attached, can form a fused aryl.

In certain embodiments, each $R_A$ is methyl.

In another aspect, the compound is a compound of formula III:

(III)

wherein
  X is N or $CR_5$;
    $R_5$ is H, alkyl, cycloalkyl, heterocycloalkyl, aryl, or heteroaryl, each of which is optionally substituted;
    $R_B$ is H, alkyl, hydroxylalkyl, aminoalkyl, alkoxyalkyl, haloalkyl, hydroxy, alkoxy, or —COO—$R_3$, each of which is optionally substituted;
  ring A is aryl or heteroaryl;
    each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  R is alkyl, cycloalkyl, heterocycloalkyl, aryl, or heteroaryl, each of which is optionally substituted;
  each $R_3$ is independently selected from the group consisting of:
    (i) H, aryl, substituted aryl, heteroaryl, or substituted heteroaryl;
    (ii) heterocycloalkyl or substituted heterocycloalkyl;
    (iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and
    (iv) NH$_2$, N=CR$_4$R$_6$;
  each $R_4$ is independently H, alkyl, alkyl, cycloalkyl, heterocycloalkyl, aryl, or heteroaryl, each of which is optionally substituted;
  or $R_3$ and $R_4$ are taken together with the nitrogen atom to which they are attached to form a 4-10-membered ring;
  $R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;
  m is 0, 1, 2, or 3;
  provided that:
    (a) if ring A is thienyl, X is N, R is phenyl or substituted phenyl, $R_8$ is methyl, then $R_3$ and $R_4$ are not taken together with the nitrogen atom to which they are attached to form a morpholino ring; and
    (b) if ring A is thienyl, X is N, R is substituted phenyl, $R_2$ is H, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl; and
  or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, $R_3$ is H, NH$_2$, or N=CR$_4$R$_6$.

In certain embodiments, each $R_4$ is independently H, alkyl, cycloalkyl, heterocycloalkyl, aryl, heteroaryl; each of which is optionally substituted.

In certain embodiments, $R_6$ is alkyl, alkenyl, cycloalkyl, cycloalkenyl, heterocycloalkyl, aryl, or heteroaryl, each of which is optionally substituted.

In another aspect, the compound is a compound of formula IV:

(IV)

wherein
  X is N or $CR_5$;
    $R_5$ is H, alkyl, cycloalkyl, heterocycloalkyl, aryl, or heteroaryl, each of which is optionally substituted;
    $R_B$ is H, alkyl, hydroxylalkyl, aminoalkyl, alkoxyalkyl, haloalkyl, hydroxy, alkoxy, or —COO—$R_3$, each of which is optionally substituted;
  ring A is aryl or heteroaryl;
    each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;
  $R_1$ is —(CH$_2$)$_n$-L, in which n is 0-3 and L is H, —COO—$R_3$, —CO—$R_3$, —CO—N(R$_3$R$_4$), —S(O)$_2$—R$_3$, —S(O)$_2$—N(R$_3$R$_4$), N(R$_3$R$_4$), N(R$_4$)C(O)R$_3$, optionally substituted aryl, or optionally substituted heteroaryl;
  $R_2$ is H, D, halogen, or optionally substituted alkyl;

each R₃ is independently selected from the group consisting of:
  (i) H, aryl, substituted aryl, heteroaryl, or substituted heteroaryl;
  (ii) heterocycloalkyl or substituted heterocycloalkyl;
  (iii) —C₁-C₈ alkyl, —C₂-C₈ alkenyl or —C₂-C₈ alkynyl, each containing 0, 1, 2, or 3 heteroatoms selected from O, S, or N; —C₃-C₁₂ cycloalkyl, substituted —C₃-C₁₂ cycloalkyl, —C₃-C₁₂ cycloalkenyl, or substituted —C₃-C₁₂ cycloalkenyl, each of which may be optionally substituted; and
  (iv) NH₂, N=CR₄R₆;
each R₄ is independently H, alkyl, alkyl, cycloalkyl, heterocycloalkyl, aryl, or heteroaryl, each of which is optionally substituted;
or R₃ and R₄ are taken together with the nitrogen atom to which they are attached to form a 4-10-membered ring;
R₆ is alkyl, alkenyl, cycloalkyl, cycloalkenyl, heterocycloalkyl, aryl, or heteroaryl, each of which is optionally substituted; or R₄ and R₆ are taken together with the carbon atom to which they are attached to form a 4-10-membered ring;
m is 0, 1, 2, or 3;
provided that
  (a) if ring A is thienyl, X is N, R₂ is H, R_B is methyl, and R₁ is —(CH₂)ₙ-L, in which n is 0 and L is —CO—N(R₃R₄), then R₃ and R₄ are not taken together with the nitrogen atom to which they are attached to form a morpholino ring;
  (b) if ring A is thienyl, X is N, R₂ is H, R_B is methyl, and R₁ is —(CH₂)ₙ-L, in which n is 0 and L is —CO—N(R₃R₄), and one of R₃ and R₄ is H, then the other of R₃ and R₄ is not methyl, hydroxyethyl, alkoxy, phenyl, substituted phenyl, pyridyl or substituted pyridyl; and
  (c) if ring A is thienyl, X is N, R₂ is H, R_B is methyl, and R₁ is —(CH₂)ₙ-L, in which n is 0 and L is —COO—R₃, then R₃ is not methyl or ethyl; or a salt, solvate or hydrate thereof.

In certain embodiments, R₁ is —(CH₂)ₙ-L, in which n is 0-3 and L is —COO—R₃, optionally substituted aryl, or optionally substituted heteroaryl; and R₃ is —C₁-C₈ alkyl, which contains 0, 1, 2, or 3 heteroatoms selected from O, S, or N, and which may be optionally substituted. In certain embodiments, n is 1 or 2 and L is alkyl or —COO—R₃, and R₃ is methyl, ethyl, propyl, i-propyl, butyl, sec-butyl, or t-butyl; or n is 1 or 2 and L is H or optionally substituted phenyl.

In certain embodiments, R₂ is H or methyl.

In certain embodiments, R_B is methyl, ethyl, hydroxy methyl, methoxymethyl, trifluoromethyl, COOH, COOMe, COOEt, COOCH₂OC(O)CH₃.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each R_A is independently an optionally substituted alkyl, or any two R_A together with the atoms to which each is attached, can form an aryl.

The methods of the invention also relate to compounds of Formulae V-XXII, and to any compound described herein.

In another aspect, the compound is a compound represented by the formula:

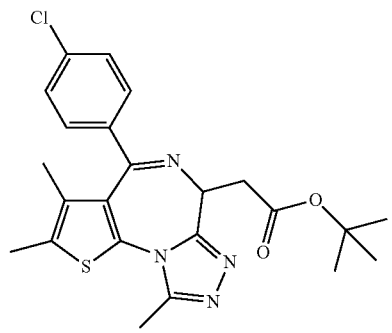 [SMILES: Cc1sc2c(c1C)C(c1ccc(Cl)cc1)=NC(CC(=O)OC(C)(C)C)c1nnc(C)n1-2]

or a salt, solvate or hydrate thereof.

In certain embodiments, the compound is (+)-JQ1:

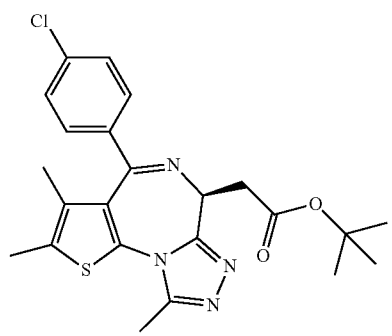 [SMILES: Cc1sc2c(c1C)C(c1ccc(Cl)cc1)=N[C@@H](CC(=O)OC(C)(C)C)c1nnc(C)n1-2]

or a salt, solvate or hydrate thereof.

In another aspect, the compound is a compound represented by the formula:

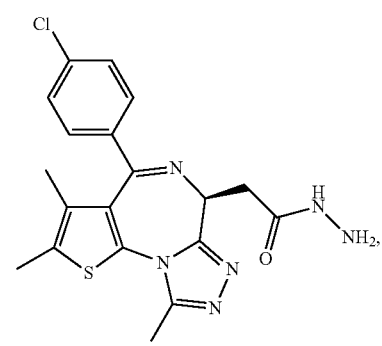

33
-continued
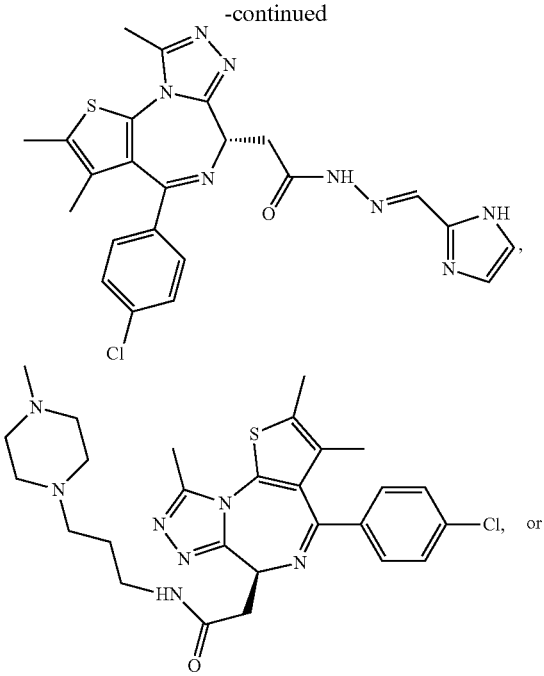
34
-continued
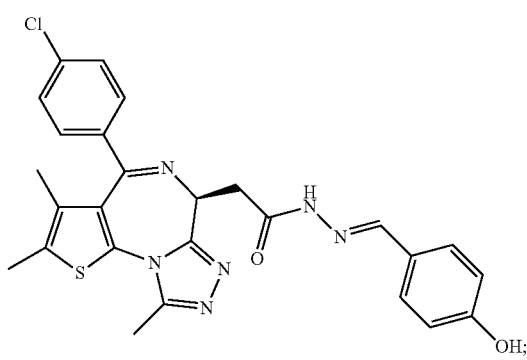
or a salt, solvate or hydrate thereof.
In another aspect, the compound is a compound represented by the formula:
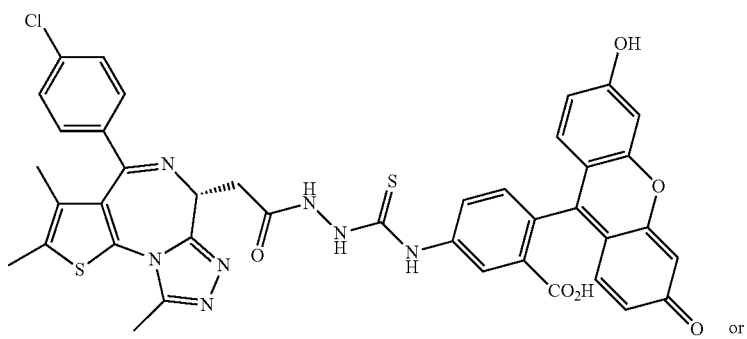
or
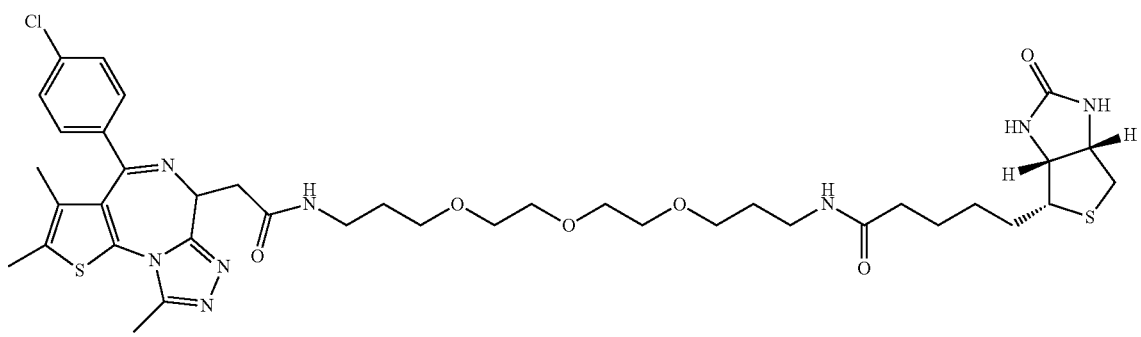
or a salt, solvate or hydrate thereof.

In another aspect, the compound is a compound represented by any one of the following formulae:
JQ1S
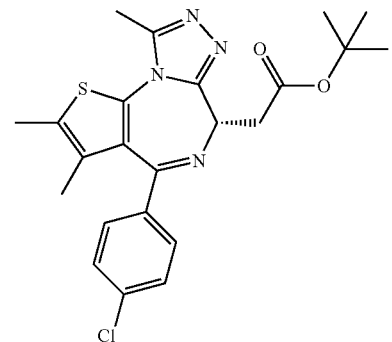
JQ6
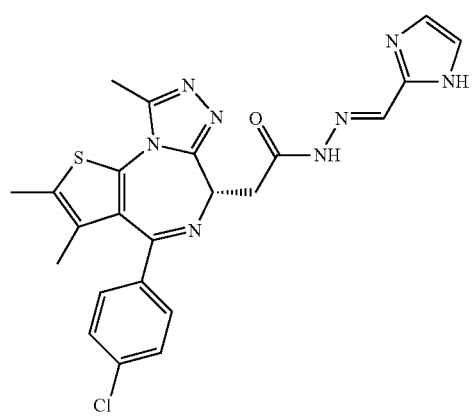
JQ11
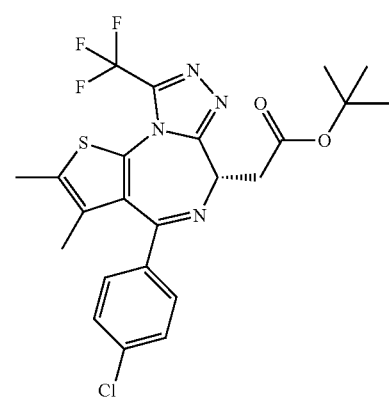
JQ1R
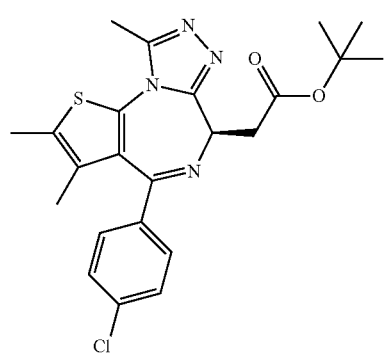
JQ13
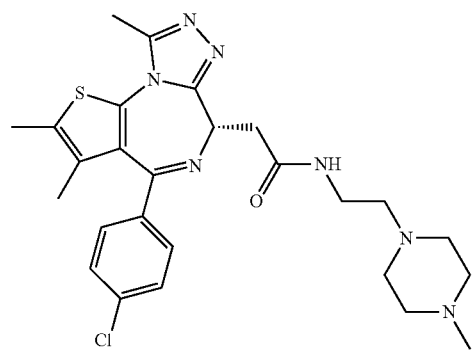
JQ21
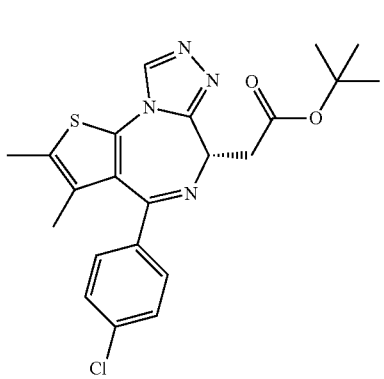
JQ20
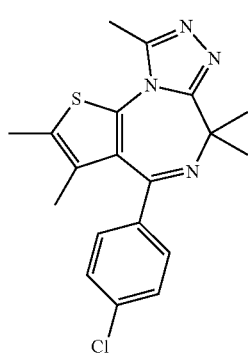
JQ19
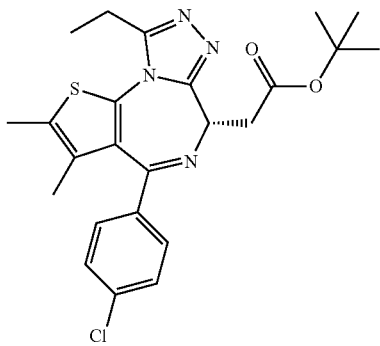

-continued
JQ24B
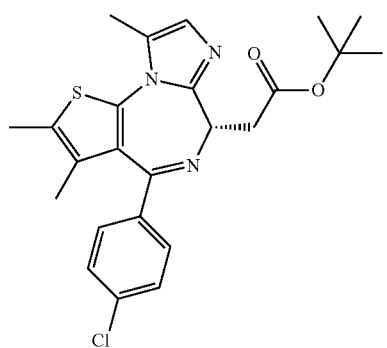
JQ8
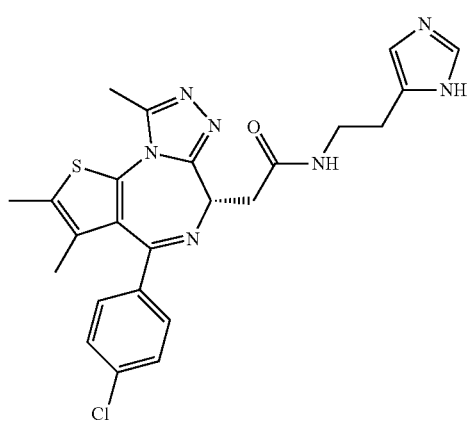
JQ18
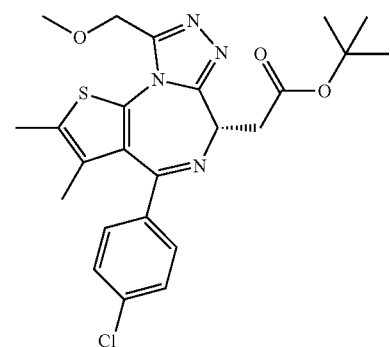
KS1
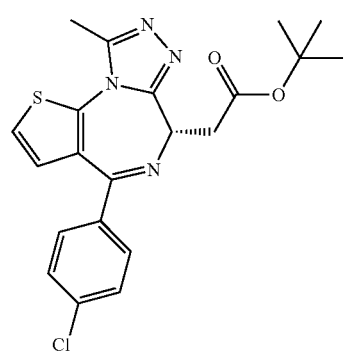
or a salt, solvate or hydrate thereof.
In another aspect, the compound is a compound represented by any one of the following formulae:
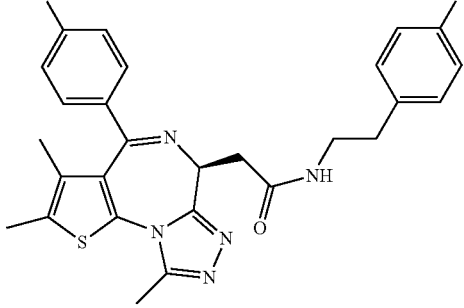
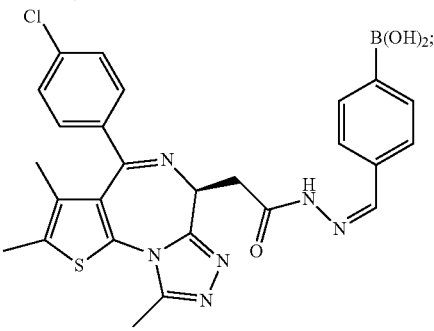
or a salt, solvate or hydrate thereof.
In another aspect, the compound is a compound represented by any one of the following structures:
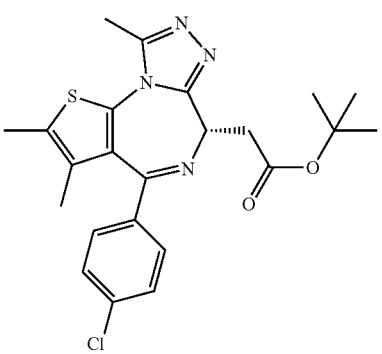
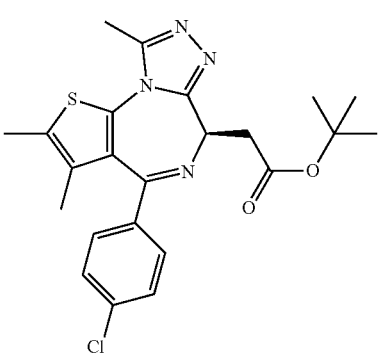

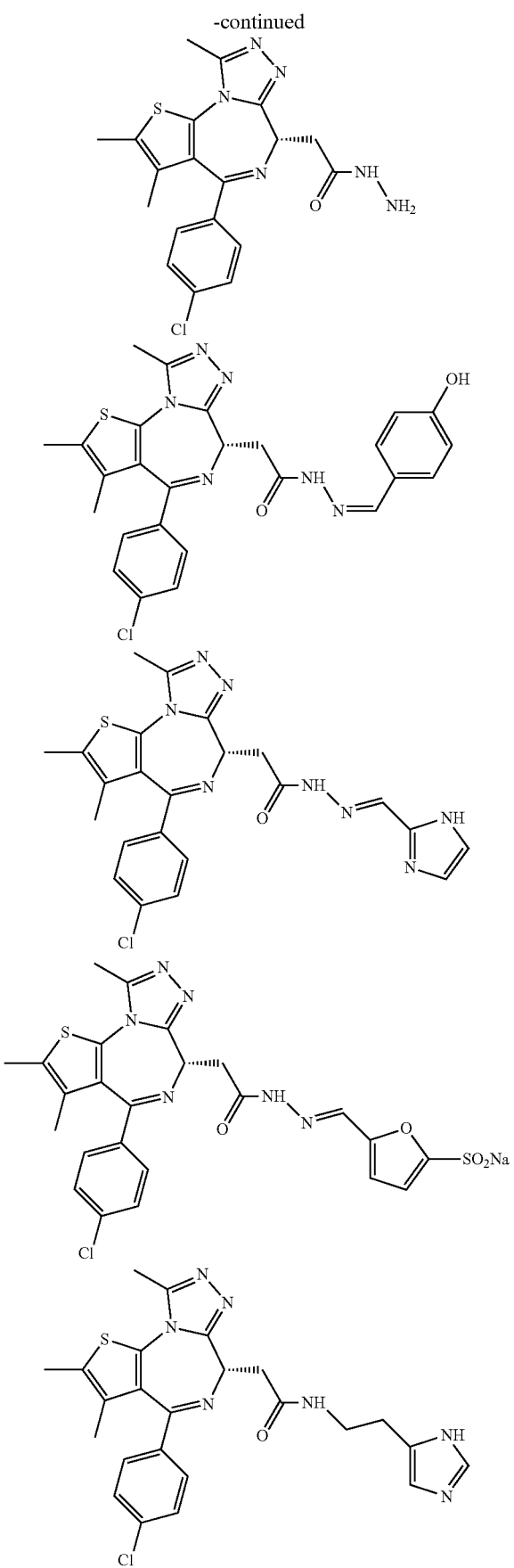
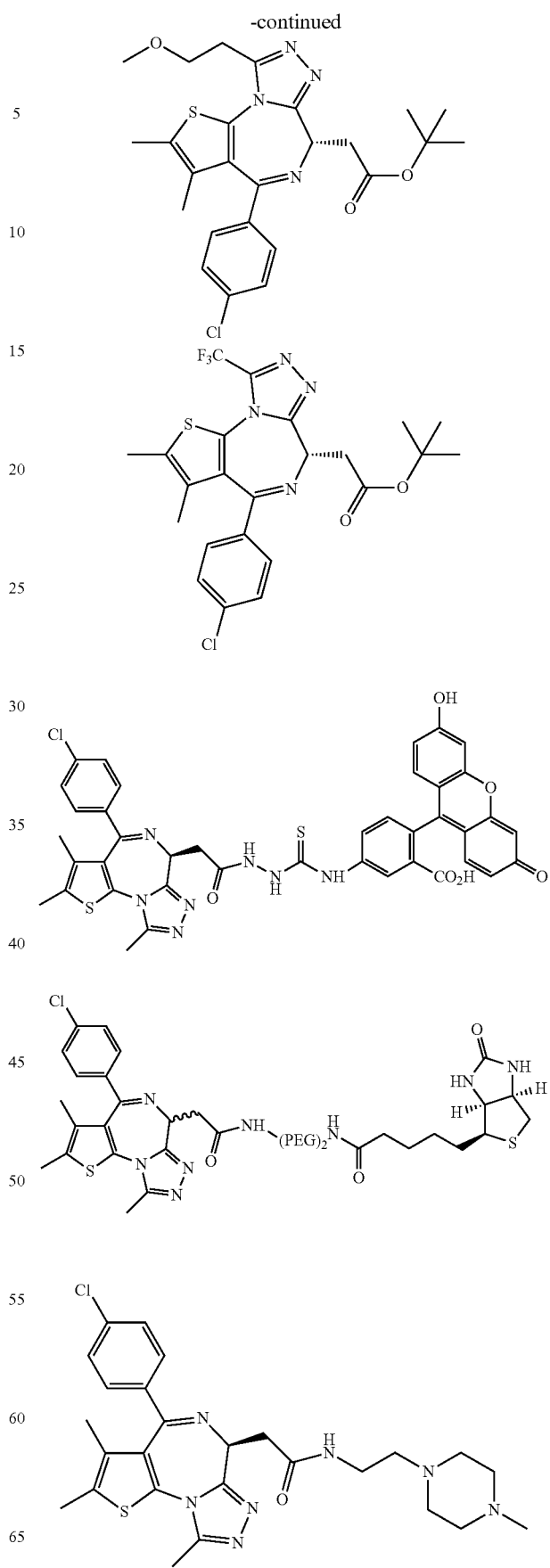

41
-continued
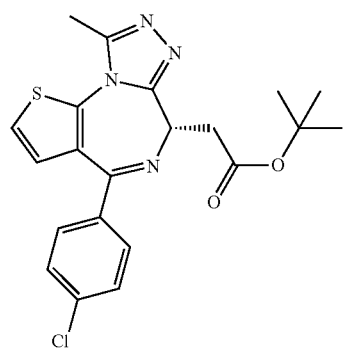
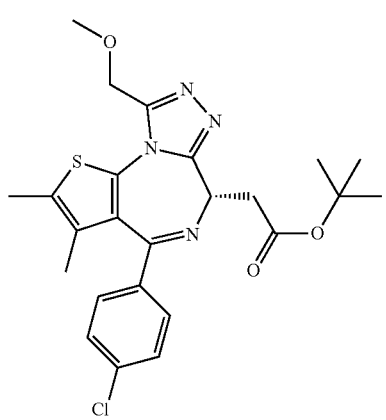
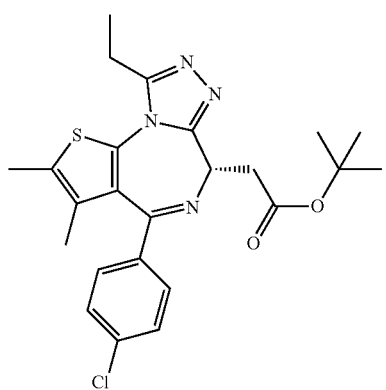
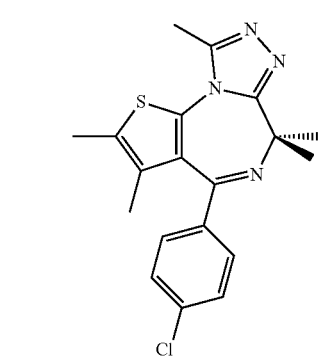
42
-continued
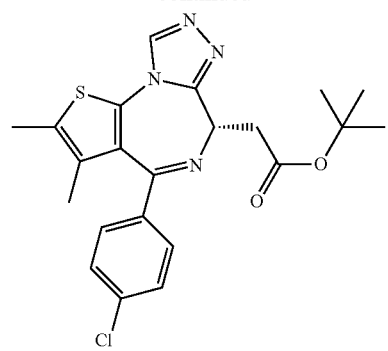
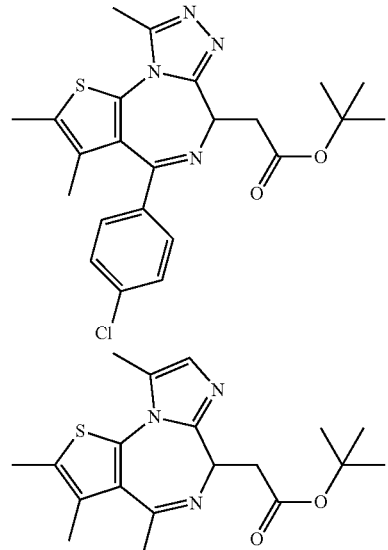
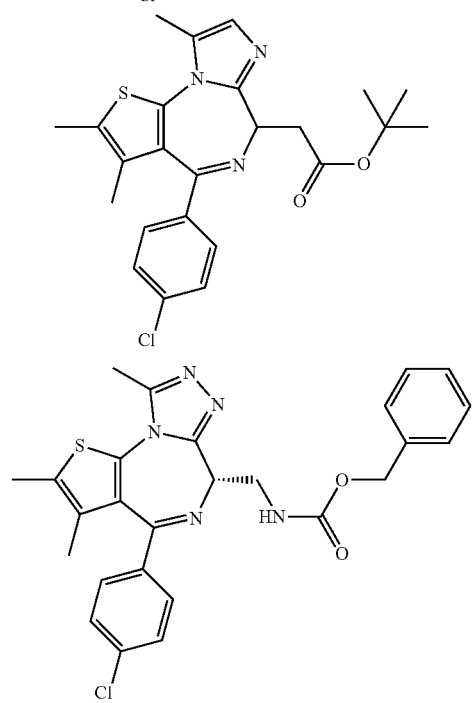
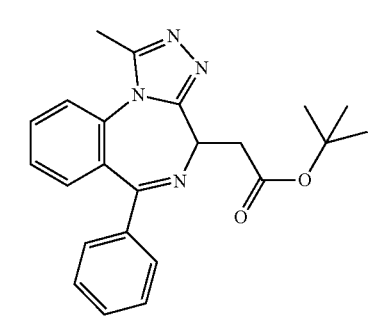

43
-continued
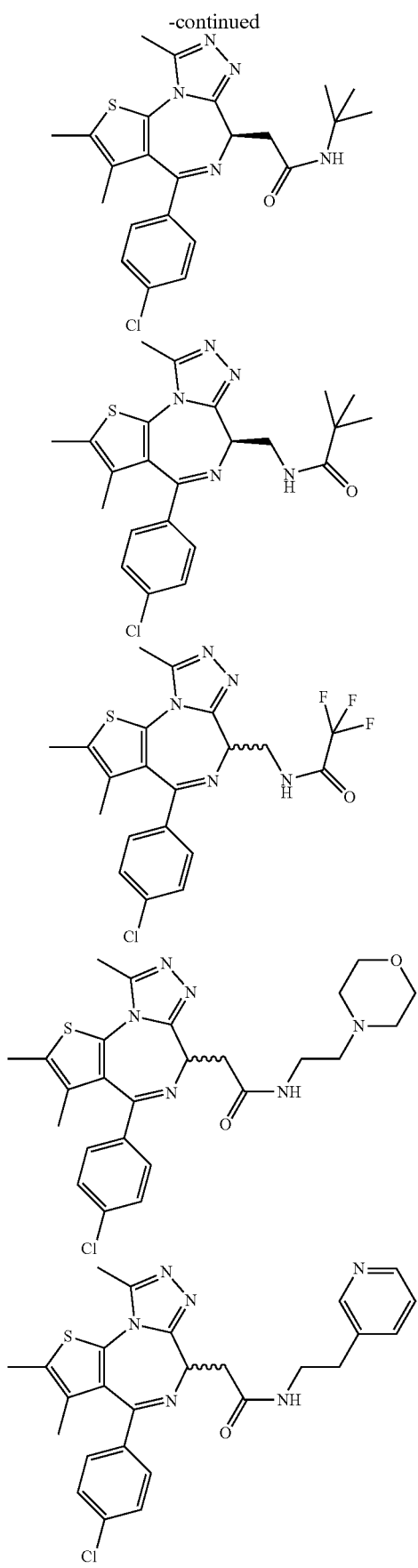
44
-continued
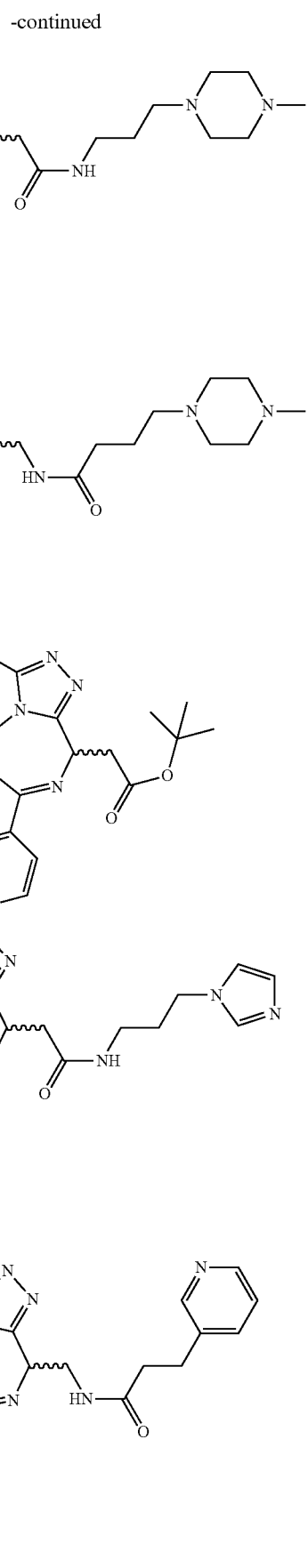

45
-continued
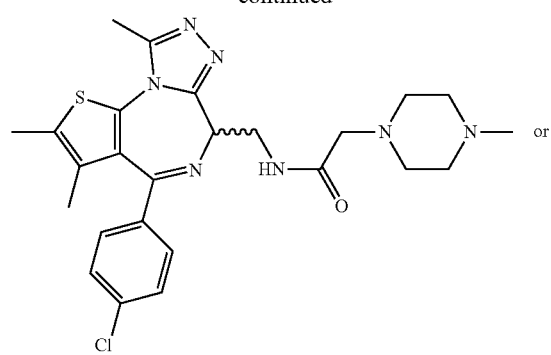
or
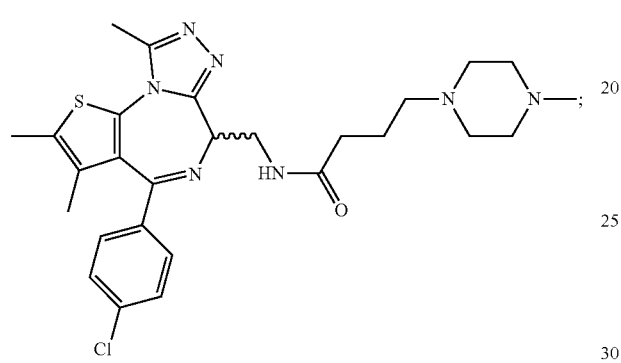
or a salt, solvate or hydrate thereof.
In certain embodiments, a compound of the invention can be represented by one of the following structures:
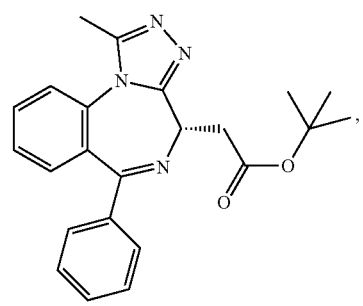
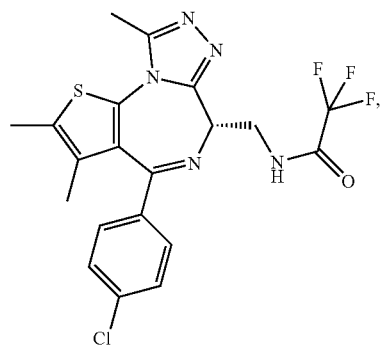
46
-continued
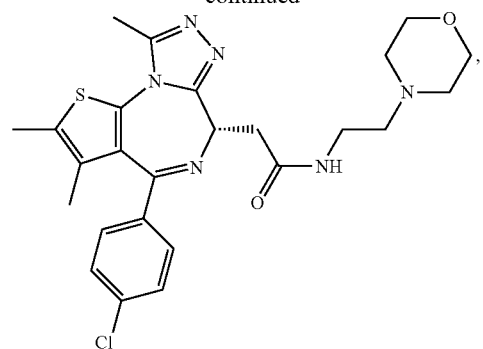
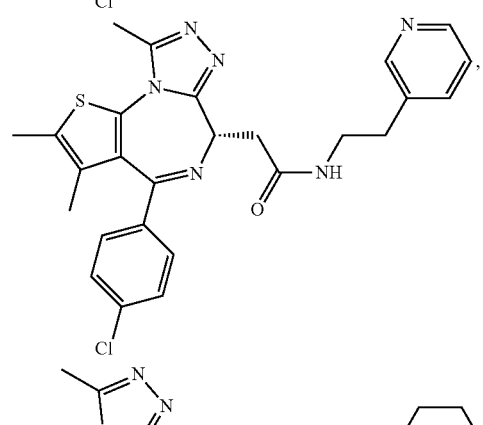
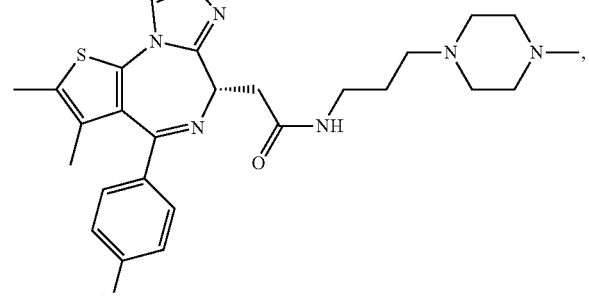
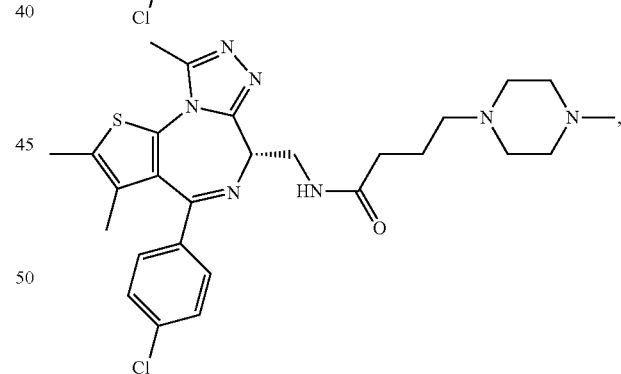
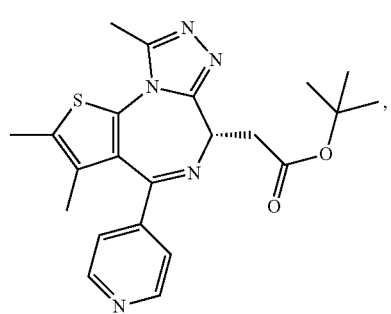

47
-continued
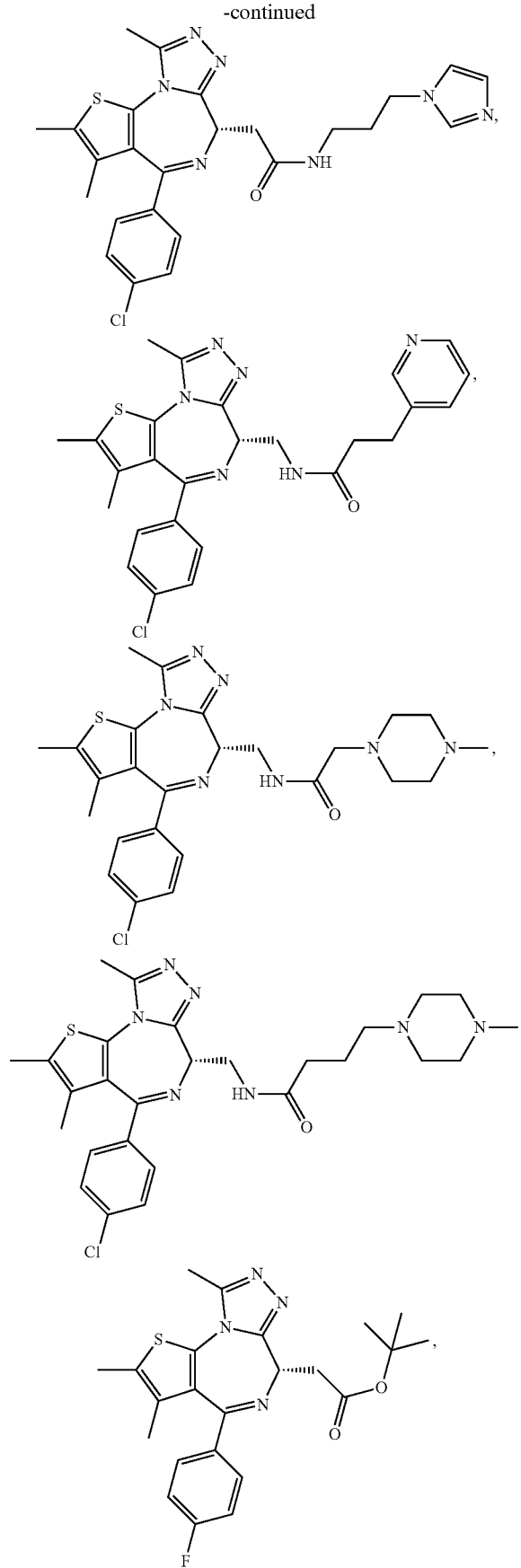
48
-continued
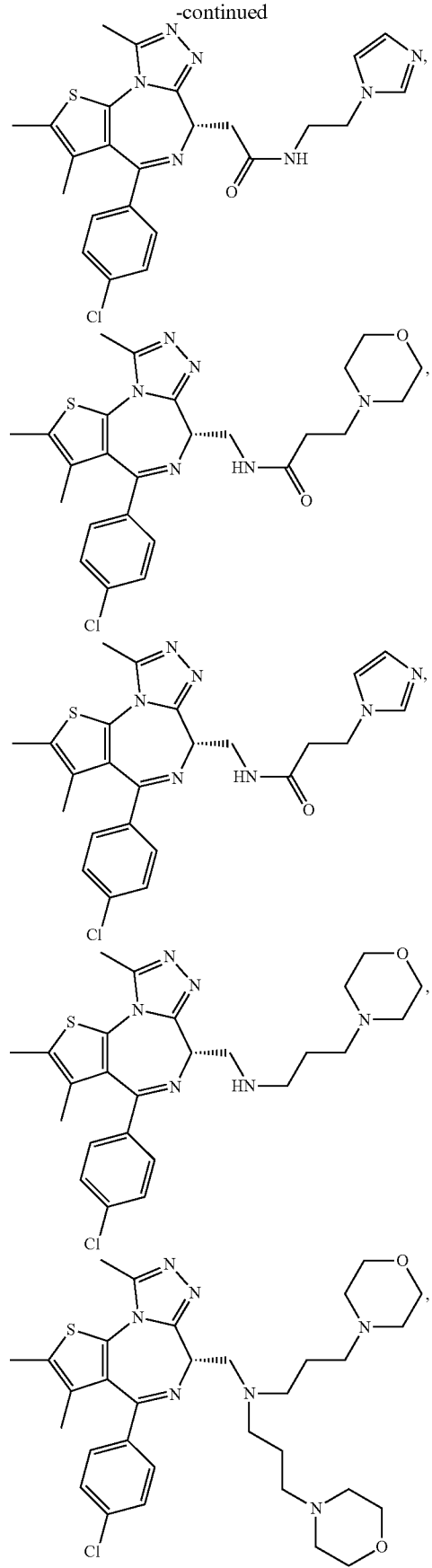

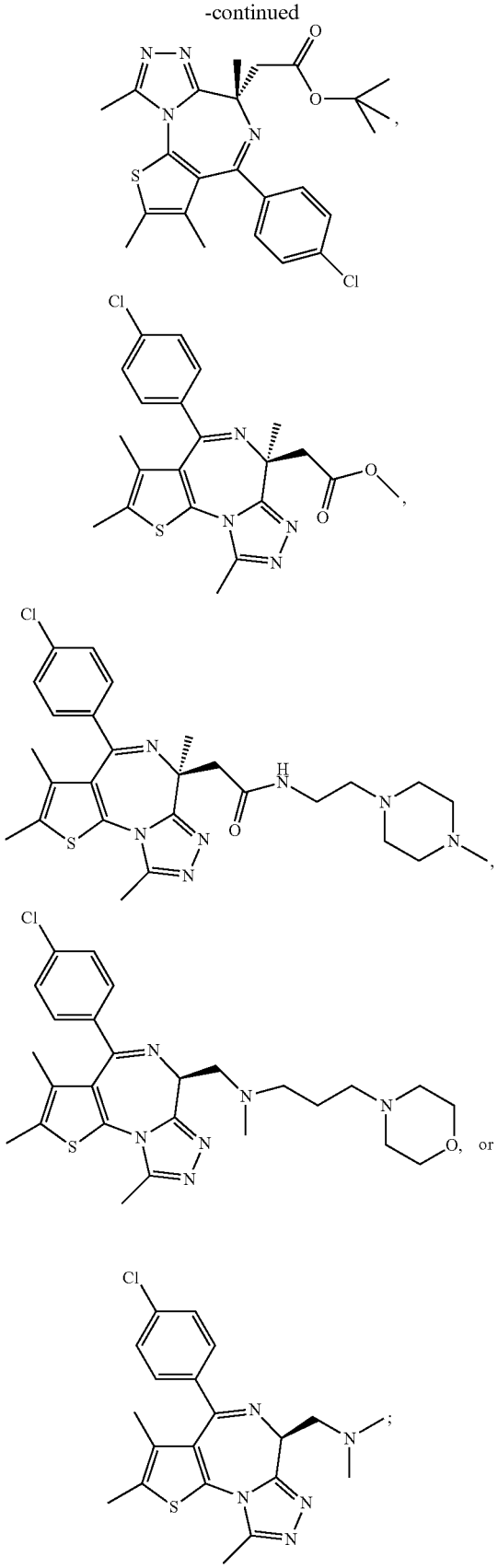

or a salt, solvate or hydrate thereof.

In one embodiment, the compound is represented by the structure:

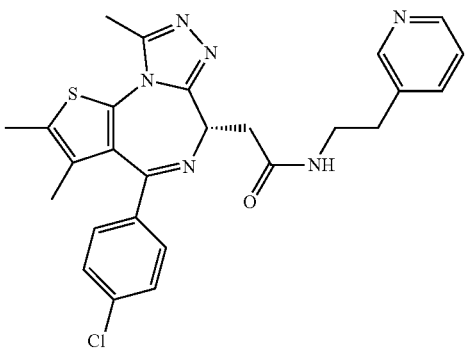 [SMILES: Cc1sc2c(c1C)C(c1ccc(Cl)cc1)=N[C@@H](CC(=O)NCCc1cccnc1)c1nnc(C)n1-2]

or a salt, solvate or hydrate thereof.

In another embodiment, the compound is represented by the structure:

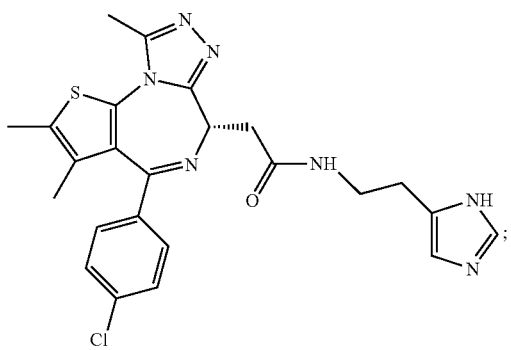 [SMILES: Cc1sc2c(c1C)C(c1ccc(Cl)cc1)=N[C@@H](CC(=O)NCCc1cnc[nH]1)c1nnc(C)n1-2]

or a salt, solvate or hydrate thereof.

In another embodiment, the compound is represented by the structure:

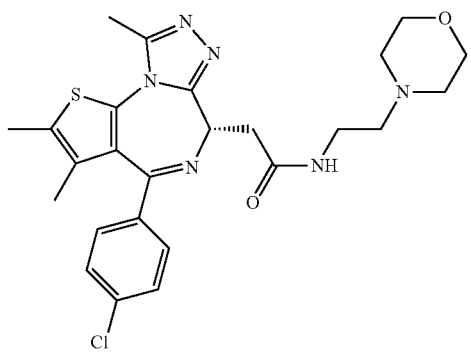

or a salt, solvate or hydrate thereof.

In certain embodiments, a compound of the invention can have the opposite chirality of any compound shown herein.

In certain embodiments, the compound is a compound represented by Formula (V), (VI), or (VII):

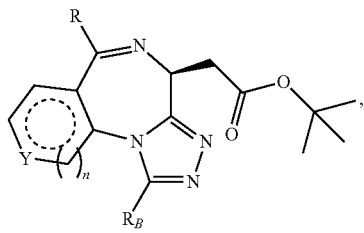
(V)

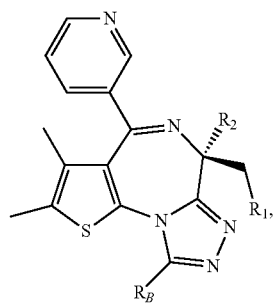
(VI)

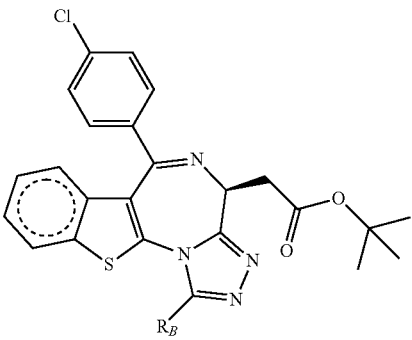
(VII)

in which R, $R_1$, and $R_2$ and $R_B$ have the same meaning as in Formula (I); Y is O, N, S, or $CR_5$, in which $R_5$ has the same meaning as in Formula (I); n is 0 or 1; and the dashed circle in Formula (VII) indicates an aromatic or non-aromatic ring; or a salt, solvate, or hydrate thereof.

In certain embodiments of any of the Formulae I-IV and VI (or any formula herein), $R_6$ represents the non-carbonyl portion of an aldehyde shown in Table A, below (i.e., for an aldehyde of formula $R_6CHO$, $R_6$ is the non-carbonyl portion of the aldehyde). In certain embodiments, $R_4$ and $R_6$ together represent the non-carbonyl portion of a ketone shown in Table A (i.e., for a ketone of formula $R_6C(O)R_4$, $R_4$ and $R_6$ are the non-carbonyl portion of the ketone).

TABLE A
Plate 1
| | 01 | 02 | 03 | 04 | 05 | 06 |
|---|---|---|---|---|---|---|
| A |  | 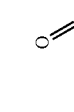 |  |  | 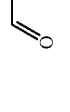 |  |
| B |  |  | 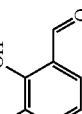 | 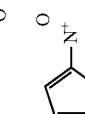 | 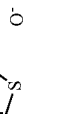 |  |
| C |  | 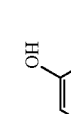 | 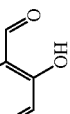 | 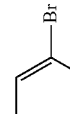 | | 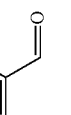 |
| D |  |  | 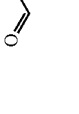 |  |  |  |
| E |  | 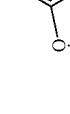 |  | 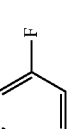 |  | 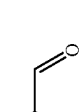 |
| F |  |  | 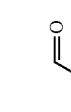 | 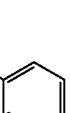 | 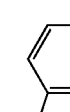 | 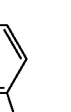 |

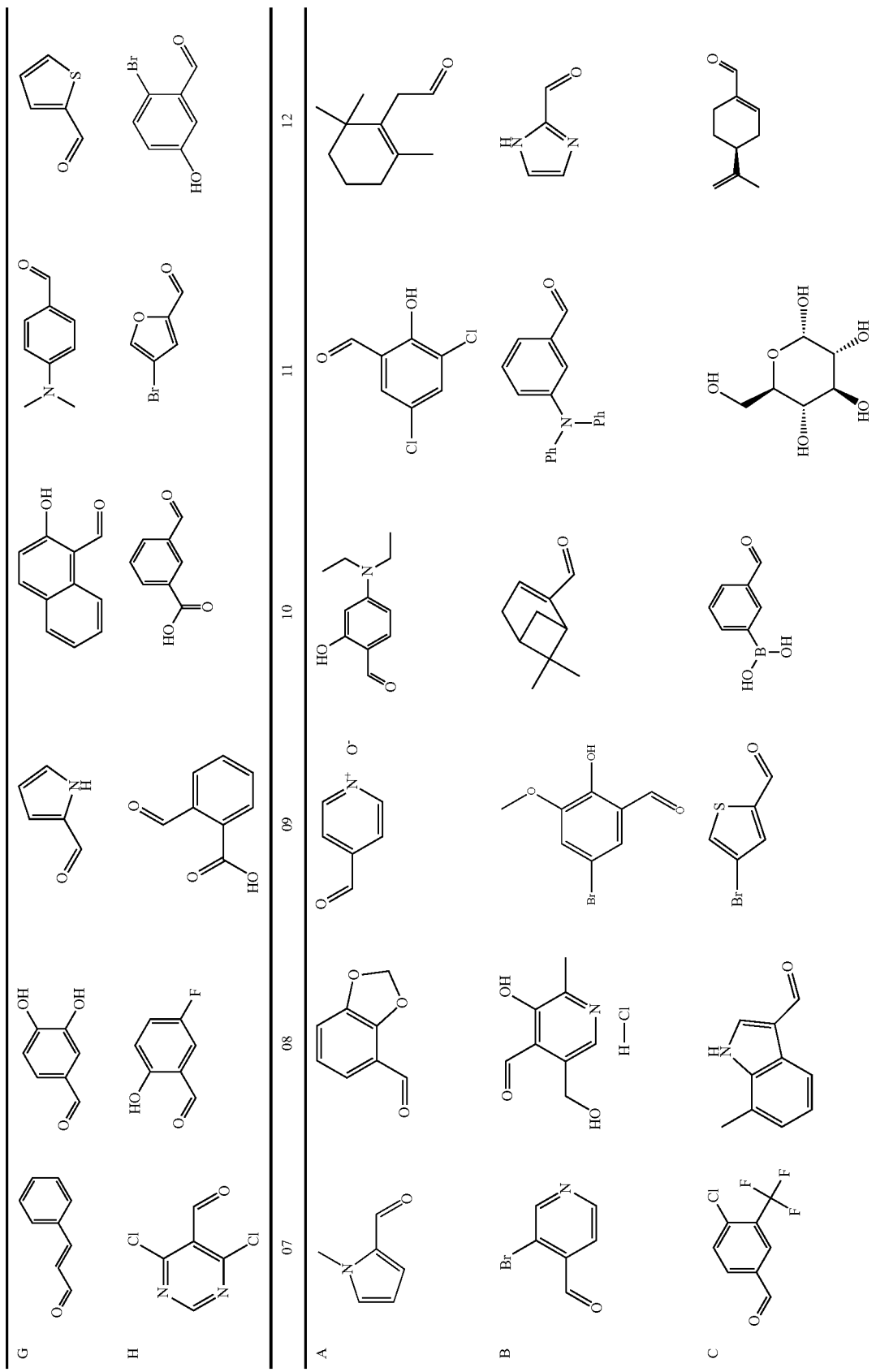

TABLE A-continued
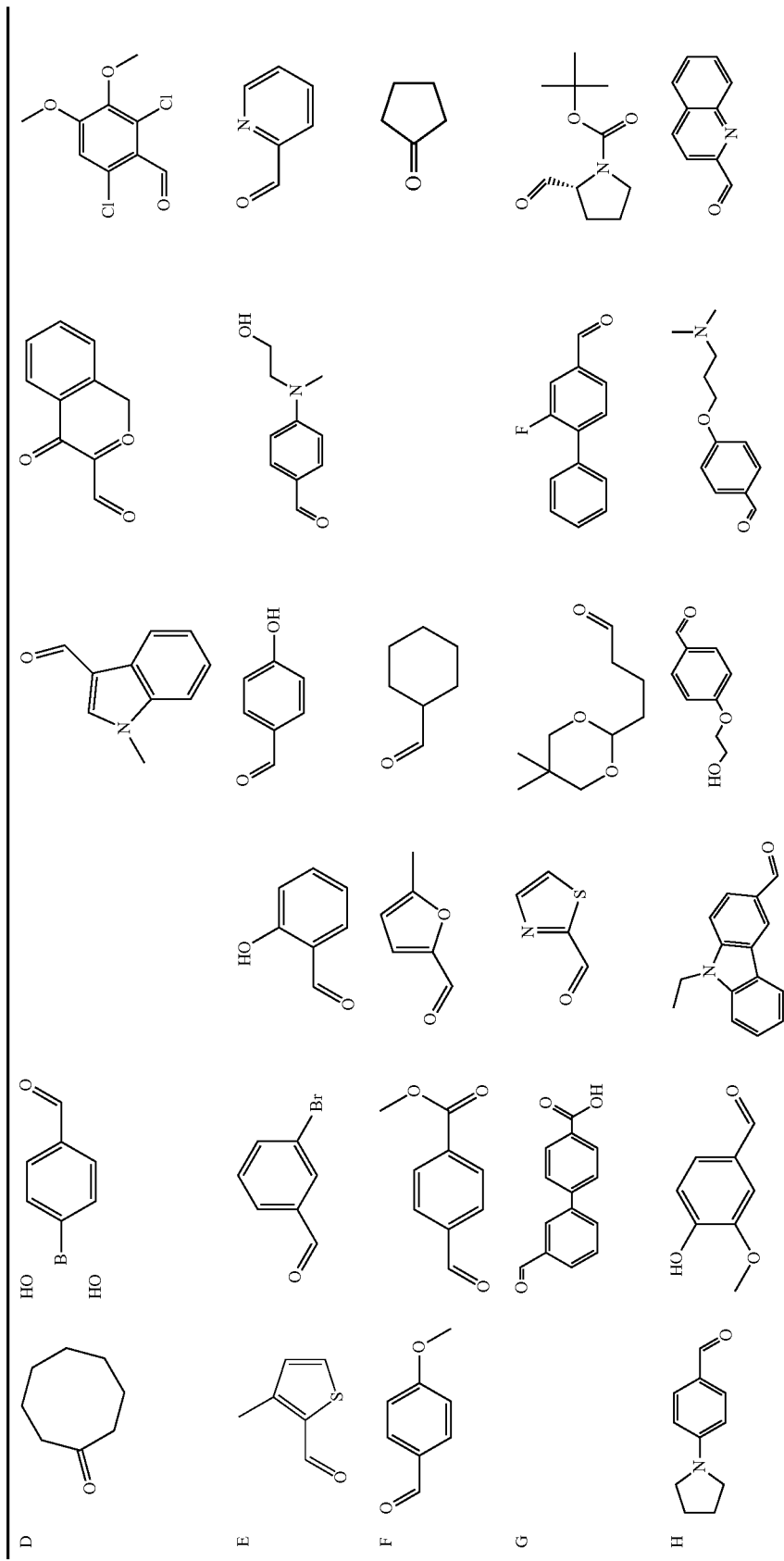

TABLE A-continued

Plate 2

TABLE A-continued

TABLE A-continued
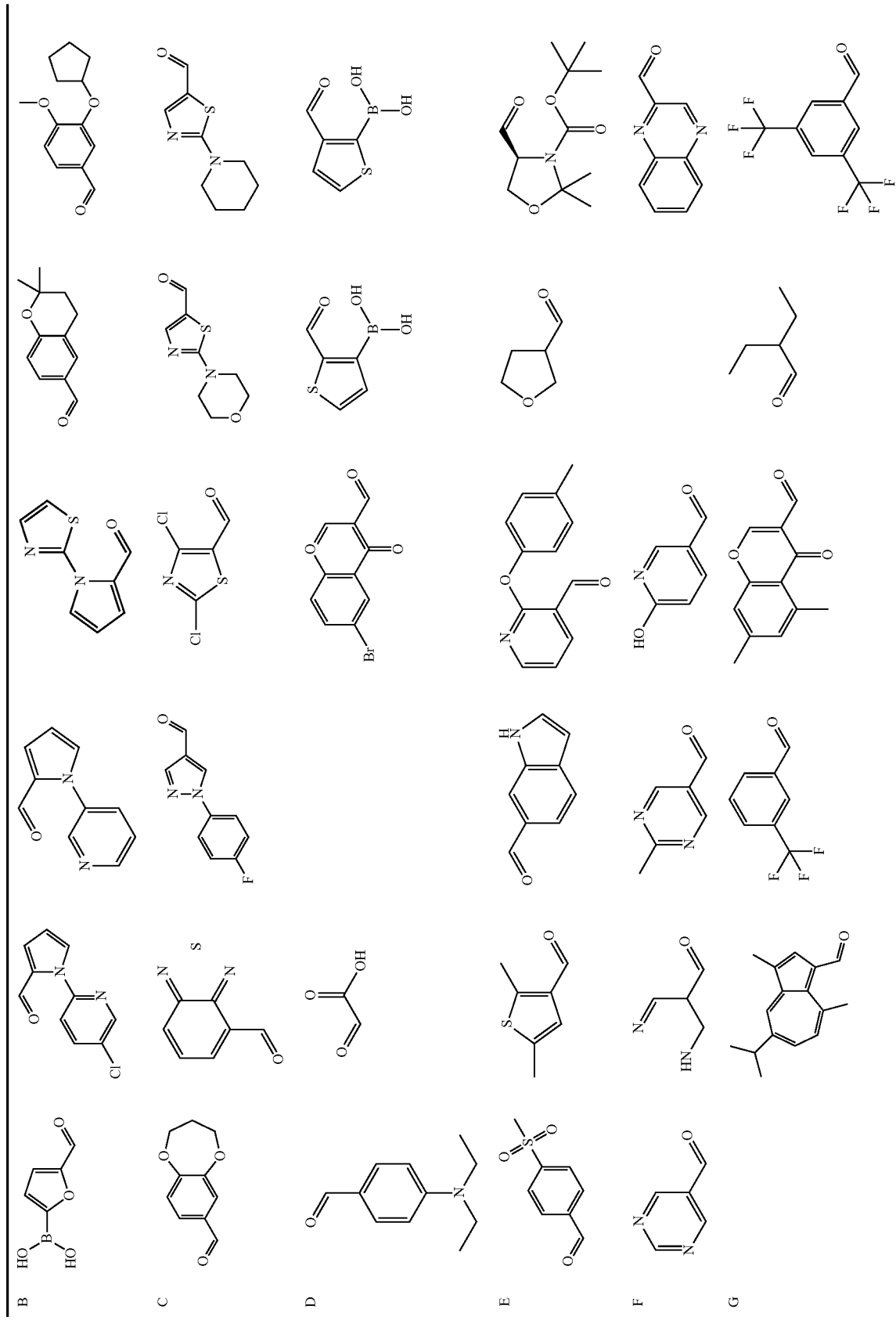

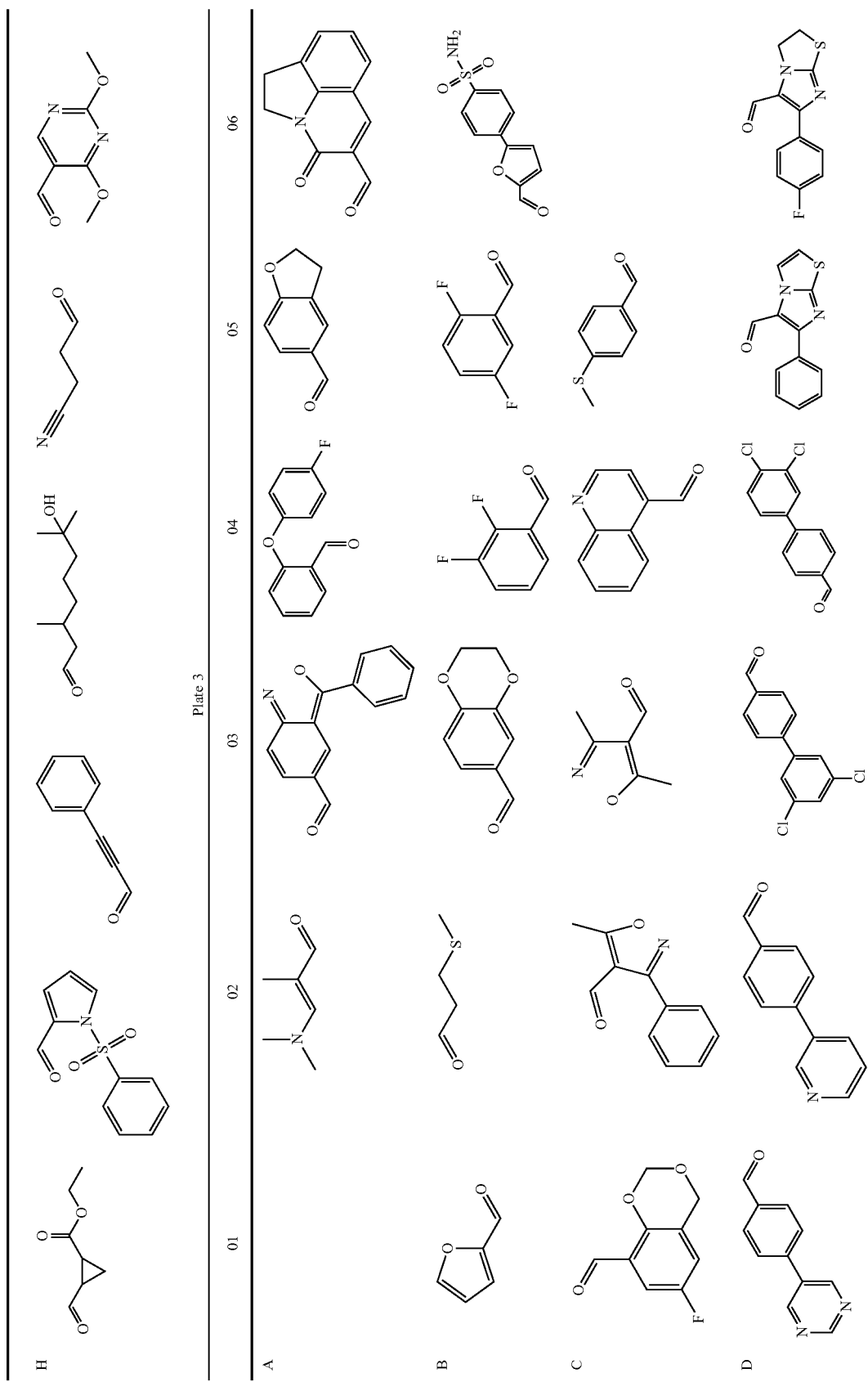

TABLE A-continued
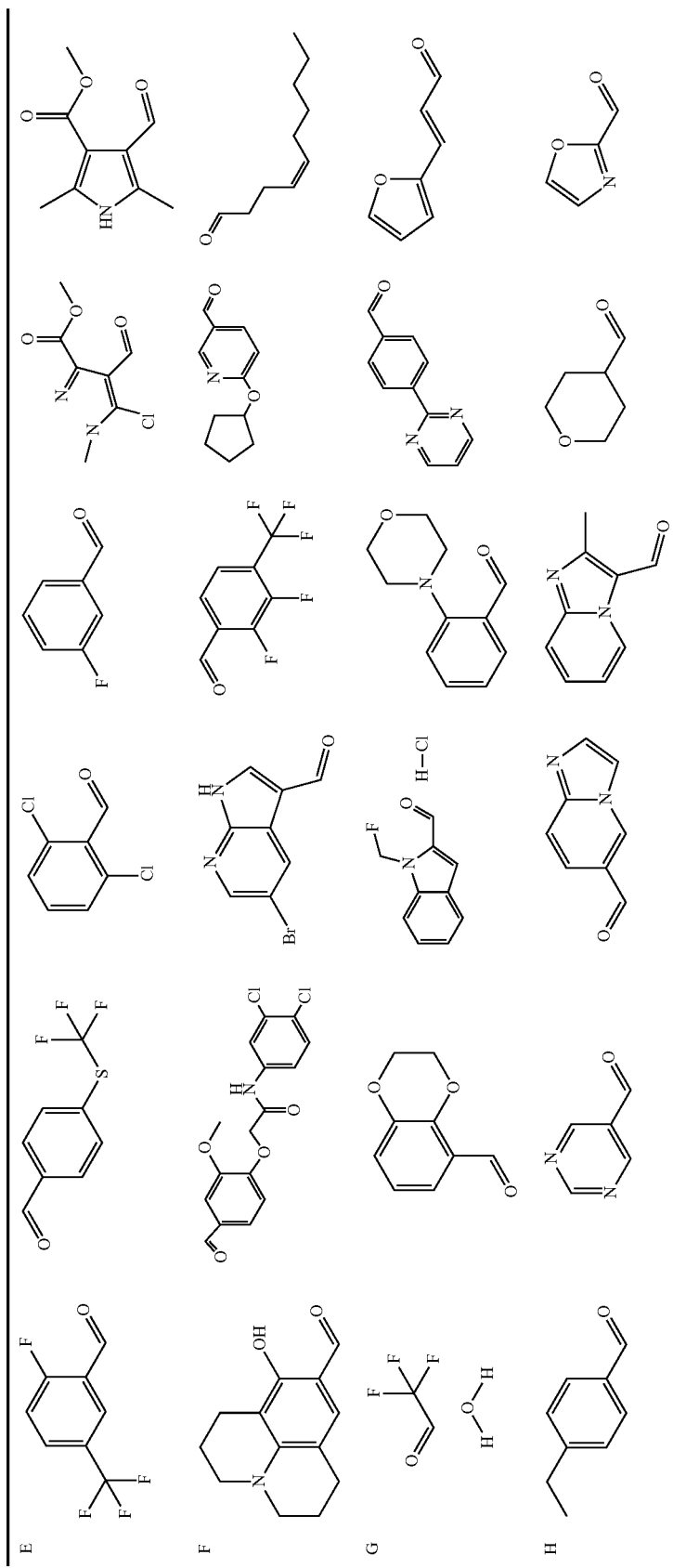
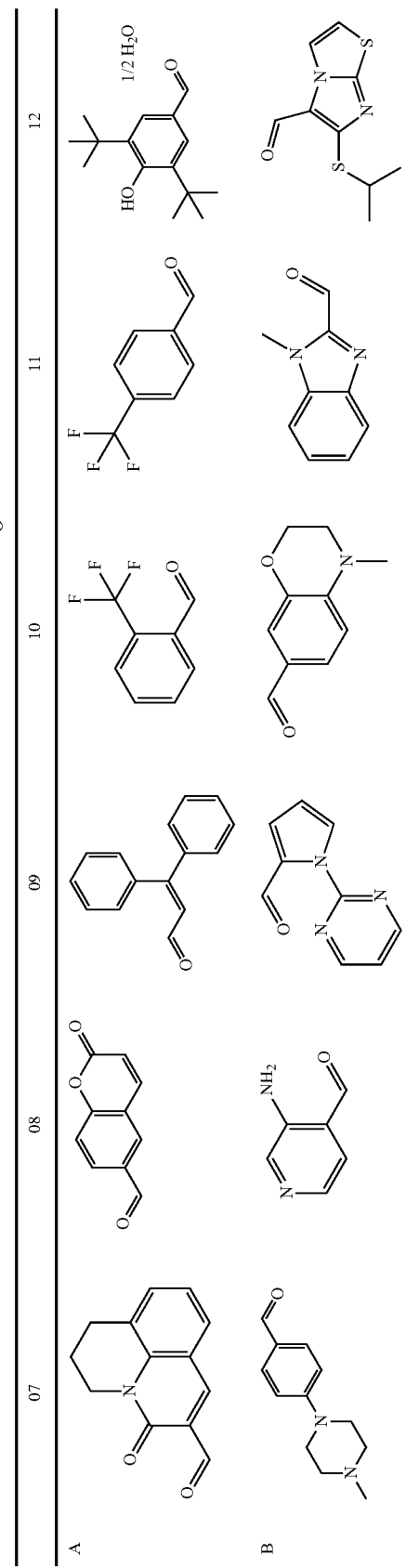

TABLE A-continued
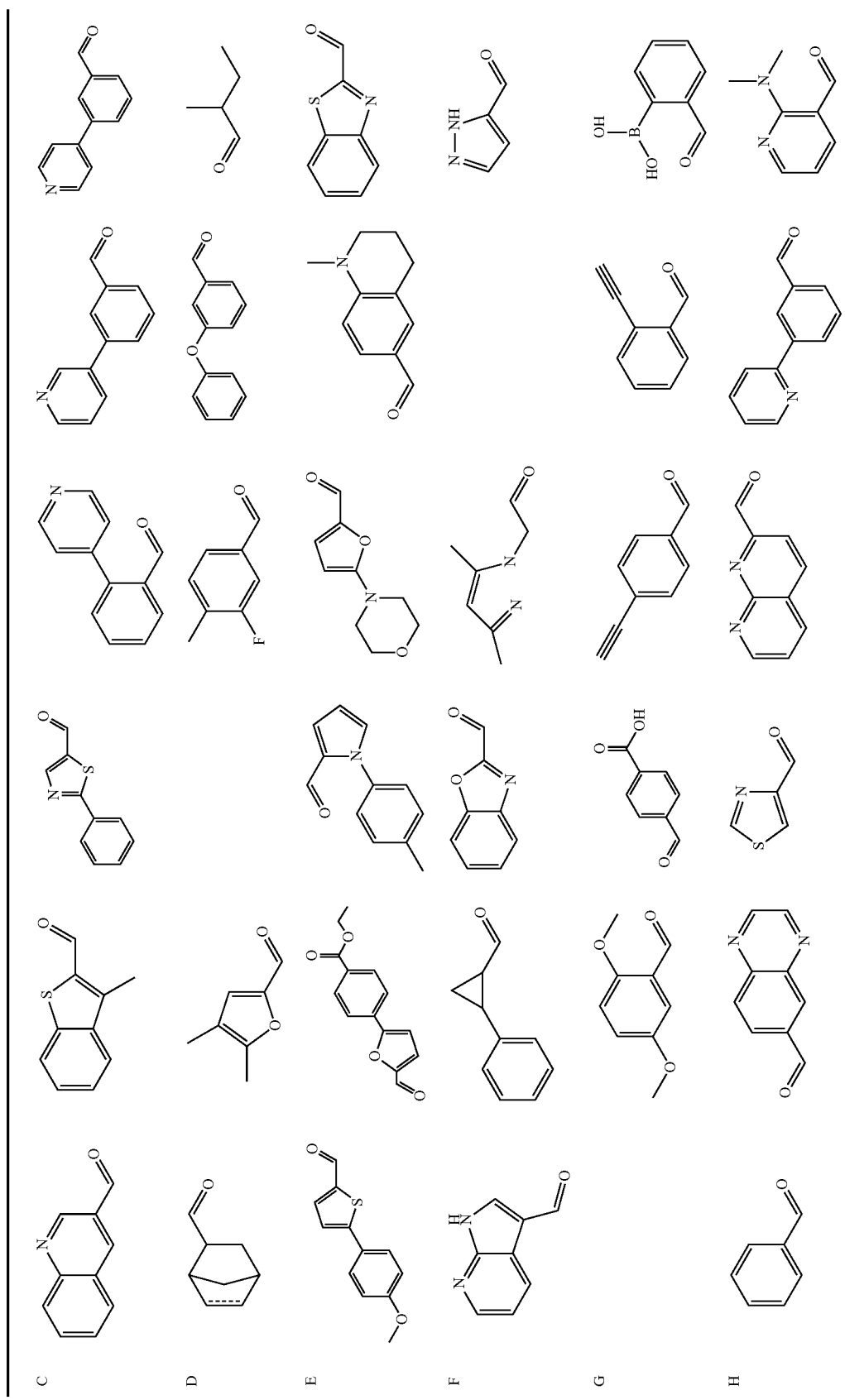

TABLE A-continued
Plate 4
| | 01 | 02 | 03 | 04 | 05 | 06 |
|---|---|---|---|---|---|---|
| A |  | 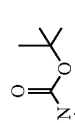 | 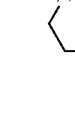 |  | 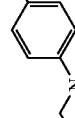 | 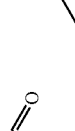 |
| B | 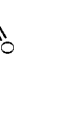 |  | 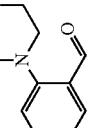 |  | 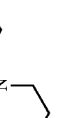 | 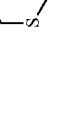 |
| C | 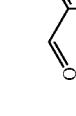 | 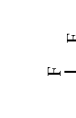 |  |  | |  |
| D |  | 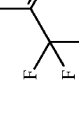 | 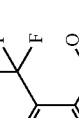 | 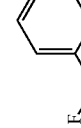 |  | 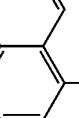 |
| E |  |  | 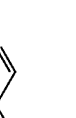 | 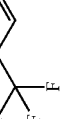 |  | 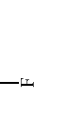 |

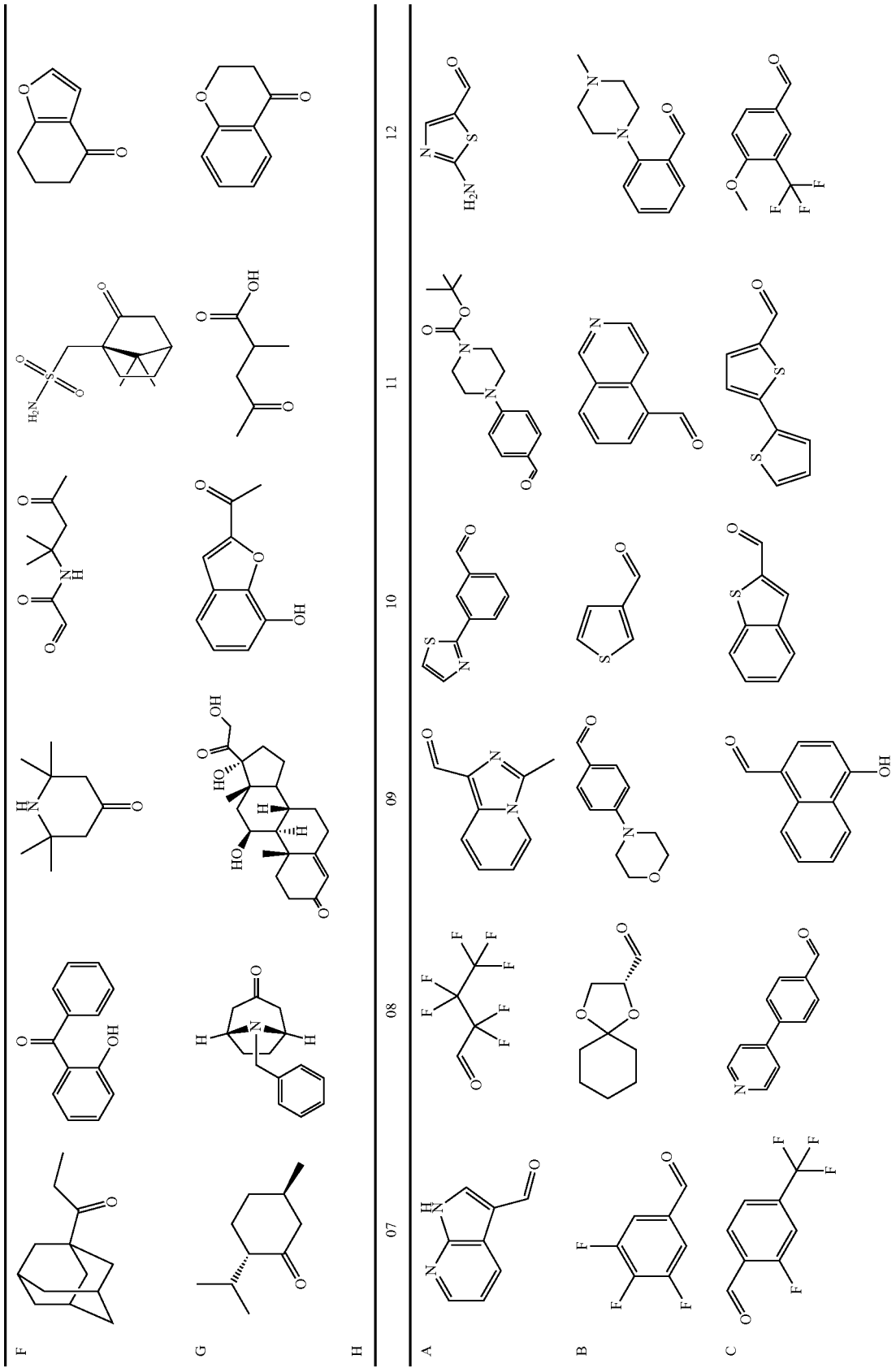

TABLE A-continued
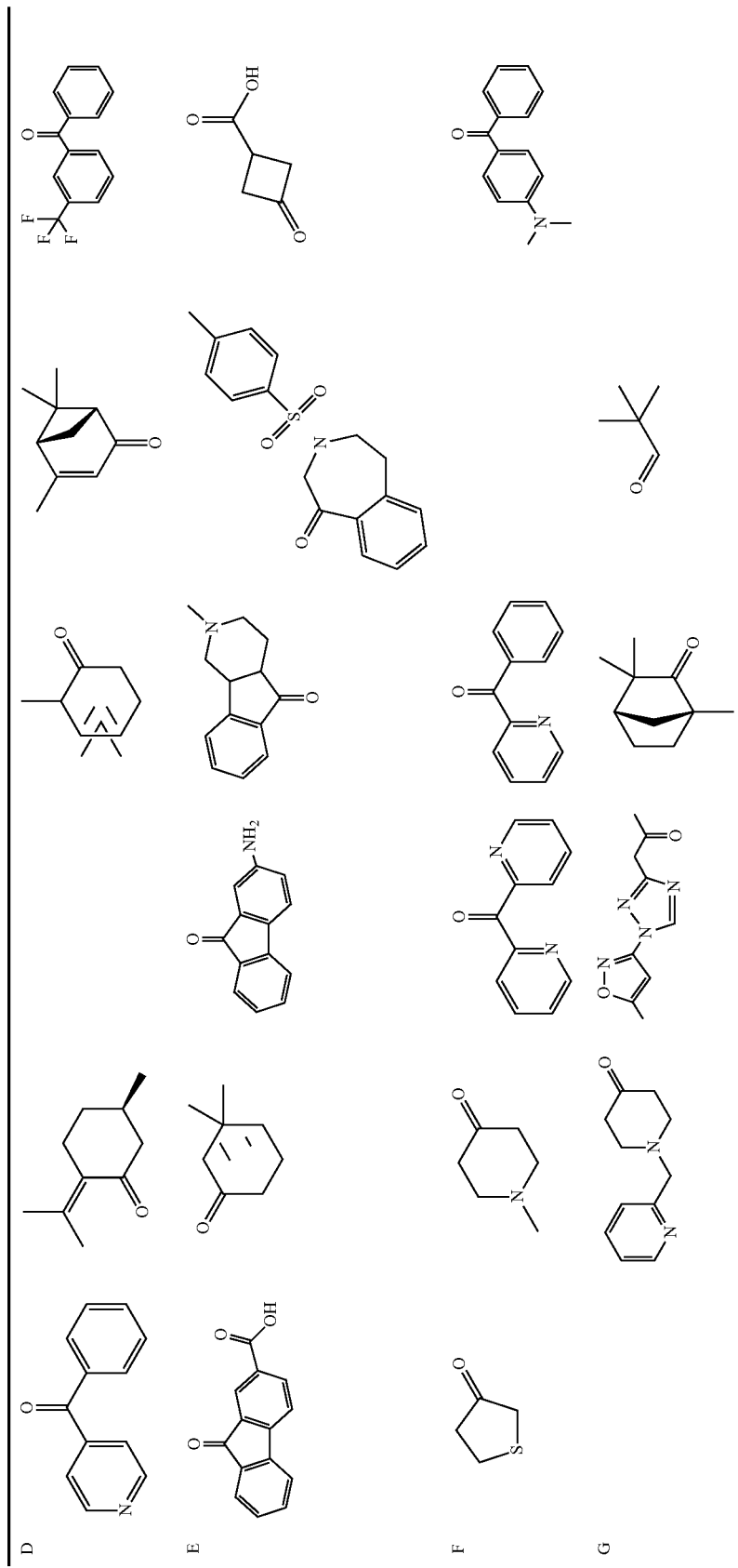

In one embodiment, the compound is a compound is represented by the formula:

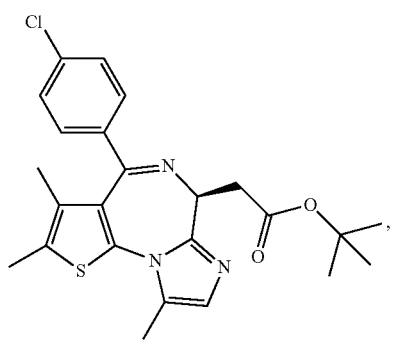
(VIII)

or a salt, solvate, or hydrate thereof.

In certain embodiments, the compound is (racemic) JQ1; in certain embodiments, the compound is (+)-JQ1. In certain embodiments, the compound is a compound selected from the group consisting of:

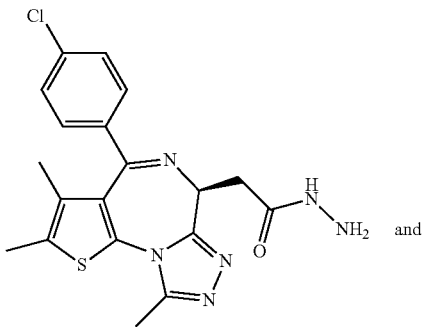
(3)

and

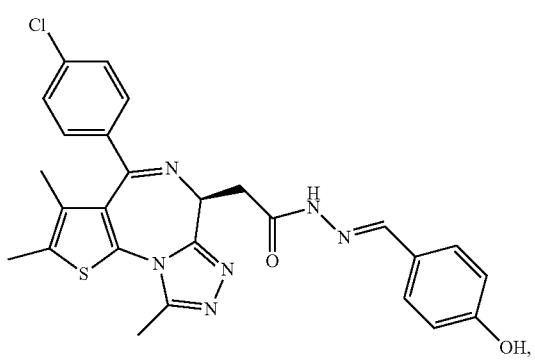
(4)

or a salt, solvate, or hydrate thereof.

Additional examples of compounds include compounds according to any of the follow formulae:

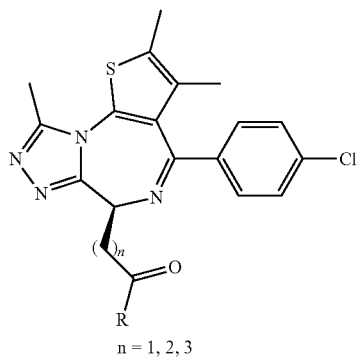
(IX)
n = 1, 2, 3

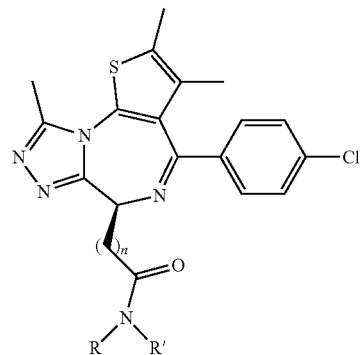
(X)
n = 1, 2, 3

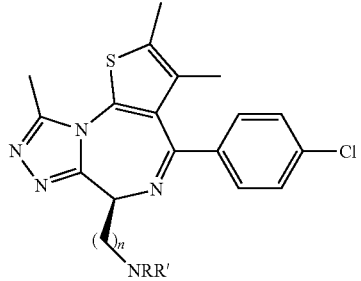
(XI)
n = 1, 2, 3

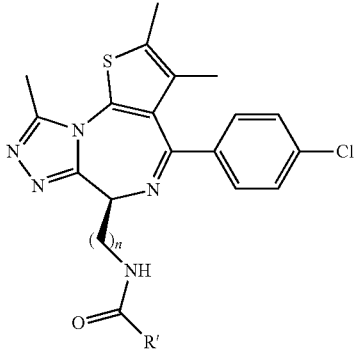
(XII)
n = 1, 2, 3

-continued
(XIII)
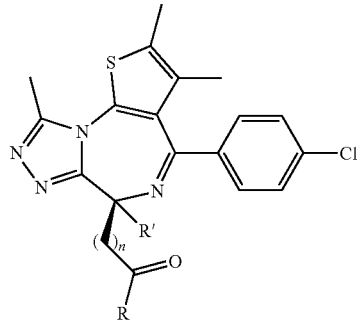
R' = H, D, Me
n = 1, 2, 3
(XIV)
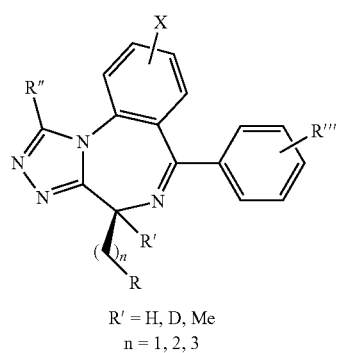
R' = H, D, Me
n = 1, 2, 3
(XV)
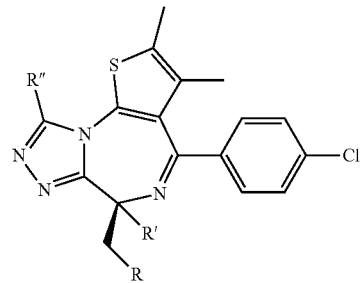
R" = OMe, CH₂OH, CH₂NH₂, CH₂OMe
(XVI)
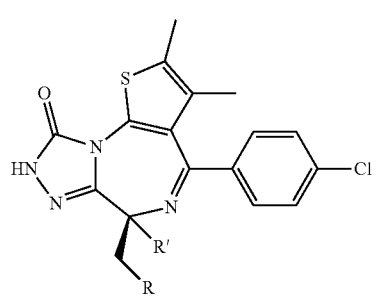
-continued
(XVII)
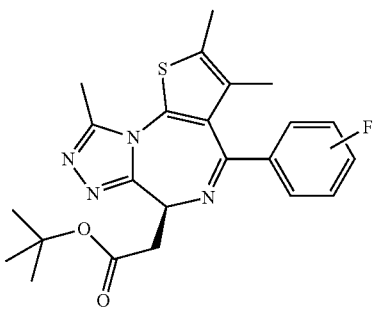
(XVIII)
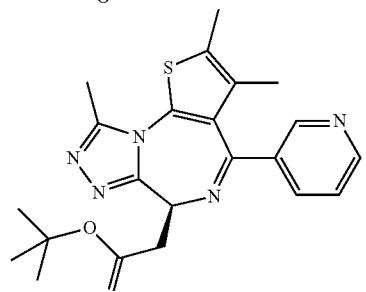
Also 2- and 4-pyridyl
(XIX)
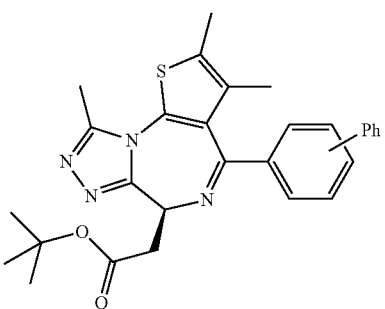
(XX)
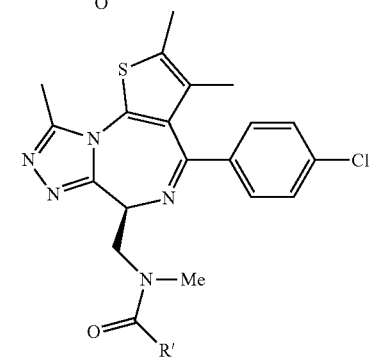
(XXI)
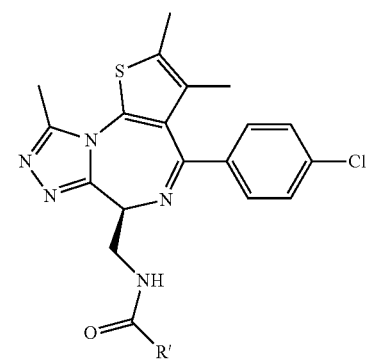

-continued (XXII)

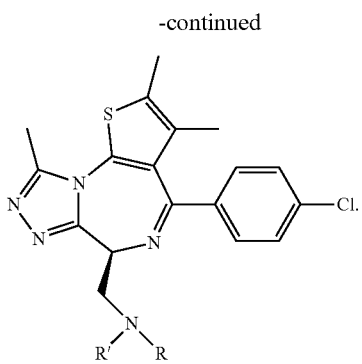

In Formulae IX-XXII, R and R' can be, e.g., H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted. In Formulae XIV, X can be any substituent for an aryl group as described herein.

Compounds of the invention can be prepared by a variety of methods, some of which are known in the art. For instance, the chemical Examples provided hereinbelow provide synthetic schemes for the preparation of the compound JQ1 (as the racemate) and the enantiomers (+)-JQ1 and (−)-JQ1 (see Schemes S1 and S2). A variety of compounds of Formulae (I)-(VIII) can be prepared by analogous methods with substitution of appropriate starting materials.

For example, starting from JQ1, the analogous amine can be prepared as shown in Scheme 1, below.

As shown in Scheme 1, hydrolysis of the t-butyl ester of JQ1 affords the carboxylic acid, which is treated with diphenylphosphoryl azide (DPPA) and subjected to Curtius rearrangement conditions to provide the Cbz-protected amine, which is then deprotected to yield the amine. Subsequent elaboration of the amine group, e.g., by reductive amination yields secondary amines, which can be further alkylated to provide tertiary amines Scheme 2

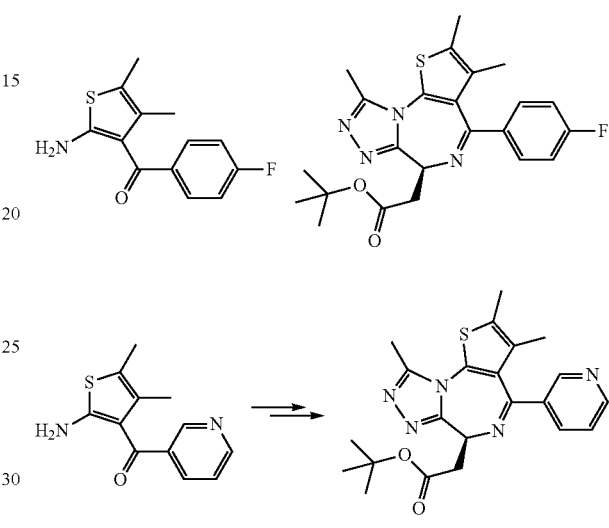

Scheme 1

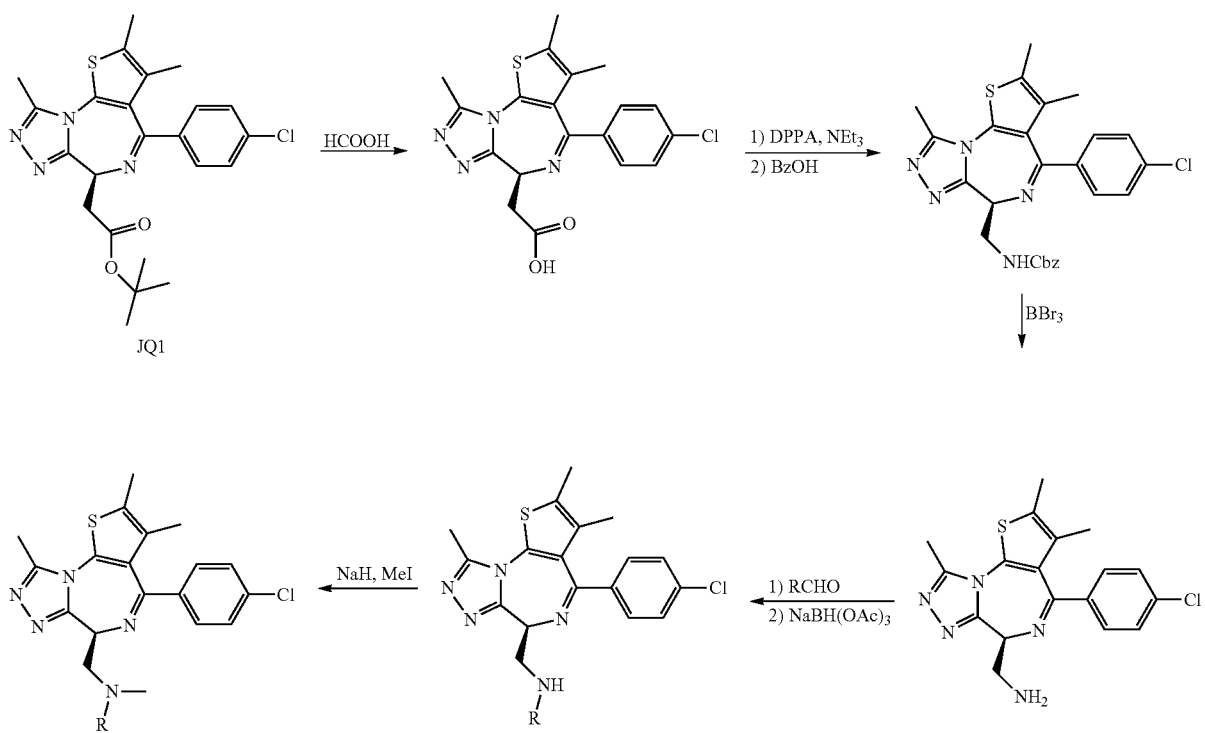

-continued

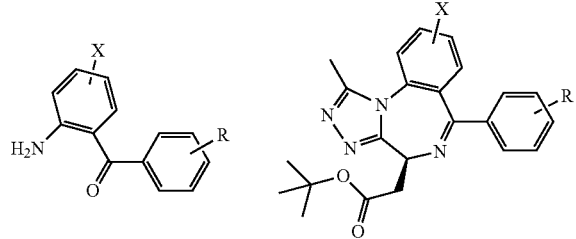

Scheme 2 shows the synthesis of further examples of the compounds of the invention, e.g., of Formula I, in which the fused ring core is modified (e.g., by substitution of a different aromatic ring as Ring A in Formula I). Use of aminodiarylketones having appropriate functionality (e.g., in place of the aminodiarylketone S2 in Scheme S1, infra) provides new compounds having a variety of fused ring cores and/or aryl group appendages (corresponding to group R in Formula I). Such aminodiarylketones are commercially available or can be prepared by a variety of methods, some of which are known in the art.

Scheme 3 provides additional exemplary synthetic schemes for preparing further compounds of the invention.

Scheme 3

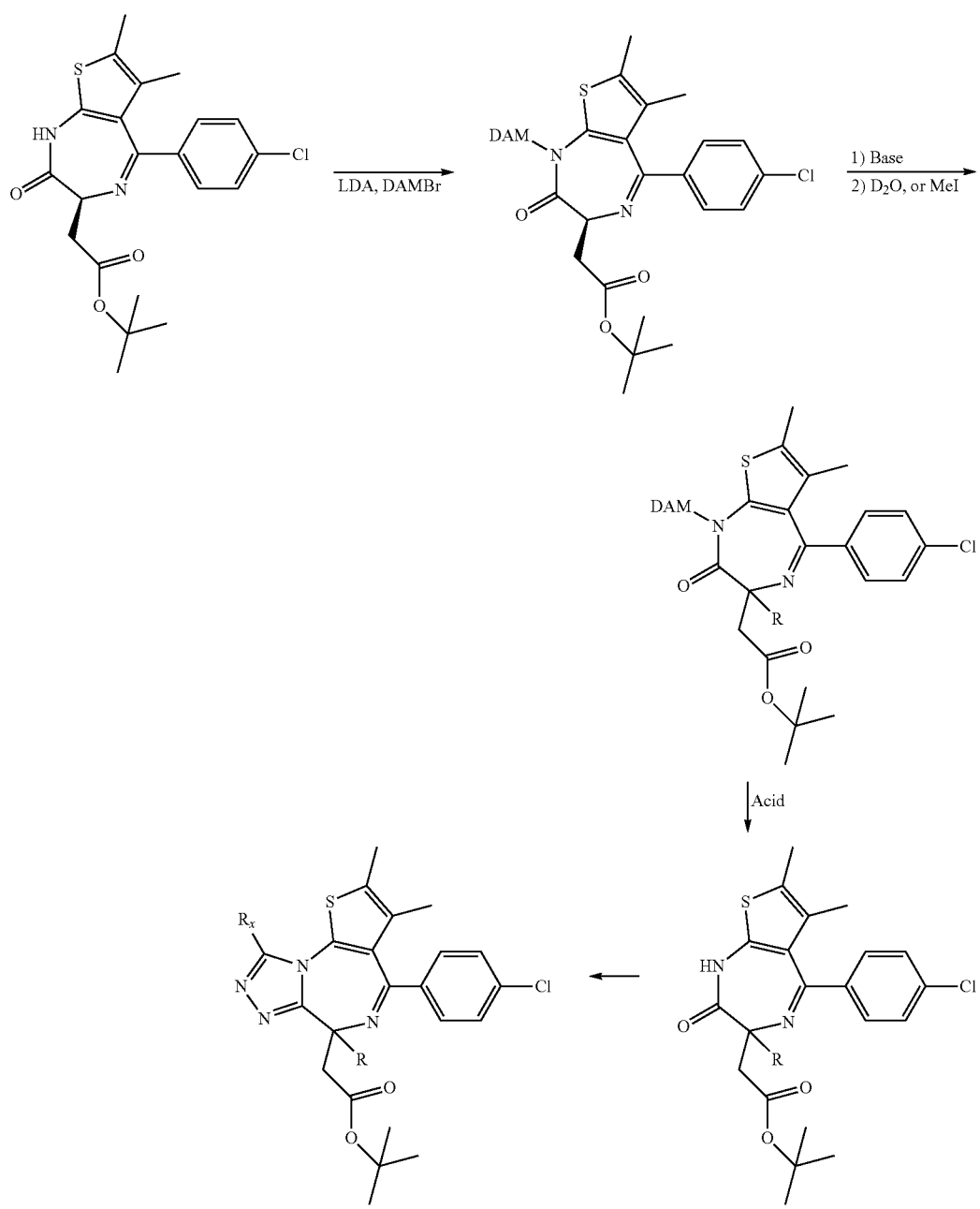

As shown in Scheme 3, a fused bicyclic precursor (see Scheme S1, infra, for synthesis of this compound) is functionalized with a moiety R (DAM=dimethylaminomethylene protecting group) and then elaborated by reaction with a hydrazide to form the tricyclic fused core. Substituent Rx can be varied by selection of a suitable hydrazide.

Additional examples of compounds of the invention (which can be prepared by the methods described herein) include:

Amides:

Amides can be prepared, e.g., by preparation of a corresponding carboxylic acid or ester, followed by amidation with an appropriate amine using standard conditions. In certain embodiments, an amide provides a two-carbon "linker" with a terminal terminal nitrogen-containing ring (e.g., pyridyl, piperidyl, piperazinyl, imidazolyl (including N-methyl-imidazolyl), morpholinyl, and the like. Exemplary amide structures include:

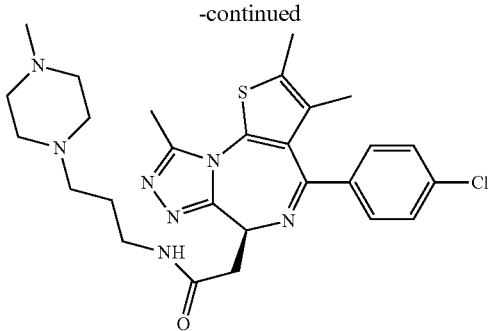

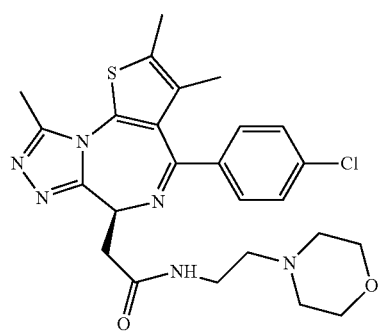

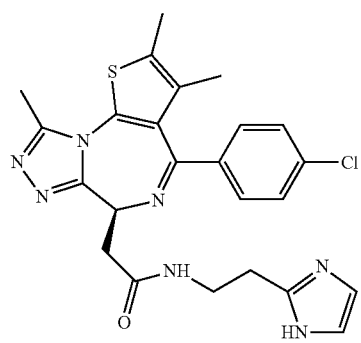

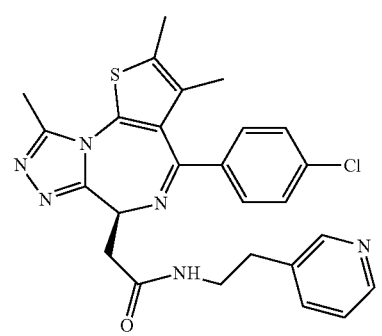

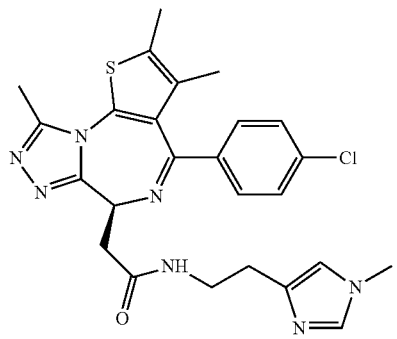 [SMILES: Cc1sc2c(c1C)C(c1ccc(Cl)cc1)=N[C@@H](CC(=O)NCCc1cn(C)cn1)c1nnc(C)n1-2]

The use of a two-carbon linker between the amide moiety and the terminal nitrogen-containing ring is preferred.

"Reverse amides":

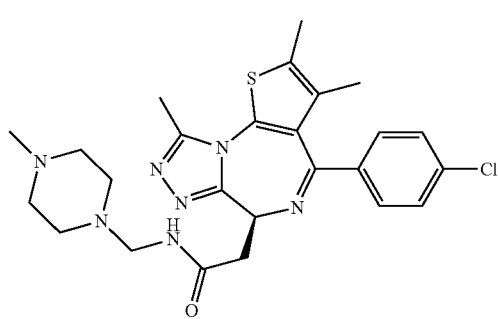

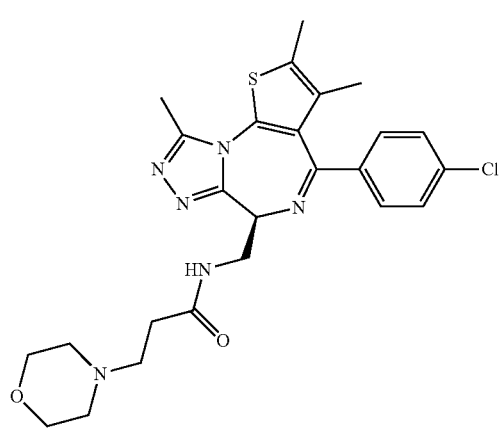

87
-continued
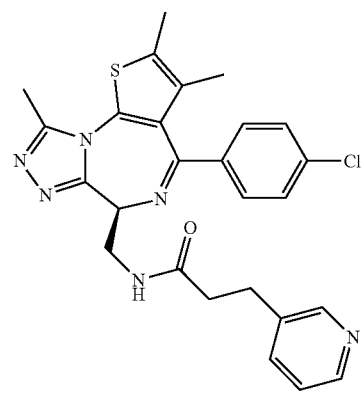
N position can be different
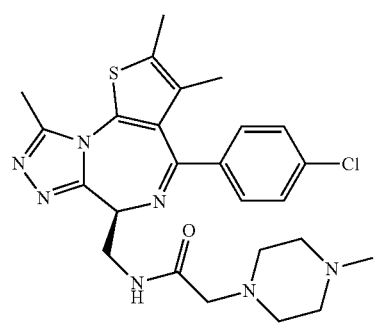
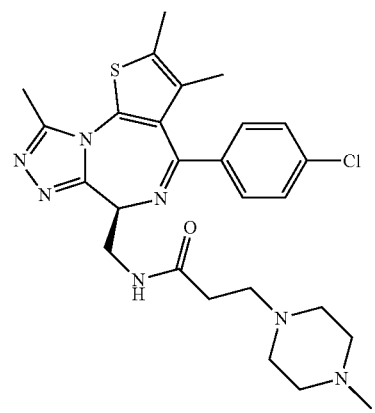
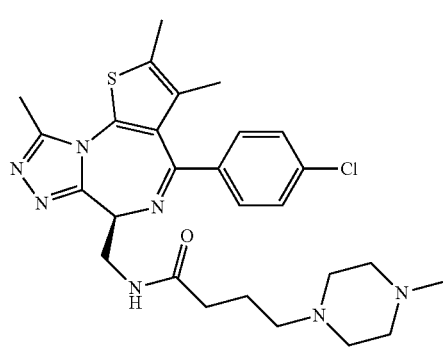
88
-continued
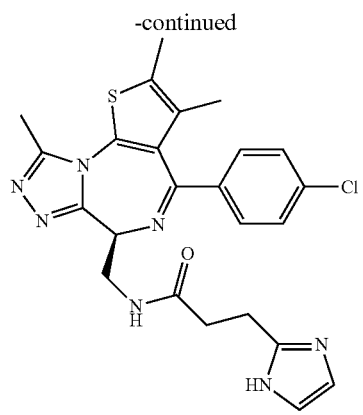
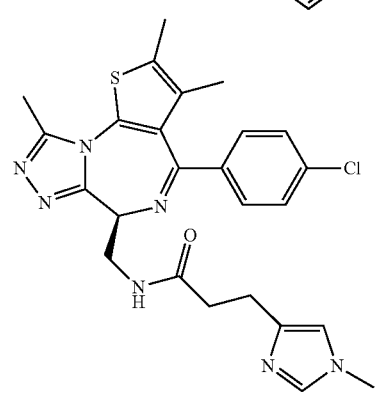
Secondary amines:
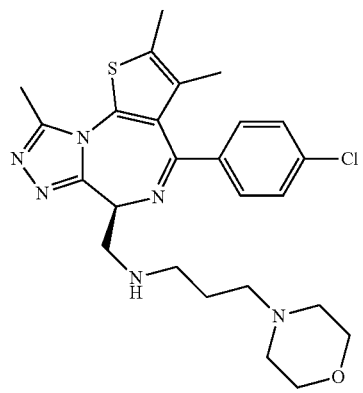
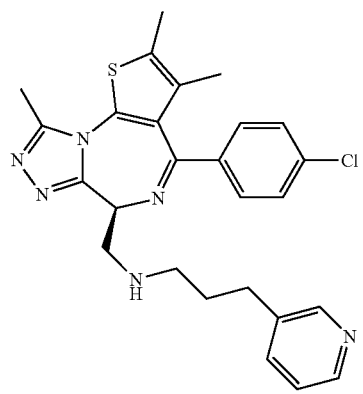

-continued

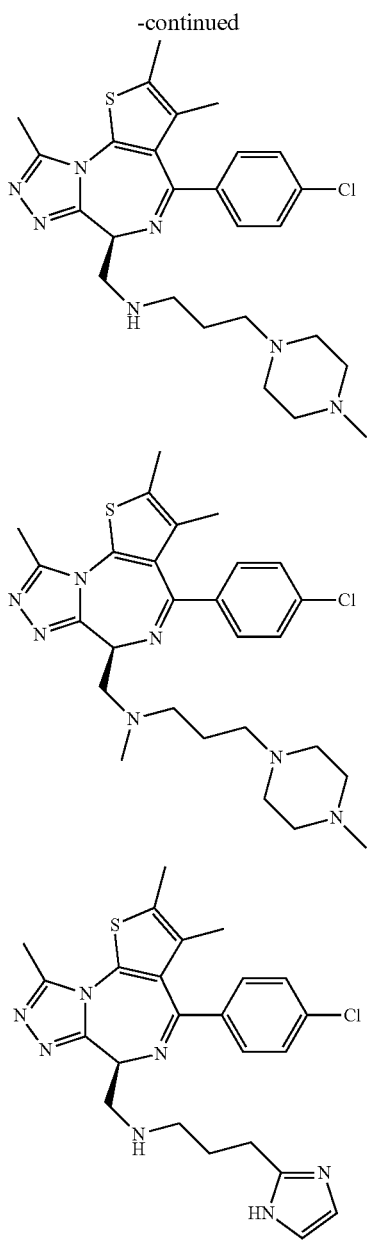

Boronic acids:

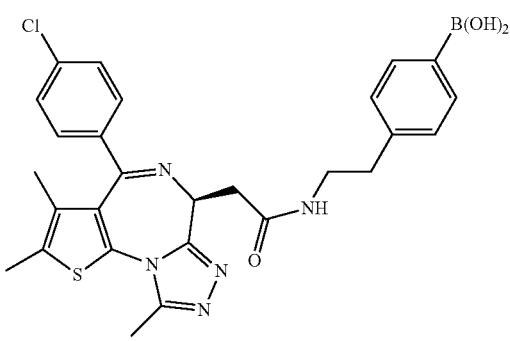

-continued

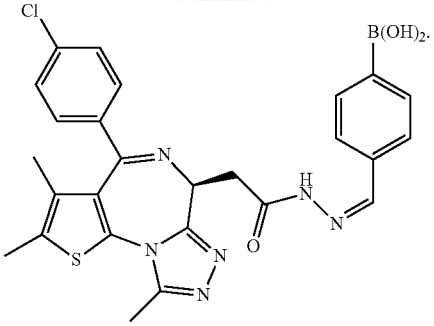

In certain embodiments, a compound having at least one chiral center is present in racemic form. In certain embodiments, a compound having at least one chiral center is enantiomerically enriched, i.e., has an enantiomeric excess (e.e.) of at least about 10%, 20%, 30%, 40%, 50%, 60%, 70%, 80%, 85%, 90%, 90%, 95%, 99%, 99% or 100%. In certain embodiments, a compound has the same absolute configuration as the compound (+)-JQ1 ((S)-tert-Butyl 2-(4-(4-chlorophenyl)-2,3,9-trimethyl-6H-thieno[3,2-f][1,2,4]triazolo[4,3-a][1,4]diazepin-6-yl)acetate) described herein.

In certain embodiments of any of the Formulae disclosed herein, the compound is not represented by the following structure:

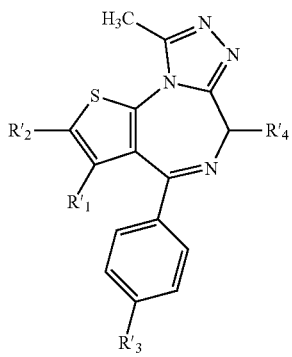

in which:

$R'_1$ is $C_1$-$C_4$ alkyl;

$R'_2$ is hydrogen, halogen, or $C_1$-$C_4$ alkyl optionally substituted with a halogen atom or a hydroxyl group;

$R'_3$ is a halogen atom, phenyl optionally substituted by a halogen atom, $C_1$-$C_4$ alkyl, $C_1$-$C_4$ alkoxy, or cyano; —$NR_5$—$(CH_2)_m$—$R_6$ wherein $R_5$ is a hydrogen atom or $C_1$-$C_4$ alkyl, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or $C_1$-$C_4$ alkyl, n is an integer of 0-2, and $R_8$ is phenyl or pyridyl optionally substituted by a halogen atom; and $R'_4$ is —$(CH_2)_a$—CO—NH—$R_9$ wherein a is an integer of 1-4, and $R_9$ is $C_1$-$C_4$ alkyl; $C_1$-$C_4$ hydroxyalkyl; $C_1$-$C_4$ alkoxy; or phenyl or pyridyl optionally substituted by $C_1$-$C_4$ alkyl, $C_1$-$C_4$ alkoxy, amino or a hydroxyl group or —$(CH_2)_b$—$COOR_{10}$ wherein b is an integer of 1-4, and $R_{10}$ is $C_1$-$C_4$ alkyl.

The term "pharmaceutically acceptable salt" also refers to a salt prepared from a compound disclosed herein (e.g., JQ1, a compound of Formulas I-XXII) or any other compound delineated herein, having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, or any other compound delineated herein, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

In addition to small compounds that inhibit Brd4, the invention further provides other agents that inhibit Brd4 expression or biological activity.

Inhibitory Nucleic Acids

The invention further provides inhibitory nucleic acid molecules that inhibit the expression or activity of Brd4, and the use of such agents for the treatment of leukemias (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative Disorders, Myelodysplasia. Such oligonucleotides include single and double stranded nucleic acid molecules (e.g., DNA, RNA, and analogs thereof) that bind a nucleic acid molecule that encodes Brd4 (e.g., antisense molecules, siRNA, shRNA) as well as nucleic acid molecules that bind directly to Brd4 to modulate its biological activity (e.g., aptamers).

Ribozymes

Catalytic RNA molecules or ribozymes that include an antisense Brd4 sequence of the present invention can be used to inhibit expression of a Brd4 nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 1988; 334:585-591 and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif Examples of such hammerhead motifs are described by Rossi et al., Aids Research and Human Retroviruses 1992; 8:183. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry 1989; 28:4929 and Hampel et al., Nucleic Acids Research 1990; 18:299. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101:25-33; Elbashir et al., Nature 2001; 411:494-498 hereby incorporated by reference). The therapeutic effectiveness of an sirNA approach in mammals was demonstrated in vivo by McCaffrey et al. Nature 2002; 418:38-39.

Given the sequence of a target gene, siRNAs may be designed to inactivate that gene. Such siRNAs, for example, could be administered directly to an affected tissue, or administered systemically. The nucleic acid sequence of an Brd4 gene can be used to design small interfering RNAs (siRNAs). The 21 to 25 nucleotide siRNAs may be used, for example, as therapeutics to treat a vascular disease or disorder.

The inhibitory nucleic acid molecules of the present invention may be employed as double-stranded RNAs for RNA interference (RNAi)-mediated knock-down of Brd4 expression. In one embodiment, Brd4 expression is reduced in a hematopoietic cell or a leukemic cell. RNAi is a method for decreasing the cellular expression of specific proteins of interest (reviewed in Tuschl, Chembiochem 2001; 2:239-245; Sharp, Genes & Devel. 2000; 15:485-490; Hutvagner and Zamore, Curr. Opin. Genet. Devel. 2002; 12:225-232; and Hannon, Nature 2002; 418:244-251. The introduction of siRNAs into cells either by transfection of dsRNAs or through expression of siRNAs using a plasmid-based expression system is increasingly being used to create loss-of-function phenotypes in mammalian cells.

In one embodiment of the invention, double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al., *Science* 2002; 296:550-553; Paddison et al., *Genes & Devel.* 2002; 16:948-958; Paul et al., *Nature Biotechnol.* 2002; 20:505-508; Sui et al., *Proc. Natl. Acad. Sci. USA* 2002; 99:5515-5520; Yu et al., *Proc. Natl. Acad. Sci. USA* 2002; 99:6047-6052; Miyagishi et al., *Nature Biotechnol.* 2002; 20:497-500; and Lee et al., *Nature Biotechnol.* 2002; 20:500-505, each of which is hereby incorporated by reference.

Small hairpin RNAs (shRNAs) comprise an RNA sequence having a stem-loop structure. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, a miRNA flanking sequence, other molecule, or some combination thereof.

As used herein, the term "small hairpin RNA" includes a conventional stem-loop shRNA, which forms a precursor miRNA (pre-miRNA). While there may be some variation in range, a conventional stem-loop shRNA can comprise a stem ranging from 19 to 29 bp, and a loop ranging from 4 to 30 bp. "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one can design and express artificial miRNAs based on the features of existing miRNA genes.

In this regard, short hairpin RNAs can be designed to mimic endogenous miRNAs. Many miRNA intermediates can be used as models for shRNA or shRNAmir, including without limitation a miRNA comprising a backbone design of miR-15a, -16, -19b, -20, -23a, -27b, -29a, -30b, -30c, -104, -132s, -181, -191, -223 (see U.S. Publication No. 2005/0075492). In some embodiments, shRNA molecules are designed based on the human miR-30 sequence, redesigned to allow expression of artificial shRNAs by substituting the stem sequences of the pri-miR-30 with unrelated base-paired sequences (Siolas et al., 2005, Nat. Biotech. 23: 227-231; Silva et al., 2005, Nat. Genet. 37: 1281-1288); Zeng et al. (2002), Molec. Cell 9: 1327-1333). The natural stem sequence of the miR-30 can be replaced with a stem sequence from about 16 to about 29 nucleotides in length, in particular from about 19 to 29 nucleotides in length. The loop sequence can be altered such that the length is from about 4 to about 23 nucleotides. In one embodiment, the stem of the shRNA molecule is about 22 nucleotides in length. In another embodiment, the stem is about 29 nucleotides in length. Thus, the invention can be practiced using shRNAs that are synthetically produced, as well as micro-RNA (miRNA) molecules that are found in nature and can be remodeled to function as synthetic silencing short hairpin RNAs.

shRNAs can be expressed from DNA vectors to provide sustained silencing and high yield delivery into almost any cell type. In some embodiments, the vector is a viral vector. Exemplary viral vectors include retroviral, including lentiviral, adenoviral, baculoviral and avian viral vectors, and including such vectors allowing for stable, single-copy genomic integrations. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

For expression within cells, DNA vectors, for example plasmid vectors comprising either an RNA polymerase II or RNA polymerase III promoter can be employed. Expression of endogenous miRNAs is controlled by RNA polymerase II (Pol II) promoters and in some cases, shRNAs are most efficiently driven by Pol II promoters, as compared to RNA polymerase III promoters (Dickins et al., 2005, Nat. Genet. 39: 914-921). In some embodiments, expression of the shRNA can be controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Small hairpin RNAs (shRNAs) comprise an RNA sequence having a stem-loop structure. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, a miRNA flanking sequence, other molecule, or some combination thereof.

As used herein, the term "small hairpin RNA" includes a conventional stem-loop shRNA, which forms a precursor miRNA (pre-miRNA). While there may be some variation in range, a conventional stem-loop shRNA can comprise a stem ranging from 19 to 29 bp, and a loop ranging from 4 to 30 bp. "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one can design and express artificial miRNAs based on the features of existing miRNA genes.

In this regard, short hairpin RNAs can be designed to mimic endogenous miRNAs. Many miRNA intermediates can be used as models for shRNA or shRNAmir, including without limitation a miRNA comprising a backbone design of miR-15a, -16, -19b, -20, -23a, -27b, -29a, -30b, -30c, -104, -132s, -181, -191, -223 (see U.S. Publication No. 2005/0075492). In some embodiments, shRNA molecules are designed based on the human miR-30 sequence, redesigned to allow expression of artificial shRNAs by substituting the stem sequences of the pri-miR-30 with unrelated base-paired sequences (Siolas et al., 2005, Nat. Biotech. 23: 227-231; Silva et al., 2005, Nat. Genet. 37: 1281-1288); Zeng et al. (2002), Molec. Cell 9: 1327-1333). The natural stem sequence of the miR-30 can be replaced with a stem sequence from about 16 to about 29 nucleotides in length, in particular from about 19 to 29 nucleotides in length. The loop sequence can be altered such that the length is from about 4 to about 23 nucleotides. In one embodiment, the stem of the shRNA molecule is about 22 nucleotides in length. In another embodiment, the stem is about 29 nucleotides in length. Thus, the invention can be practiced using shRNAs that are synthetically produced, as well as micro-RNA (miRNA) molecules that are found in nature and can be remodeled to function as synthetic silencing short hairpin RNAs.

shRNAs can be expressed from DNA vectors to provide sustained silencing and high yield delivery into almost any cell type. In some embodiments, the vector is a viral vector. Exemplary viral vectors include retroviral, including lentiviral, adenoviral, baculoviral and avian viral vectors, and including such vectors allowing for stable, single-copy genomic integrations. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

For expression within cells, DNA vectors, for example plasmid vectors comprising either an RNA polymerase II or RNA polymerase III promoter can be employed. Expression of endogenous miRNAs is controlled by RNA polymerase II (Pol II) promoters and in some cases, shRNAs are most efficiently driven by Pol II promoters, as compared to RNA polymerase III promoters (Dickins et al., 2005, Nat. Genet. 39: 914-921). In some embodiments, expression of the shRNA can be controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Delivery of Nucleobase Oligomers

Naked inhibitory nucleic acid molecules, or analogs thereof, are capable of entering mammalian cells and inhibiting expression of a gene of interest, e.g., Brd4. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Pharmaceutical Therapeutics

In other embodiments, agents discovered to have medicinal value (e.g., JQ1 or a compound of a formula delineated herein) using the methods described herein are useful as a drug or as information for structural modification of existing compounds, e.g., by rational drug design. For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the leukemia (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia and Myeloproliferative Disorders). Generally, amounts will be in the range of those used for other agents used in the treatment of other diseases associated with leukemias, although in certain instances lower amounts will be needed because of the increased specificity of the compound. A compound is administered at a dosage that reduces the proliferation, growth or survival of a cancer cell as determined by a method known to one skilled in the art, or using any that assay that measures cell proliferation or viability.

Formulation of Pharmaceutical Compositions

The administration of a compound for the treatment of a leukemia may be by any suitable means that results in a concentration of the therapeutic that, combined with other components, is effective in reducing the proliferation or survival of a leukemic cell. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). In one particular embodiment, an agent of the invention is directly administered to a subject systemically.

Human dosage amounts can initially be determined by extrapolating from the amount of compound used in mice, as a skilled artisan recognizes it is routine in the art to modify the dosage for humans compared to animal models. In one embodiment, an agent of the invention is administered orally or systemically at 50 mg/kg. In certain other embodiments it is envisioned that the dosage may vary from between about 1 μg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 100 mg compound/Kg body. In other embodiments the doses may be about 5, 10, 15, 20, 25, 30, 35, 40, 45, 50, 55, 60, 65, 70, 75, 80, 85, 90, 95, 100 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a leukemia, including but not limited to acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia, and Myeloproliferative Disorders. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces the growth, proliferation or survival of a leukemic cell, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutaminine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

At least two therapeutics may be mixed together in the tablet, or may be partitioned. In one example, the first active therapeutic is contained on the inside of the tablet, and the second active therapeutic is on the outside, such that a substantial portion of the second therapeutic is released prior to the release of the first therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

Optionally, a therapeutic for the treatment of leukemia including but not limited to acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia, and Myeloproliferative Disorders, is administered alone or in combination with other standard therapies for treating cancer; such methods are known to the skilled artisan and described in Remington's Pharmaceutical Sciences by E. W. Martin. If desired, agents of the invention (e.g., JQ1, compounds of formulas delineated herein, and derivatives thereof) are administered in combination with any conventional chemotherapeutic useful for the treatment of a cancer.

Kits or Pharmaceutical Systems

The present compositions may be assembled into kits or pharmaceutical systems for use in the treatment of leukemia (e.g., acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia, and Myeloproliferative Disorders). Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention.

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

As described above, if desired, treatment with a compound of the invention (e.g., JQ1), a an inhibitory nucleic acid molecule that targets Brd4 may be combined with therapies for the treatment of proliferative disease (e.g., radiotherapy, surgery, or chemotherapy). The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

I. Chemical Examples—Synthesis and Methods of Preparation

Compounds of the invention can be synthesized by methods described herein, and/or according to methods known to one of ordinary skill in the art in view of the description herein.

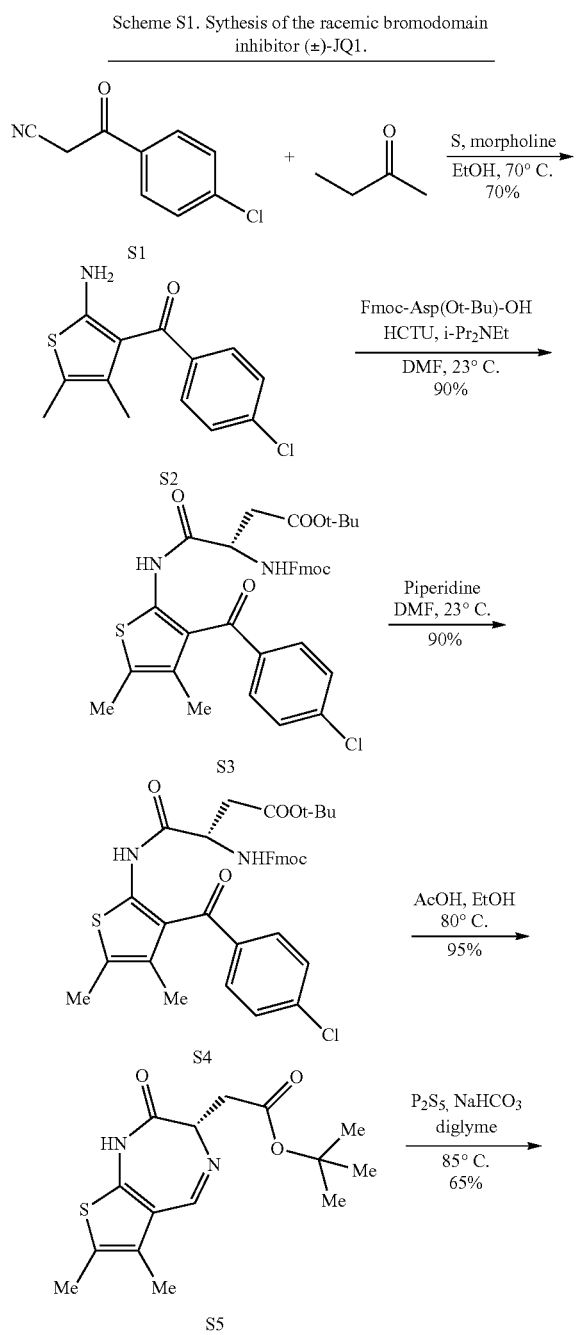

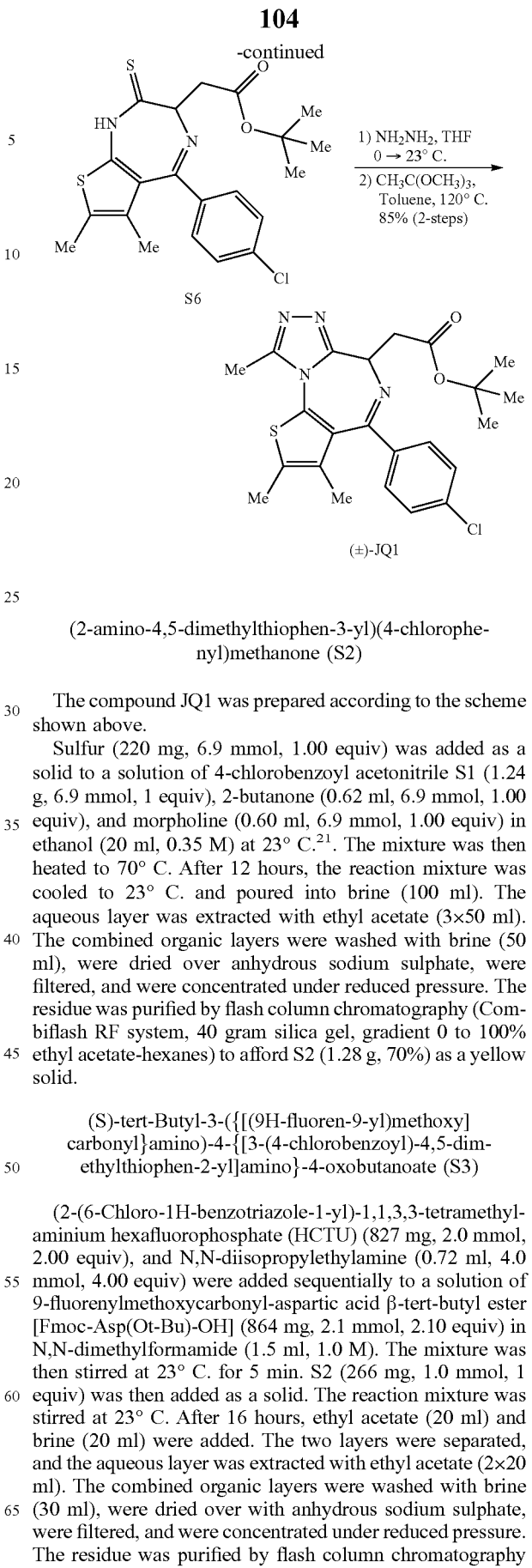

(2-amino-4,5-dimethylthiophen-3-yl)(4-chlorophenyl)methanone (S2)

The compound JQ1 was prepared according to the scheme shown above.

Sulfur (220 mg, 6.9 mmol, 1.00 equiv) was added as a solid to a solution of 4-chlorobenzoyl acetonitrile S1 (1.24 g, 6.9 mmol, 1 equiv), 2-butanone (0.62 ml, 6.9 mmol, 1.00 equiv), and morpholine (0.60 ml, 6.9 mmol, 1.00 equiv) in ethanol (20 ml, 0.35 M) at 23° C.[21] The mixture was then heated to 70° C. After 12 hours, the reaction mixture was cooled to 23° C. and poured into brine (100 ml). The aqueous layer was extracted with ethyl acetate (3×50 ml). The combined organic layers were washed with brine (50 ml), were dried over anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S2 (1.28 g, 70%) as a yellow solid.

(S)-tert-Butyl-3-({[(9H-fluoren-9-yl)methoxy] carbonyl}amino)-4-{[3-(4-chlorobenzoyl)-4,5-dimethylthiophen-2-yl]amino}-4-oxobutanoate (S3)

(2-(6-Chloro-1H-benzotriazole-1-yl)-1,1,3,3-tetramethylaminium hexafluorophosphate (HCTU) (827 mg, 2.0 mmol, 2.00 equiv), and N,N-diisopropylethylamine (0.72 ml, 4.0 mmol, 4.00 equiv) were added sequentially to a solution of 9-fluorenylmethoxycarbonyl-aspartic acid β-tert-butyl ester [Fmoc-Asp(Ot-Bu)-OH] (864 mg, 2.1 mmol, 2.10 equiv) in N,N-dimethylformamide (1.5 ml, 1.0 M). The mixture was then stirred at 23° C. for 5 min. S2 (266 mg, 1.0 mmol, 1 equiv) was then added as a solid. The reaction mixture was stirred at 23° C. After 16 hours, ethyl acetate (20 ml) and brine (20 ml) were added. The two layers were separated, and the aqueous layer was extracted with ethyl acetate (2×20 ml). The combined organic layers were washed with brine (30 ml), were dried over with anhydrous sodium sulphate, were filtered, and were concentrated under reduced pressure. The residue was purified by flash column chromatography (Combiflash RF, 40 gram silica gel, gradient 0 to 100% ethyl acetate-hexanes) to afford S3 (625 mg, 90%) as brown oil.

(S)-tert-butyl 3-amino-4-((3-(4-chlorobenzoyl)-4,5-dimethylthiophen-2-yl)amino)-4-oxobutanoate (S4)

Compound S3 (560 mg, 0.85 mmol, 1 equiv) was dissolved into 20% piperidine in DMF solution (4.0 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford free amine S4 (370 mg, 90%) as yellow solid. The enantiomeric purity dropped to 75% (determined with Berger Supercritical Fluid Chromatography (SFC) using AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (280 mg, 0.63 mmol) was dissolved in 10% acetic acid ethanol solution (21 ml, 0.03 M). The reaction mixture was heated to 85° C. After 30 minutes, all solvents were removed under reduced pressure. The residue was purified by flash column chromatography (Combiflash RF system, 12 gram silica gel, gradient 0 to 100% ethyl acetate-hexanes) to afford compound S5 (241 mg, 95%) as white solid. Enantiomeric purity of S5 was 67% (determined with Berger Supercritical Fluid Chromatography (SFC) using an AS-H column).

tert-Butyl 2-(5-(4-chlorophenyl)-6,7-dimethyl-2-thioxo-2,3-dihydro-1H-thieno[2,3-e][1,4]diazepin-3-yl)acetate (S6)

Phosphorus pentasulfide (222 mg, 1.0 mmol, 2.00 equiv), sodium bicarbonate (168 mg, 2.0 mmol, 4.00 equiv) were added sequentially to a solution of S5 (210 mg, 0.5 mmol, 1 equiv) in diglyme (1.25 ml, 0.4M). The reaction mixture was heated to 90° C. After 16 h, brine (20 ml) and ethyl acetate (35 ml) were added. The two layers were separated, and the aqueous layer was extracted with ethyl acetate (3×30 ml). The combined organic layers were washed with brine (2×15 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexanes) to afford S6 (141 mg, 65%) as brown solid with recovered S5 (73 mg, 34%).

tert-Butyl 2-(4-(4-chlorophenyl)-2,3,9-trimethyl-6H-thieno[3,2-f][1,2,4]triazolo[4,3-a][1,4]diazepin-6-yl)acetate [(±)JQ1]

Hydrazine (0.015 ml, 0.45 mmol, 1.25 equiv) was added to a solution of S6 (158 mg, 0.36 mmol, 1 equiv) in THF (2.6 ml, 0.14 M) at 0° C. The reaction mixture was warmed to 23° C., and stirred at 23° C. for 1 h. All solvents were removed under reduced pressure. The resulting hydrazine was used directly without purification. The hydrazine was then dissolved in a 2:3 mixture of trimethyl orthoacetate and toluene (6 ml, 0.06 M). The reaction mixture was heated to 120° C. After 2 h, all the solvents were removed under reduced pressure. The residue was purified by flash column chromatography (Combiflash system, 4 g silica gel, gradient 0 to 100% ethyl acetate-hexanes) to afford JQ1 (140 mg, 85% in 2 steps) as white solid. The reaction conditions further epimerized the stereogenic center, resulting in the racemate, JQ1 (determined with Berger Supercritical Fluid Chromatography (SFC) with an AS-H column).

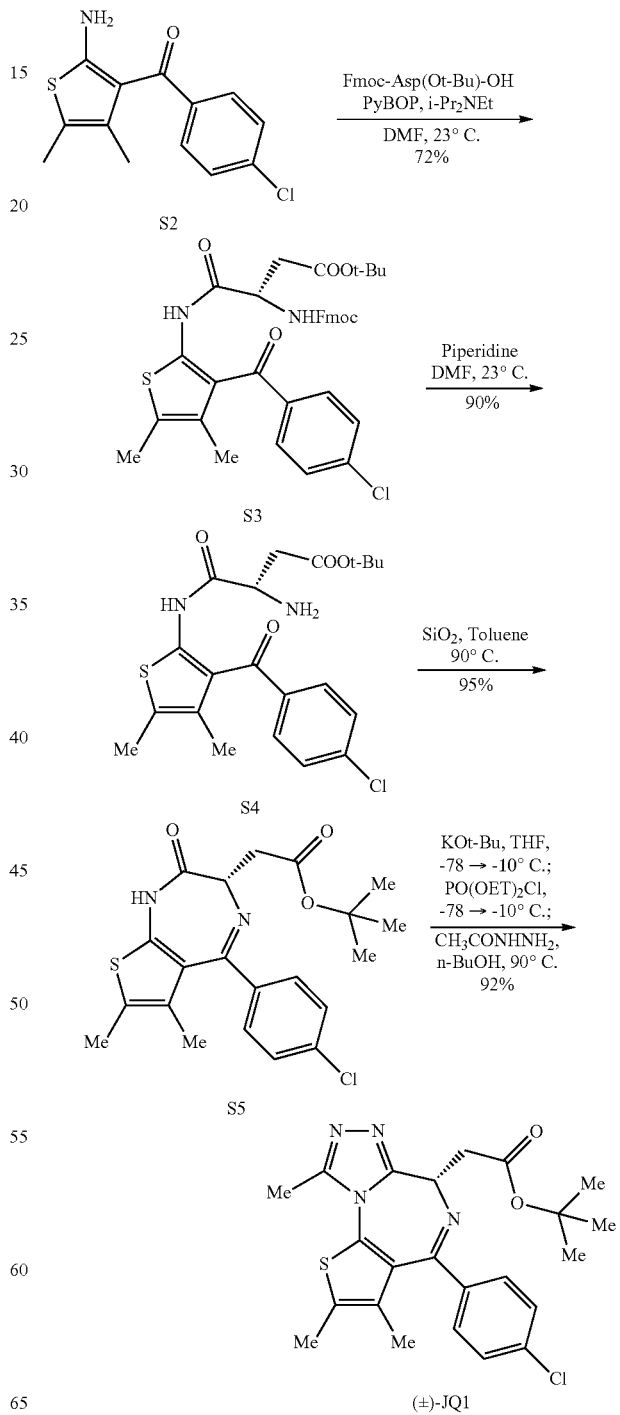

Scheme S2. Sythesis of enantiomerically enriched (±)-JQ1.

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(Benzotriazol-1-yloxyl)tripyrrolidinophosphonium (PyBOP) (494 mg, 0.95 mmol, 0.95 equiv), N,N-diisopropylethylamine (0.50 ml, 2.8 mmol, 2.75 equiv) were added sequentially to a solution of 9-fluorenylmethoxycarbonyl-aspartic acid β-tert-butyl ester [Fmoc-Asp(Ot-Bu)-OH] (411 mg, 1.00 mmol, 1.0 equiv) in N,N-dimethylformamide (1.0 ml, 1.0 M). The mixture was then stirred at 23° C. for 5 min. S2 (266 mg, 1.0 mmol, 1 equiv) was then added as solid. The reaction mixture was stirred at 23° C. After 4 h, ethyl acetate (20 ml) and brine (20 ml) were added. The two layers were separated, and the aqueous layer was extracted with ethyl acetate (2×20 ml). The combined organic layers were washed with brine, were dried over with anhydrous sodium sulphate, were filtered, and were concentrated under reduced pressure. The residue was purified by flash column chromatography (Combiflash RF system, 40 gram silica gel, gradient 0 to 100% ethyl acetate-hexanes) to afford S3 (452 mg, 72%) as brown oil.

(S)-tert-butyl 3-amino-4-((3-(4-chlorobenzoyl)-4,5-dimethylthiophen-2-yl)amino)-4-oxobutanoate (S4)

Compound S3 (310 mg, 0.47 mmol, 1 equiv) was dissolved into 20% piperidine in DMF solution (2.2 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), were dried over anhydrous sodium sulphate, were filtered, and were concentrated under reduced pressure. The residue was purified by flash column chromatography (Combiflash RF system, 24 gram silica gel, gradient 0 to 100% ethyl acetate-hexane) to afford free amine S4 (184 mg, 90%) as yellow solid. The enantiomeric purity was 91% (checked with Berger Supercritical Fluid Chromatography (SFC) using an AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (184 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography (Combiflash RF system, 12 gram silica gel, gradient 0 to 100% ethyl acetate-hexanes) to afford compound S5 (168 mg, 95%) as white solid. Enantiomeric purity of S5 was 90% (determined with Berger Supercritical Fluid Chromatography (SFC) using an AS-H column).

(S)-tert-Butyl 2-(4-(4-chlorophenyl)-2,3,9-trimethyl-6H-thieno[3,2-f][1,2,4]triazolo[4,3-a][1,4]diazepin-6-yl)acetate [(+)JQ1]

Potassium tert-butoxide (1.0 M solution in THF, 0.3 ml, 0.30 mmol, 1.10 equiv) was added to a solution of S5 (114 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 ml, 0.32 mmol, 1.20 equiv) was added to reaction mixture[22]. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 1 h, all solvents were removed under reduce pressure. The residue was purified with flash column chromatography (Combiflash system, 4 g silica gel, gradient 0 to 100% ethyl acetate-hexanes) to afford (+)-JQ1 (114 mg, 92%) as white solid with 90% enantiomeric purity (determined with Berger Supercritical Fluid Chromatography (SFC) using AS-H column, 85% hexanes-methanol, 210 nm, $t_R$ (R-enantiomer)=1.59 min, $t_R$ (S-enantiomer)=3.67 min). The product was further purified by chiral preparative HPLC (Agilent High Pressure Liquid Chromatography using an OD-H column) to provide the S-enantiomer in greater than 99% ee.

$^1$H NMR (600 MHz, CDCl$_3$, 25° C.) δ 7.39 (d, J=8.4 Hz, 2H), 7.31 (d, J=8.4 Hz, 2H), 4.54 (t, J=6.6 MHz, 1H), 3.54-3.52 (m, 2H), 2.66 (s, 3H), 2.39 (s, 3H), 1.67 (s, 3H), 1.48 (s, 9H).

$^{13}$C NMR (150 MHz, CDCl$_3$, 25° C.) δ 171.0, 163.8, 155.7, 150.0, 136.9, 131.1, 130.9, 130.6, 130.3, 128.9, 81.2, 54.1, 38.1, 28.4, 14.6, 13.5, 12.1.

HRMS (ESI) calc'd for $C_{21}H_{24}ClN_2O_3S$ [M+H]$^+$: 457.1460. found 457.1451 m/z.

TLC (EtOAc), Rf: 0.32 (UV)

$[\alpha]^{22}_D$=+75 (c 0.5, CHCl$_3$)

(−)-JQ1 was synthesized in a similar manner, employing Fmoc-D-Asp(Ot-Bu)-OH as a starting material, and was further purified by chiral preparative HPLC (Agilent High Pressure Liquid Chromatography using an OD-H column) to afford the R-enantiomer in greater than 99% ee. $[\alpha]^{22}_D$=−72 (c 0.5, CHCl$_3$)

Synthesis of Additional Compounds

Additional compounds of the invention were prepared as illustrated in Scheme S3.

Scheme S3. Synthesis of hydrazine derivatives.

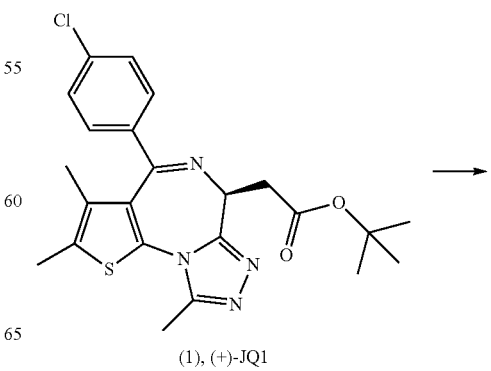

(1), (+)-JQ1

-continued

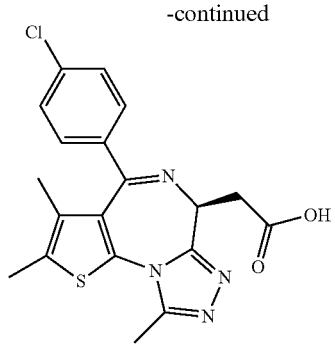

(2)

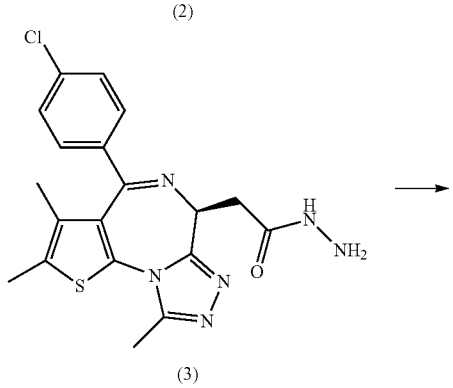

(3)

-continued

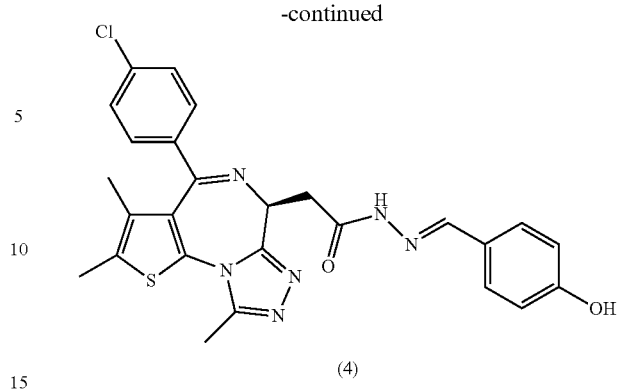

(4)

As shown in Scheme S3, the t-butyl ester of (+)-JQ1 (1) was cleaved to yield the free acid (2), which was coupled with hydrazine to yield the hydrazide (3). Reaction with 4-hydroxybenzaldehyde yielded the hydrazone (4).

Both hydrazide (3) and hydrazone (4) showed activity in at least one biological assay.

A library of compounds was prepared by reaction of the hydrazide (3) with a variety of carbonyl-containing compounds (see Table A, above).

Additional compounds were prepared for use, e.g., as probes for assay development. An exemplary synthesis is shown in Scheme S4, below.

Scheme S4. Synthesis of derivatives useful as probes.

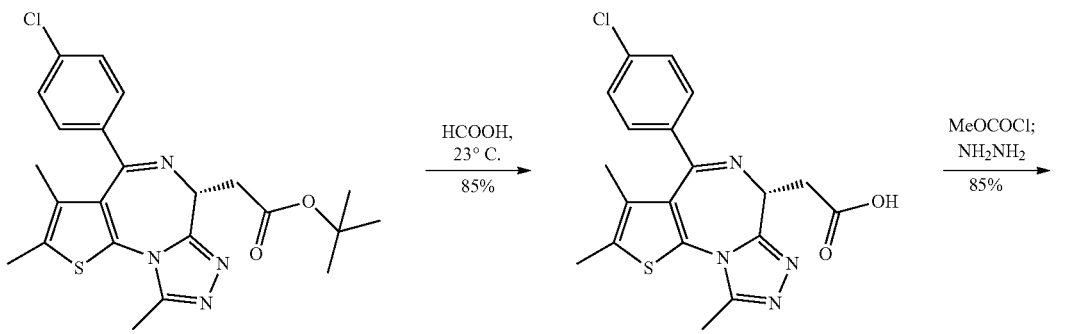

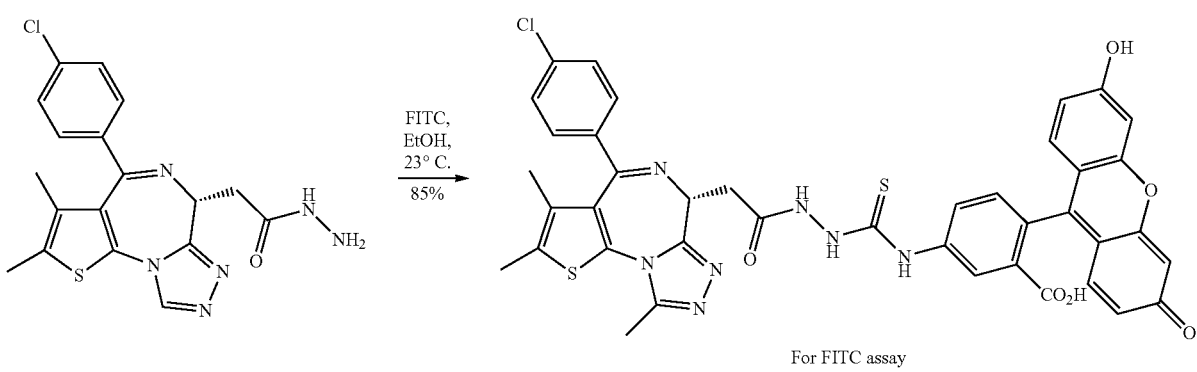

For FITC assay

-continued
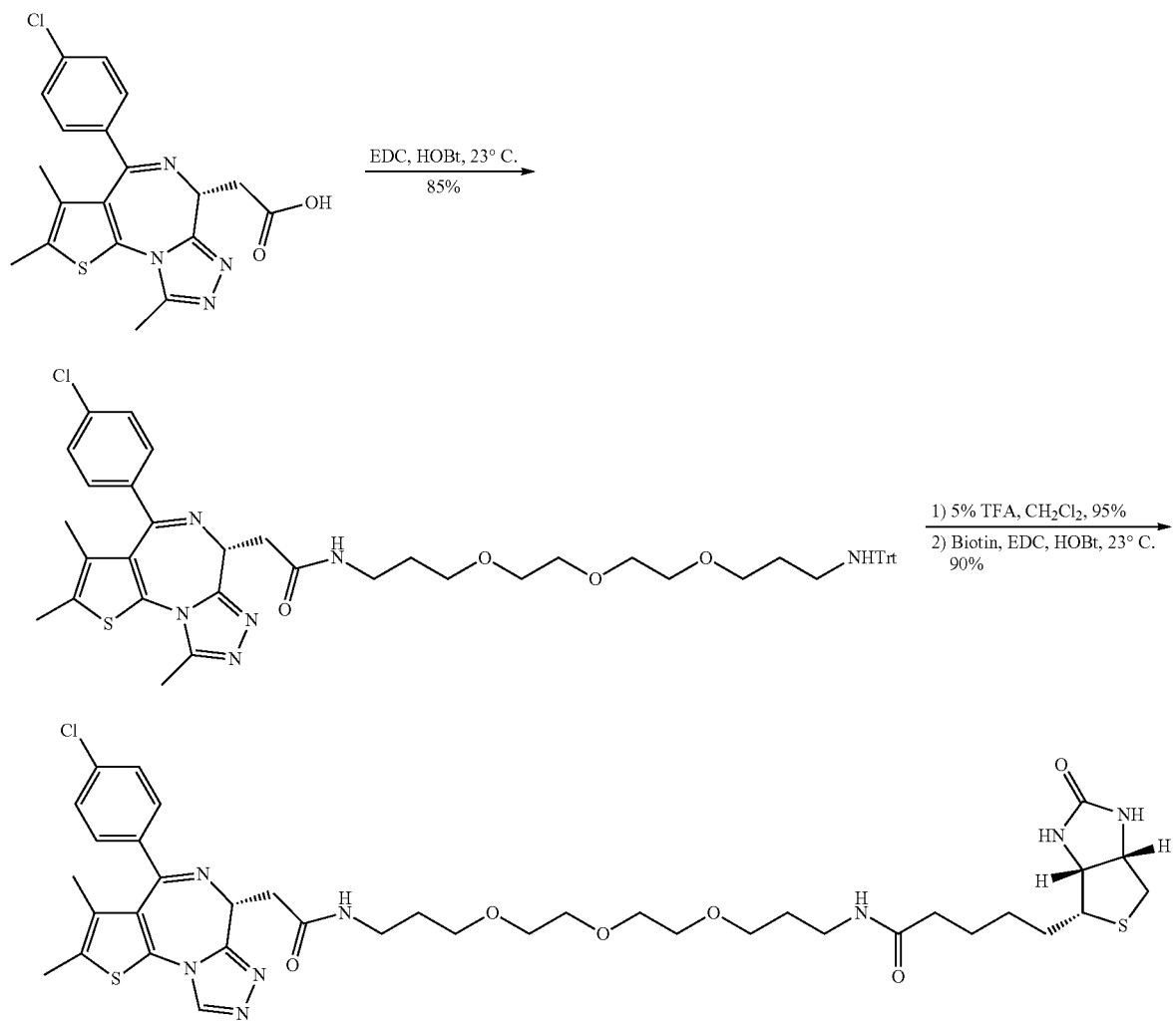
For Alpha assay
Additional compounds were prepared as shown in the table below:
| Compound Name | Structure | MS [M + H]+ m/z (Observed) |
|---|---|---|
| (S)-JQ1 | 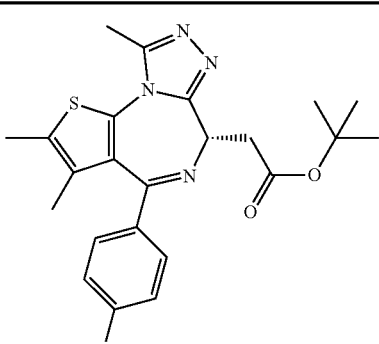 | 457.1 |

-continued
| Compound Name | Structure | MS [M + H]+ m/z (Observed) |
|---|---|---|
| (R)-JQ1 | 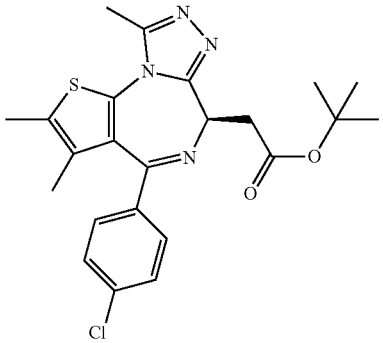 [SMILES: Cc1sc2c(c1C)C(c1ccc(Cl)cc1)=N[C@H](CC(=O)OC(C)(C)C)c1nnc(C)n1-2] | 457.1 |
| JQ3 | 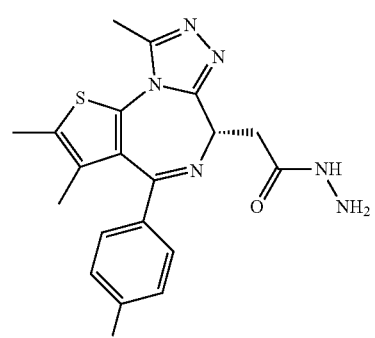 | 415.1 |
| JQ4 | 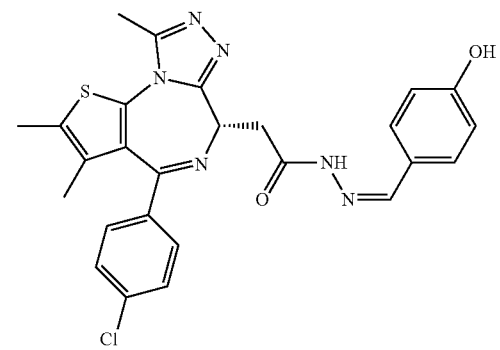 [SMILES: Cc1sc2c(c1C)C(c1ccc(Cl)cc1)=N[C@@H](CC(=O)N/N=C\c1ccc(O)cc1)c1nnc(C)n1-2] | 519.1 |
| JQ6 | 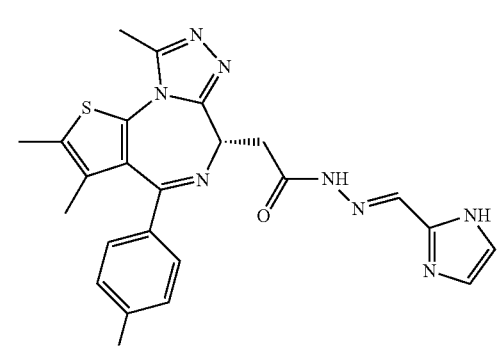 | 493.1 |

-continued

| Compound Name | Structure | MS [M + H]+ m/z (Observed) |
|---|---|---|
| JQ7 | 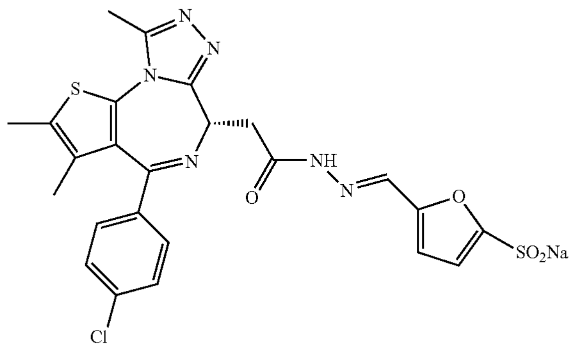 | 579.0 |
| JQ8 | 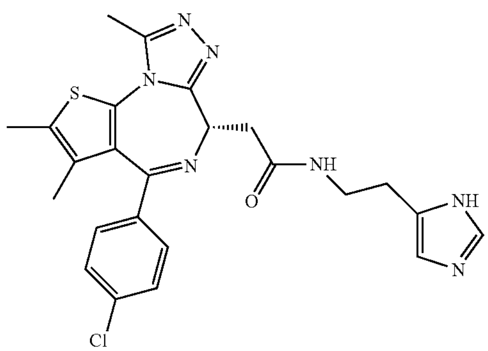 [SMILES: Cc1sc2c(c1C)C(c1ccc(Cl)cc1)=N[C@@H](CC(=O)NCCc1cnc[nH]1)c1nnc(C)n1-2] | 494.1 |
| JQ10 | 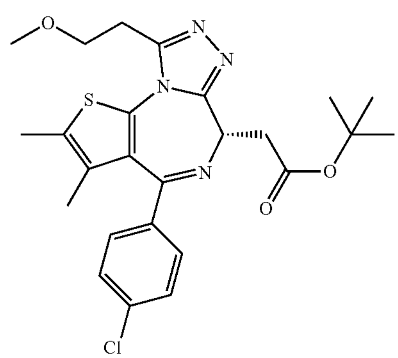 [SMILES: COCCc1nnc2n1-c1sc(C)c(C)c1C(c1ccc(Cl)cc1)=N[C@H]2CC(=O)OC(C)(C)C] | 501.1 |
| JQ11 | 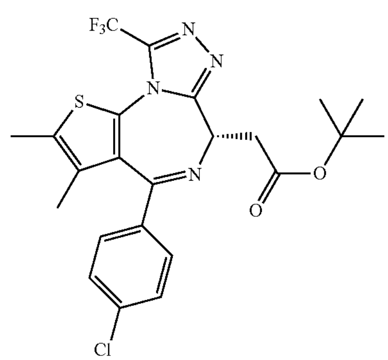 [SMILES: Cc1sc2c(c1C)C(c1ccc(Cl)cc1)=N[C@@H](CC(=O)OC(C)(C)C)c1nnc(C(F)(F)F)n1-2] | 511.1 |

-continued

| Compound Name | Structure | MS [M + H]+ m/z (Observed) |
|---|---|---|
| JQ1-FITC | 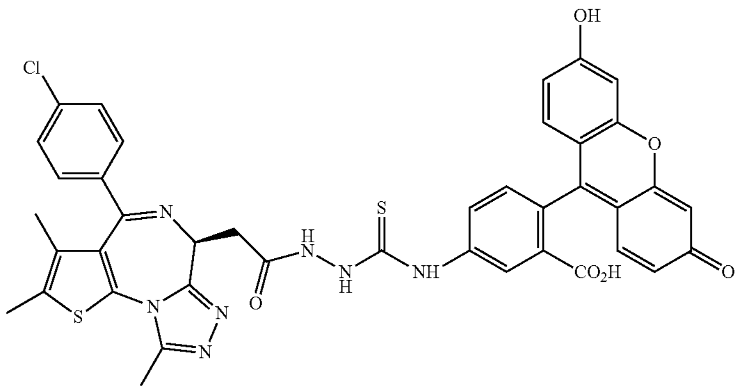 [SMILES: Cc1sc2c(c1C)C(c1ccc(Cl)cc1)=N[C@@H](CC(=O)NNC(=S)Nc1ccc(-c3c4ccc(=O)cc-4oc4cc(O)ccc34)c(C(=O)O)c1)c1nnc(C)n1-2] | 804.1 |
| JQ1-Biotin | 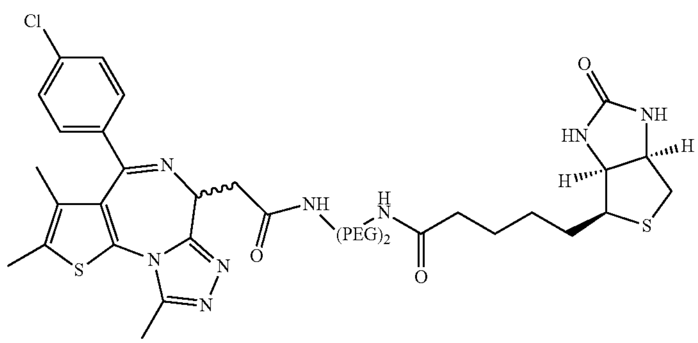 | 829.3 |
| JQ13 | 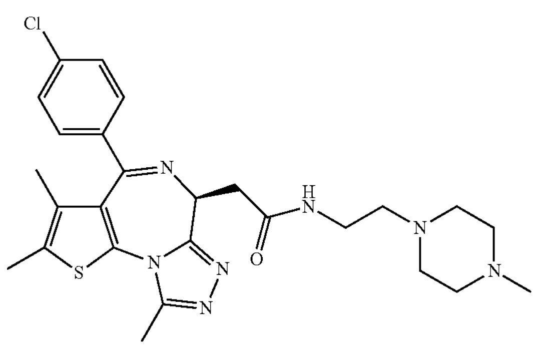 | 526.2 |
| KS1 | 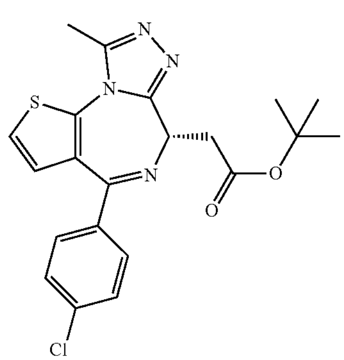 [SMILES: Cc1nnc2n1-c1sccc1C(c1ccc(Cl)cc1)=N[C@H]2CC(=O)OC(C)(C)C] | 429.1 |

| Compound Name | Structure | MS [M + H]+ m/z (Observed) |
|---|---|---|
| JQ18 | 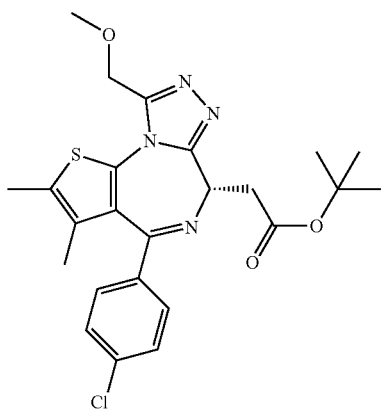 [SMILES: COCc1nnc2n1-c1sc(C)c(C)c1C(c1ccc(Cl)cc1)=N[C@H]2CC(=O)OC(C)(C)C]  Chemical Formula: C$_{24}$H$_{27}$ClN$_4$O$_3$S  Exact Mass: 486.14924  Molecular Weight: 487.01418 | 487.1 |
| JQ19 | 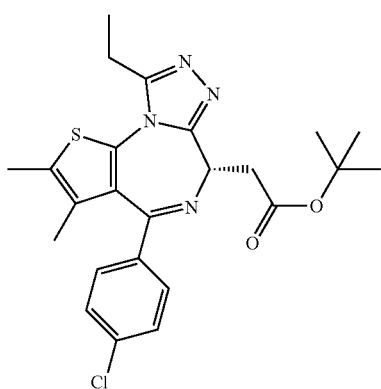 [SMILES: CCc1nnc2n1-c1sc(C)c(C)c1C(c1ccc(Cl)cc1)=N[C@H]2CC(=O)OC(C)(C)C]  Chemical Formula: C$_{24}$H$_{27}$ClN$_4$O$_2$S  Exact Mass: 470.15432  Molecular Weight: 471.01478 | 471.1 |
| JQ20 | 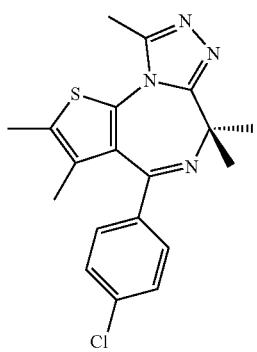  Chemical Formula: C$_{19}$H$_{19}$ClN$_4$S  Exact Mass: 370.10190  Molecular Weight: 370.89896  JQI-II-023 | 370.1 |

| Compound Name | Structure | MS [M + H]+ m/z (Observed) |
|---|---|---|
| JQ21 | JQI-II-024<br>Chemical Formula: $C_{22}H_{23}ClN_4O_2S$<br>Exact Mass: 442.12302<br>Molecular Weight: 442.96162 | 443.1 |
| JQ24A | Chemical Formula: $C_{24}H_{26}ClN_3O_2S$<br>Exact Mass: 455.1434<br>Molecular Weight: 456.0001 | 456.1 |
| JQ24B | Chemical Formula: $C_{24}H_{26}ClN_3O_2S$<br>Exact Mass: 455.1434<br>Molecular Weight: 456.0001 | 456.1 |

| Compound Name | Structure | MS [M + H]+ m/z (Observed) |
|---|---|---|
| JQ25 | Chemical Formula: $C_{26}H_{24}ClN_5O_2S$<br>Exact Mass: 505.1339<br>Molecular Weight: 506.0191 | 506.1 |
| JQB | Chemical Formula: $C_{23}H_{24}N_4O_2$<br>Exact Mass: 388.1899<br>Molecular Weight: 388.4623 | 389.2 |
| JQ30 | Chemical Formula: $C_{23}H_{26}ClN_5OS$<br>Exact Mass: 455.1547<br>Molecular Weight: 456.0034 | 456.2 |
| JQ31 | Chemical Formula: $C_{23}H_{26}ClN_5OS$<br>Exact Mass: 455.1547<br>Molecular Weight: 456.0034 | 456.2 |

| Compound Name | Structure | MS [M + H]+ m/z (Observed) |
|---|---|---|
| JQ32 | 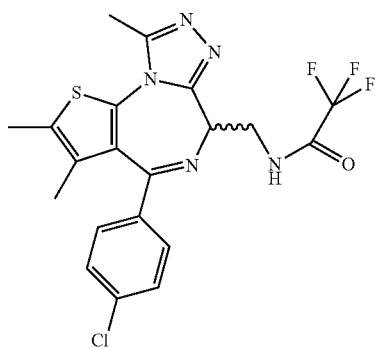 [SMILES: Cc1sc2c(c1C)C(c1ccc(Cl)cc1)=NC(CNC(=O)C(F)(F)F)c1nnc(C)n1-2]<br>Chemical Formula: C$_{20}$H$_{17}$ClF$_3$N$_5$OS<br>Exact Mass: 467.0794<br>Molecular Weight: 467.8951 | 468.1 |
| JQ33 | 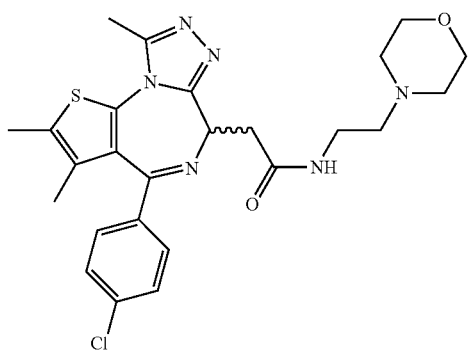 [SMILES: Cc1sc2c(c1C)C(c1ccc(Cl)cc1)=NC(CC(=O)NCCN1CCOCC1)c1nnc(C)n1-2]<br>Chemical Formula: C$_{25}$H$_{29}$ClN$_6$O$_2$S<br>Exact Mass: 512.1761<br>Molecular Weight: 513.0548 | 512.2 |
| JQ34 | 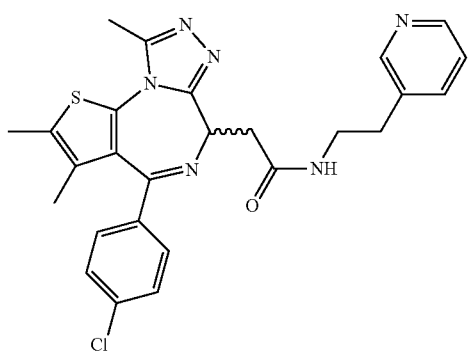 [SMILES: Cc1sc2c(c1C)C(c1ccc(Cl)cc1)=NC(CC(=O)NCCc1cccnc1)c1nnc(C)n1-2]<br>Chemical Formula: C$_{26}$H$_{25}$ClN$_6$OS<br>Exact Mass: 504.1499<br>Molecular Weight: 505.0343 | 505.1 |

| Compound Name | Structure | MS [M + H]+ m/z (Observed) |
|---|---|---|
| JQ35 | 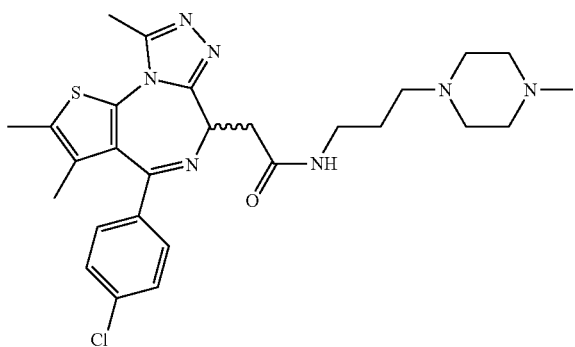<br>Chemical Formula: C_{27}H_{34}ClN_7OS<br>Exact Mass: 539.2234<br>Molecular Weight: 540.1232 | 540.2 |
| JQ36 | 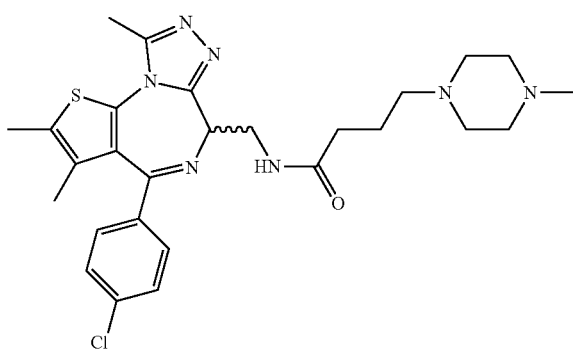<br>Chemical Formula: C_{27}H_{34}ClN_7OS<br>Exact Mass: 539.2234<br>Molecular Weight: 540.1232 | 540.2 |
| JQ37 | 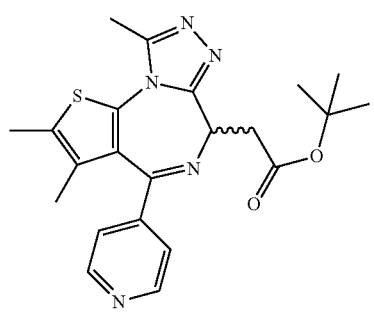 [SMILES: Cc1sc2c(c1C)C(c1ccncc1)=NC(CC(=O)OC(C)(C)C)c1nnc(C)n1-2]<br>Chemical Formula: C_{22}H_{25}N_5O_2S<br>Exact Mass: 423.1729<br>Molecular Weight: 423.5312 | 424.2 |

| Compound Name | Structure | MS [M + H]+ m/z (Observed) |
|---|---|---|
| JQ38 | 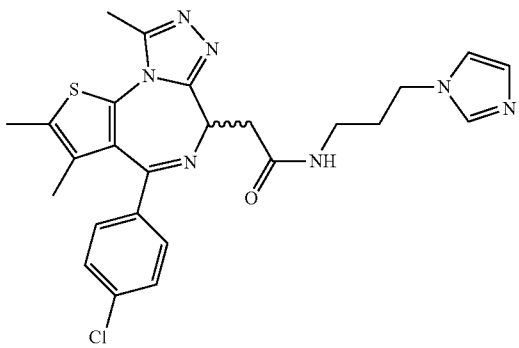 [SMILES: Cc1sc2c(c1C)C(c1ccc(Cl)cc1)=NC(CC(=O)NCCCn1ccnc1)c1nnc(C)n1-2]<br>Chemical Formula: C$_{25}$H$_{26}$ClN$_7$OS<br>Exact Mass: 507.1608<br>Molecular Weight: 508.0382 | 508.2 |
| JQ39 | 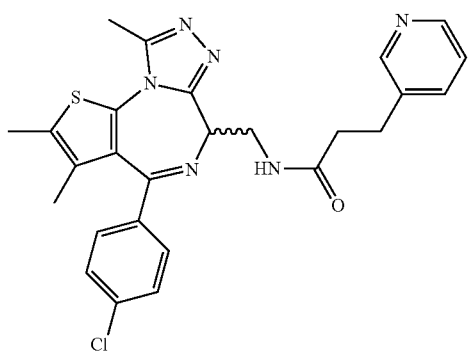 [SMILES: Cc1sc2c(c1C)C(c1ccc(Cl)cc1)=NC(CNC(=O)CCc1cccnc1)c1nnc(C)n1-2]<br>Chemical Formula: C$_{26}$H$_{25}$ClN$_6$OS<br>Exact Mass: 504.1499<br>Molecular Weight: 505.0343 | 505.1 |
| JQ40 | 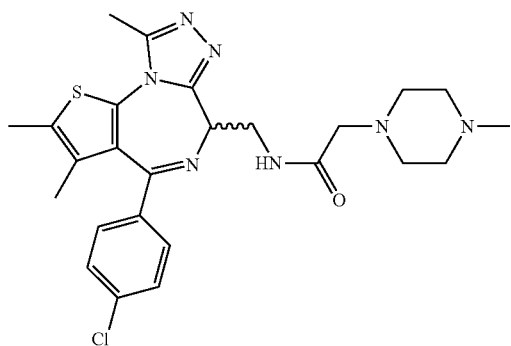<br>Chemical Formula: C$_{25}$H$_{30}$ClN$_7$OS<br>Exact Mass: 511.1921<br>Molecular Weight: 512.0700 | 512.2 |

| Compound Name | Structure | MS [M + H]+ m/z (Observed) |
|---|---|---|
| JQ41 | 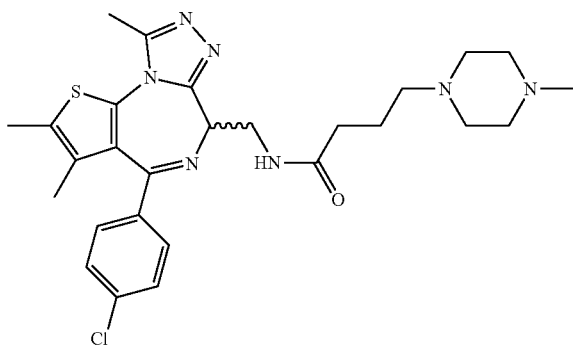<br>Chemical Formula: C$_{27}$H$_{34}$ClN$_7$OS<br>Exact Mass: 539.2234<br>Molecular Weight: 540.1232 | 540.2 |
| JQ42 | 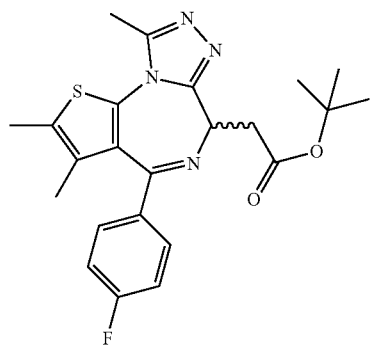 [SMILES: Cc1sc2c(c1C)C(c1ccc(F)cc1)=NC(CC(=O)OC(C)(C)C)c1nnc(C)n1-2]<br>Chemical Formula: C$_{23}$H$_{25}$FN$_4$O$_2$S<br>Exact Mass: 440.1682<br>Molecular Weight: 440.5336 | 441.2 |
| JQ43 | 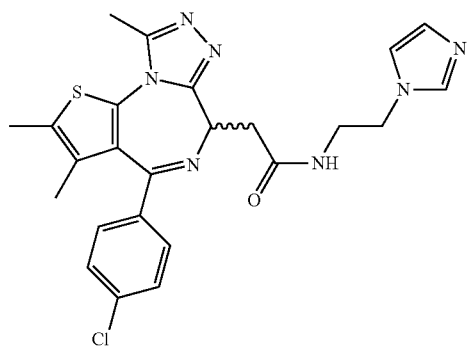 [SMILES: Cc1sc2c(c1C)C(c1ccc(Cl)cc1)=NC(CC(=O)NCCn1ccnc1)c1nnc(C)n1-2]<br>Chemical Formula: C$_{24}$H$_{24}$ClN$_7$OS<br>Exact Mass: 493.1452<br>Molecular Weight: 494.0117 | 494.1 |

| Compound Name | Structure | MS [M + H]+ m/z (Observed) |
|---|---|---|
| JQ44 | 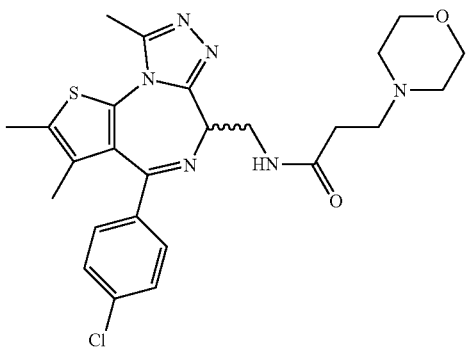 [SMILES: Cc1sc2c(c1C)C(c1ccc(Cl)cc1)=NC(CNC(=O)CCN1CCOCC1)c1nnc(C)n1-2]<br>Chemical Formula: C$_{25}$H$_{29}$ClN$_6$O$_2$S<br>Exact Mass: 512.1761<br>Molecular Weight: 513.0548 | 513.2 |
| JQ45 | 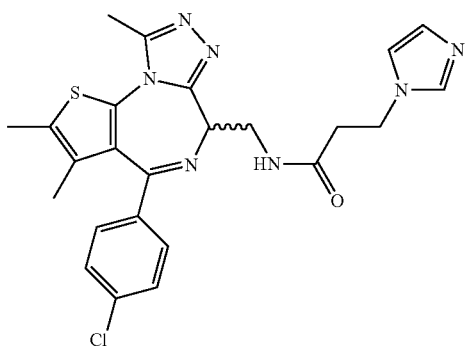 [SMILES: Cc1sc2c(c1C)C(c1ccc(Cl)cc1)=NC(CNC(=O)CCn1ccnc1)c1nnc(C)n1-2]<br>Chemical Formula: C$_{24}$H$_{24}$ClN$_7$OS<br>Exact Mass: 493.1452<br>Molecular Weight: 494.0117 | 494.1 |
| JQ46 | 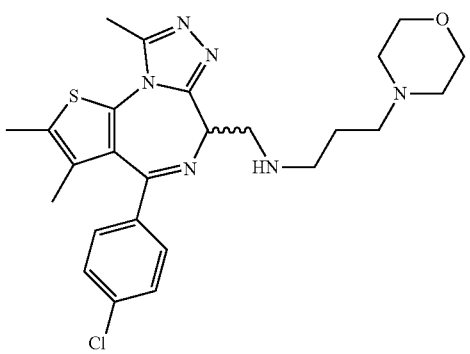 [SMILES: Cc1sc2c(c1C)C(c1ccc(Cl)cc1)=NC(CNCCCN1CCOCC1)c1nnc(C)n1-2]<br>Chemical Formula: C$_{25}$H$_{31}$ClN$_6$OS<br>Exact Mass: 498.1969<br>Molecular Weight: 499.0712 | 499.2 |

-continued

| Compound Name | Structure | MS [M + H]+ m/z (Observed) |
|---|---|---|
| JQ47 | Chemical Formula: C₃₂H₄₄ClN₇O₂S<br>Exact Mass: 625.2966<br>Molecular Weight: 626.2555 | 626.3 |
| JQ48 | Exact Mass: 470.1543<br>Molecular Weight: 471.0148 | 471.2 |
| JQ49 | Exact Mass: 428.1074<br>Molecular Weight: 428.9350 | 429.1 |
| JQ50 | Exact Mass: 539.2234<br>Molecular Weight: 540.1232 | 540.2 |

| Compound Name | Structure | MS [M + H]+ m/z (Observed) |
|---|---|---|
| JQ51 | 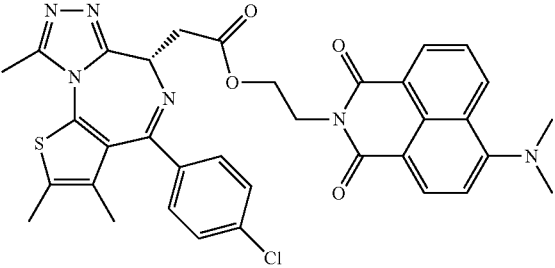<br>JQI-II-114<br>Exact Mass: 666.1816<br>Molecular Weight: 667.1764 | 667.2 |
| JQ52 | 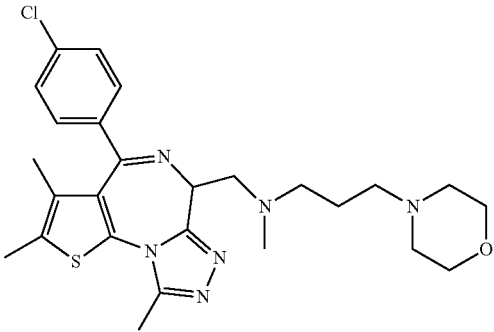 [SMILES: Cc1sc2c(c1C)C(c1ccc(Cl)cc1)=NC(CN(C)CCCN1CCOCC1)c1nnc(C)n1-2]<br>Exact Mass: 512.2125<br>Molecular Weight: 513.0978 | 513.2 |
| JQ53 | 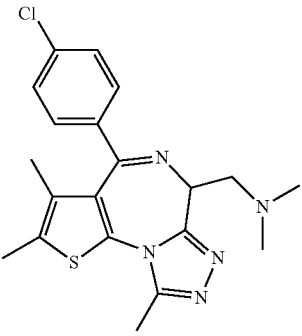<br>Exact Mass: 399.1284<br>Molecular Weight: 399.9402 | 400.1 |

Spectral data for each compound were consistent with the assigned structure.

II. Biological Activity and Methods of Treatment

Figure 1B:
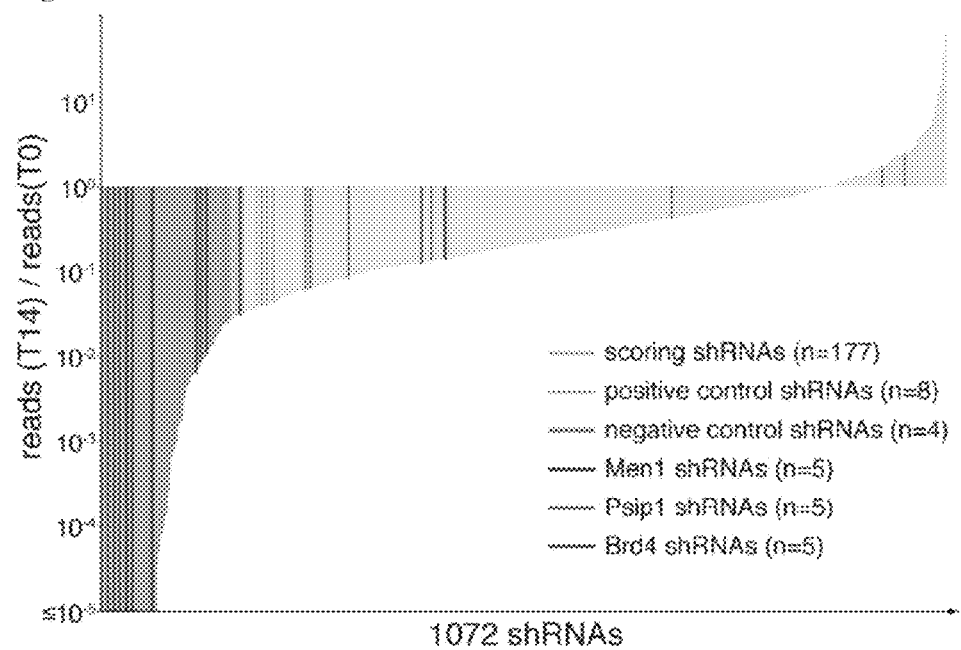
Figure 3A:
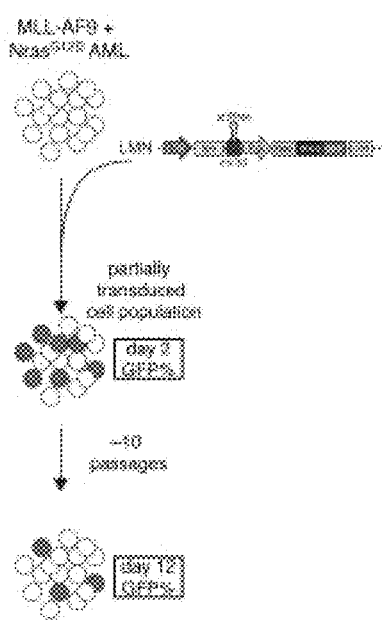
FIGS. 3A and 3B validate the screening strategy.
Figure 3B:
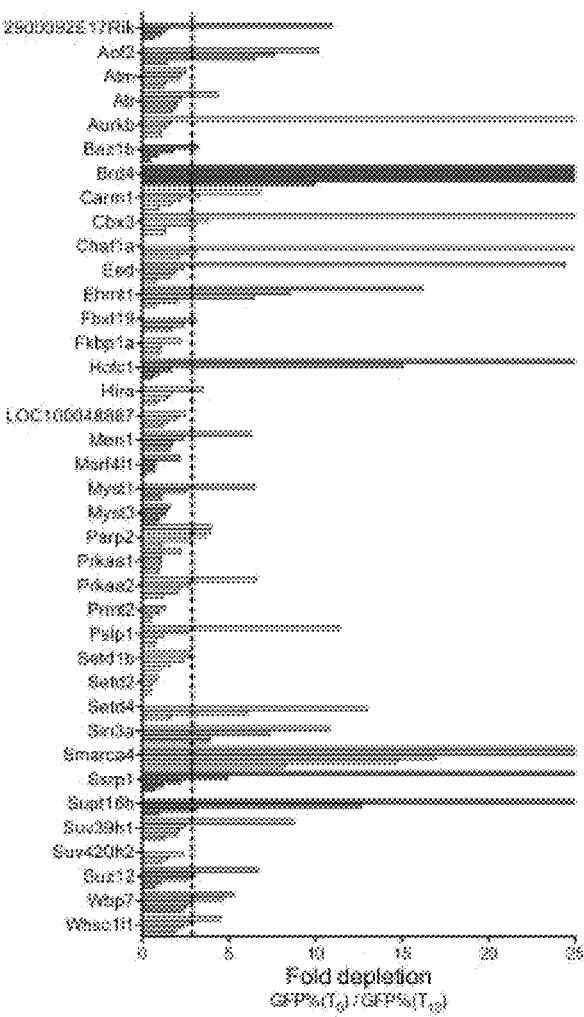

Example 1: Brd4 is Critically and Specifically Required for Proliferation of Acute Myeloid Leukemia Cells To systematically probe epigenetic pathways required for Acute Myeloid Leukemia (AML) maintenance, a shRNA screen was undertaken. For this, a custom shRNA library which targeted the 243 known chromatin regulators was built. This library included most 'writers', 'readers', and 'erasers' of epigenetic marks (FIG. 1A). This library of 1,095 shRNAs (three to six per gene) was constructed in TRMPV, a vector optimized for negative-selection. RNAi screening. In a primary screen, the library was transduced as one pool into an established Tet-On competent AML mouse model-cell line that included a MLL-AF9 and Nras$^{G12D}$ fusion gene (Zuber et al., Nat Biotechnol 2011; 29:79-83). Following drug selection, shRNA expression was induced by addition of doxycycline (dox). Changes in library representation after fourteen days of culture were monitored using deep-sequencing of shRNA guide strands amplified from genomic DNA (FIGS. 1B and 2A-2D). In each of two independent replicates, 177 shRNAs exhibited greater than twenty-fold depletion, which was used as the scoring criterion. Positive scoring was achieved for all eight positive control shRNAs that target essential genes (Rpa1, Rpa3, Pcna, Polr2b) as well as several shRNAs that target two known MLL-AF9 cofactors (Men1 and Psip1). Genes having at least two independent shRNAs that achieved the scoring criterion in the primary screen underwent an extensive one-by-one validation using an independent MLL-AF9/Nras$^{G12D}$ AML line and vector system (FIG. 3A) (for additional details, see PCT Publication No. WO/2010/111712). In both primary screens and validation stages, shRNAs that targeted the transcription factor Brd4 were among the most strongly depleted. Overall, Brd4 was identified as the most responsive gene to the experimental conditions of this shRNA screen (FIGS. 1B and 3B).

Figure 4A:
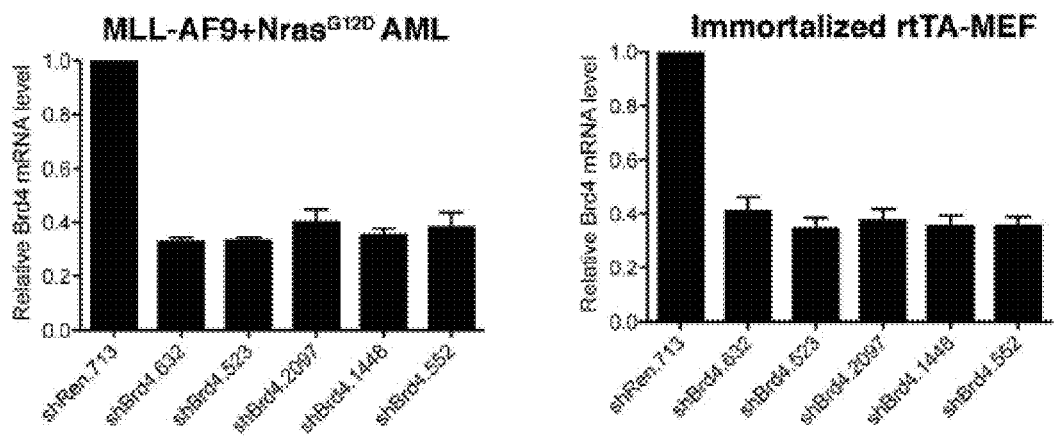
FIGS. 4A-4E show comparisons of Brd4-shRNA effects in leukemia, MEF, and G1E cells. In each of the experiments shown, doxycycline-inducible shRNAs in the TtTMPV vector were transduced into Tet-On competent cells, followed by G418 selection.
Figure 4B:
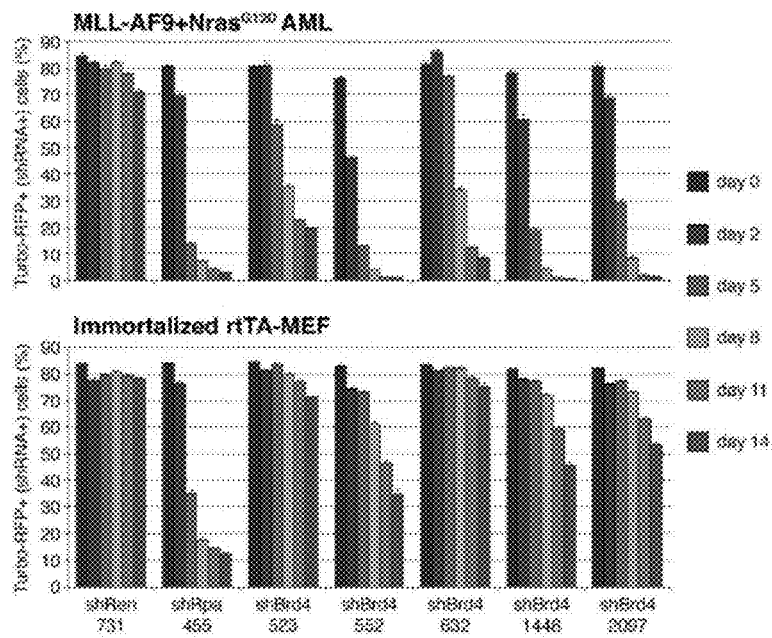
Figure 4C:
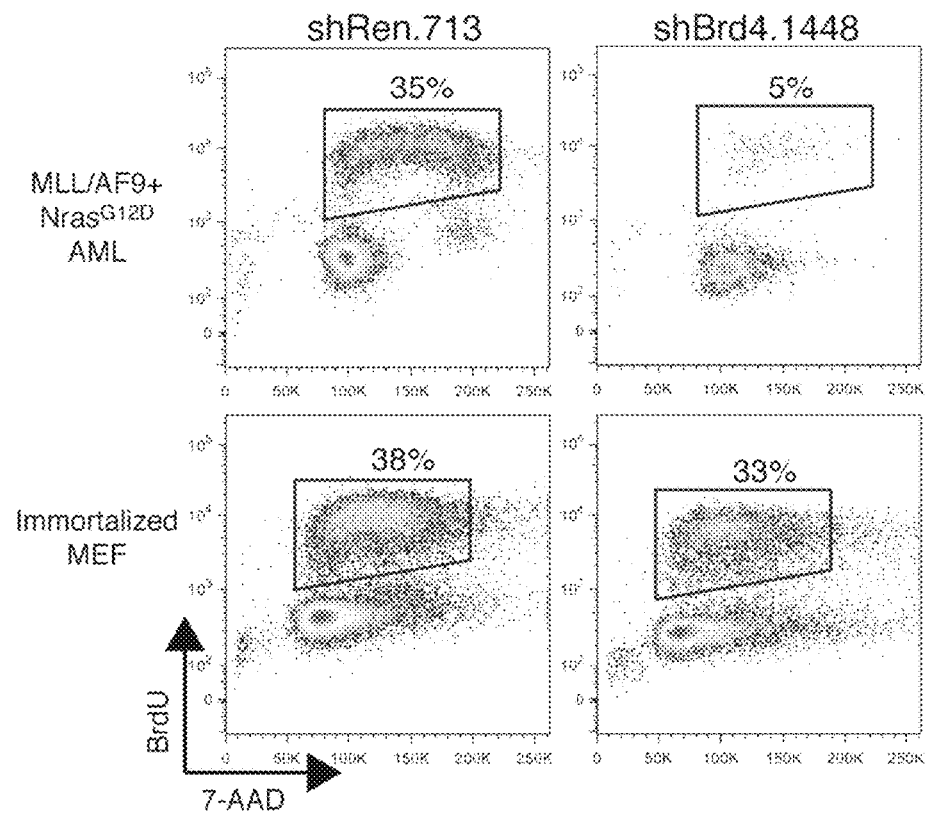
Figure 4D:
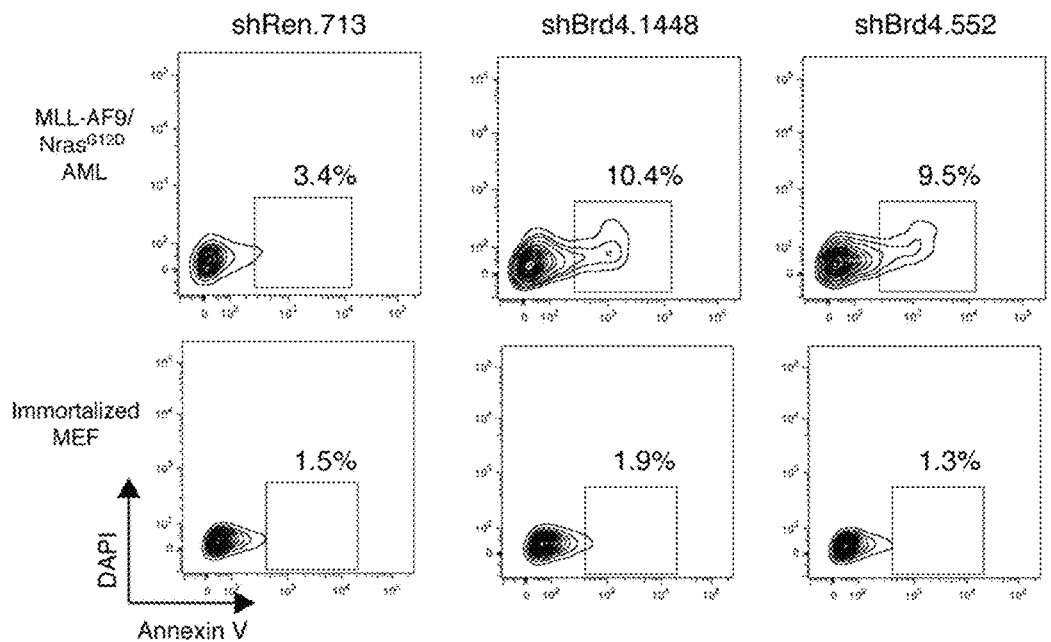
Figure 4E:
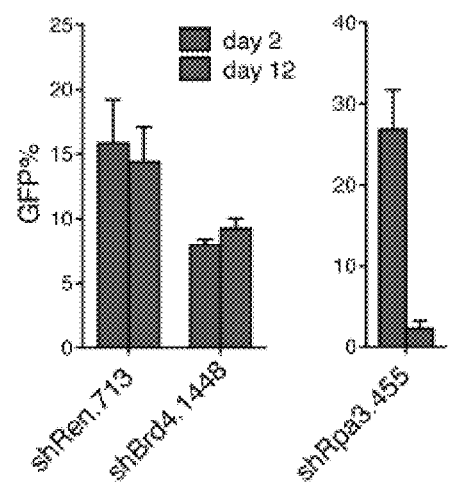
Figure 5A:
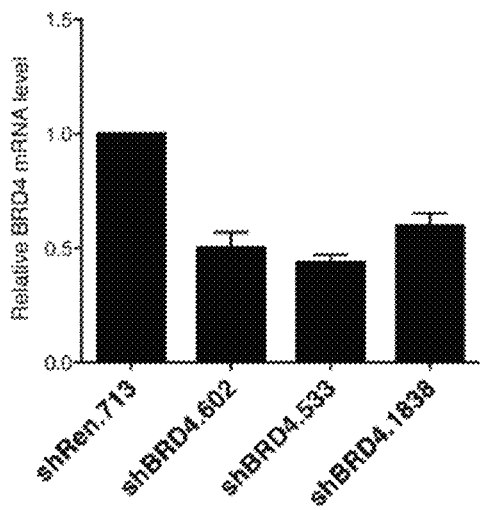
FIGS. 5A-5D show that shRNA knockdown of BRD4 is sufficient to inhibit growth of human AML cell lines THP-1 and MOLM-13. shRNAs targeting human BRD4 were cloned into TRMPV-Neo vector, followed by retroviral transduction of Eco-receptor+/Tet-On competent human AML cell lines THP-1 and MOLM-13. Cells were selected with G418 for one week.
Figure 5B:
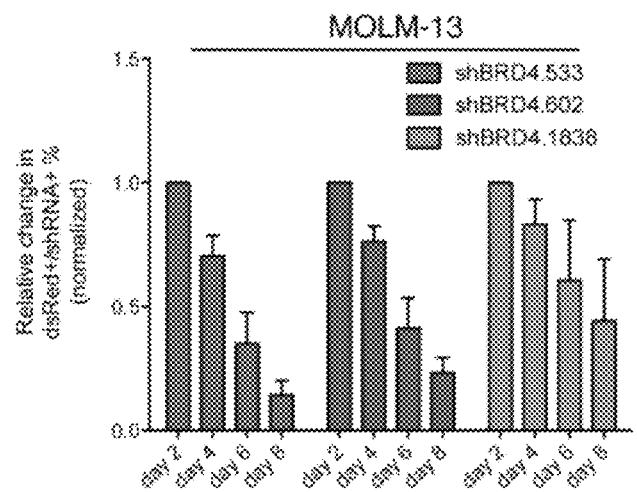
Figure 5C:
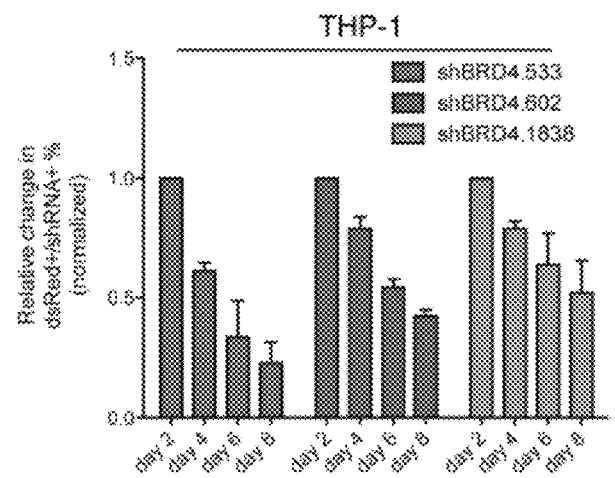
Figure 5D:
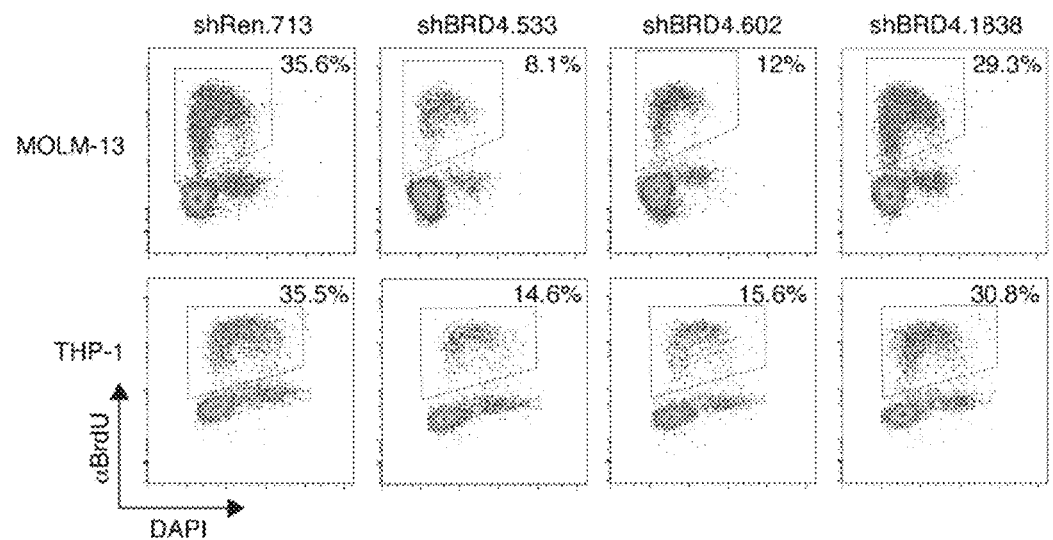
Figure 6A:
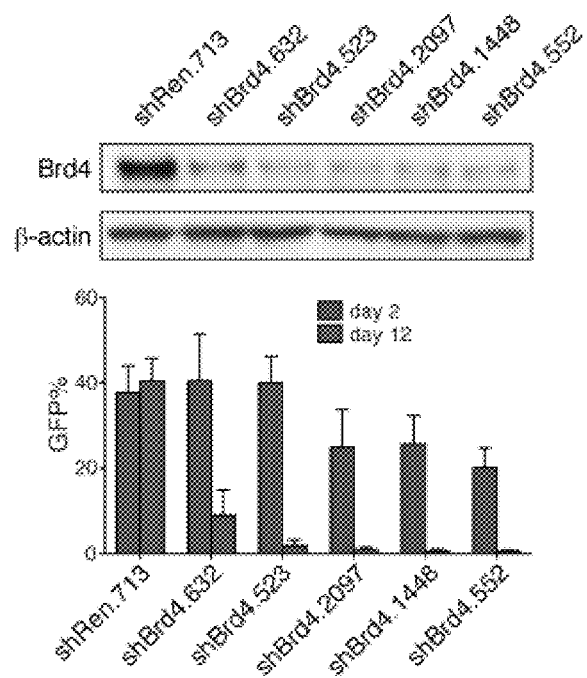
FIGS. 6A-6E show that AML growth is sensitive to Brd4-inhibition.
Figure 6B:
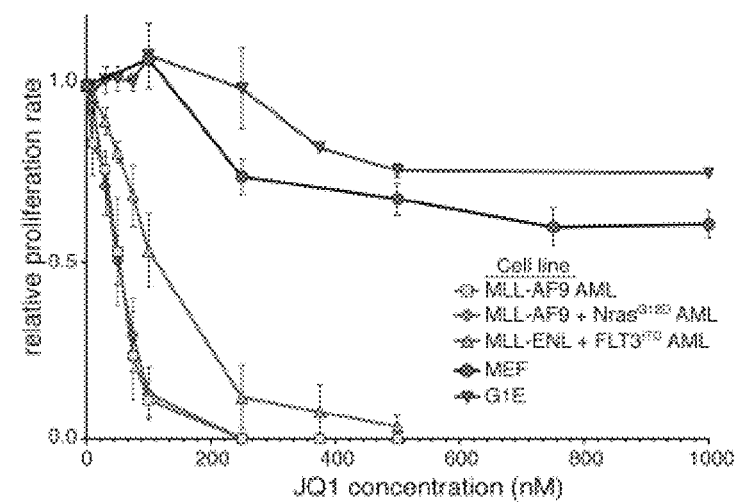

Brd4 is a member of the BET family of bromodomain-containing proteins that bind to acetylated histones to influence transcription. BRD4 is also a proto-oncogene that is mutated, via chromosomal translocation, in a rare form of squamous cell carcinoma. A role for Brd4 in leukemia has not been described. The recent development of small-molecule BET bromodomain inhibitors (Filippakopoulos et al., Nature 2010; 468:1067-73), together with Brd4's identification as the most responsive gene in the above-mentioned shRNA screen, suggested that Brd4 is a novel drug target for AML treatment. Five independent Brd4 shRNAs showed a close correspondence between knockdown efficiency and growth inhibition, indicating on-target effects (FIGS. 6A and 6B). Brd4-suppression led to cell cycle arrest and apoptosis of leukemia cells whereas equivalent knockdown in immortalized murine embryonic fibroblasts (MEF) led to only modest cell cycle inhibition without cytotoxicity (FIGS. 4A-4D). Brd4 knockdown also failed to influence growth of a non-transformed G1E erythroblast cells (FIG. 4E). In addition, shRNAs targeting BRD4 were also sufficient to induce cell-cycle arrest in two MLL-AF9+ human AML lines (FIG. 5A-5D). Together, these results indicated that Brd4 is a critical requirement in MLL-AF9+ AML.

Example 2: Acute Myeloid Leukemia (AML) Cell Proliferation is Specifically Blocked by the Bromodomain Protein Inhibitor JQ1

Figure 6C:
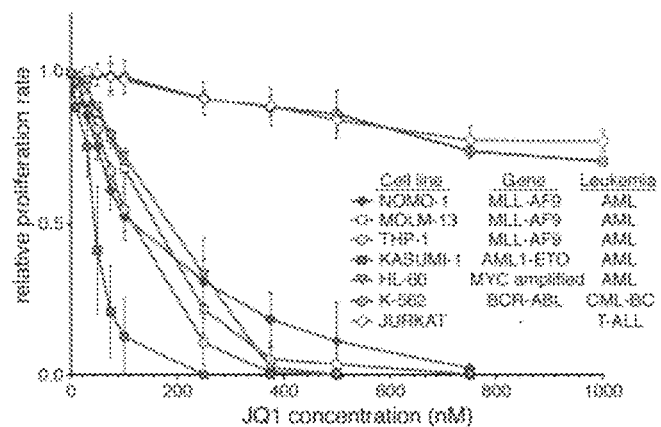
Figure 6D:
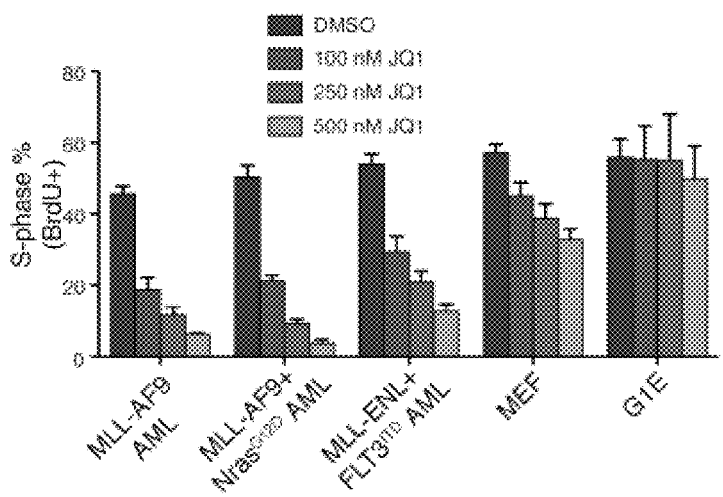
Figure 6E:
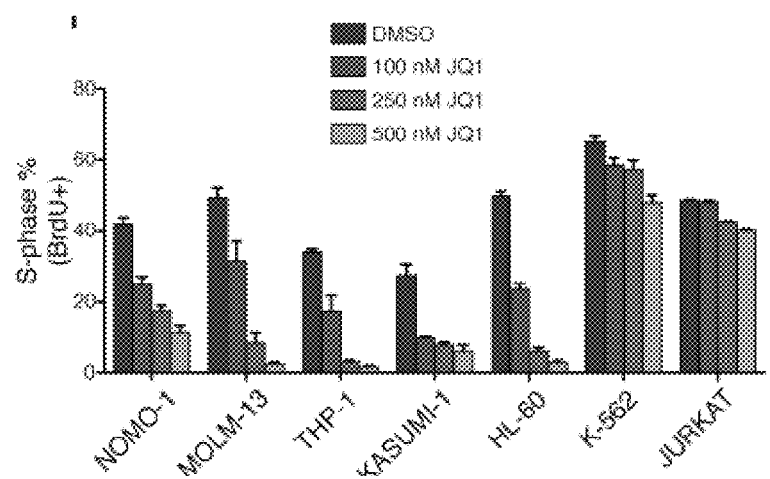
Figure 7A:
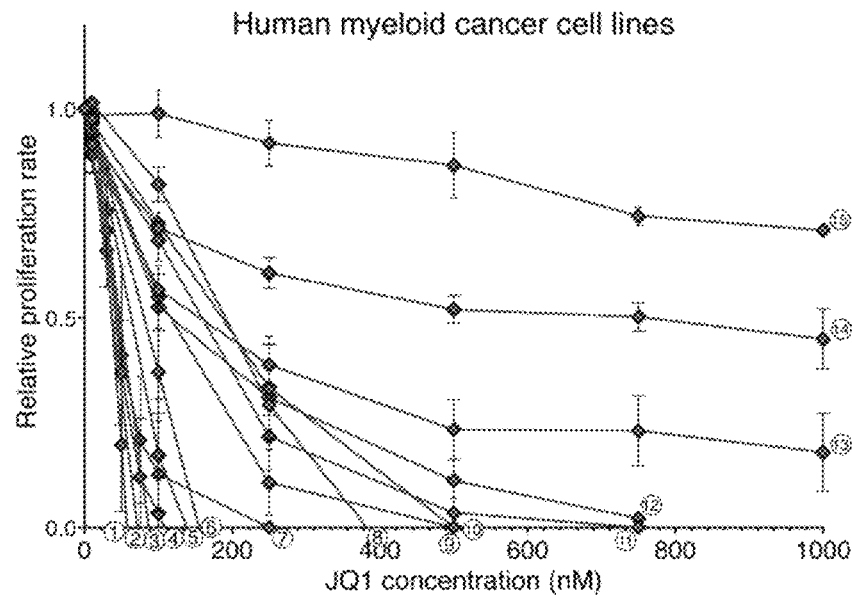
FIGS. 7A and 7B show that JQ1 displays a broad anti-leukemia activity in diverse human leukemia cell lines.
Figure 7B:
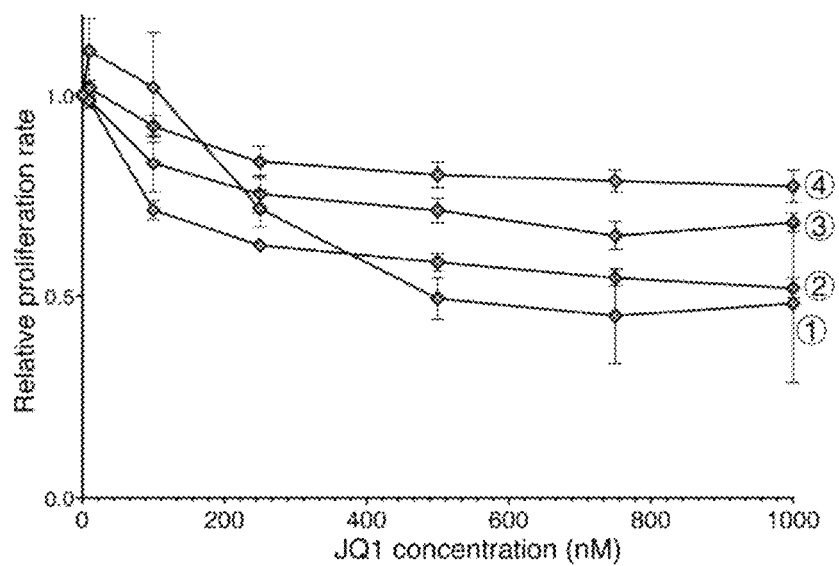
Figure 8C:
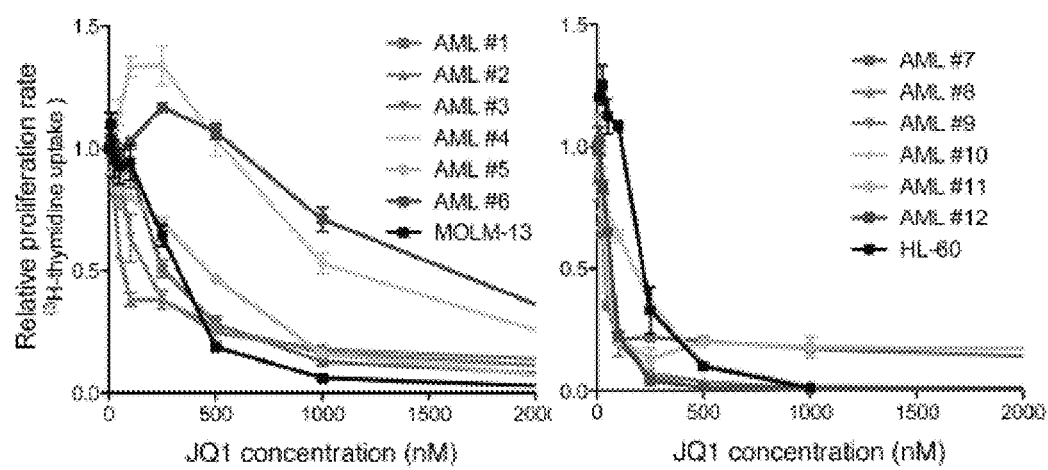
Figure 8D:
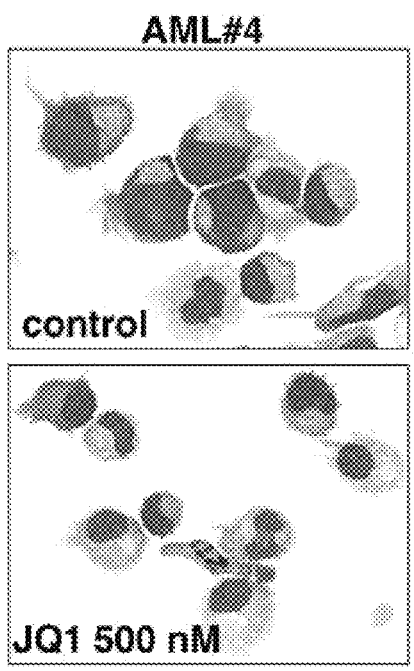
Figure 9C:
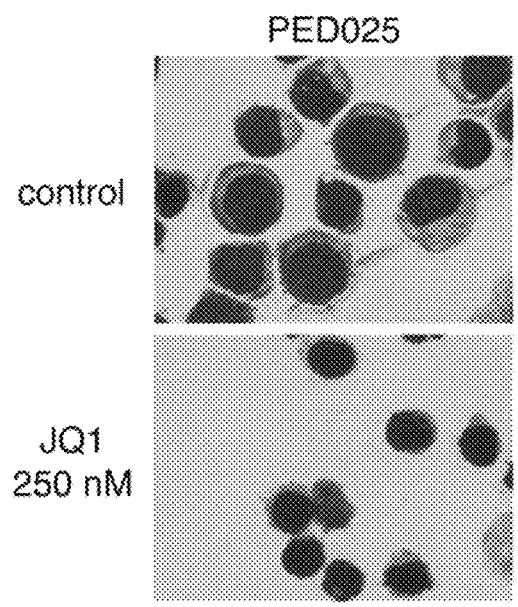
Figure 10A:
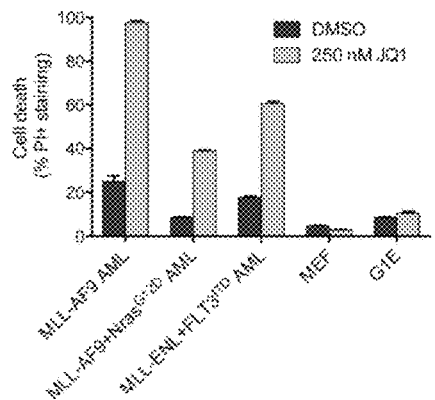
FIGS. 10A-10C show that JQ1 treatment leads to apoptosis of leukemic cells.
Figure 10B:
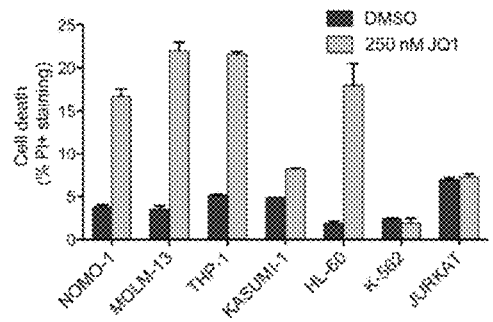
Figure 10C:
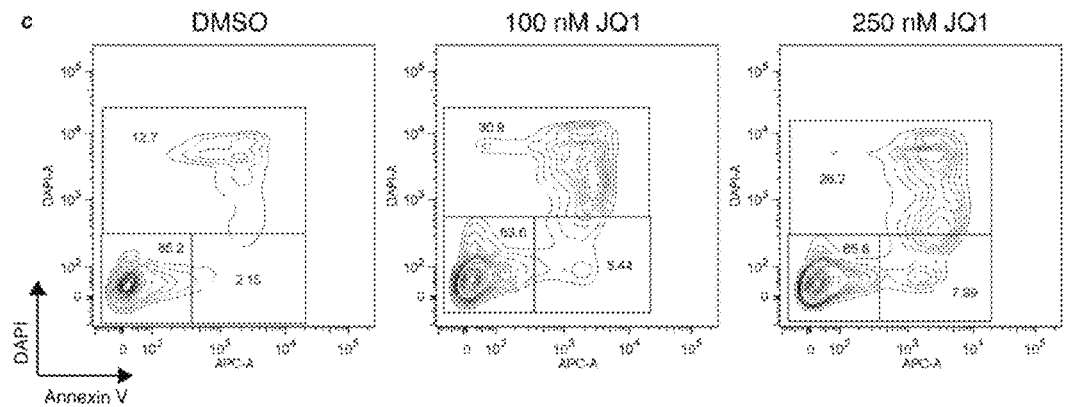
Figure 11A:
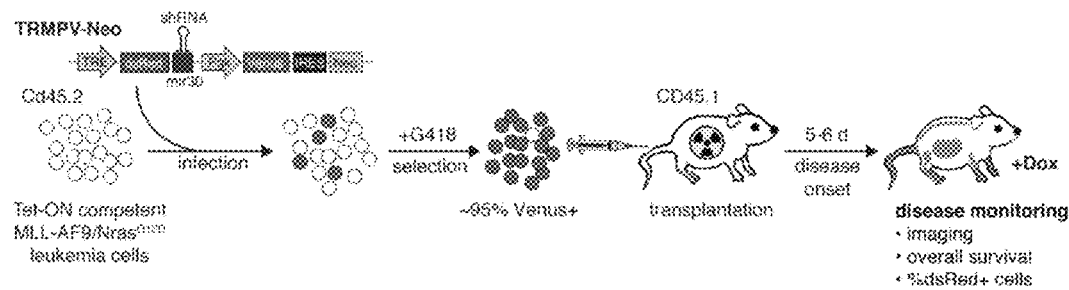
FIGS. 11A-11F show that clonal TRMPV-Neo leukemia lines display robust disease inhibition upon doxycycline induction of shRNA expression. TRMPV-Neo clones were generated by performing limiting serial dilutions.
Figure 11B:
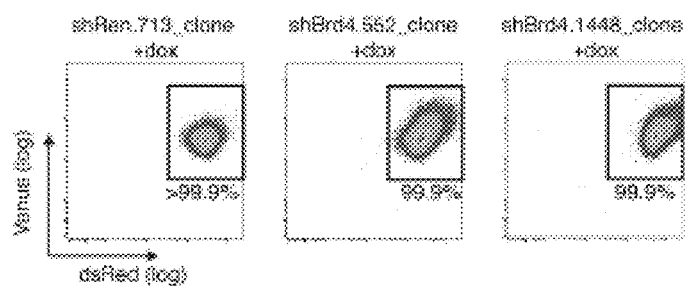
Figure 11C:
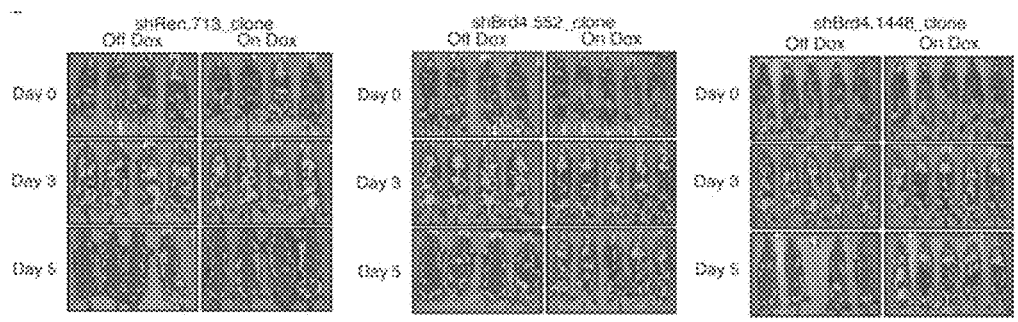
Figure 11D:
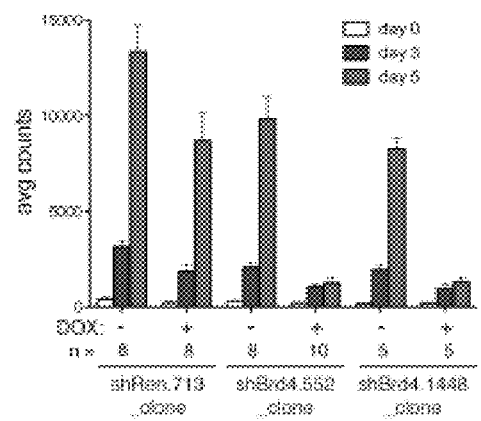
Figure 11E:
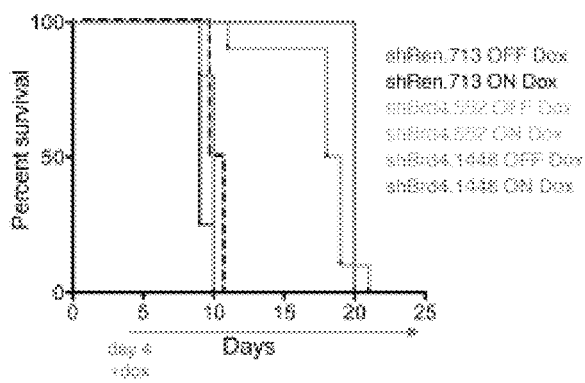
Figure 11F:
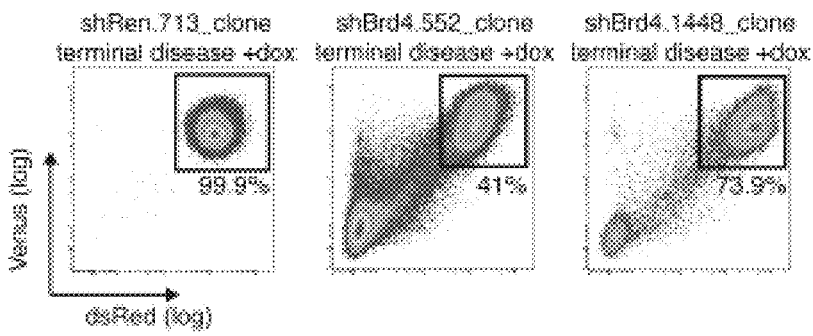

The effects of JQ1, a first-in-class small-molecule inhibitor of BET bromodomains with highest affinity for the first bromodomain of Brd4 (Filippakopoulos et al., 2010), was tested on a variety of leukemia cell types. Proliferation of mouse MLL-fusion leukemia cells was strikingly sensitive to sub-micromolar JQ1 concentrations as compared to fibroblasts and G1E (FIG. 6B), in agreement with the relative impact of Brd4-shRNAs on proliferation of these different cell types. The growth-inhibitory effects of JQ1 in a series of established human leukemia cell lines as in adult and pediatric primary leukemia samples were also examined Broad growth-suppressive activity of JQ1 (IC50<500 nM) was observed in 13/14 AML cell lines, (FIGS. 6C and 7A) and 12/15 primary AMLs across diverse genetic subtypes (FIGS. 8 and 9). In addition, 3/3 tested primary MLL-rearranged pediatric leukemias were highly sensitive to JQ1 (FIGS. 9A and 9B), while other tested non-AML leukemia and solid tumor cell lines showed minimal sensitivity to the compound (FIGS. 6C and 7B). In all tested AML lines, JQ1 treatment universally triggered cell-cycle arrest and apoptosis, similar to effects seen after shRNA-mediated Brd4 knockdown (FIGS. 6D, 6E, 8A-8D, 9A-9C, 10A-10C). Together, these data indicate that Brd4 is important for AML growth in vitro that can be effectively targeted using the bromodomain inhibitor JQ1.

Example 3: Leukemia Progression In Vivo is Inhibited by Suppression of Brd4

Figure 12A:
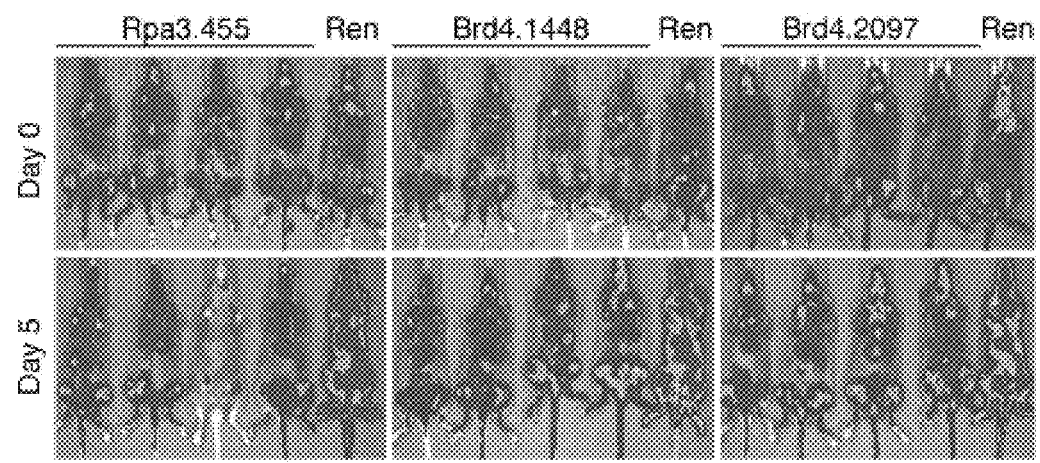
FIGS. 12A-12I show that Brd4 is required for leukemia progression in vivo.
Figure 12B:
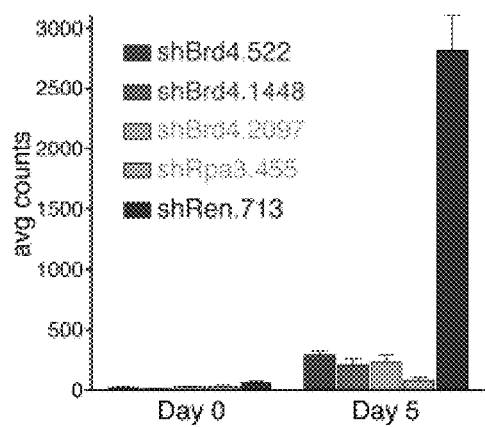
Figure 12C:
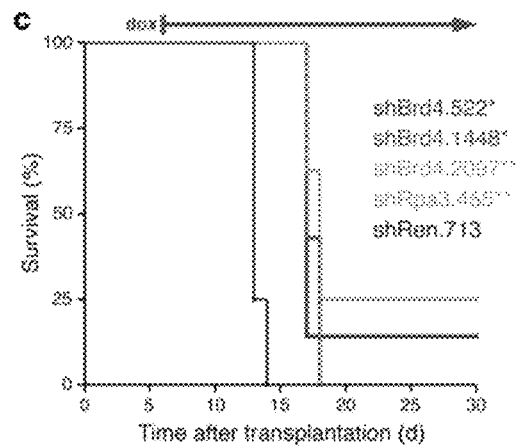
Figure 12D:
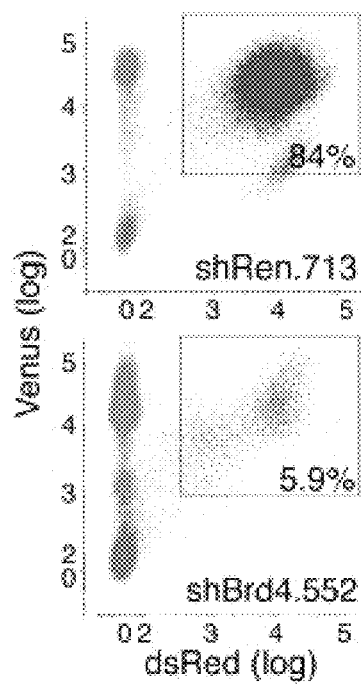
Figure 12E:
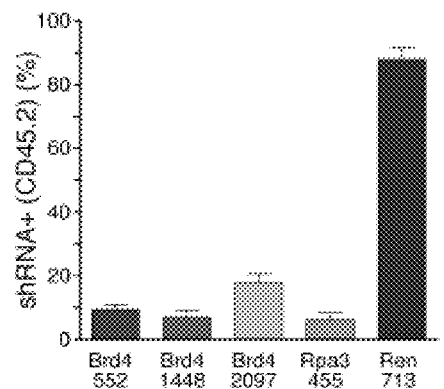

The in vivo relevance of Brd4 to AML progression was investigated. To suppress Brd4 in established AML in mice, Tet-On competent MLL-AF9/Nras$^{G12D}$ leukemia cells were transduced with TRMPV constructs containing anti-Brd4 shRNAs or containing control shRNAs. These cells were then transplanted into secondary recipient mice who had previously been sublethally irradiated. Following disease onset, which was confirmed by bioluminescent imaging, shRNA expression was induced by doxycycline (dox) administration (FIGS. 11A-11F). Subsequent monitoring revealed that Brd4 suppression resulted in a marked delay in leukemia progression and provided a significant survival benefit (FIGS. 12A-12C). Taking advantage of the dsRed reporter linked to shRNA expression in the TRMPV vector (Zuber et al., Nat Biotechnol 2011; 29:79-83), flow-cytometry analysis verified that Brd4-shRNA-positive cells were depleted within the terminal leukemia burden as compared to controls. This data indicates that lethality in the studied mice was a consequence of an outgrowth of Brd4-shRNA-negative cells (FIGS. 12D and 12E). Together, these data indicate that RNAi-mediated suppression of Brd4 inhibits leukemia expansion in vivo.

Example 4: JQ1 Treatment Inhibits Established AML In Vivo

Figure 12F:
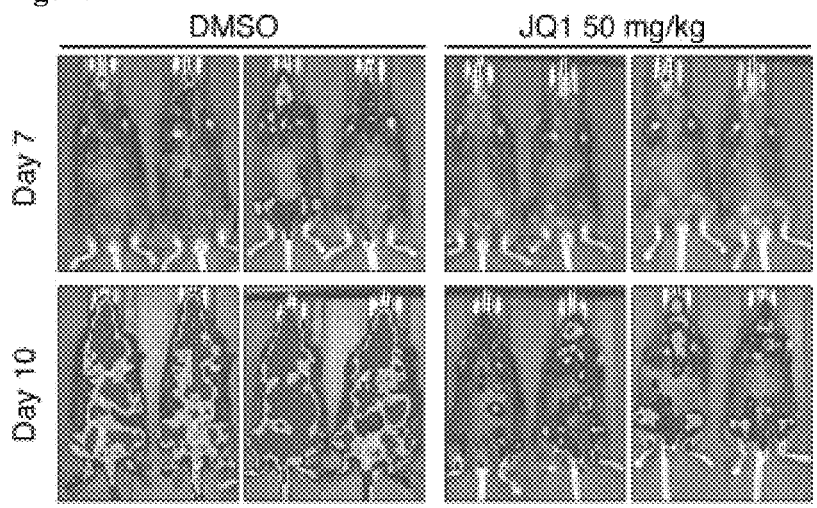
Figure 12G:
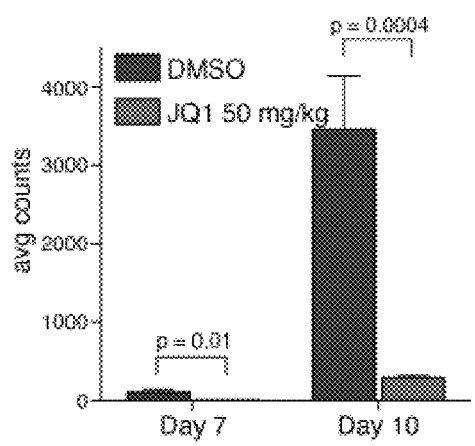
Figure 12H:
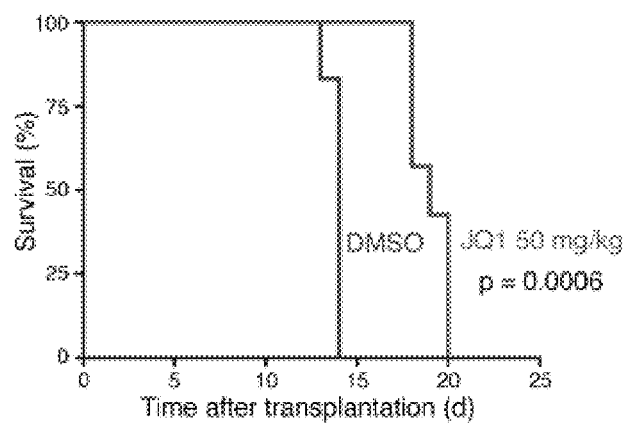
Figure 12I:
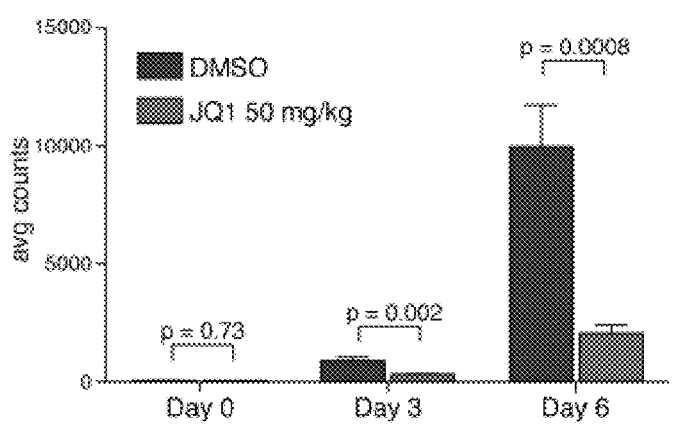
Figure 13A:
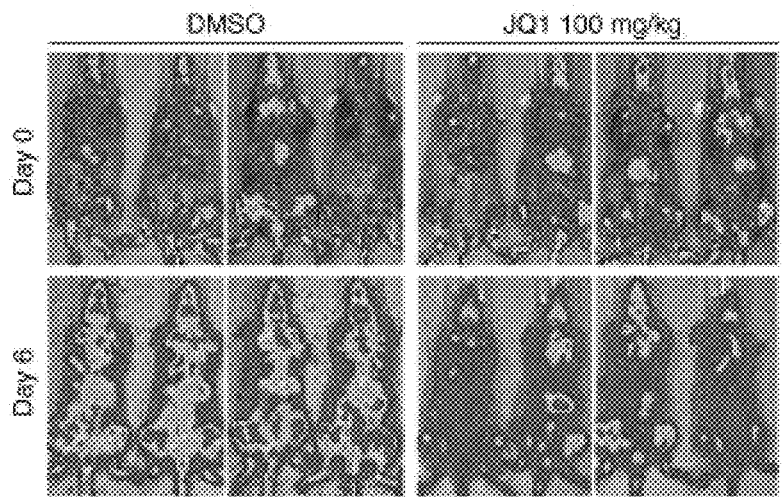
FIGS. 13A-13E show that 100 mg/kg/d and 50 mg/kg/d JQ1 treatments display single agent activity in established MLL-AF9/NrasG12D leukemia.
Figure 13B:
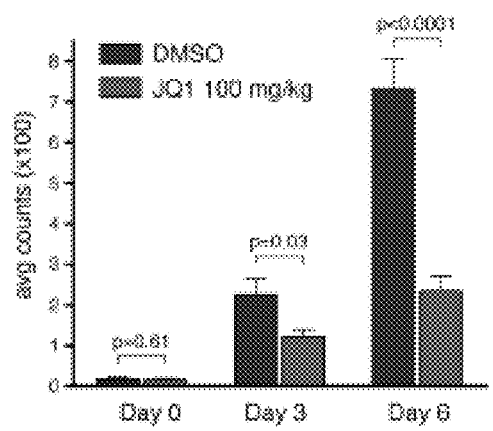
Figure 13C:
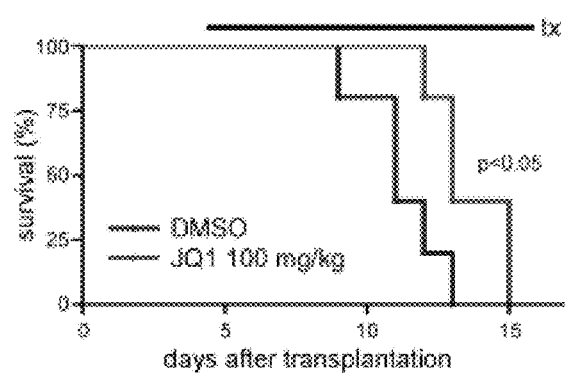
Figure 13D:
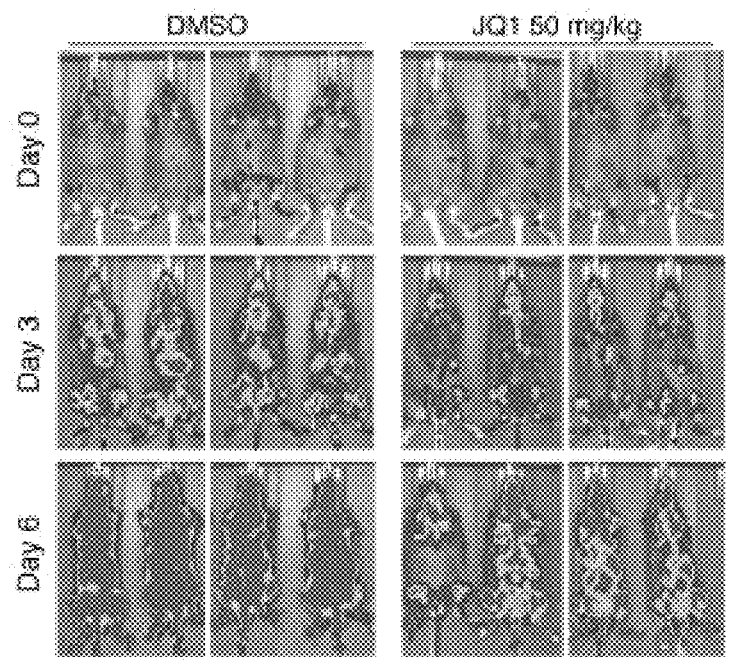
Figure 13E:
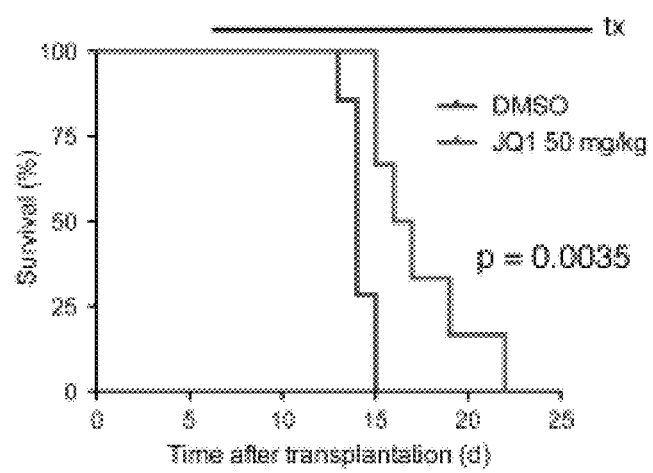
Figure 14A:
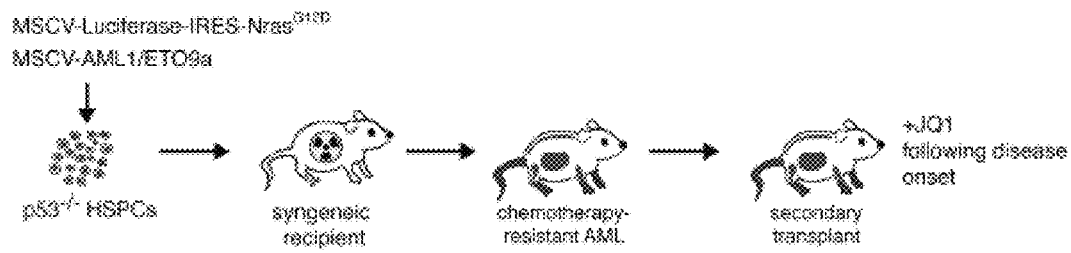
FIGS. 14A-14C show that JQ1 displays single-agent anti-leukemia activity in the AML1-ETO9a/Nras$^{G12D}$/p53$^{-/-}$ AML mouse model.
Figure 14B:
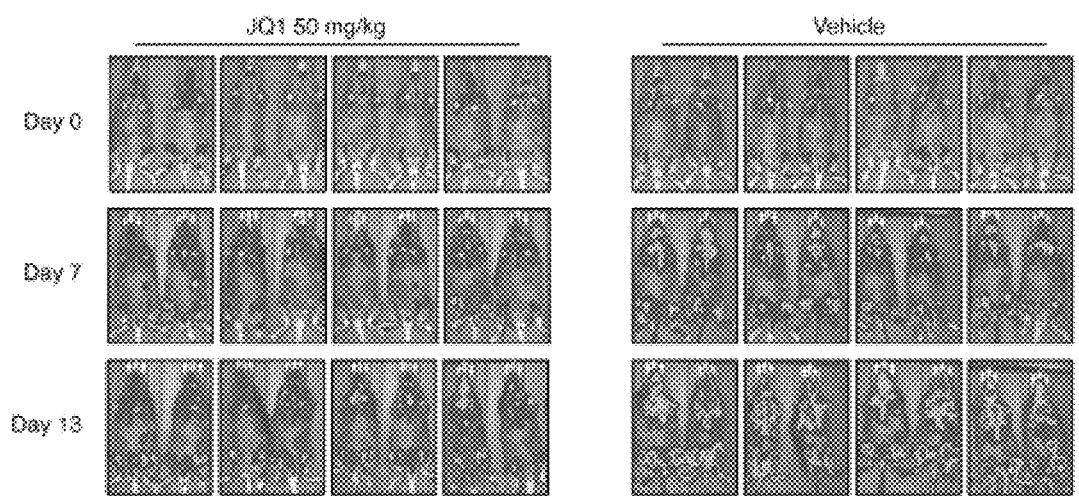
Figure 14C:
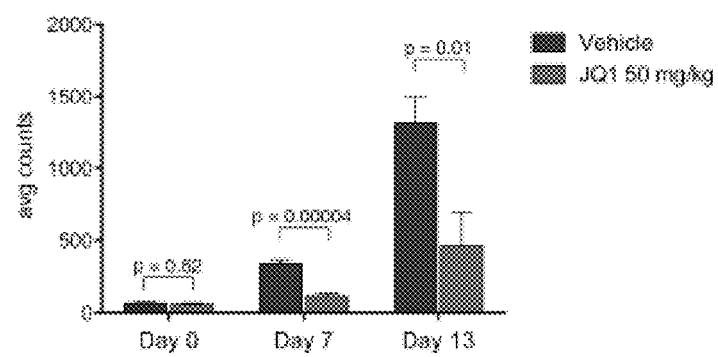
Figure 15:
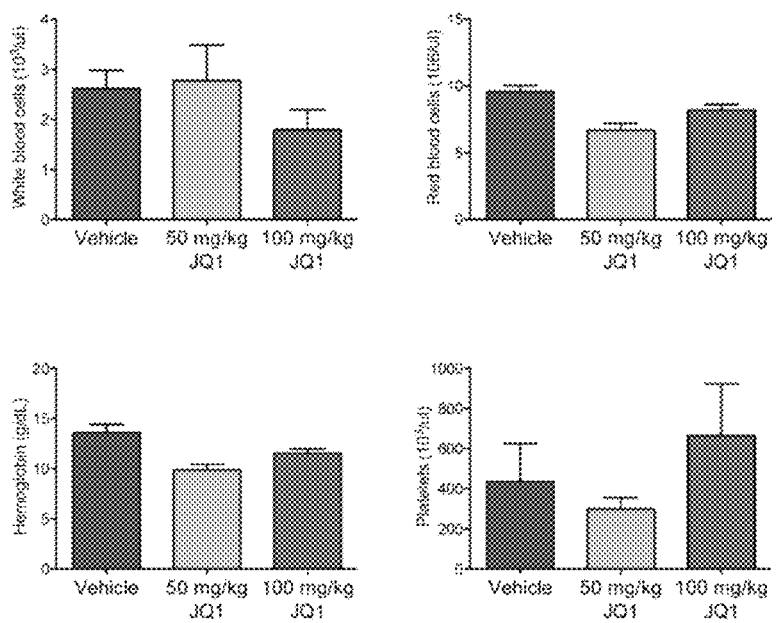
FIG. 15 includes graphs showing the effects of JQ1 treatment on peripheral hematopoietic cell counts. Healthy C57Bl/6 mice were treated with either JQ1 (50 or 100 mg/kg/d) or DMSO-carrier (400 ul/d), both administered by intraperitoneal injection for 20 days. Peripheral blood was collected by submandibular bleeding and analyzed using a Hemavet 950 analyzer (Drew Scientific). Values represent average values of 3 replicate mice; error bars indicate s.e.m.
Figure 16:
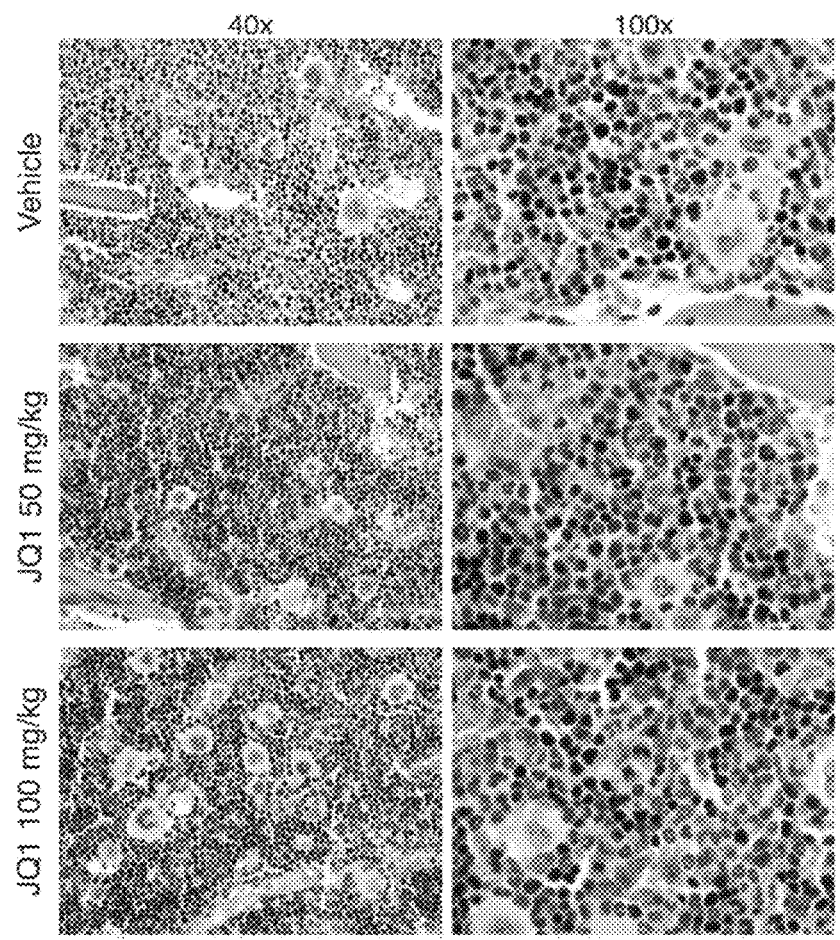
FIG. 16 includes cellular stains showing that 20 days of JQ1 administration has minimal impact on normal bone marrow hematopoiesis. Healthy C57BL/6 mice were treated with daily intraperitoneal injections of 50 mg/kg or 100 mg/kg JQ1 for 20 days prior to bone marrow analysis. H&E stained histopathology of sternal bone marrows from mice treated with vehicle or with JQ1 showed a normal cellularity and normal mixed hematopoiesis. n=3-5 mice for each treatment group. Representative images are shown.
Figure 17A:
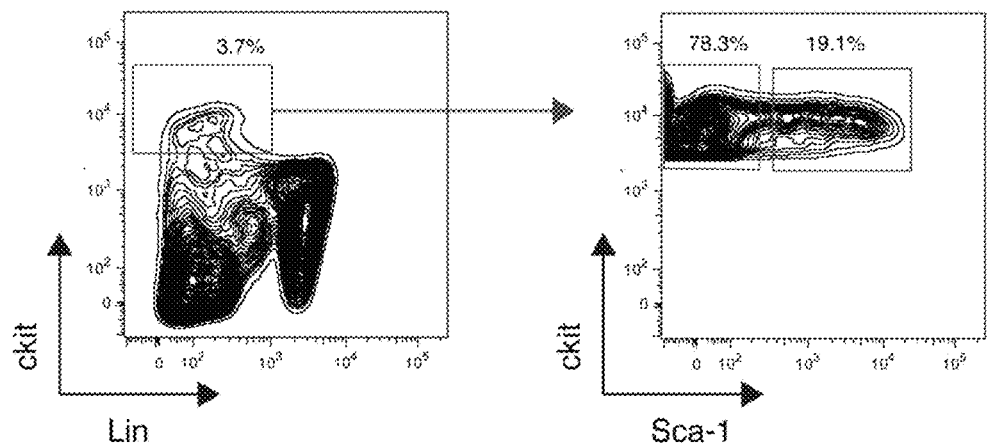
FIGS. 17A and 17B show that daily JQ1 administration has a minimal impact on normal hematopoiesis. Healthy C57BL/6 mice were treated with daily injections of 50 mg/kg or 100 mg/kg JQ1 for 20 days prior to bone marrow FACS analysis.
Figure 17B:
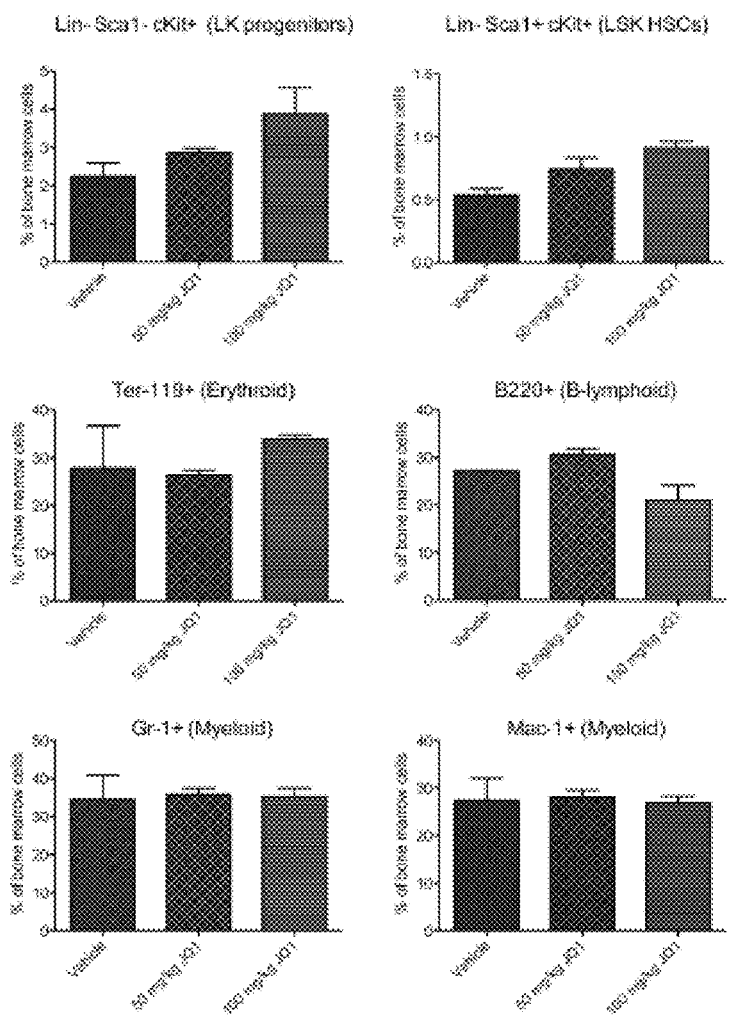

To examine whether JQ1 has single-agent activity in AML, mice transplanted with MLL-AF9/Nras$^{G12D}$ leukemia cells were treated with either daily injections of JQ1 (50 mg/kg) or vehicle. JQ1 administration led to a marked delay in disease progression and significantly extended survival (FIGS. 12F-12H). JQ1 also displayed single-agent activity in the setting of established disease, as seen in MLL-AF9Nras$^{G12D}$ and in AML1-ETO9a/Nras$^{G12D}$/p53$^{-/-}$ AML models (FIGS. 12I, 13A-13E, and 14A-14C), both of which are known to be insensitive to conventional chemotherapy (Zuber et al., Genes Dev 2009; 23:877-89). Consistent with prior findings (Filippakopoulos et al., Nature 2010; 468: 1067-73), JQ1 treatment was well-tolerated in mice, with little if any impact on normal hematopoiesis (FIGS. 15, 16, 17A and 17B). These findings demonstrate that JQ1 has potent and leukemia-specific effects as a single agent in vivo.

Figure 18A:
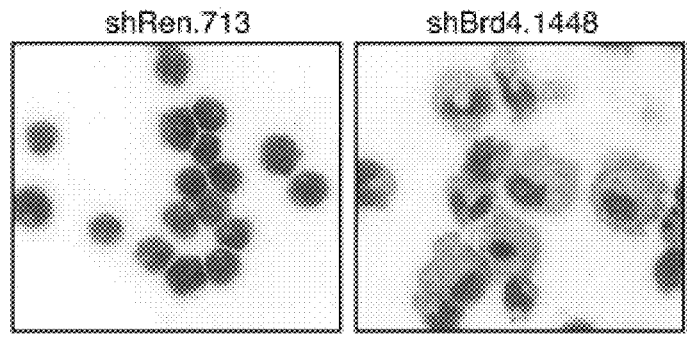
FIGS. 18A-18I show that Brd4-inhibition leads to myeloid differentiation and leukemia stem cell depletion.
Figure 18B:
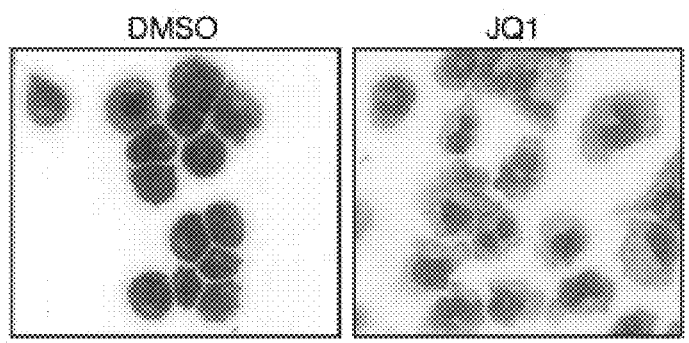
Figure 18C:
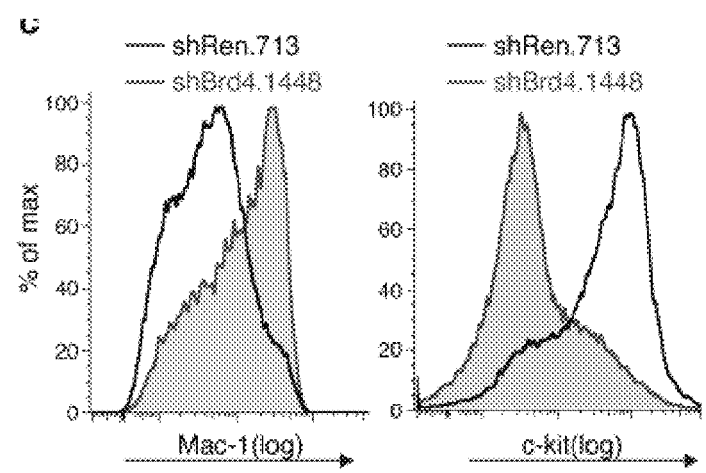
Figure 18D:
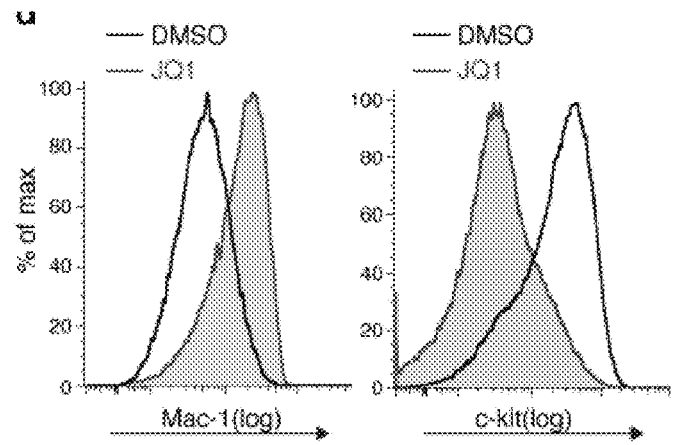

Example 5: Brd4 Inhibition, by shRNA or JQ1, Reduces the Stem Cell Potential of Leukemia Cells and Induces their Differentiation AML is characterized by an expanded self-renewal capacity linked with an inability to complete terminal myeloid differentiation. Thus, whether the presence of Brd4 influences the differentiation state of leukemia cells was considered next. Both Brd4 shRNA-expression and JQ1 treatment altered the morphology of MLL-AF9/Nras$^{G12D}$ leukemia cells from myelomonocytic blasts into cells having a macrophage-like appearance (FIGS. 18A and 18B). Upon Brd4 inhibition, either by shRNA or JQ1 treatment, upregulated genes involved in macrophage functions and Mac-1, a myeloid differentiation marker. Brd4 inhibition downregulated c-kit, whose levels correlate with leukemic stem cell (LSC) frequencies in MLL-rearranged leukemia (FIGS. 18C and 18D). In addition, JQ1 treatment induced morphologic signs of maturation phenotypes in the majority of tested primary leukemia samples, albeit to varying degrees (FIGS. 8 and 9).

Figure 18E:
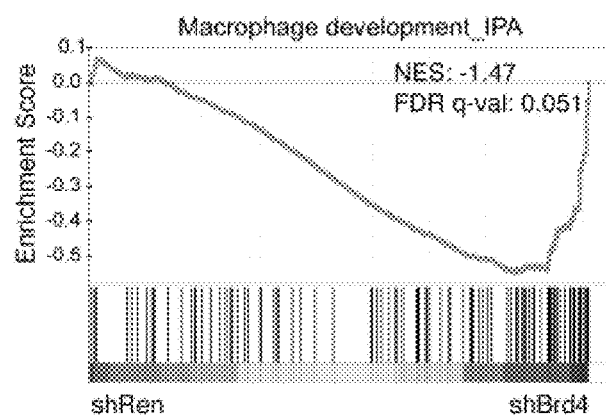
Figure 18F:
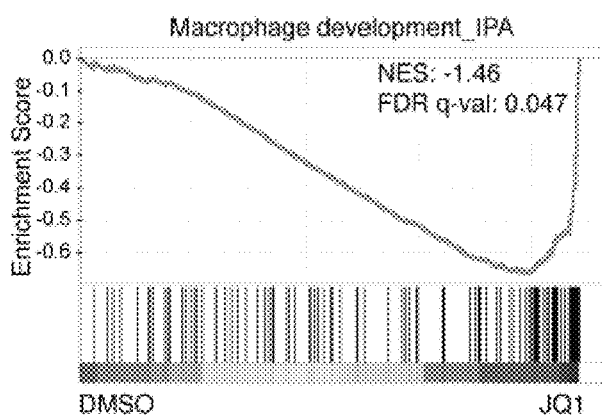
Figure 18G:
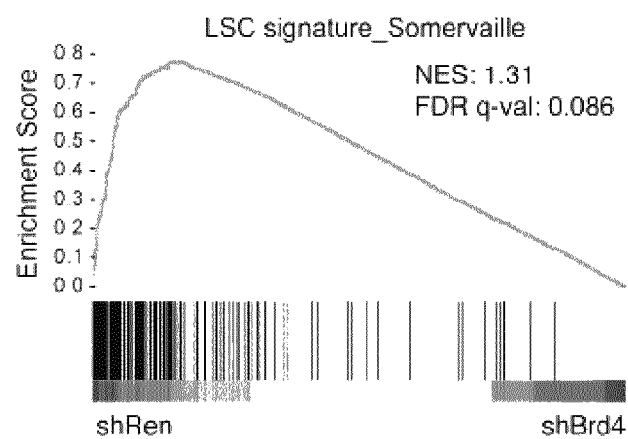
Figure 18H:
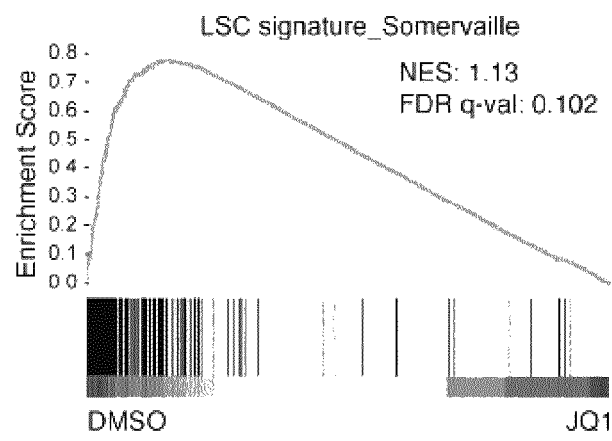
Figure 18I:
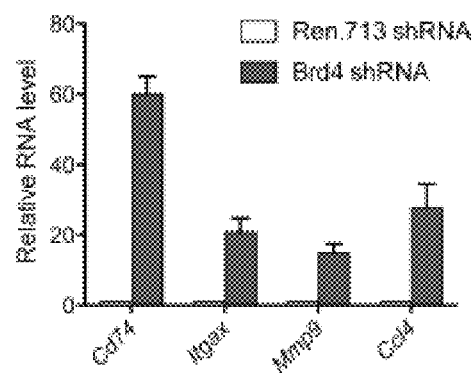
Figure 18I:
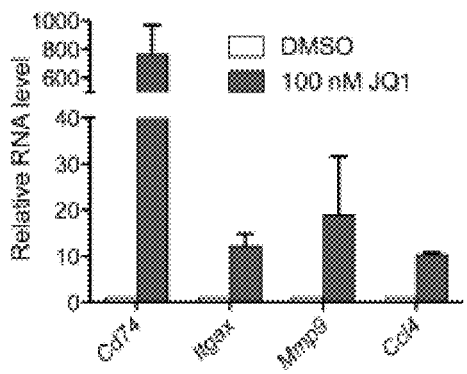

To further validate whether suppression of Brd4 eradicates the LSC compartment, Gene Set Enrichment Analysis (GSEA) was conducted on expression microarrays obtained from Brd4-shRNA and JQ1-treated leukemia cells (Subramanian et al., *Proc Natl Acad Sci USA* 2005; 102:15545-50). GSEA revealed significant upregulation of macrophage-specific gene expression following Brd4-inhibition (FIGS. 18E and 18F), as well as global loss of a gene expression signature previously shown to discriminate LSCs from non-self-renewing leukemia cell subsets (FIGS. 18G and 18H) (Somervaille et al., *Cell Stem Cell* 2009; 4:129-40). FIG. 18I includes graphs showing RT-qPCR results. A similar profile of gene expression changes was seen in a JQ1-treated human AML cell line THP-1 (FIG. 19) Importantly, the strong phenotypic resemblance between Brd4 knockdown via shRNA and pharmacologic BET bromodomain inhibition among these assays establishes that Brd4 is a target of JQ1. Accordingly, these results reveal that Brd4 is essential for maintaining leukemic stem cell populations and for preventing their terminal differentiation.

Figure 20A:
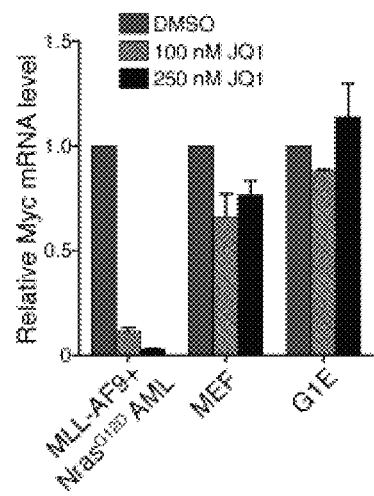
FIGS. 20A-20H show that JQ1 suppresses the Myc pathway in leukemia cells.
Figure 20B:
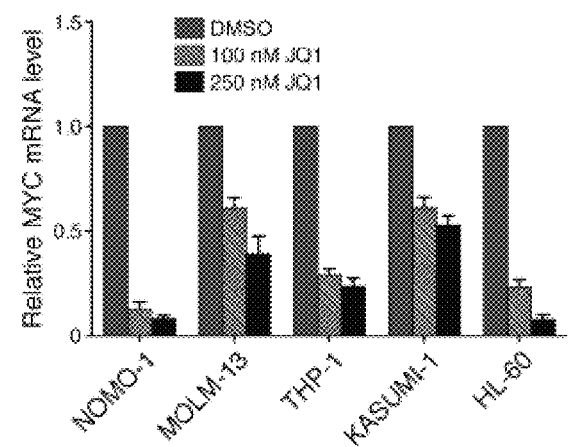
Figure 20C:
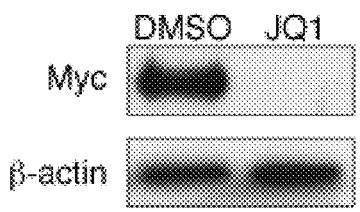
Figure 20D:
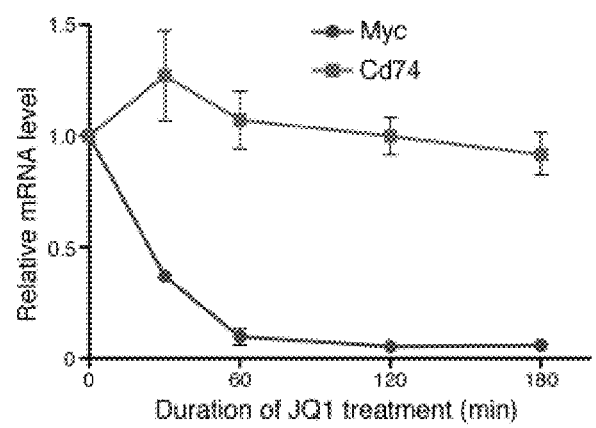
Figure 20E:
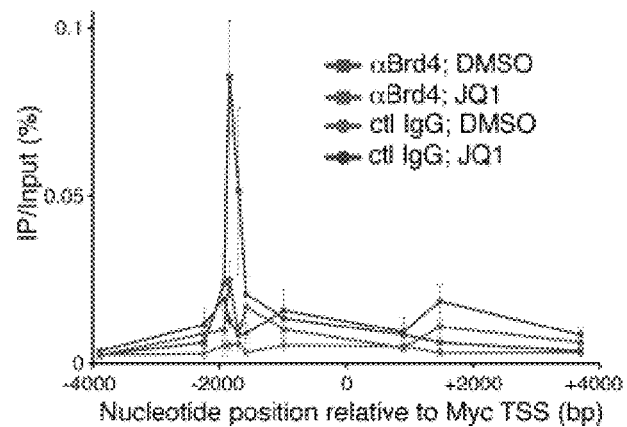
Figure 21A:
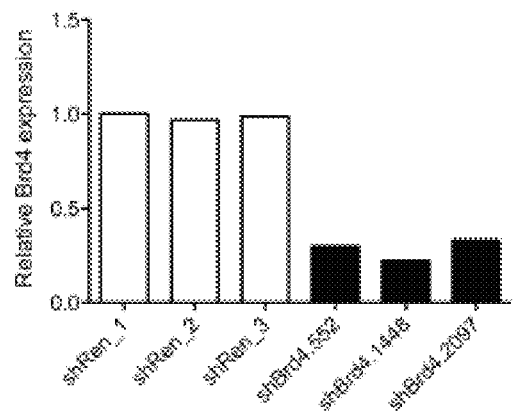
FIGS. 21A-21D show that Brd4 knockdown via shRNA leads to downregulation of Myc levels and downregulation of Myc target gene expression.
Figure 21B:
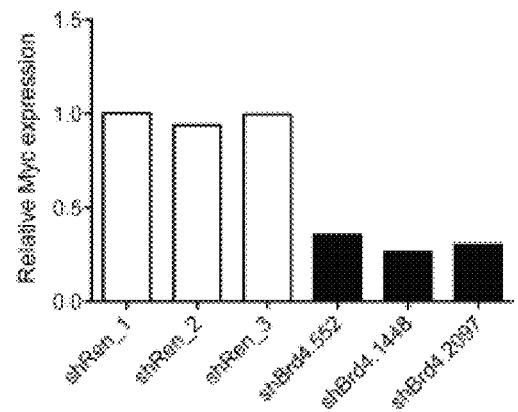
Figure 21C:
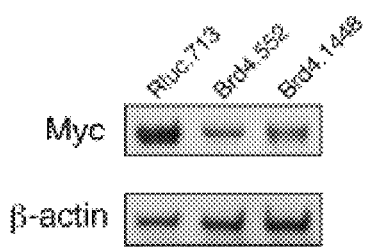
Figure 21D:
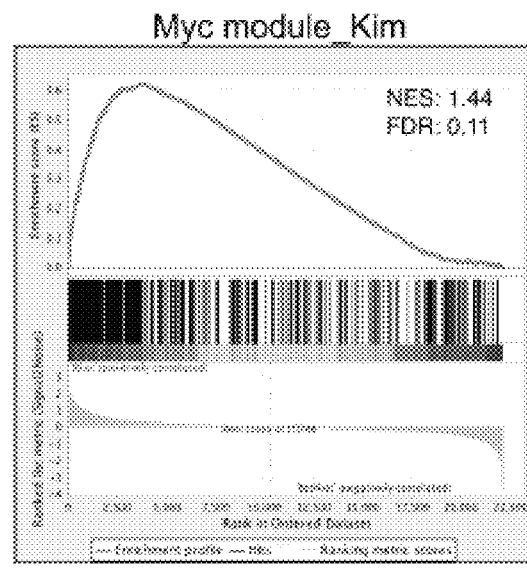
Figure 21D:
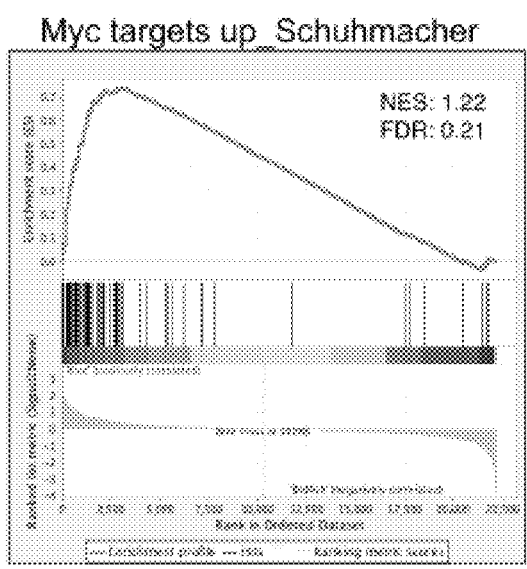
Figure 22:
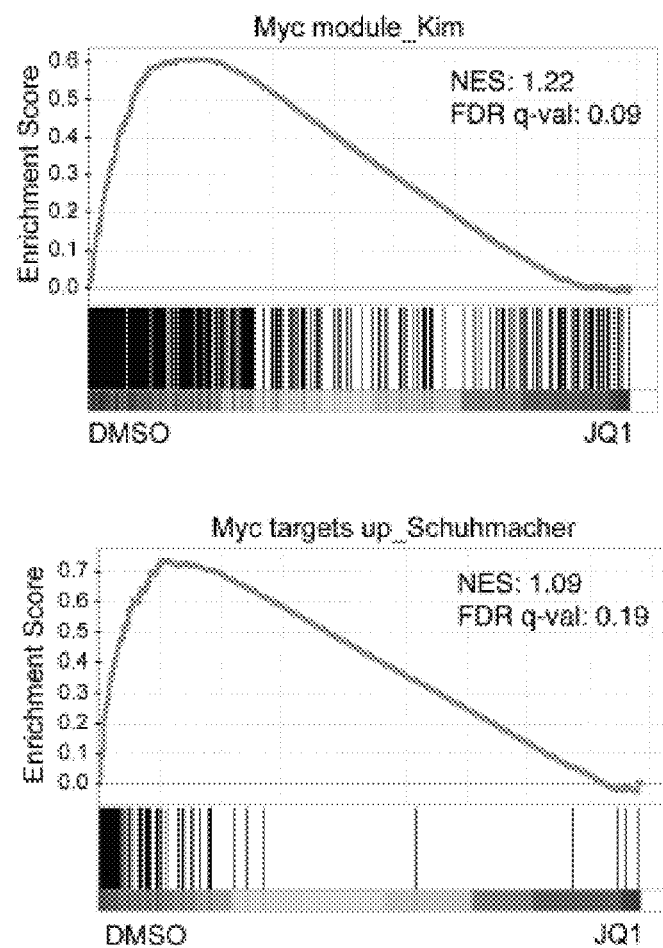
FIG. 22 shows that JQ1 triggers downregulation of Myc target gene expression.
Figure 23A:
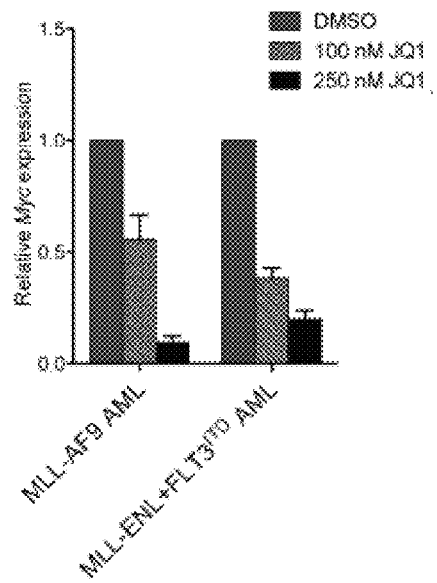
FIGS. 23A and 23B show that 48 hours of JQ1 treatment suppresses Myc expression selectively in leukemia cells.
Figure 23B:
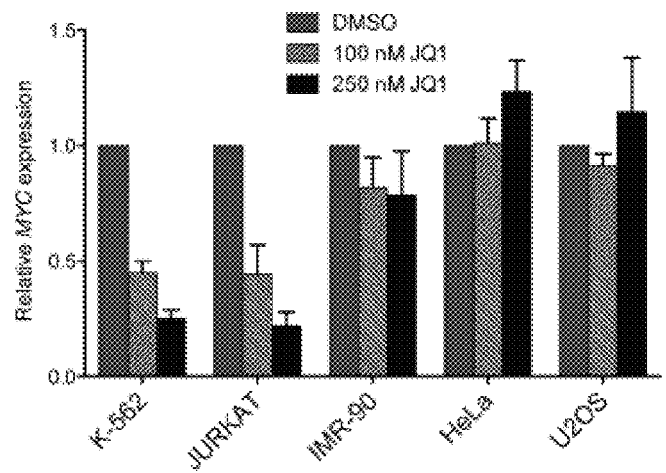

Example 6: In Murine and Human Leukemia Cells, JQ1 Suppresses the Myc Pathway, a Pathway Associated with Leukemic Stem Cell Self-Renewal Since the Myc pathway is associated with leukemic stem cell self-renewal and Myc appears to be a downstream target of Brd4, the effects of Brd4 inhibition on Myc levels was studied. In mouse MLL-AF9/Nras$^{G12D}$ leukemia cells, Brd4 inhibition via shRNAs or JQ1 treatment led to a dramatic reduction in Myc mRNA levels and Myc protein levels; in contrast, Brd4 inhibition had minimal effects in MEF or G1E cells (FIGS. 20A-20C, 21A, and 21B). Downregulation of Myc mRNA levels occurred within 60 minutes of JQ1 exposure, qualitatively preceding the increased expression of genes related to macrophage differentiation, such as Cd74 (FIG. 20D). Further supporting a direct transcriptional regulation, chromatin immunoprecipitation experiments identified a region of focal Brd4 occupancy ~2 kilobases upstream of the Myc promoter which was eliminated following exposure to JQ1 (FIG. 20E). As expected, RNAi- or JQ1-induced suppression of Brd4 inhibition with shRNA or with JQ1 also led to a global reduction in Myc target gene expression (FIGS. 21C and 22) (See also, Kim et al., *Cell* 2010; 143:313-24; and Schuhmacher et al., *Nucleic Acids Res* 2001; 29:397-406). Strikingly, JQ1 treatment triggered Myc down-regulation in a broad array of mouse and human leukemia cell lines examined (FIGS. 20A-20C, FIGS. 23A and 23B), indicating that JQ1 provide a means to suppress the Myc pathway in a range of leukemia subtypes. FIG. 21D includes GSEA plots evaluating changes in Myc downstream target gene expression.

Example 7: Brd4 Regulates Cell Survival Through a Myc-Independent Pathway

Figure 20F:
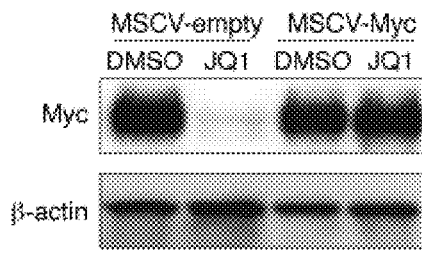
Figure 20G:
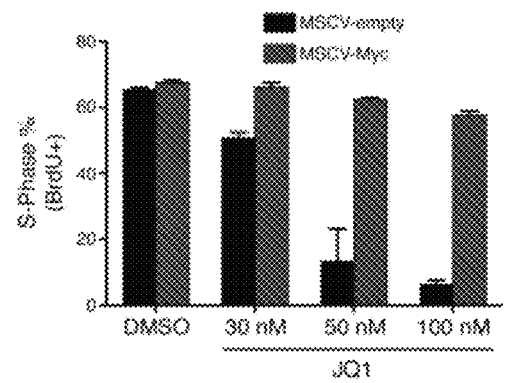
Figure 20H:
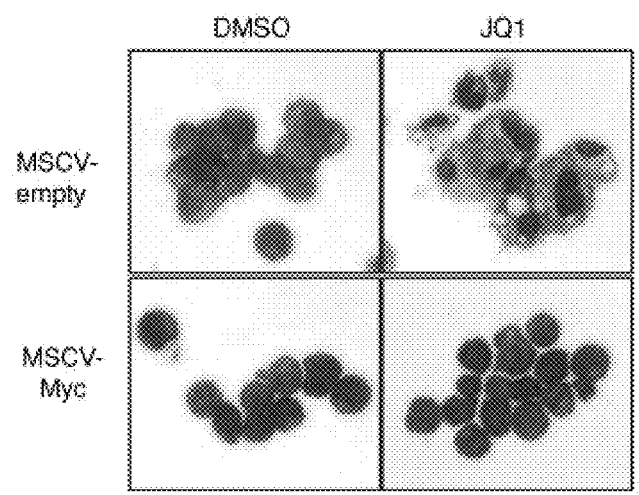
Figure 24A:
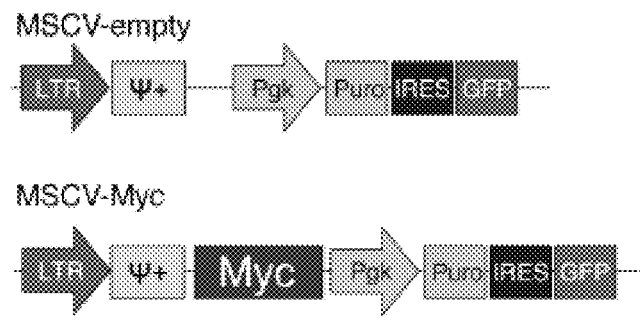
FIGS. 24A-24D show the impact of retroviral Myc overexpression on sensitivity of leukemia cells to JQ1.
Figure 24B:
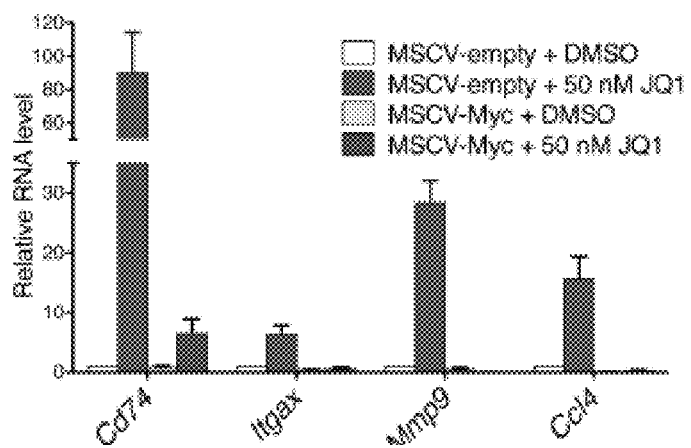
Figure 24C:
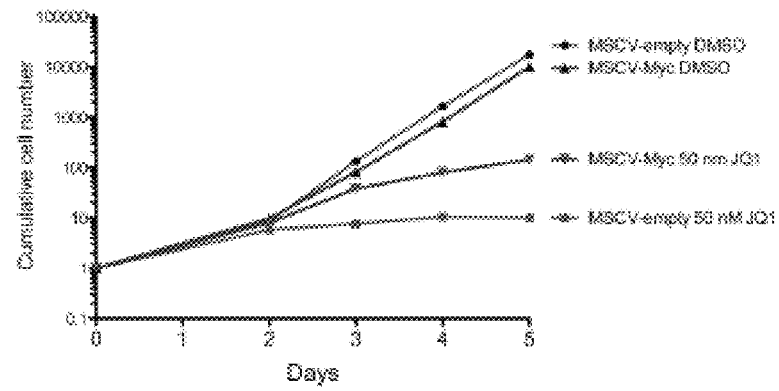
Figure 24D:
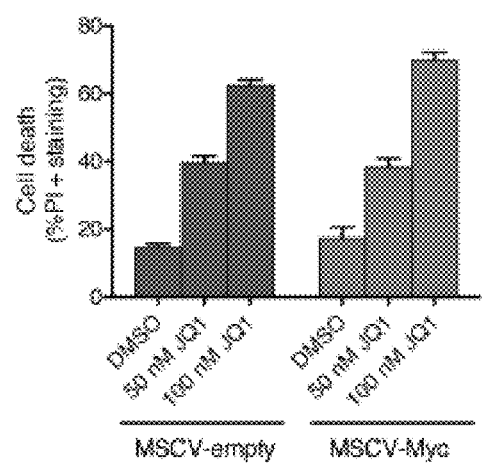
Figure 25A:
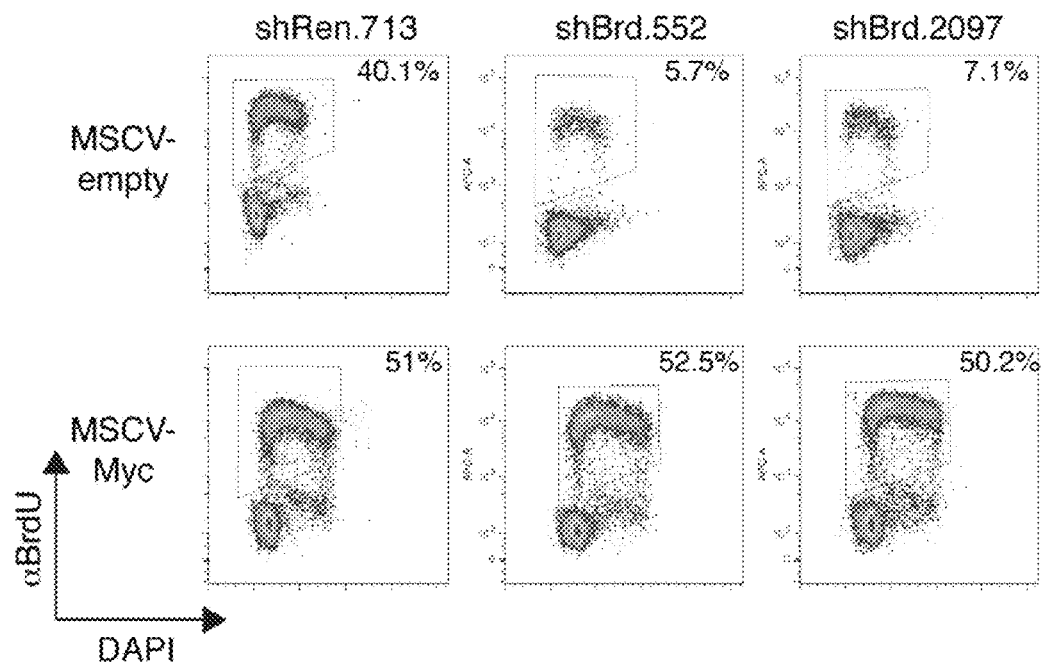
FIGS. 25A-25D show that Myc overexpression prevents Brd4 shRNA-induced cell-cycle arrest and macrophage differentiation.
Figure 25B:
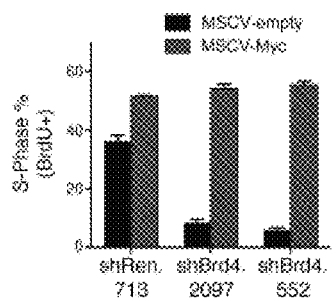
Figure 25C:
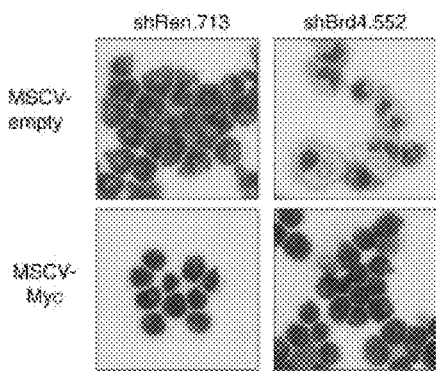
Figure 25D:
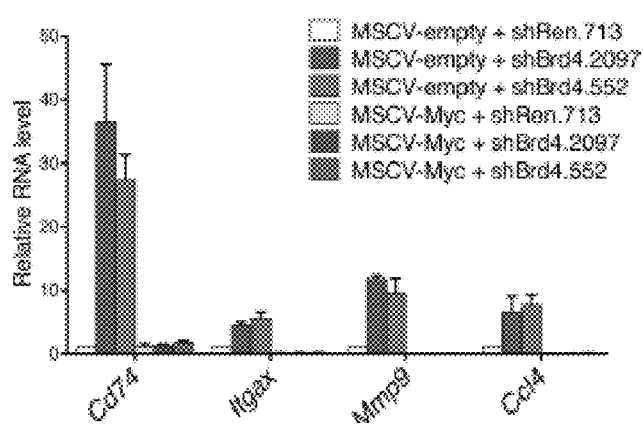
Figure 26A:
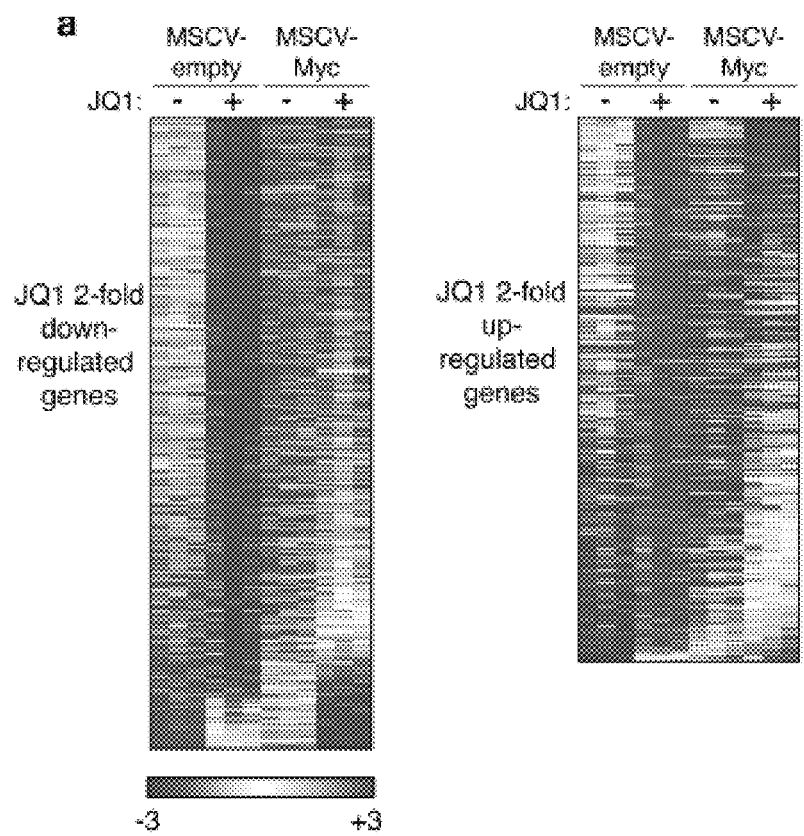
FIGS. 26A-26C show that the majority of JQ1-induced gene expression changes are secondary effects of Myc inhibition. MLL-AF9/Nras$^{G12D}$ leukemia cells transduced with MSCV-Myc or empty vector control were treated with 100 nM JQ1 for 48 hours, followed by collection of RNA for expression microarray analysis.
Figure 26B:
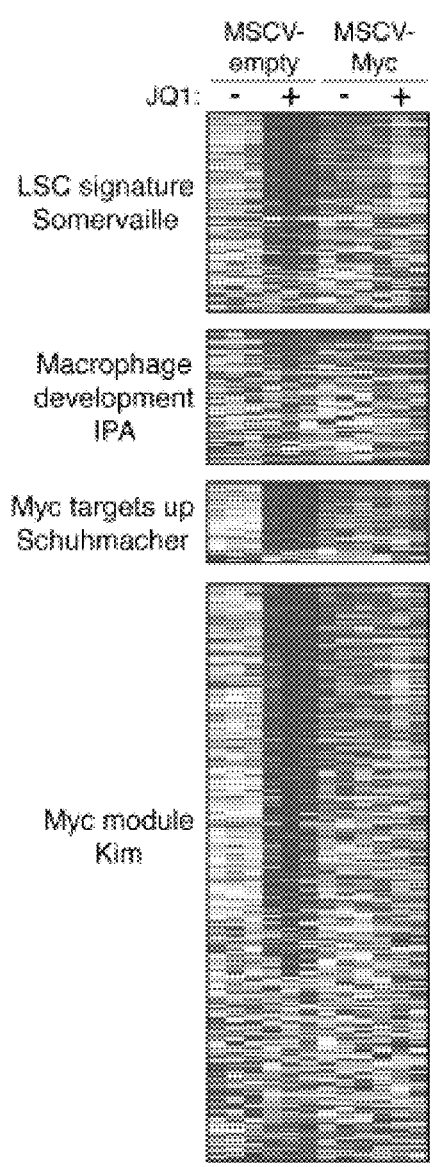
Figure 26C:
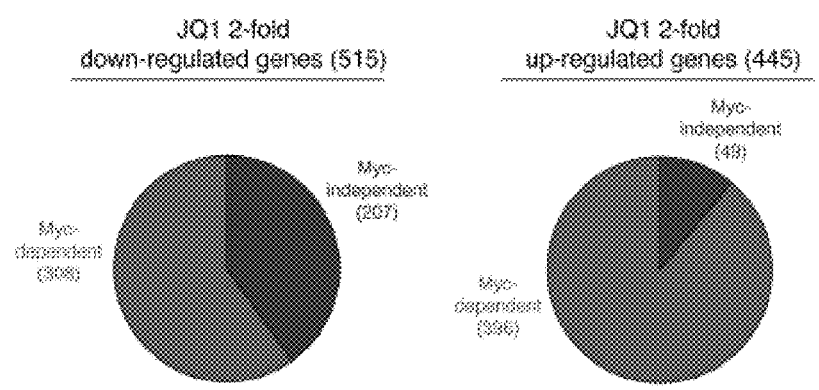
Figure 27A:
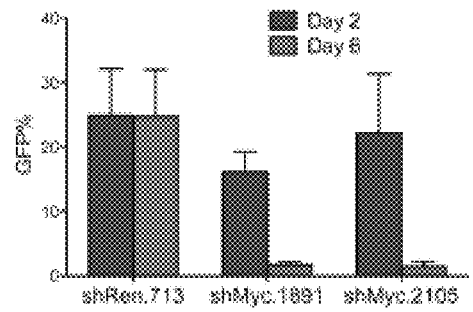
FIGS. 27A-27D show that shRNA knockdown of Myc inhibits MLL-AF9/Nras$^{G12D}$ leukemia growth and triggers terminal myeloid differentiation.
Figure 27B:
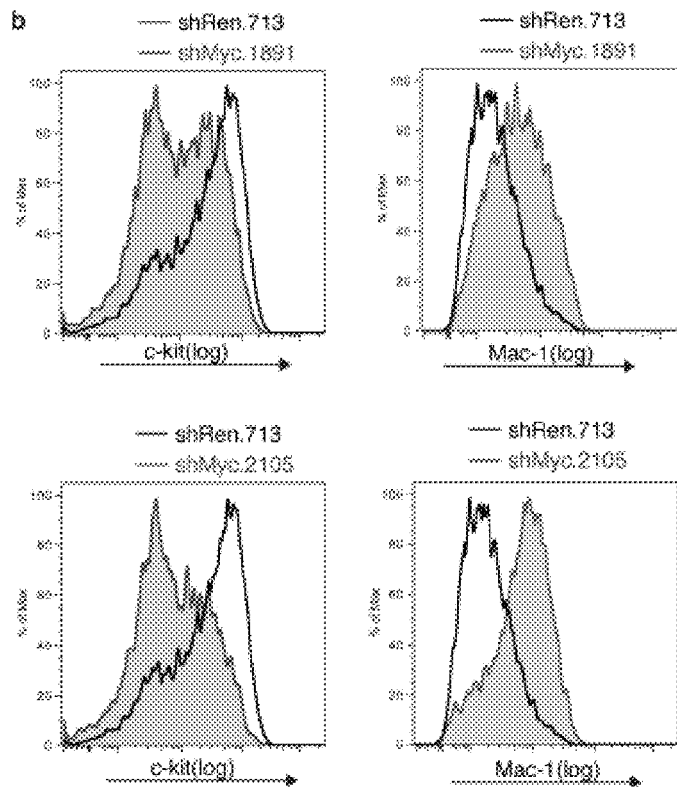
Figure 27C:
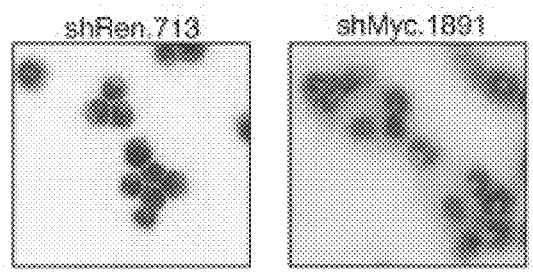
Figure 27D:
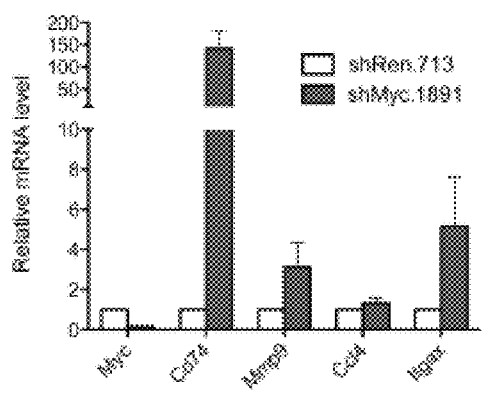

Next, experiments were conducted to further evaluate whether the anti-proliferation effects of JQ1 treatment occur via suppression of Myc activity. Here, MLL-AF9/Nras$^{G12D}$ leukemia cultures were generated so that Myc cDNA was ectopically expressed from a retroviral promoter, which resulted in slight but constitutive Myc overexpression that was entirely resistant to JQ1-induced transcriptional suppression (FIGS. 20F, 24A and 24B). Notably, ectopic Myc conferred nearly complete resistance to JQ1, Brd4 shRNA-induced cell cycle arrest, and macrophage differentiation (FIGS. 20G, 20H, and 25A-D). Furthermore, global expression profiling revealed that the vast majority of JQ1-induced transcriptional changes are in fact secondary effects of Myc downregulation (FIGS. 26A-26C). shRNA knockdown of Myc itself also triggered a pattern of growth arrest and myeloid differentiation resembling Brd4 inhibition (FIGS. 27A-D), further supporting Myc as an important mediator of JQ1-induced effects. Importantly, ectopic Myc expression was unable to prevent JQ1-induced cell death, suggesting additional Myc-independent roles for Brd4 in regulating cell survival (FIGS. 24C and 24D). These findings indicate that Brd4 has an important role in maintaining Myc activation to preserve an undifferentiated cellular state in leukemia.

Figure 28A:
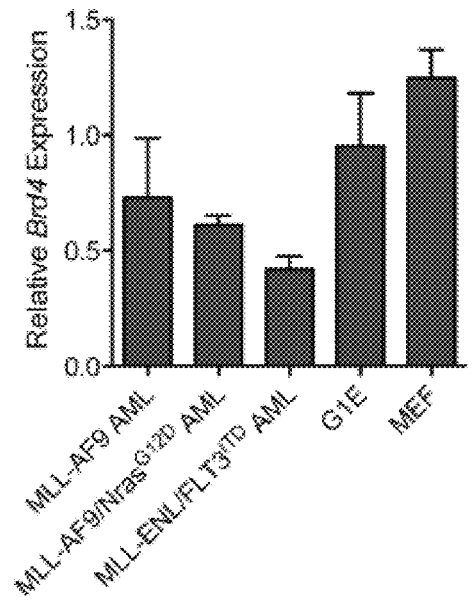
FIGS. 28A and 28B show that Brd4 is not consistently overexpressed in AML relative to other cell types.
Figure 28B:
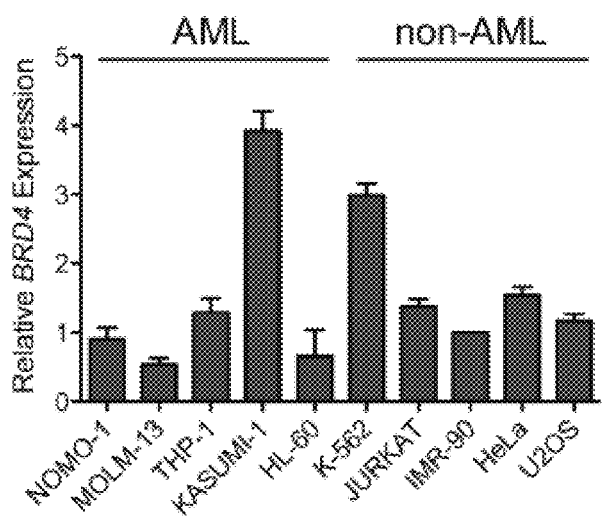
Figures 29A, 29B:
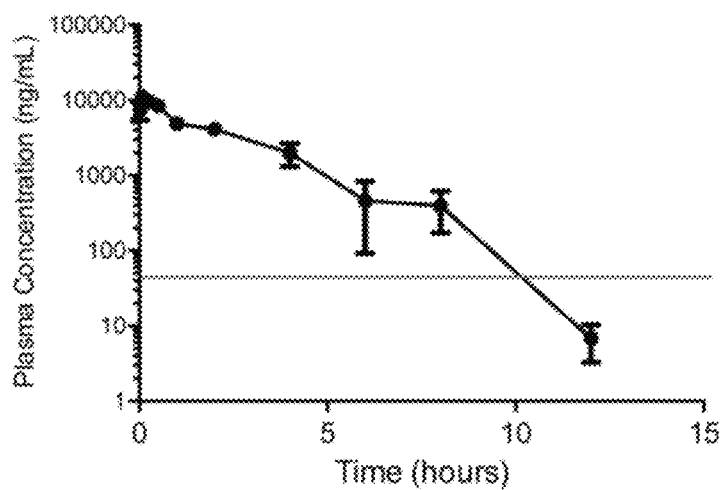
FIGS. 29A and 29B show the results from the pharmacokinetic study of (+)-JQ1 in mice.

By taking a non-biased screening approach targeting epigenetic regulators, Brd4 was identified as a critical factor required for AML disease maintenance. As Brd4 is not evidently mutated or overexpressed in AML (FIGS. 28A and 28B), the exquisite sensitivity of leukemia cells to Brd4 inhibition would not have been revealed simply through genetic or transcriptional characterization of this disease. In addition, the results described herein demonstrate that the bromodomain inhibitor JQ1 has broad activity in different AML contexts, and by comparing its effects to those induced by Brd4-shRNAs, provide evidence that Brd4 is the relevant target for the anti-leukemic activity of JQ1. JQ1 is a robust anti-leukemic molecule with a half-life in rodents of about one hour (FIG. 29). Such effects are also observed in vivo with Brd4 shRNAs, unambiguously highlighting the utility of RNAi screening in revealing novel drug targets in cancer.

Figure 30A:
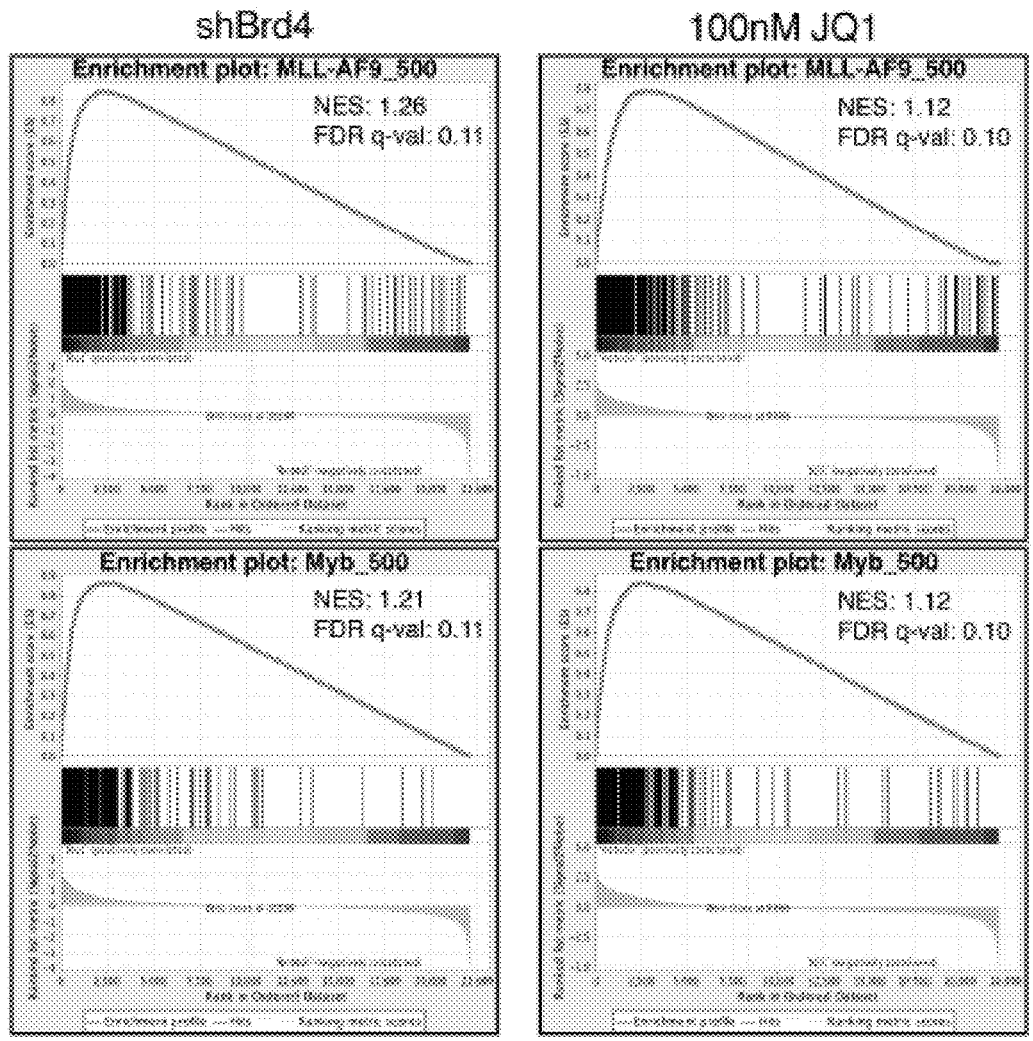
FIGS. 30A-30C show the broadly overlapping transcriptional effects elicited upon suppressing Brd4, Myb, and MLL-AF9 with downregulation of Myc upon suppressing any of the three factors.
Figure 30B:
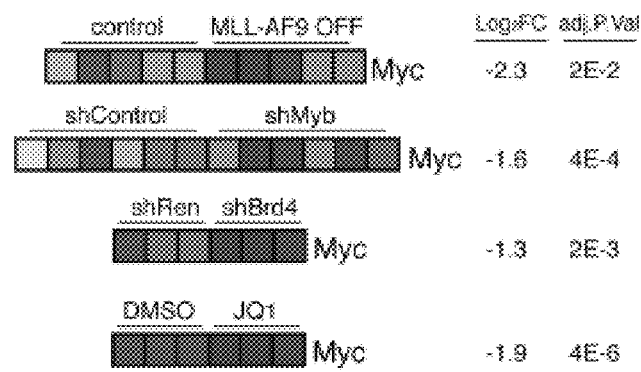
Figure 30C:
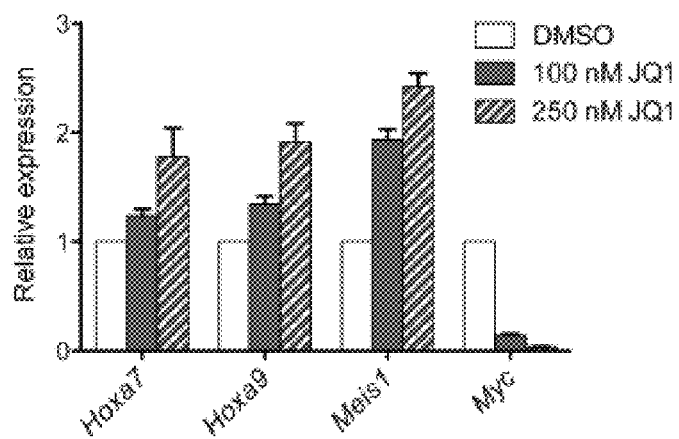

As a competitive inhibitor of the acetyl-lysine binding domain, JQ1 interferes with the ability of Brd4 to 'read' histone acetylation marks that facilitate transcriptional activation (Filippakopoulos et al., 2010). When applied to leukemia cells, JQ1 interferes with transcriptional circuits supporting self-renewal; thus, JQ1 induces terminal differentiation in leukemic stem cells (LSCs). Myb is a central mediator of MLL-AF9-induced transcriptional programs and is important for aberrant self-renewal states, such that Myb inhibition is sufficient to eradicate disease (Zuber et al., submitted). Interestingly, gene expression changes generated following genetic or pharmacologic inhibition of Brd4 are remarkably similar to those observed upon suppressing MLL-AF9 or Myb (FIGS. 30A-30C). However, JQ1 treatment does not influence expression of Hoxa7, Hoxa9, or Meis1, which are well established direct targets of MLL-AF9. This indicates that Brd4 inhibition does not neutralize the global function of MLL-AF9, but instead suppresses a large subsets of other downstream targets, e.g. via an inhibition of Myc. Together, it appears that MLL-AF9, Myb, and Brd4 functionally intersect within a common transcriptional circuit essential for malignant self-renewal. A key effector of this program is the oncoprotein Myc (Zuber et al, submitted), which has been validated as an attractive therapeutic target but is not amenable to traditional pharmacological inhibition.

The above-mentioned examples decisively demonstrate that targeting Brd4 extinguishes Myc expression and limits self renewal with selectivity for the leukemic context, thus averting hematopoietic toxicities potentially associated with systemic Myc inhibition. Consequently, inhibiting Brd4 via RNAi knockdown or JQ1 treatments defines a specific and effective strategy for disarming elusive oncogenic pathways relating to murine and human leukemias through the direct modulation of the epigenetic machinery.

The results reported herein in the above Examples were obtained using the following materials and methods.

Plasmids

For conditional RNAi experiments, shRNAs were expressed from either the TRMPV-Neo vector or TtTMPV-Neo vector, which have been described previously (Zuber et al., Nat Biotechnol 2011; 29:79-83). For screen validation, shRNAs were cloned into LMN (MSCV-miR30-PGK-NeoR-IRES-GFP), which was generated based on LMP3 by replacing the PuroR transgene with a NeoR cassette. For Myc rescue experiments, the wild-type mouse Myc cDNA was subcloned into MSCV-PGK-Puro-IRES-GFP (MSCV-PIG) (Hemann et al., Nat Genet 2003; 33:396-400).

Pooled Negative-Selection RNAi Screening

A custom shRNA library targeting 243 chromatin regulating mouse genes was designed using miR30-adapted BIOPREDsi predictions (Huesken et al., Nature Biotechnology 2005; 23:995-1001) (6 shRNAs/gene) and constructed by PCR-cloning a pool of oligonucleotides synthesized on 55 k customized arrays (Agilent Technologies, Lexington, Mass.) as previously described (Zuber et al., 2011). Following sequence verification, 1095 shRNAs (3-6/gene) were combined together with several positive and negative control shRNAs at equal concentrations in one pool. This pool was subcloned into TRMPV-Neo and transduced into Tet-On MLL-AF9/Nras$^{G12D}$ leukemia cells using conditions that predominantly lead to a single retroviral integration and represent each shRNA in a calculated number of >500 cells (30 million cells total at infection, 2% transduction efficiency). Transduced cells were selected for 5 days using 1 mg/ml G418 (Invitrogen, Carlsbad, Calif.); at each passage >20 million cells were maintained to preserve library representation throughout the experiment. Following drug selection T0 samples were obtained (~20 million cells per replicate) and cells were subsequently cultured under addition of 0.5 mg/ml G418 and 1 µg/ml doxycycline to induce shRNA expression. After 14 days (=12 passages, T14), for each replicate ~15 million shRNA expressing (dsRed+Nenus+) cells were sorted using a FACSAriaII™ (BD Biosciences, Sparks, Md.). Genomic DNA from T0 and T14 samples was isolated by two rounds of phenol extraction using PhaseLock™ tubes (5prime, Gaithersburg, Md.) followed by isopropanol precipitation. Deep sequencing template libraries were generated by PCR amplification of shRNA guide strands as previously described (Zuber et al., 2011). Libraries were analyzed on an Illumina® Genome Analyzer (San Diego, Calif.) at a final concentration of 8 pM; 18 nt were sequenced using a primer that reads in reverse into the guide strand (miR30EcoRISeq, TAGC-CCCTTGAATTCCGAGGCAGTAGGCA (SEQ ID NO: 5). To provide a sufficient baseline for detecting shRNA depletion in experimental samples, it was desirable to acquire >500 reads per shRNA in the T0 sample, which required >10 million reads per sample to compensate for disparities in shRNA representation inherent in the pooled plasmid preparation or introduced by PCR biases. With these conditions, T0 baselines of >500 reads for 1072 (97% of all) shRNAs were acquired. Sequence processing was performed using a customized Galaxy platform (Taylor et al., Curr Protoc Bioinformatics Chapter 10, Unit 10 5 (2007)). For each shRNA and condition, the number of matching reads was normalized to the total number of library specific reads per lane and imported into a database for further analysis.

Cell Culture

All mouse MLL-leukemia cell lines were derived from bone marrow obtained from terminally ill recipient mice, cultured in RPMI1640 supplemented with 10% fetal bovine serum (FBS) and penicillin/streptomycin. MLL-AF9 (alone), MLL-AF9/Nras$^{G12D}$, Tet-On MLL-AF9/Nras$^{G12D}$, and MLL-ENL/FLT3$^{ITD}$ cell cultures were derived as described previously (Zuber. et al., Genes Dev 2009; 23:877-89 and Zuber et al., 2011). Tet-On immortalized MEF cultures were described previously (Zuber et al., 2011). G1E cells were kindly provided by Mitchell Weiss (University of Pennsylvania). MEF cells were grown in DMEM with 10% FBS and 1% glutamine (GIBCO®, Carlsbad, Calif.). G1E cells were grown in IMDM with 15% FBS, 2 U/ml erythropoietin (Sigma-Adrich), and 10% kit ligand conditioned medium. All human leukemia cell lines were cultured in RPMI1640/10% FBS, except KASUMI-1 cells were cultured in 20% FBS. NOMO-1 and MOLM-13 were purchased from DSMZ. KASUMI-1, HL-60, and IMR-90 were obtained from ATCC. K-562 and THP-1 were kindly provided by Martin Carroll (University of Pennsylvania). U2OS, HeLa, and Jurkat were provided by the CSHL tissue culture service.

Western Blot

For Brd4 Western blots, 30 µg of whole cell lysate RIPA extract (25 mM Tris pH7.6, 150 mM NaCl, 1% NP-40, 1% Sodium deoxycholate, 0.1% SDS) was loaded into each lane. For Myc Western blots, cells were lysed directly in Laemmli buffer. About 50,000 cell equivalents were loaded in each lane. Protein extracts were resolved by SDS-PAGE electrophoresis and transferred to nitrocellulose for blotting.

Proliferation Assay

Proliferation assays were performed by counting the increase in viable cell number over seventy-two hours. Dead cells were excluded by incubating with propidium iodide (PI). Cell concentration measurements were performed on a Guava Easycyte (Millipore, Billerica, Mass.), gating only viable cells using forward/side scatter/PI-cells. Proliferation rate was calculated using the equation: ln(cell concentration$_{72\,h}$/cell concentration$_{0\,h}$)/72. Relative proliferation rate was calculated by normalizing to rate of DMSO-treated cells.

May-Grunwald-Giemsa Cytospin Staining

MLL-AF9/Nras$^{G12D}$ leukemia cells were treated with 1 ug/ml doxycycline to induce TRMPV shRNA or with 100 nM JQ1 for 2 days. 50,000 cells were resuspend in 100 µl FACS buffer (5% FBS, 0.05% NaN3 in PBS) cytospun onto glass slides using Shandon Cytospin 2 Centrifuge at 500 rpm for 5 min. May-Grunwald (Sigma-Aldrich, #019K4368) and Giemsa (Sigma-Aldrich, #010M4338) stainings were performed according to manufacturer's protocols. Images were collected using a Zeiss Observer Microscope with a 40× objective.

BrdU Cell Cycle Analysis and Annexin V Flow Cytometry

BrdU incorporation assays were performed according to the manufacturer's protocol (BD, APC BrdU Flow Kit, #552598), where cells were pulsed with BrdU for 30 min. Cells were co-stained with 7-AAD or DAPI for DNA content measurement. For all conditional shRNA experiments, the analysis was gated on shRNA+/dsRed+ cell populations. Annexin V staining for apoptosis was performed according to manufacturer's protocol (BD Biosciences, APC Annexin V, #550475). In FIG. 4e, Annexin V gating was performed on live cells (FSC/SCC) and dsRed+/shRNA+ population, to ensure a clear readout of shRNA effects. This gating method selectively visualizes early apoptotic cells (Annexin V+, DAPI−), hence the apparent lack of accumulated dead cells (Annexin V+, DAPI+) in the plots. All analyses were performed using Flowjo software.

shRNA Experiments in Human AML Cell Lines

Human shRNAs were cloned into the TRMPV-Neo vector followed by retroviral transduction of THP-1 and MOLM- 13 cells, modified to express the Ecotropic Receptor and rtTA3 using the MSCV-RIEP plasmid (rtTA-ires-EcoR-PGK-Puro). Cells were selected with 400 μg/ml G418 for 1 week. Cells were treated 1 μg/ml doxycycline to induce shRNA expression. The relative change in dsRed+/shRNA+ cells using FACS was used to monitor growth inhibition. BrdU cell cycle analysis was performed as described above.

Adult Primary Leukemia Sample Analysis (FIG. 8)

Primary leukemic cells were obtained from peripheral blood (PB) or bone marrow (BM) aspirate samples of 12 (untreated) patients with AML at diagnosis (n=10) or at relapse (n=2). Diagnoses were established according to criteria provided by the French-American-British (FAB) Cooperative Study Group (Delhommeau et al., N Engl J Med 2009; 360:2289-301; and Ley et al., N Engl J Med 2010; 363:2424-33) and the World Health Organization (WHO) (Zuber et al., Nat Biotechnol 2011; 29:79-83). Mononuclear cells (MNC) were prepared using Ficoll and stored in liquid nitrogen until used. Informed consent was obtained prior to blood donation or BM puncture in each case. The study was approved by the Institutional Review Board (Ethics Committee) of the Medical University of Vienna. HL60 and MOLM13 cell lines were included as controls (German Collection of Microorganisms and Cell Cultures, DSMZ, Braunschweig, Germany). After thawing, the viability of AML cells ranged from 70% to 99% as assessed by trypan blue exclusion.

Primary cells (thawed MNC, 5-10×$10^4$ cells/well) and cell lines (1-5×$10^4$ cells/well) were cultured in 96-well microtiter plates (TPP, Trasadingen, Switzerland) in RPMI 1640 medium (PAA laboratories, Pasching, Austria) plus 10% fetal calf serum (FCS, Pasching) in the absence or presence of JQ1 (10-5,000 nM) at 37° C. (5% $CO_2$) for 48 hours. In select experiments, primary AML cells were incubated with JQ1 in the presence or absence of a cocktail of proliferation-inducing cytokines: recombinant human (rh) G-CSF, 100 ng/ml (Amgen, Thousand Oaks, Calif.), rhSCF, 100 ng/ml (Peprotech, Rocky Hill, N.J.), and rhIL-3, 100 ng/ml (Novartis, Vienna, Austria). After 48 hours, 0.5 μCi $^3$H-thymidine was added (16 hours). Cells were then harvested on filter membranes in a Filtermate 196 harvester (Packard Bioscience, Meriden, Conn.). Filters were air-dried, and the bound radioactivity was measured in a β-counter (TopCount NXT, Packard Bioscience). All experiments were performed in triplicates. Proliferation was calculated as percent of control (cells kept in control medium), and the inhibitory effects of JQ1 were expressed as $IC_{50}$ values. In 7/12 patients, drug-exposed cells were analyzed for morphologic signs of differentiation by Wright-Giemsa staining on cytospin slides.

Pediatric Primary Leukemia Sample Analysis (FIG. 9)

Diagnostic bone marrow samples were collected under institutional review board-approved protocols from newly diagnosed children with acute leukemia. Informed consent was obtained in accordance with the Helsinki protocol. At the time of collection, primary leukemic cells were enriched by density centrifugation using Ficoll-Paque PLUS (GE Healthcare, Piscataway, N.J.) and subsequently stored in liquid nitrogen. Vials of cryopreserved cells were thawed, resuspended in media, and live leukemic cells were enriched by density centrifugation. Cells were maintained in supplemented media with 20% fetal bovine serum. All leukemia cell cultures were incubated at 37° C. in 5% $CO_2$.

Primary leukemia samples were treated with dose ranges of JQ1 and vehicle control for 72 hours in 96 well plates. For the annexin binding assays, cells were harvested and stained with Annexin V-PE and 7-AAD (BD Pharmingen, San Diego, Calif.), read on a FACSCalibur, and analyzed with FlowJo software (Tree Star, Inc., Ashland, Oreg.). For the WST-1 assays, WST-1 reagent (Roche Diagnostics, Mannheim, Germany) was added to the culture medium (1:10 dilution) and absorbance was measured at 450 nm using a Bio-Rad model 680 microplate reader (Bio Rad Laboratories, Hercules, Calif.). WST-1 assays were performed in triplicate.

Primary leukemia samples were treated with 250 nM of JQ1 and vehicle control for 48 hours in 96 well plates. Cytospins were prepared at baseline, 24 hours and 48 hours and stained with Wright-Giemsa solution (Sigma-Aldrich, St. Louis, Mo.). Images were acquired using a Nikon Eclipse E600 microscope system.

Histological Analysis of Bone Marrow

Paraffin embedded sections were stained with hematoxylin & eosin (H&E). Photographs were taken on a Nikon Eclipse 80i microscope with a Nikon Digital Sight camera using NIS-Elements F2.30 software at a resolution of 2560× 1920. Using Adobe Photoshop CS2, images were re-sized and set at a resolution of 300 pixels/inch, autocontrast was applied, and unsharp mask was used to improve image clarity.

FACS Evaluation of Normal Hematopoiesis (FIG. 17)

Human shRNAs were cloned into the TRMPV-Neo vector followed by retroviral transduction of THP-1 and MOLM-13 cells, modified to express the Ecotropic Receptor and rtTA3 using the MSCV-RIEP plasmid (rtTA-ires-EcoR-PGK-Puro). Cells were selected with 400 μg/ml G418 for 1 week. Cells were treated 1 μg/ml doxycycline to induce shRNA expression. The relative change in dsRed+/shRNA+ cells using FACS was used to monitor growth inhibition. BrdU cell cycle analysis was performed as described above.

Expression Microarrays

Microarrays were performed through the CSHL microarray shared resource. RNA was isolated from 107 cells using RNeasy® Mini Kit (QIAGEN, Germantown, Md., #74104). RNA quality was assessed on an Agilent 2100 Bioanalyzer, RNA 6000 Pico Series II Chips (Agilent, Palo Alto, Calif., USA). Samples with assessed by a RIN score (2.0 or greater were passed). RNA was amplified by a modified Eberwine Technique, aRNA was then cDNA converted, using an Ambion® WT Expression Kit (Ambion, Austin, Tex.). Size distribution of aRNA and cDNA was assessed for 3' bias was performed on all samples using Agilent 2100 Bioanalyzer RNA 6000 Nano Series II Chips (Agilent, Palo Alto, Calif., USA). The cDNA was then fragmented and terminally labeled with biotin, using the Affymetrix® GeneChip WT Terminal Labeling kit (Affymetrix, Santa Clara, Calif.). Samples were then prepared for hybridization, hybridized, washed, and scanned according to the manufacturer's instructions on Mouse Gene ST 1.0 GeneChips (Affymetrix, Santa Clara, Calif.). Affymetrix Expression Console QC metrics were used to pass the image data. Raw data was processed by Affymetrix and Limma package in R based Bioconductor.

Heat map shown in FIG. 25 was made by using GenePattern software (Yokoyama et al., Cancer Cell 2008; 14:36-46). Briefly, RMA-processed microarray data was converted into log 2 scale. The selected lists of gene were then row-normalized and run through a Heat mapImage module on GenePattern.

Gene Set Enrichment Analysis (GSEA) analysis

Gene set enrichment analysis (Subramanian et al., Proc Natl Acad Sci USA 2005; 102:15545-50) were performed using GSEA v2.07 software (Broad Institute, Cambridge, Mass.) with 1000 phenotype permutation. Leukemia stem cell and Myc gene sets were obtained from indicated publications (Kim et al., *Cell* 2010; 143:313-24, Schuhmacher et al., *Nucleic Acids Res* 2001; 29:397-406, and Somervaille et al, *Cell Stem Cell* 2009; 4:129-40). Macrophage development gene set was obtained from the Ingenuity® Pathway Analysis (IPA) software (Ingenuity, Redwood City, Calif.). The Myb signature gene set (top 500 downregulated genes in shMyb MLL-AF9/Nras$^{G12D}$ leukemia cells) and MLL-AF9 signature gene set (top 500 downregulated genes in MLL-AF9 Tet-OFF MLL-AF9/Nras$^{G12D}$ leukemia cells) were obtained from microarray data from an unpublished study from the Lowe/Vakoc laboratories (Zuber et al, submitted).

Figure 19:
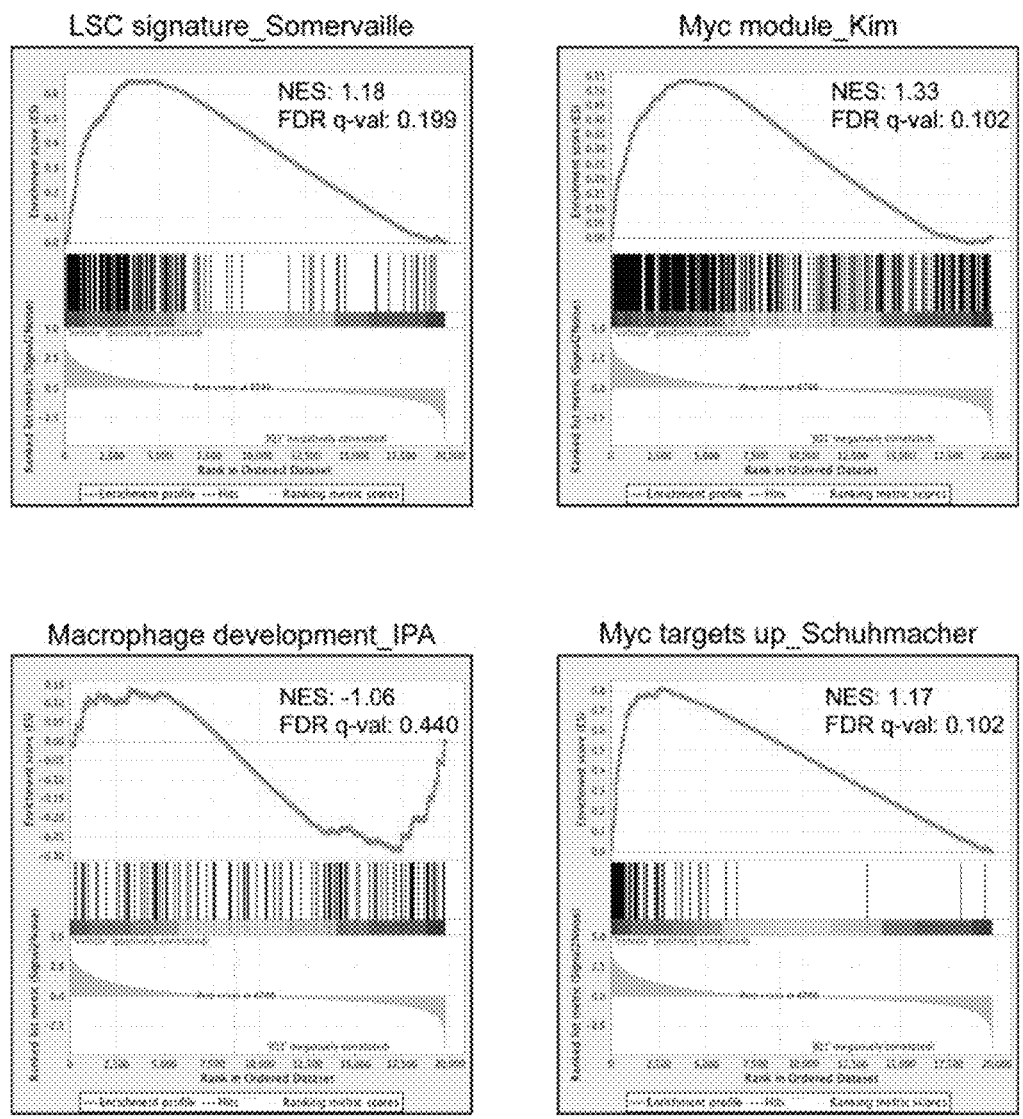
FIG. 19 includes GSEA plots showing that JQ1 triggers a similar pattern of gene expression changes in THP-1 human AML cells as seen in murine MLL-AF9/Nras$^{G12D}$ AML model. THP-1 cells were treated with 250 nM JQ1 for 48 hours prior to RNA collection. Expression arrays were performed using Affymetrix human gene ST 1.0 arrays. GSEA was performed to evaluate changes in macrophage, LSC, and Myc gene signatures upon Brd4 inhibition are shown.

In FIG. 19, to perform GSEA on human microarray data, the mouse gene sets were first converted into human gene names using bioDBNet dbWalk module (http://biodbnet.ab-cc.ncifcrf.gov/db/dbWalk.php) or manually using the NCBI database. A detailed description of GSEA methodology and interpretation is provided at (http://www.broadinstitute.org/gsea/doc/GSEAUserGuideFrame.html). In short, the Normalized Enrichment Score (NES) provides "the degree to which a gene set is overrepresented at the top or bottom of a ranked list of genes". The False Discovery Rate q-value (FDR q-val) "is the estimated probability that a gene set with a given NES represents a false positive finding." "In general, given the lack of coherence in most expression datasets and the relatively small number of gene sets being analyzed, an FDR cutoff of 25% is appropriate."

Chromatin Immunoprecipitation

ChIP assays were performed exactly as described (Filippakopoulos et al.). Crosslinking was performed with sequential EGS (Pierce)/formaldehyde (Nicodeme et al., *Nature* 2010; 468:1119-23). All results were quantified by qPCR performed using SYBR green (ABI) on an ABI 7900HT. Each IP signal was referenced to an input standard curve dilution series (IP/Input) to normalize for differences in starting cell number and for primer amplification efficiency.

RT-qPCR

RNA was prepared using Trizol® reagent (Invitrogen, Carlsbad, Calif.). cDNA synthesis was performed using gScript™ cDNA SuperMix (Quanta Biosciences, Gaithersburg, Md., #101414-106). Quantitative PCR (qPCR) analysis was performed on an ABI™ 7900HT with Sybr green (ABI, Carlsbad, Calif., #4364344). All signals were quantified using the delta-Ct method. All signals were normalized to the levels of GAPDH.

Primers

```
Mouse RT-qPCR primers (written 5' to 3')
Bim:
CCTGCTTTGCTCTCTCCATTTT      (SEQ ID NO: 6)
and

CCCCACCCCAGACACAAGTA        (SEQ ID NO: 7)

Brd4:
CCATGGACATGAGCACAATC        (SEQ ID NO: 8)
and

TGGAGAACATCAATCGGACA        (SEQ ID NO: 9)

Ccl4:
CCCGAGCAACACCATGAAG         (SEQ ID NO. 10)
and

CCACGAGCAAGAGGAGAGA         (SEQ ID NO. 11)

Cd74:
CCAACGCGACCTCATCTCTAA       (SEQ ID NO. 12)
and

AGGGCGGTTGCCCAGTA           (SEQ ID NO. 13)

Gapdh:
TTCACCACCATGGAGAAGGC        (SEQ ID NO: 14)
and

CCCTTTTGGCTCCACCCT          (SEQ ID NO: 15)

Hoxa7:
AGTTCAGGACCCGACAGGAA        (SEQ ID NO: 16)
and

CAGGTAGCGGTTGAAATGGAA       (SEQ ID NO: 17)

Hoxa9:
CCGAAAACAATGCCGAGAA         (SEQ ID NO: 18)
and

CCGGGTTATTGGGATCGAT         (SEQ ID NO: 19)

Itgax:
CCAGGTTGCCCAGTGAGAA         (SEQ ID NO: 20)
and

CTCAGATGGGCGGGTTCA          (SEQ ID NO: 21)

Mmp9:
CATTCGCGTGGATAAGGAGT        (SEQ ID NO: 22)
and

TCACACGCCAGAAGAATTTG        (SEQ ID NO: 23)

Myc:
GCCGATCAGCTGGAGATGA         (SEQ ID NO: 24)
and

GTCGTCAGGATCGCAGATGAAG      (SEQ ID NO: 25)

Human RT-qPCR primers (written 5' to 3')
BIM:
CACCGTGTCCATTACAGCAG        (SEQ ID NO: 26)
and

CTAAAATGCAGGAGGCCAAG        (SEQ ID NO: 27)

BRD4:
CCCCTCGTGGTGGTGAAG          (SEQ ID NO: 28)
and

GCTCGCTGCGGATGATG           (SEQ ID NO: 29)

GAPDH:
CCTGACCTGCCGTCTAGAAA        (SEQ ID NO: 30)
and

CTCCGACGCCTGCTTCAC          (SEQ ID NO: 31)

MYC:
AGGGATCGCGCTGAGTATAA        (SEQ ID NO: 32)
and

TGCCTCTCGCTGGAATTACT        (SEQ ID NO: 33)

Mouse Myc ChIP primers (written 5' to 3')
Myc -3.8 kb:
TGTGGCTTTCCTGTCCTTTT        (SEQ ID NO: 34)
and

AGGGGACATCCCCATTTTAC        (SEQ ID NO: 35)

Myc -2.2 kb:
ATTCATTTTCCCCATCCACA        (SEQ ID NO: 36)
and

TTGCAAAGAGGGGAGTAGA         (SEQ ID NO: 37)
```

-continued

| | | |
|---|---|---|
| Myc -1.9 kb: | | |
| ACAAATCCGAGAGCCACAAC | (SEQ ID NO: 38) | |
| and | | |
| AACACCAAGAGCCACCAATC | (SEQ ID NO: 39) | |
| Myc -1.8 kb: | | |
| GGTGGCTCTTGGTGTTTGAG | (SEQ ID NO: 40) | |
| and | | |
| TCGAGCTCATTGCACAATTC | (SEQ ID NO: 41) | |
| Myc -1.7 kb: | | |
| CAACTTTGAACAATGAGCACCT | (SEQ ID NO: 42) | |
| and | | |
| CTCTCACTGCTACCCGGTTT | (SEQ ID NO: 43) | |
| Myc -1.5 kb: | | |
| CGAGGAGTCCGGAATAAGAA | (SEQ ID NO: 44) | |
| and | | |
| TCTTTTGCTCTGTGCATTGG | (SEQ ID NO: 45) | |
| Myc -1 kb: | | |
| GCCTCTTGTGAAAACCGACT | (SEQ ID NO: 46) | |
| and | | |
| CCGGTCTACACCCCATACAC | (SEQ ID NO: 47) | |
| Myc + 1 kb: | | |
| TGGAATCCTGAGGTCTTTGG | (SEQ ID NO: 48) | |
| and | | |
| CAGAAATGCACCAAGCTGAA | (SEQ ID NO: 49) | |
| Myc + 1.5 kb: | | |
| CCCTCCCCTTTTATTTCGAG | (SEQ ID NO: 50) | |
| and | | |
| GCTTTTCTTTCCGATTGCTG | (SEQ ID NO: 51) | |
| Myc + 3.7 kb: | | |
| TGCTTTGGGTGTGTCTGAAG | (SEQ ID NO: 52) | |
| and | | |
| CTCCCAGAAAGGCAGAACAG | (SEQ ID NO: 53) | |

Antibodies

The anti-Brd4 antibody used for Western Blotting was a gift from Gerd Blobel and anti-Brd4 antibody used for ChIP was purchased from Sigma (#HPA015055). The anti-Myc antibody was purchased from Epitomics (#1472-1). Antibodies used in FACS: APC anti-mouse CD117/ckit (Biolegend #105811), APC anti-mouse CD11b (Biolegend #101211), Pacific Blue anti-mouse CD45.2 (Biolegend #109820), mouse hematopoietic lineage eFluor® 450 cocktail (ebioscience #88-7772-72), APC anti-mouse CD45R/B220 (Biolegend #103212), APC anti-mouse TER-119/Erythroid Cells (Biolegend #116212), APC anti-mouse Ly-6G/Gr-1 (ebioscience #17-5931), PE-Cy7 anti-mouse CD117/ckit (ebioscience #25-1171-82) and APC anti-mouse Sca-1 (ebioscience #17-5981-81). The anti-β-actin HRP antibody was purchased from Sigma (#A3854).

The anti-Brd4 antibody was a gift from Gerd Blobel. anti-Myc antibody (Epitomics, Burlingame, Calif., #1472-1). The antibodies used for FACS were purchased from Biolegend (San Diego, Calif.), APC anti-mouse CD117/ckit (#105811), APC anti-mouse CD11b (#101211) and Pacific Blue anti-mouse CD45.2 (#109820). The anti-β-actin HRP antibody was purchased from Sigma (#A3854).

Animal Studies

For conditional RNAi experiments in vivo, Tet-On MLL-AF9/Nras$^{G12D}$ leukemia cells were transduced with TRMPV-shRNA constructs. Leukemia cells were transplanted by tail-vein injection of $1\times10^6$ cells into sublethally (5.5 Gy) irradiated B6/SJL(CD45.1) recipient mice.

For whole body bioluminescent imaging mice were intraperitoneally injected with 50 mg/kg D-Luciferin (Goldbio, St. Louis, Mo.), and after 10 min. analyzed using an IVIS® Spectrum system (Caliper LifeSciences, Waltham, Mass.). Quantification was performed using Living Image software (Caliper LifeSciences) and standardized rectangular region of interests covering the mouse trunk and extremities.

For shRNA induction, animals were treated with doxycycline in both drinking water (2 mg/ml with 2% sucrose; Sigma-Aldrich, St. Louis, Mo.) and food (625 mg/kg, Harlan Laboratories, Indianapolis, Ind.). For JQ1 treatment trials, a stock of 100 mg/ml JQ1 in DMSO was 20-fold diluted by dropwise addition of a 10% 2-Hydroxypropyl-β-cyclodextrin (Sigma-Aldrich) carrier under vortexing, yielding a final concentration of 5 mg/ml. Mice transplanted with MLL-AF9/Nras$^{G12D}$ leukemia cells were injected intraperitoneally (IP) daily with freshly prepared carrier-diluted JQ1 (100 mg/kg) or 400 µl carrier (containing 5% DMSO).

Microarray Analysis

Expression microarrays were performed using Affymetrix ST 1.0 GeneChips. Pathway analysis was performed using GSEA v2.07 software with 1000 phenotype permutations (Subramanian et al.).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for treating a leukemia or related disorder in a subject, the method comprising administering to the subject an effective amount of at least one agent that inhibits Brd4 or a derivative thereof represented by the following structural formulas

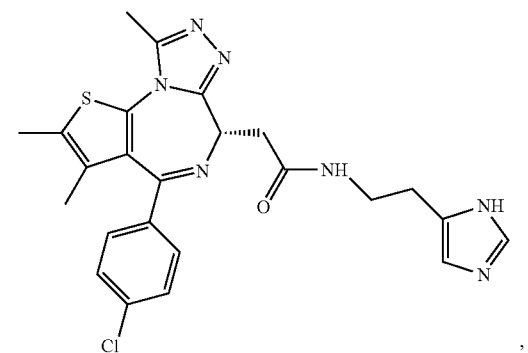

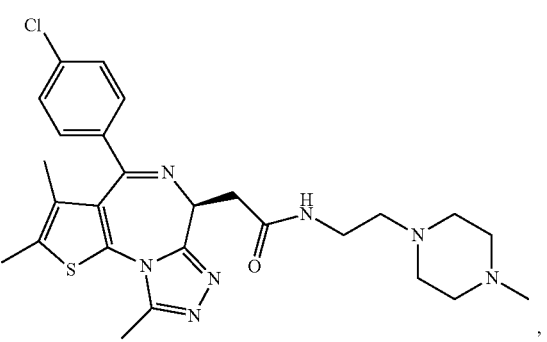

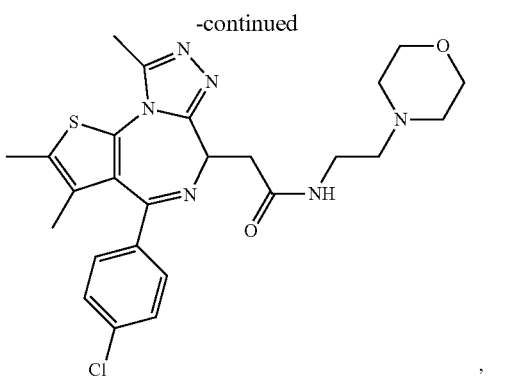

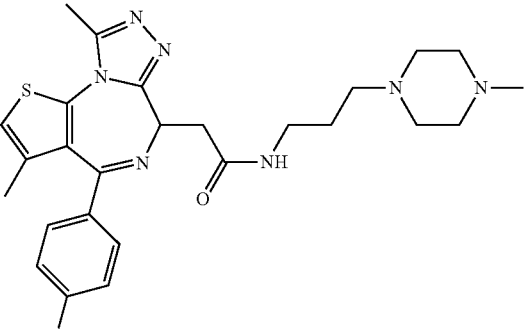

or a pharmaceutically acceptable salt thereof.

2. The method of claim 1, wherein the leukemia is acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myeloproliferative disorders or Myelodysplastic syndromes.

3. A method for reducing the growth, proliferation or survival of a leukemic cell, the method comprising contacting the cell with an effective amount of at least one agent that inhibits Brd4 or a derivative thereof,
represented by the following structural formulas

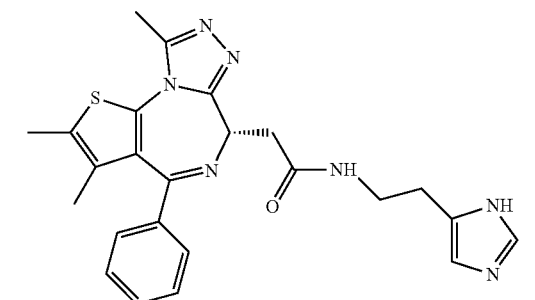

,

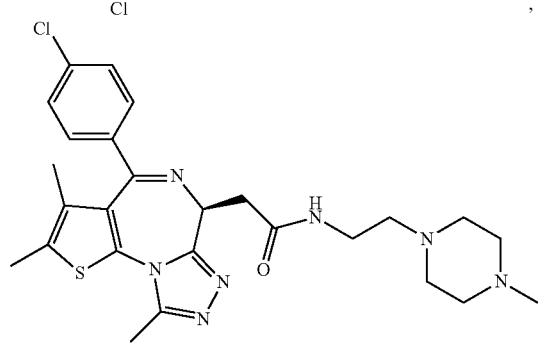

,

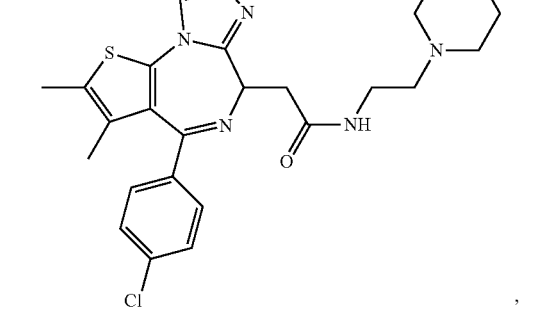

,

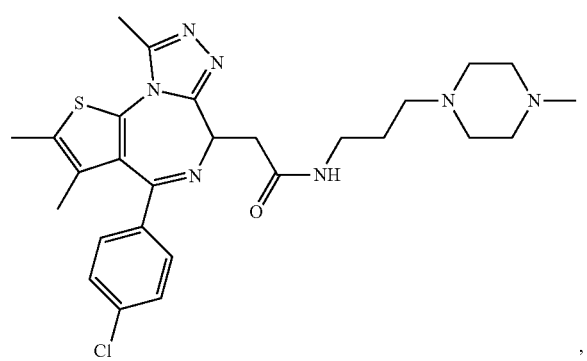

, or a pharmaceutically acceptable salt thereof,
thereby reducing the growth, proliferation or survival of a leukemic cell.

4. A method of inducing cell death or terminal differentiation in a leukemic cell, the method comprising contacting the cell with an effective amount of at least one agent that inhibits Brd4 or a derivative thereof, represented by the following structural formulas

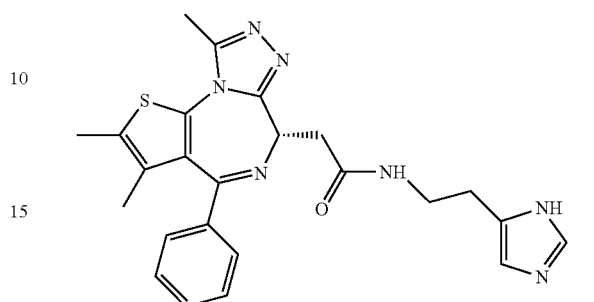

,

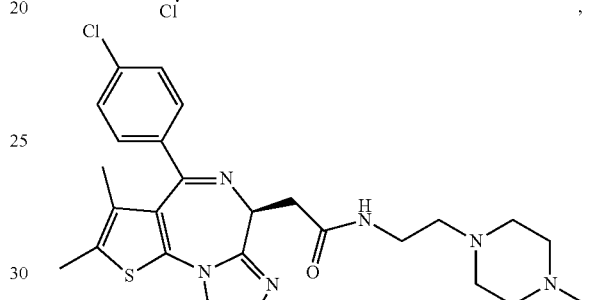

,

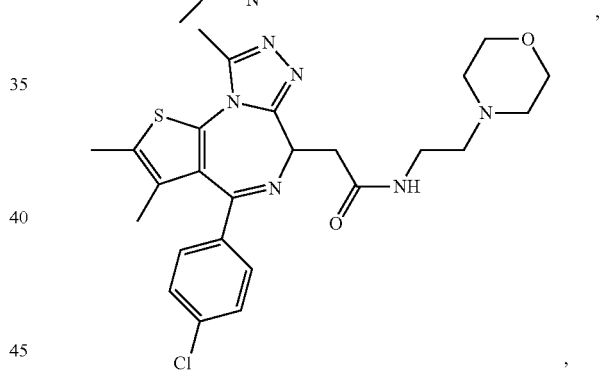

, and

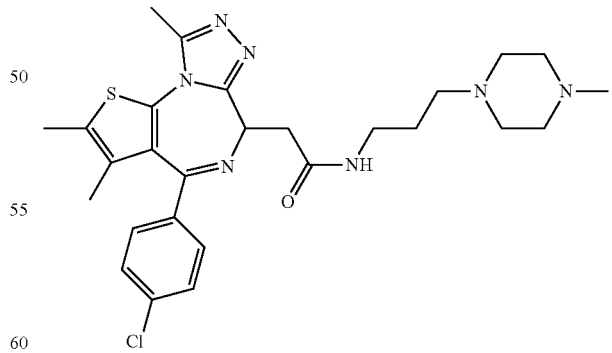

, or a pharmaceutically acceptable salt thereof,
thereby inducing cell death or terminal differentiation in the leukemic cell.

5. The method of claim 3 or 4, wherein the cell is in a subject.

6. The method of claim 3 or 4, wherein the cell is derived from an acute myeloid leukemia (AML), Chronic Lymphocydic Leukemia (CLL), Acute Lymphocytic Leukemia (ALL), Chronic Myeloid Leukemia (CML), Chronic Myelomonocytic Leukemia (CMML), Eosinophilic Leukemia, Hairy Cell Leukemia, Hodgkin Lymphoma, Multiple Myeloma, Non-Hodgkin Lymphoma, Myelodysplasia or Myeloproliferative Disorders.

7. A method of treating acute myeloid leukemia in a subject, the method comprising administering to a subject in need thereof an effective amount of at least one agent that inhibits Brd4, represented by the following structural formulas

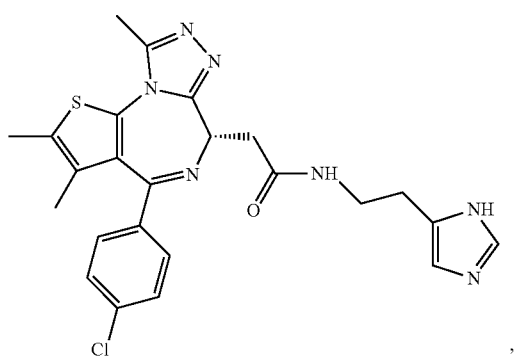

,

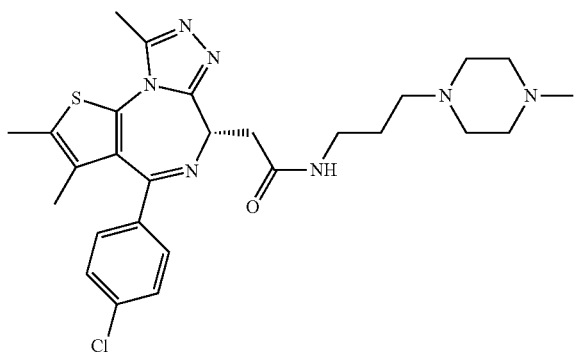

, or a pharmaceutically acceptable salt thereof,
thereby treating acute myeloid leukemia in a subject.

8. The method of claim 7, wherein the subject is a mammal.

9. The method of claim 8, wherein the subject is a human patient.

10. The method of claim 9, wherein the human patient is an adult.

11. The method of claim 9, wherein the human patient is a child.

12. The method of claim 7, wherein the method reduces the growth, proliferation or survival of a leukemic cell in a subject.

13. A method of any one of claim 1, 3, 4 or 7, wherein the at least one agent is represented by any one of the following structural formulas:

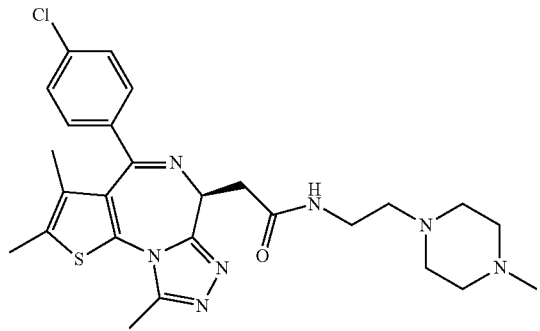

,

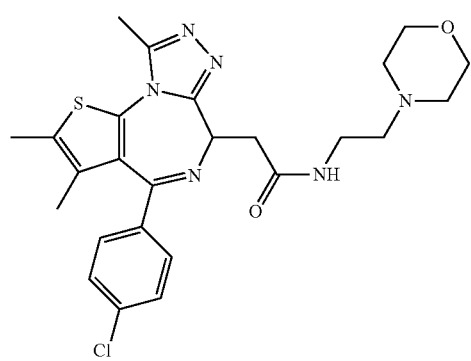

and

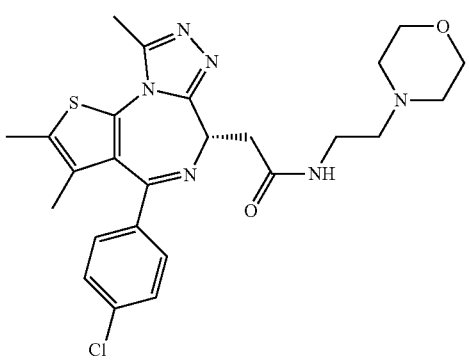

or

.

* * * * *

SEQUENCE LISTING

<160> NUMBER OF SEQ ID NOS: 53

<210> SEQ ID NO 1
<211> LENGTH: 801
<212> TYPE: PRT
<213> ORGANISM: Homo sapiens

<400> SEQUENCE: 1

-continued

```
Met Leu Gln Asn Val Thr Pro His Asn Lys Leu Pro Gly Glu Gly Asn
 1               5                  10                  15

Ala Gly Leu Leu Gly Leu Gly Pro Glu Ala Ala Pro Gly Lys Arg
             20                  25                  30

Ile Arg Lys Pro Ser Leu Leu Tyr Glu Gly Phe Glu Ser Pro Thr Met
             35                  40                  45

Ala Ser Val Pro Ala Leu Gln Leu Thr Pro Ala Asn Pro Pro Pro
 50                  55                  60

Glu Val Ser Asn Pro Lys Pro Gly Arg Val Thr Asn Gln Leu Gln
 65                  70                  75                  80

Tyr Leu His Lys Val Val Met Lys Ala Leu Trp Lys His Gln Phe Ala
                 85                  90                  95

Trp Pro Phe Arg Gln Pro Val Asp Ala Val Lys Leu Gly Leu Pro Asp
                 100                 105                 110

Tyr His Lys Ile Ile Lys Gln Pro Met Asp Met Gly Thr Ile Lys Arg
             115                 120                 125

Arg Leu Glu Asn Asn Tyr Tyr Trp Ala Ala Ser Glu Cys Met Gln Asp
     130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                 165                 170                 175

Val Ala Ser Met Pro Gln Glu Glu Gln Leu Val Val Thr Ile Pro
             180                 185                 190

Lys Asn Ser His Lys Lys Gly Ala Lys Leu Ala Ala Leu Gln Gly Ser
             195                 200                 205

Val Thr Ser Ala His Gln Val Pro Ala Val Ser Ser Val Ser His Thr
     210                 215                 220

Ala Leu Tyr Thr Pro Pro Glu Ile Pro Thr Thr Val Leu Asn Ile
225                 230                 235                 240

Pro His Pro Ser Val Ile Ser Ser Pro Leu Leu Lys Ser Leu His Ser
                 245                 250                 255

Ala Gly Pro Pro Leu Leu Ala Val Thr Ala Ala Pro Pro Ala Gln Pro
             260                 265                 270

Leu Ala Lys Lys Lys Gly Val Lys Arg Lys Ala Asp Thr Thr Thr Pro
             275                 280                 285

Thr Pro Thr Ala Ile Leu Ala Pro Gly Ser Pro Ala Ser Pro Pro Gly
     290                 295                 300

Ser Leu Glu Pro Lys Ala Ala Arg Leu Pro Pro Met Arg Arg Glu Ser
305                 310                 315                 320

Gly Arg Pro Ile Lys Pro Pro Arg Lys Asp Leu Pro Asp Ser Gln Gln
                 325                 330                 335

Gln His Gln Ser Ser Lys Lys Gly Lys Leu Ser Glu Gln Leu Lys His
             340                 345                 350

Cys Asn Gly Ile Leu Lys Glu Leu Leu Ser Lys Lys His Ala Ala Tyr
             355                 360                 365

Ala Trp Pro Phe Tyr Lys Pro Val Asp Ala Ser Ala Leu Gly Leu His
             370                 375                 380

Asp Tyr His Asp Ile Ile Lys His Pro Met Asp Leu Ser Thr Val Lys
385                 390                 395                 400

Arg Lys Met Glu Asn Arg Asp Tyr Arg Asp Ala Gln Glu Phe Ala Ala
                 405                 410                 415

Asp Val Arg Leu Met Phe Ser Asn Cys Tyr Lys Tyr Asn Pro Pro Asp
```

```
                420                 425                 430
His Asp Val Val Ala Met Ala Arg Lys Leu Gln Asp Val Phe Glu Phe
            435                 440                 445
Arg Tyr Ala Lys Met Pro Asp Glu Pro Leu Glu Pro Gly Pro Leu Pro
        450                 455                 460
Val Ser Thr Ala Met Pro Pro Gly Leu Ala Lys Ser Ser Ser Glu Ser
465                 470                 475                 480
Ser Ser Glu Glu Ser Ser Ser Glu Ser Ser Glu Glu Glu Glu
                485                 490                 495
Glu Asp Glu Glu Asp Glu Glu Glu Glu Ser Glu Ser Ser Asp Ser
            500                 505                 510
Glu Glu Glu Arg Ala His Arg Leu Ala Glu Leu Gln Glu Gln Leu Arg
        515                 520                 525
Ala Val His Glu Gln Leu Ala Ala Leu Ser Gln Gly Pro Ile Ser Lys
        530                 535                 540
Pro Lys Arg Lys Arg Glu Lys Glu Lys Lys Lys Arg Lys Ala
545                 550                 555                 560
Glu Lys His Arg Gly Arg Ala Gly Ala Asp Glu Asp Lys Gly Pro
            565                 570                 575
Arg Ala Pro Arg Pro Gln Pro Lys Ser Lys Lys Ala Ser Gly
        580                 585                 590
Ser Gly Gly Gly Ser Ala Ala Leu Gly Pro Ser Gly Phe Gly Pro Ser
        595                 600                 605
Gly Gly Ser Gly Thr Lys Leu Pro Lys Ala Thr Lys Thr Ala Pro
        610                 615                 620
Pro Ala Leu Pro Thr Gly Tyr Asp Ser Glu Glu Glu Glu Ser Arg
625                 630                 635                 640
Pro Met Ser Tyr Asp Glu Lys Arg Gln Leu Ser Leu Asp Ile Asn Lys
            645                 650                 655
Leu Pro Gly Glu Lys Leu Gly Arg Val Val His Ile Ile Gln Ala Arg
            660                 665                 670
Glu Pro Ser Leu Arg Asp Ser Asn Pro Glu Glu Ile Glu Ile Asp Phe
        675                 680                 685
Glu Thr Leu Lys Pro Ser Thr Leu Arg Glu Leu Glu Arg Tyr Val Leu
        690                 695                 700
Ser Cys Leu Arg Lys Lys Pro Arg Lys Pro Tyr Thr Ile Lys Lys Pro
705                 710                 715                 720
Val Gly Lys Thr Lys Glu Glu Leu Ala Leu Glu Lys Lys Arg Glu Leu
            725                 730                 735
Glu Lys Arg Leu Gln Asp Val Ser Gly Gln Leu Asn Ser Thr Lys Lys
            740                 745                 750
Pro Pro Lys Lys Ala Asn Glu Lys Thr Glu Ser Ser Ser Ala Gln Gln
        755                 760                 765
Val Ala Val Ser Arg Leu Ser Ala Ser Ser Ser Ser Asp Ser Ser
        770                 775                 780
Ser Ser Ser Ser Ser Ser Ser Ser Asp Thr Ser Asp Ser Asp Ser
785                 790                 795                 800
Gly

<210> SEQ ID NO 2
<211> LENGTH: 726
<212> TYPE: PRT
<213> ORGANISM: Homo sapiens
```

```
<400> SEQUENCE: 2

Met Ser Thr Ala Thr Val Ala Pro Ala Gly Ile Pro Ala Thr Pro
  1               5                  10                  15

Gly Pro Val Asn Pro Pro Pro Glu Val Ser Asn Pro Ser Lys Pro
             20                  25                  30

Gly Arg Lys Thr Asn Gln Leu Gln Tyr Met Gln Asn Val Val Lys
         35                  40                  45

Thr Leu Trp Lys His Gln Phe Ala Trp Pro Phe Tyr Gln Pro Val Asp
 50                  55                  60

Ala Ile Lys Leu Asn Leu Pro Asp Tyr His Lys Ile Ile Lys Asn Pro
 65                  70                  75                  80

Met Asp Met Gly Thr Ile Lys Lys Arg Leu Glu Asn Asn Tyr Tyr Trp
                 85                  90                  95

Ser Ala Ser Glu Cys Met Gln Asp Phe Asn Thr Met Phe Thr Asn Cys
            100                 105                 110

Tyr Ile Tyr Asn Lys Pro Thr Asp Asp Ile Val Leu Met Ala Gln Ala
        115                 120                 125

Leu Glu Lys Ile Phe Leu Gln Lys Val Ala Gln Met Pro Gln Glu Glu
    130                 135                 140

Val Glu Leu Leu Pro Pro Ala Pro Lys Gly Lys Gly Arg Lys Pro Ala
145                 150                 155                 160

Ala Gly Ala Gln Ser Ala Gly Thr Gln Gln Val Ala Ala Val Ser Ser
                165                 170                 175

Val Ser Pro Ala Thr Pro Phe Gln Ser Val Pro Pro Thr Val Ser Gln
            180                 185                 190

Thr Pro Val Ile Ala Ala Thr Pro Val Pro Thr Ile Thr Ala Asn Val
        195                 200                 205

Thr Ser Val Pro Val Pro Pro Ala Ala Pro Pro Pro Pro Ala Thr
    210                 215                 220

Pro Ile Val Pro Val Val Pro Thr Pro Pro Val Val Lys Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Pro Leu Ser Asp Pro Lys Gln
                260                 265                 270

Ala Lys Val Val Ala Arg Arg Glu Ser Gly Gly Arg Pro Ile Lys Pro
            275                 280                 285

Pro Lys Lys Asp Leu Glu Asp Gly Glu Val Pro Gln His Ala Gly Lys
        290                 295                 300

Lys Gly Lys Leu Ser Glu His Leu Arg Tyr Cys Asp Ser Ile Leu Arg
305                 310                 315                 320

Glu Met Leu Ser Lys Lys His Ala Ala Tyr Ala Trp Pro Phe Tyr Lys
                325                 330                 335

Pro Val Asp Ala Glu Ala Leu Glu Leu His Asp Tyr His Asp Ile Ile
            340                 345                 350

Lys His Pro Met Asp Leu Ser Thr Val Lys Arg Lys Met Asp Gly Arg
        355                 360                 365

Glu Tyr Pro Asp Ala Gln Gly Phe Ala Ala Asp Val Arg Leu Met Phe
    370                 375                 380

Ser Asn Cys Tyr Lys Tyr Asn Pro Pro Asp His Glu Val Val Ala Met
385                 390                 395                 400

Ala Arg Lys Leu Gln Asp Val Phe Glu Met Arg Phe Ala Lys Met Pro
                405                 410                 415
```

```
Asp Glu Pro Val Glu Ala Pro Ala Leu Pro Ala Pro Ala Ala Pro Met
            420                 425                 430

Val Ser Lys Gly Ala Glu Ser Arg Ser Ser Glu Ser Ser Ser
            435                 440             445

Asp Ser Gly Ser Ser Asp Ser Glu Glu Arg Ala Thr Arg Leu Ala
            450                 455                 460

Glu Leu Gln Glu Gln Leu Lys Ala Val His Glu Gln Leu Ala Ala Leu
465                 470                 475                 480

Ser Gln Ala Pro Val Asn Lys Pro Lys Lys Lys Glu Lys Lys Glu
            485                 490                 495

Lys Glu Lys Lys Lys Asp Lys Glu Lys Glu Lys Glu Lys His Lys
            500                 505                 510

Val Lys Ala Glu Glu Lys Lys Ala Lys Val Ala Pro Pro Ala Lys
            515                 520                 525

Gln Ala Gln Gln Lys Lys Ala Pro Ala Lys Lys Ala Asn Ser Thr Thr
            530                 535                 540

Thr Ala Gly Arg Gln Leu Lys Lys Gly Gly Lys Gln Ala Ser Ala Ser
545                 550                 555                 560

Tyr Asp Ser Glu Glu Glu Glu Gly Leu Pro Met Ser Tyr Asp Glu
            565                 570                 575

Lys Arg Gln Leu Ser Leu Asp Ile Asn Arg Leu Pro Gly Glu Lys Leu
            580                 585                 590

Gly Arg Val Val His Ile Ile Gln Ser Arg Glu Pro Ser Leu Arg Asp
            595                 600                 605

Ser Asn Pro Asp Glu Ile Glu Ile Asp Phe Glu Thr Leu Lys Pro Thr
            610                 615                 620

Thr Leu Arg Glu Leu Glu Arg Tyr Val Lys Ser Cys Leu Gln Lys Lys
625                 630                 635                 640

Gln Arg Lys Pro Phe Ser Ala Ser Gly Lys Lys Gln Ala Ala Lys Ser
            645                 650                 655

Lys Glu Glu Leu Ala Gln Glu Lys Lys Lys Glu Leu Glu Lys Arg Leu
            660                 665                 670

Gln Asp Val Ser Gly Gln Leu Ser Ser Ser Lys Lys Pro Ala Arg Lys
            675                 680                 685

Glu Lys Pro Gly Ser Ala Pro Ser Gly Gly Pro Ser Arg Leu Ser Ser
            690                 695                 700

Ser Ser Ser Ser Glu Ser Gly Ser Ser Ser Ser Gly Ser Ser Ser
705                 710                 715                 720

Asp Ser Ser Asp Ser Glu
            725

<210> SEQ ID NO 3
<211> LENGTH: 722
<212> TYPE: PRT
<213> ORGANISM: Homo sapiens

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
                20                  25                  30

Ala Gln Pro Gln Pro Ala Asn Ala Ala Ser Thr Asn Pro Pro Pro
            35                  40                  45

Glu Thr Ser Asn Pro Asn Lys Pro Lys Arg Gln Thr Asn Gln Leu Gln
```

-continued

```
                50                  55                  60
Tyr Leu Leu Arg Val Val Leu Lys Thr Leu Trp Lys His Gln Phe Ala
 65                  70                  75                  80

Trp Pro Phe Gln Gln Pro Val Asp Ala Val Lys Leu Asn Leu Pro Asp
                 85                  90                  95

Tyr Tyr Lys Ile Ile Lys Thr Pro Met Asp Met Gly Thr Ile Lys Lys
                100                 105                 110

Arg Leu Glu Asn Asn Tyr Tyr Trp Asn Ala Gln Glu Cys Ile Gln Asp
                115                 120                 125

Phe Asn Thr Met Phe Thr Asn Cys Tyr Ile Tyr Asn Lys Pro Gly Asp
            130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175

Lys Gly Arg Gly Arg Gly Arg Lys Glu Thr Gly Thr Ala Lys Pro Gly
                180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr Pro His Pro
            210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                245                 250                 255

Pro Gln Pro Pro Pro Ala Pro Ala Pro Gln Pro Val Gln Ser His Pro
                260                 265                 270

Pro Ile Ile Ala Ala Thr Pro Gln Pro Val Lys Thr Lys Lys Gly Val
            275                 280                 285

Lys Arg Lys Ala Asp Thr Thr Thr Pro Thr Thr Ile Asp Pro Ile His
            290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
            355                 360                 365

His Ala Ala Tyr Ala Trp Pro Phe Tyr Lys Pro Val Asp Val Glu Ala
            370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
                420                 425                 430

Asn Pro Pro Asp His Glu Val Val Ala Met Ala Arg Lys Leu Gln Asp
            435                 440                 445

Val Phe Glu Met Arg Phe Ala Lys Met Pro Asp Glu Pro Glu Glu Pro
            450                 455                 460

Val Val Ala Val Ser Ser Pro Ala Val Pro Pro Pro Thr Lys Val Val
465                 470                 475                 480
```

```
Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
                500                 505                 510

Glu Leu Gln Glu Gln Leu Lys Ala Val His Glu Gln Leu Ala Ala Leu
            515                 520                 525

Ser Gln Pro Gln Gln Asn Lys Pro Lys Lys Glu Lys Asp Lys Lys
        530                 535                 540

Glu Lys Lys Lys Glu Lys His Lys Arg Lys Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
            580                 585                 590

Ser Lys Pro Pro Pro Thr Tyr Glu Ser Glu Glu Glu Asp Lys Cys Lys
        595                 600                 605

Pro Met Ser Tyr Glu Glu Lys Arg Gln Leu Ser Leu Asp Ile Asn Lys
        610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
                660                 665                 670

Ser Cys Leu Arg Lys Lys Arg Lys Pro Gln Ala Glu Lys Val Asp Val
            675                 680                 685

Ile Ala Gly Ser Ser Lys Met Lys Gly Phe Ser Ser Ser Glu Ser Glu
690                 695                 700

Ser Ser Ser Glu Ser Ser Ser Asp Ser Glu Asp Ser Glu Thr Gly
705                 710                 715                 720

Pro Ala

<210> SEQ ID NO 4
<211> LENGTH: 947
<212> TYPE: PRT
<213> ORGANISM: Homo sapiens

<400> SEQUENCE: 4

Met Ser Leu Pro Ser Arg Gln Thr Ala Ile Ile Val Asn Pro Pro Pro
  1               5                  10                  15

Pro Glu Tyr Ile Asn Thr Lys Lys Asn Gly Arg Leu Thr Asn Gln Leu
                20                  25                  30

Gln Tyr Leu Gln Lys Val Val Leu Lys Asp Leu Trp Lys His Ser Phe
            35                  40                  45

Ser Trp Pro Phe Gln Arg Pro Val Asp Ala Val Lys Leu Gln Leu Pro
        50                  55                  60

Asp Tyr Tyr Thr Ile Ile Lys Asn Pro Met Asp Leu Asn Thr Ile Lys
65                  70                  75                  80

Lys Arg Leu Glu Asn Lys Tyr Tyr Ala Lys Ala Ser Glu Cys Ile Glu
                85                  90                  95

Asp Phe Asn Thr Met Phe Ser Asn Cys Tyr Leu Tyr Asn Lys Pro Gly
            100                 105                 110

Asp Asp Ile Val Leu Met Ala Gln Ala Leu Glu Lys Leu Phe Met Gln
        115                 120                 125
```

```
Lys Leu Ser Gln Met Pro Gln Glu Glu Gln Val Val Gly Val Lys Glu
    130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Glu Lys Val Phe Lys Gln Gln Glu
                165                 170                 175

Ile Pro Ser Val Phe Pro Lys Thr Ser Ile Ser Pro Leu Asn Val Val
                180                 185                 190

Gln Gly Ala Ser Val Asn Ser Ser Gln Thr Ala Ala Gln Val Thr
            195                 200                 205

Lys Gly Val Lys Arg Lys Ala Asp Thr Thr Pro Ala Thr Ser Ala
    210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
                245                 250                 255

Ser Gln Gln Gln Tyr Asn Val Val Lys Thr Val Lys Val Thr Glu Gln
                260                 265                 270

Leu Arg His Cys Ser Glu Ile Leu Lys Glu Met Leu Ala Lys Lys His
        275                 280                 285

Phe Ser Tyr Ala Trp Pro Phe Tyr Asn Pro Val Asp Val Asn Ala Leu
    290                 295                 300

Gly Leu His Asn Tyr Tyr Asp Val Val Lys Asn Pro Met Asp Leu Gly
305                 310                 315                 320

Thr Ile Lys Glu Lys Met Asp Asn Gln Glu Tyr Lys Asp Ala Tyr Lys
                325                 330                 335

Phe Ala Ala Asp Val Arg Leu Met Phe Met Asn Cys Tyr Lys Tyr Asn
                340                 345                 350

Pro Pro Asp His Glu Val Val Thr Met Ala Arg Met Leu Gln Asp Val
                355                 360                 365

Phe Glu Thr His Phe Ser Lys Ile Pro Ile Glu Pro Val Glu Ser Met
    370                 375                 380

Pro Leu Cys Tyr Ile Lys Thr Asp Ile Thr Glu Thr Thr Gly Arg Glu
385                 390                 395                 400

Asn Thr Asn Glu Ala Ser Ser Glu Gly Asn Ser Ser Asp Asp Ser Glu
                405                 410                 415

Asp Glu Arg Val Lys Arg Leu Ala Lys Leu Gln Glu Gln Leu Lys Ala
                420                 425                 430

Val His Gln Gln Leu Gln Val Leu Ser Gln Val Pro Phe Arg Lys Leu
    435                 440                 445

Asn Lys Lys Lys Glu Lys Ser Lys Lys Glu Lys Lys Lys Glu Lys Val
450                 455                 460

Asn Asn Ser Asn Glu Asn Pro Arg Lys Met Cys Glu Gln Met Arg Leu
465                 470                 475                 480

Lys Glu Lys Ser Lys Arg Asn Gln Pro Lys Arg Lys Gln Gln Phe
                485                 490                 495

Ile Gly Leu Lys Ser Glu Asp Glu Asp Asn Ala Lys Pro Met Asn Tyr
                500                 505                 510

Asp Glu Lys Arg Gln Leu Ser Leu Asn Ile Asn Lys Leu Pro Gly Asp
        515                 520                 525

Lys Leu Gly Arg Val Val His Ile Ile Gln Ser Arg Glu Pro Ser Leu
    530                 535                 540
```

```
Ser Asn Ser Asn Pro Asp Glu Ile Glu Ile Asp Phe Glu Thr Leu Lys
545                 550                 555                 560

Ala Ser Thr Leu Arg Glu Leu Glu Lys Tyr Val Ser Ala Cys Leu Arg
            565                 570                 575

Lys Arg Pro Leu Lys Pro Pro Ala Lys Lys Ile Met Met Ser Lys Glu
        580                 585                 590

Glu Leu His Ser Gln Lys Lys Gln Glu Leu Glu Lys Arg Leu Leu Asp
    595                 600                 605

Val Asn Asn Gln Leu Asn Ser Arg Lys Arg Gln Thr Lys Ser Asp Lys
610                 615                 620

Thr Gln Pro Ser Lys Ala Val Glu Asn Val Ser Arg Leu Ser Glu Ser
625                 630                 635                 640

Ser Ser Ser Ser Ser Ser Ser Glu Ser Glu Ser Ser Ser Ser Ser Asp
            645                 650                 655

Leu Ser Ser Ser Asp Ser Ser Asp Ser Glu Ser Glu Met Phe Pro Lys
            660                 665                 670

Phe Thr Glu Val Lys Pro Asn Asp Ser Pro Ser Lys Gly Asn Val Lys
        675                 680                 685

Lys Met Lys Asn Glu Cys Ile Leu Pro Glu Gly Arg Thr Gly Val Thr
690                 695                 700

Gln Ile Gly Tyr Cys Val Gln Asp Thr Thr Ser Ala Asn Thr Thr Leu
705                 710                 715                 720

Val His Gln Thr Thr Pro Ser His Val Met Pro Pro Asn His His Gln
                725                 730                 735

Leu Ala Phe Asn Tyr Gln Glu Leu Glu His Leu Gln Thr Val Lys Asn
            740                 745                 750

Ile Ser Pro Leu Gln Ile Leu Pro Pro Ser Gly Asp Ser Glu Gln Leu
        755                 760                 765

Ser Asn Gly Ile Thr Val Met His Pro Ser Gly Asp Ser Asp Thr Thr
770                 775                 780

Met Leu Glu Ser Glu Cys Gln Ala Pro Val Gln Lys Asp Ile Lys Ile
785                 790                 795                 800

Lys Asn Ala Asp Ser Trp Lys Ser Leu Gly Lys Pro Val Lys Pro Ser
                805                 810                 815

Gly Val Met Lys Ser Ser Asp Glu Leu Phe Asn Gln Phe Arg Lys Ala
            820                 825                 830

Ala Ile Glu Lys Glu Val Lys Ala Arg Thr Gln Glu Leu Ile Arg Lys
        835                 840                 845

His Leu Glu Gln Asn Thr Lys Glu Leu Lys Ala Ser Gln Glu Asn Gln
850                 855                 860

Arg Asp Leu Gly Asn Gly Leu Thr Val Glu Ser Phe Ser Asn Lys Ile
865                 870                 875                 880

Gln Asn Lys Cys Ser Gly Glu Glu Lys Glu His Gln Gln Ser Ser
                885                 890                 895

Glu Ala Gln Asp Lys Ser Lys Leu Trp Leu Leu Lys Arg Asp Leu
            900                 905                 910

Ala Arg Gln Lys Glu Gln Glu Arg Arg Arg Glu Ala Met Val Gly
        915                 920                 925

Thr Ile Asp Met Thr Leu Gln Ser Asp Ile Met Thr Met Phe Glu Asn
            930                 935                 940

Asn Phe Asp
945
```

```
<210> SEQ ID NO 5
<211> LENGTH: 29
<212> TYPE: DNA
<213> ORGANISM: Artificial Sequence
<220> FEATURE:
<223> OTHER INFORMATION: Synthetic primer

<400> SEQUENCE: 5 tagcccttg aattccgagg cagtaggca                                   29

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
cctgctttgc tctctccatt tt                                         22

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ccccacccca gacacaagta                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccatggacat gagcacaatc                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
tggagaacat caatcggaca                                            20

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
cccgagcaac accatgaag                                             19

<210> SEQ ID NO 11
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 11
ccacgagcaa gaggagagag a                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ccaacgcgac ctcatctcta a                                              21

<210> SEQ ID NO 13
<211> LENGTH: 17
<212> TYPE: DNA
<213> ORGANISM: Artificial Sequence
<220> FEATURE:
<223> OTHER INFORMATION: Synthetic primer

<400> SEQUENCE: 13
agggcggttg cccagta                                                   17

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ttcaccacca tggagaaggc                                                20

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15 ccctttggc tccaccct                                                   18

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
agttcaggac ccgacaggaa                                                20

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
caggtagcgg ttgaaatgga a                                              21

<210> SEQ ID NO 18
<211> LENGTH: 19
```

```
<212> TYPE: DNA
<213> ORGANISM: Artificial Sequence
<220> FEATURE:
<223> OTHER INFORMATION: Synthetic primer

<400> SEQUENCE: 18
ccgaaaacaa tgccgagaa                                                   19

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
ccgggttatt gggatcgat                                                   19

<210> SEQ ID NO 20
<211> LENGTH: 19
<212> TYPE: DNA
<213> ORGANISM: Artificial Sequence
<220> FEATURE:
<223> OTHER INFORMATION: Synthetic primer

<400> SEQUENCE: 20
ccaggttgcc cagtgagaa                                                   19

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
ctcagatggg cgggttca                                                    18

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
cattcgcgtg gataaggagt                                                  20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tcacacgcca gaagaatttg                                                  20

<210> SEQ ID NO 24
<211> LENGTH: 19
<212> TYPE: DNA
<213> ORGANISM: Artificial Sequence
<220> FEATURE:
<223> OTHER INFORMATION: Synthetic primer

<400> SEQUENCE: 24
```

```
gccgatcagc tggagatga                                                        19

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
gtcgtcagga tcgcagatga ag                                                    22

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
caccgtgtcc attacagcag                                                       20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
ctaaaatgca ggaggccaag                                                       20

<210> SEQ ID NO 28
<211> LENGTH: 18
<212> TYPE: DNA
<213> ORGANISM: Artificial Sequence
<220> FEATURE:
<223> OTHER INFORMATION: Synthetic primer

<400> SEQUENCE: 28
cccctcgtgg tggtgaag                                                         18

<210> SEQ ID NO 29
<211> LENGTH: 17
<212> TYPE: DNA
<213> ORGANISM: Artificial Sequence
<220> FEATURE:
<223> OTHER INFORMATION: Synthetic primer

<400> SEQUENCE: 29
gctcgctgcg gatgatg                                                          17

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
cctgacctgc cgtctagaaa                                                       20

<210> SEQ ID NO 31
<211> LENGTH: 18
<212> TYPE: DNA
<213> ORGANISM: Artificial Sequence
```

```
<220> FEATURE:
<223> OTHER INFORMATION: Synthetic primer

<400> SEQUENCE: 31
ctccgacgcc tgcttcac                                              18

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
agggatcgcg ctgagtataa                                            20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
tgcctctcgc tggaattact                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
tgtggctttc ctgtcctttt                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35 agggacatc cccattttac                                             20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
attcattttc cccatccaca                                            20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
ttgcaaagag ggggagtaga                                            20
```

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
acaaatccga gagccacaac                                                   20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
aacaccaaga gccaccaatc                                                   20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
ggtggctctt ggtgtttgag                                                   20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
tcgagctcat tgcacaattc                                                   20

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
caactttgaa caatgagcac ct                                                22

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
ctctcactgc tacccggttt                                                   20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
cgaggagtcc ggaataagaa                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
tcttttgctc tgtgcattgg                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
gcctcttgtg aaaaccgact                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
ccggtctaca ccccatacac                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
tggaatcctg aggtctttgg                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
cagaaatgca ccaagctgaa                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
ccctcccctt ttatttcgag                    20

<210> SEQ ID NO 51

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
gcttttcttt ccgattgctg                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
tgctttgggt gtgtctgaag                                           20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
ctcccagaaa ggcagaacag                                           20
```